US010639098B2

(12) United States Patent
Cosman et al.

(10) Patent No.: US 10,639,098 B2
(45) Date of Patent: May 5, 2020

(54) ELECTROSURGICAL GENERATOR

(71) Applicant: COSMAN INSTRUMENTS, LLC, Burlington, MA (US)

(72) Inventors: Eric R. Cosman, Belmont, MA (US); Eric R. Cosman, Belmont, MA (US)

(73) Assignee: COSMAN INSTRUMENTS, LLC, Burlington, MA (US)

( * ) Notice: Subject to any disclaimer, the term of this patent is extended or adjusted under 35 U.S.C. 154(b) by 0 days.

(21) Appl. No.: 14/325,303

(22) Filed: Jul. 7, 2014

(65) Prior Publication Data
US 2015/0320481 A1 Nov. 12, 2015

Related U.S. Application Data

(60) Provisional application No. 61/989,479, filed on May 6, 2014.

(51) Int. Cl.
*A61B 18/14* (2006.01)
*A61B 18/12* (2006.01)
(Continued)

(52) U.S. Cl.
CPC ...... *A61B 18/1482* (2013.01); *A61B 18/1233* (2013.01); *A61B 18/14* (2013.01);
(Continued)

(58) Field of Classification Search
CPC . A61B 18/1482; A61B 18/1233; A61B 18/16; A61B 18/14; A61B 2018/00577;
(Continued)

(56) References Cited

U.S. PATENT DOCUMENTS 4,411,266 A 10/1983 Cosman
4,565,200 A 1/1986 Cosman
(Continued)

FOREIGN PATENT DOCUMENTS

WO WO 99/40859 8/1999
WO WO 99/40860 8/1999
WO WO 00/59394 10/2000

OTHER PUBLICATIONS

Cosman et al. "Theoretical Aspects of Radiofrequency Lesions in the Dorsal Root Entry Zone," *Neurosurgery*, vol. 15, No. 6, pp. 945-950 (1984).

*Primary Examiner* — Michael F Peffley
(74) *Attorney, Agent, or Firm* — Steptoe & Johnson LLP

(57) ABSTRACT

This invention relates to high-frequency ablation of tissue in the body using a cooled high-frequency electrode connected to a high frequency generator including a computer graphic control system and an automatic controller for control the signal output from the generator, and adapted to display on a real time graphic display a measured parameter related to the ablation process and visually monitor the variation of the parameter of the signal output that is controlled by the controller during the ablation process. In one example, one or more measured parameters are displayed simultaneously to visually interpret the relation of their variation and values. In one example, the displayed one or more parameters can be taken from the list of measured voltage, current, power, impedance, electrode temperature, and tissue temperature related to the ablation process. The graphic display gives the clinician an instantaneous and intuitive feeling for the dynamics and stability of the ablation process for safety and control. This invention relates to monitoring and controlling multiple ground pads to optimally carry return currents during high-frequency tissue ablation, and to prevent of ground-pad skin burns. This invention relates to the use of (Continued)

ultrasound imaging intraoperatively during a tissue ablation procedure. This invention relates to the use of nerve stimulation and blocking during a tissue ablation procedure.

28 Claims, 23 Drawing Sheets

(51) Int. Cl.
    *A61B 34/10*     (2016.01)
    *A61B 90/00*     (2016.01)
    *A61B 18/16*     (2006.01)
    *A61B 18/00*     (2006.01)

(52) U.S. Cl.
    CPC .............. *A61B 18/16* (2013.01); *A61B 34/10* (2016.02); *A61B 90/37* (2016.02); *A61B 2018/00023* (2013.01); *A61B 2018/0072* (2013.01); *A61B 2018/00434* (2013.01); *A61B 2018/00577* (2013.01); *A61B 2018/00702* (2013.01); *A61B 2018/00708* (2013.01); *A61B 2018/00714* (2013.01); *A61B 2018/00732* (2013.01); *A61B 2018/00755* (2013.01); *A61B 2018/00767* (2013.01); *A61B 2018/00779* (2013.01); *A61B 2018/00791* (2013.01); *A61B 2018/00827* (2013.01); *A61B 2018/00833* (2013.01); *A61B 2018/00875* (2013.01); *A61B 2018/00892* (2013.01); *A61B 2018/124* (2013.01); *A61B 2018/165* (2013.01)

(58) Field of Classification Search
    CPC ........ A61B 2018/124; A61B 2018/165; A61B 2018/00791; A61B 2018/00708
    See application file for complete search history.

(56) References Cited

U.S. PATENT DOCUMENTS

| | | | |
|---|---|---|---|
| 4,566,454 A | 1/1986 | Mehl et al. | |
| 4,597,379 A | 7/1986 | Kihn et al. | |
| 4,727,874 A | 3/1988 | Bowers et al. | |
| 4,807,620 A | 2/1989 | Strul et al. | |
| 5,233,515 A * | 8/1993 | Cosman | A61B 5/042 600/509 |
| 5,433,739 A | 7/1995 | Sluijter et al. | |
| 5,571,147 A | 11/1996 | Sluijter et al. | |
| 5,769,847 A | 6/1998 | Paneseu et al. | |
| 5,951,546 A | 9/1999 | Lorentzen | |
| 5,983,141 A | 11/1999 | Sluijter et al. | |
| 6,104,959 A | 8/2000 | Spertell | |
| 6,161,048 A | 12/2000 | Sluijter et al. | |
| 6,246,912 B1 | 6/2001 | Sluijter et al. | |
| 6,259,952 B1 | 7/2001 | Sluijter et al. | |
| 6,301,506 B1 | 10/2001 | Den Boer et al. | |
| 6,321,120 B1 | 11/2001 | Surbeck et al. | |
| 6,397,106 B1 | 5/2002 | DeBrouse | |
| 6,402,739 B1 | 6/2002 | Neev | |
| 6,428,537 B1 | 8/2002 | Swanson et al. | |
| 6,440,127 B2 | 8/2002 | McGovern et al. | |
| 6,447,505 B2 | 9/2002 | McGovern et al. | |
| 6,482,204 B1 | 11/2002 | Lax et al. | |
| 6,517,534 B1 | 2/2003 | McGovern et al. | |
| 6,530,922 B2 | 3/2003 | Cosman et al. | |
| 6,692,493 B2 | 2/2004 | McGovern et al. | |
| 6,743,226 B2 | 6/2004 | Cosman et al. | |
| 6,843,789 B2 | 1/2005 | Goble | |
| 6,853,864 B2 | 2/2005 | Litovitz | |
| 6,869,430 B2 | 3/2005 | Balbierz et al. | |
| 7,522,953 B2 | 4/2009 | Kaula et al. | |
| 7,553,309 B2 | 6/2009 | Buysse et al. | |
| 7,566,332 B2 * | 7/2009 | Jarrard | A61B 18/1233 606/32 |
| 7,574,257 B2 | 8/2009 | Rittman, III | |
| 7,722,603 B2 * | 5/2010 | McPherson | A61B 18/16 606/32 |
| 7,736,357 B2 * | 6/2010 | Lee, Jr. | A61B 18/1233 606/32 |
| 7,938,825 B2 * | 5/2011 | Sturm | A61B 18/1233 606/35 |
| 2002/0156472 A1 | 10/2002 | Lee et al. | |
| 2002/0165531 A1 | 11/2002 | Goble | |
| 2003/0032951 A1 | 2/2003 | Rittman et al. | |
| 2003/0212390 A1 | 11/2003 | Chen et al. | |
| 2007/0032835 A1 | 2/2007 | Rittman | |
| 2008/0262490 A1 | 10/2008 | Williams | |
| 2009/0036885 A1 * | 2/2009 | Gregg | A61B 18/1233 606/35 |
| 2009/0187177 A1 * | 7/2009 | Epstein | A61B 18/16 606/33 |

\* cited by examiner

ELECTROSURGICAL GENERATOR

This application claims priority to U.S. Provisional Application No. 61/989,479, filed May 6, 2014, which is incorporated by reference in its entirety.

TECHNICAL FIELD

This invention relates generally to the advances in medical systems and procedures for prolonging and improving human life. The present invention relates generally to a system and method for applying energy, particularly radiofrequency (RF) or microwave (MW) energy, to a living body. The present invention also relates generally to a system and method for apply energy for the purpose of tissue ablation.

BACKGROUND

The use of radiofrequency (RF) and microwave (MW) generators connected to non-cooled electrodes inserted into the tissue of the body so that the signal output from the high frequency (HF) generator ablates the tissue has been used for decades. Both RF and MW generators are considered HF generators here. Use of cooled RF and MW electrode systems have also been in use for decades. Computer graphic systems have been described in use with high frequency ablation systems. The Cosman G4 Radiofrequency generator (Cosman Medical, Inc., Burlington, Mass.) is an example of a modern RF lesion generator that includes a graphic display, and the Cosman G4 brochure printed in 2011 is hereby incorporated by reference herein in its entirety.

A research paper by E. R. Cosman, et al., entitled "Theoretical Aspects of Radio Frequency Lesions in the Dorsal Root Entry Zone," *Neurosurgery*, Vol. 15, No. 6, pp. 945-0950 (1984), describes various techniques associated with radio frequency lesions and is hereby incorporated by reference herein in its entirety. Also, research papers by S. N. Goldberg, et al., entitled "Tissue Ablation with Radiofrequency: Effect of Probe Size, Gauge, Duration, and Temperature on Lesion Volume," *Acad. Radiol.*, Vol. 2, pp. 399-404 (1995), and "Thermal Ablation Therapy for Focal Malignancy," *AJR*, Vol. 174, pp. 323-331 (1999), described techniques and considerations relating to tissue ablation with radio frequency energy and are hereby incorporated by reference herein in its entirety. Examples of high-frequency (HF) generators and electrodes are given in the papers of entitled "Theoretical Aspects of Radiofrequency Lesions and the Dorsal Root Entry Zone," by Cosman, E. R., et al., *Neurosurg* 15:945-950, 1984; and "Methods of Making Nervous System Lesions," by Cosman, E. R. and Cosman, B. J. in Wilkins R. H., Rengachary S. S. (eds): *Neurosurgery*, New York, McGraw-Hill, Vol. Ill. pp. 2490-2498, 1984, and are hereby incorporated by reference herein in their entirety. A paper by D. A. Gervais, et al., entitled "Radiofrequency Ablation of Renal Cell Carcinoma: early Clinical Experience," Radiology, Vol. 217, No. 2, pp. 665-672 (2000), describes using a rigid tissue perforating and penetrating electrode that has a sharpened tip to self-penetrate the skin and tissue of the patient for the ablation of kidney tumors, and this paper is hereby incorporated by reference herein in its entirety.

United States patents by E. R. Cosman and W. J. Rittman, III, entitled "Cool-Tip Electrode Thermal Surgery System," U.S. Pat. No. 6,506,189 B1, date of patent Jan. 14, 2003; "Cluster Ablation Electrode System," U.S. Pat. No. 6,530,922 B1, date of patent Mar. 11, 2003; and "Cool-Tip Radiofrequency Thermosurgery Electrode System For Tumor Ablation", U.S. Pat. No. 6,575,969 B1, date of patent Jun. 10, 2003 describe systems and methods related to tissue ablation with radiofrequency energy, generators, and internally-cooled RF electrodes, and they are hereby incorporated by reference herein in their entirety. One electrode system described in these patents comprises an electrode with an insulated shaft except for a fixed uninsulated tip exposure of an uninsulated exposed length, the electrode being internally cooled so that the uninsulated exposed tip is cooled. The electrode shaft is a rigid and self tissue piercing with a sharp pointed distal tip on the electrode shaft. This is essentially the configuration of cooled electrode offered by the Radionics Cool-Tip Electrode System (Radionics, Inc., Burlington Mass.) and the Valley Lab Cool-Tip Electrode System (Valley lab, Inc., Boulder Colo.). One cooled-RF electrode shown in patent '189 includes an extension tip including a temperature sensor at its distal end. In a patent by Mark Leung, et al., entitled "Electrosurgical Tissue Treatment Method", U.S. Pat. No. 7,294,127 B2, date of patent: Nov. 13, 2007, a cooled RF electrode is shown. These patents are hereby incorporated by reference herein in its entirety. The cooled RF system manufactured by Baylis Medical Company (Canada) includes an RF generator maintains the temperature of an internally-cooled RF electrode substantially below the tissue boiling point, wherein the electrode includes a temperature sensor positioned in an extension tip at the distal end of the electrode shaft.

United States patent applications by E. R. Cosman Jr and E. R. Cosman Sr. "Cool RF Electrode" application Ser. No. 13/153,696, "Cool RF Electrode" application Ser. No. 14/072,588, and "Cool RF Electrode" application Ser. No. 14/076,113, describe systems and methods related to tissue ablation with radiofrequency energy, generators, internally-cooled RF electrodes, and RF cannulae, and they are hereby incorporated by reference herein in their entirety.

The following patents describe microwave tissue ablation devices and are herein incorporated by reference in their entireties: U.S. Pat. Nos. 4,641,649, 5,246,438, 5,405,346, 5,314,466, 5,800,494, 5,957,969, 6,471,696, 6,878,147, and 6,962,586. Microwave energy is typically delivered to tissue by application of a high frequency electromagnetic signal to an elongated antenna probe placed in bodily tissue, without the use of a reference ground pad, wherein the frequency is in the range 800 MHz to 6 GHz, for example. Currently the frequencies that are approved by the U.S. Food and Drug Administration for clinical work are 915 MHz and 2.45 GHz. Examples of companies with MW ablation systems includes Evident, Covidien, Mansfield, Mass.; MicrothermX, BSD Medical, Salt Lake City, Utah; Avecure, Medwaves, San Diego, Calif.; Certus 140, Neuwave, Madison, Wis.; Amica, Hospital Service, Rome, Italy; and Acculis MTA, Microsulis, Hampshire, England.

Examples of non-cooled electrode systems are in the product lines of the companies Cosman Medical, NeuroTherm, Radionics, ValleyLab, Baylis, Kimberly Clark, Stryker, and Diros Medical. Examples of non-cooled electrode systems with computer graphic display are given in the product lines of Cosman Medical, NeuroTherm, Stryker, Baylis, Kimberly Clark, and Diros. Examples of cooled high-frequency electrode system are shown in the product lines of Covidian, HS Medical, Boston Scientific, and Kimberly Clark. Generator systems for RF nerve ablation are included in the product lines of Cosman Medical, NeuroTherm, Radionics, ValleyLab, Baylis, Kimberly Clark, Stryker, and Diros Medical, and they produce maximum power 50 Watts, attach to up to four electrodes, and attach to one ground pad. Generator systems for RF tumor ablation are included in the product lines of Covidian, HS Medical, and Boston Scientific, and they produce maximum power 200 or 250 Watts, attach to up to three electrodes, and attach to up to four ground pads. One limitation of these RF generators is that they do not provide real-time graphic display of impedance as function of time. One limitation of these RF generators is that they do not provide real-time graphic display of current as function of time. One limitation of these RF generators is that they do not provide real-time graphic display of both current and impedance as function of time. One limitation of these generators is that they do not provide real-time graphic display of both impedance and the generator output level as function of time. One limitation of these generators is that they do not provide real-time graphic display of impedance, current, and temperature as function of time. One limitation of these generators is that they do not provide real-time graphic display any two of the following list: current, voltage, power, impedance, or mathematical functions with these parameters as arguments. One limitation of these RF generators that are configured for cooled RF tissue ablation by means of an automated impedance-driven pulsing process is that they do not provide a graphic display of any measured parameter as a function of time axis. While some generator systems in the prior art have allowed for export of generator readings which could be used to plot parameters on the same time axis after the ablation procedure, this does not provide instant feedback that would allow a clinician to monitor the ablation process as it progresses and to make adjustments if necessary. This advantage of real-time graphical doctor feedback has special importance for cooled-RF tissue ablation, because a single RF electrode can deliver very high current and heating power to influence tissue several centimeters away from that RF electrode (in contrast to typical non-cooled monopolar and bipolar surgical coagulation, for example), and because the amplitude and timing of impedance and output-level signals can indicate irregularities that can arise from heating over a large volume of tissue that may include multiple tissue types within different electrical and thermal characteristics.

U.S. Pat. No. 5,233,515 A, date of patent Aug. 3, 1993, entitled "Real-time graphic display of heat lesioning parameters in a clinical lesion generator system", by E. R. Cosman and W. J. Rittman, 111, describes a system for non-cooled RF ablation wherein temperature and impedance are plotted on the same time axis, and is hereby incorporated by reference herein in its entirety. One limitation of '515 is that no parameter of the RF generator signal output level (eg voltage, current, power) is plotted as a function of a time. Another limitation of '515 is that the RF generator signal output level (eg voltage, current, power) is not plotted on the same time axis as the impedance. Another limitation of '515 is that the system does not pertain to RF ablation using an internally-cooled RF electrode. Another limitation of '515 is that it does not pertain to automated methods of repeatedly pulsing the RF signal output.

U.S. Pat. No. 6,241,725, date of patent Jun. 5, 2001, entitled "High frequency thermal ablation of cancerous tumors and functional targets with image data assistance", by E. R. Cosman, describes a system for planning non-cooled RF ablation using temperature monitoring and control, including plots of various RF parameters. One limitation of '725 is that the system does not pertain to RF ablation using an internally-cooled RF electrode. Another limitation of '725 is that it does not pertain to automated methods for impedance-feedback control of a cooled RF electrode. Another limitation of '725 is that it does not pertain to automated methods comprising repeated pulsing the RF signal output.

Control methods for cooled RF electrodes exist in the prior art wherein the generator signal alternates between a high range and a low range in response to impedance spikes indicative of tissue boiling, which produces high-impedance gaseous vapor bubbles around the electrode active tip. The paper entitled "Percutaneous radiofrequency tissue ablation: optimization of pulsed-RF technique to increase coagulation necrosis" by S. N. Goldberg et al. (J Vasc Interv Radiol 1999; 10(7):907-916) and the paper entitled "High-Power Generator for Radiofrequency Ablation: Larger Electrodes and Pulsing Algorithms in Bovine ex Vivo and Porcine in Vivo Settings" by S. A. Solazzo et al. (Radiology 2007; 242(3):743-750) are hereby incorporated by reference in full and describe pulsing processes wherein the RF signal is delivered at a high, constant-current level until impedance rises above a threshold indicative of boiling (the "up time"); then the RF signal level is substantially reduced for a predetermined duration (the "down time"); then the RF output level is returned either to the previous high constant-current level or to a constant-current level 100 mA below the previous high constant-current level depending on whether the duration of the previous "up time" was above or below a threshold, respectively; and then the cycle of up times and down times repeats throughout the ablation process. Therefore, after an initial rapid ramp (in Solazzo, the initial predetermined current level is achieved in at most 30 seconds, at a rate of 67 mA/sec or 134 mA/sec) to bring the RF output to its initial set level, the level of successive constant-amplitude RF pulses monotonically decreases during the ablation process. One challenge in cooled RF control by means of impedance-based pulsing methods is the selection of a target radiofrequency signal level, eg current, that can produce a stable ablation process, because the maximum signal level that particular tissue can carry without overheating and limiting ablation size, can vary across tissue types, patients, and bodily locations. One limitation of the prior art in impedance-based pulsing methods for cooled RF ablation control is that the initial output level ramp is too fast to discriminate the maximum output level ramp that the tissue can stably carry during the ablation process. One limitation of the prior art in impedance-based pulsing methods for cooled RF ablation control is that the output level, namely the current level, does not increase from the initial set value during the ablation process. One limitation of the prior art in impedance-based RF pulsing methods is that if the output level is set low to avoid the risk of overheating the tissue, then the maximum ablation size may not achieved, or the maximum lesion size may be not achieved as efficiently as possible. In one aspect, the present invention seeks to overcome these limitations by means of an RF pulsing method that can both increase and decrease the generator output level during up times, eg current, in response to measured ablation parameters. Another limitation of the prior art in pulsing methods for cooled RF ablation is that the "down times" (that is, the inter-pulse cooling times) do not vary during an ablation session. The down times do not vary either in accordance with a predetermined schedule or in response to a measured parameter. This is an important limitation because the extent of the region of boiling tissue bubbles can change during the ablation process, and/or because the heat distribution around the bubble zone changes the rate of dissipation of the bubbles, and/or because a predetermined down-time duration may not be well matched to the every ablation scenario, leading to a situation where more or less inter-pulse cooling time is required for optimal dissipation of vapor bubbles in the tissue. In one aspect, the present invention seeks to overcome these limitations by means of an RF pulsing method wherein the down-time durations (ie the cooling time in between pulses) can vary during the ablation process. In some embodiments of the present invention, the variation of down times can include a component that is predetermined, as in the example of a predetermined schedule of increase in the down-times durations. In some embodiments of the present invention, the variation of down times can include a component that is influenced by one or more measured parameters during the ablation process. In various embodiments of the present invention, the variation of down times can either strictly increase, strictly decrease, or both increase and decrease. Another limitation of prior systems for RF tissue ablation is that they do not plot both the impedance and the generator output level (eg voltage, current, or power) on the same time axis in real time. Another limitation in the prior art is that prior systems for RF tissue ablation do not include a plot of two or more of the parameters impedance, voltage, current, and power. Another limitation in the prior art is that prior systems for RF tissue ablation do not include both an automatic method for output-level pulsing (eg for cooled RF tissue ablation) and a real-time graphical plot of a parameter of the generator output (eg voltage, current or power, impedance) as a function of time. Several aspects of the present invention seek to overcome these limitations.

In U.S. Pat. Nos. 8,152,801 and 8,357,151 by Goldberg and Young, an RF pulsing method for non-cooled RF ablation is proposed wherein the level of successive constant-amplitude RF pulses monotonically decreases during the ablation process in response to impedance variations indicative of tissue moisture content.

The use of radiofrequency (RF) generators and electrodes to be applied to tissue for pain relief or functional modification is well known. Related information is given in the paper by Cosman E R and Cosman B J, "Methods of Making Nervous System Lesions", in Wilkins R H, Rengachary S (eds.); Neurosurgery, New York, McGraw Hill, Vol. 3, 2490-2498; and is hereby incorporated by reference in its entirety. Related information is given in the book chapter by Cosman E R Sr and Cosman E R Jr. entitled "Radiofrequency Lesions.", in Andres M. Lozano, Philip L. Gildenberg, and Ronald R. Tasker, eds., Textbook of Stereotactic and Functional Neurosurgery (2nd Edition), 2009, and is hereby incorporated by reference in its entirety. For example, the RFG-3C plus RF lesion generator of Radionics, Inc., Burlington, Mass. and its associated electrodes enable electrode placement of the electrode near target tissue and heating of the target tissue by RF power dissipation of the RF signal output in the target tissue. For example, the G4 generator of Cosman Medical, Inc., Burlington, Mass. and its associated electrodes such as the Cosman CSK, and cannula such as the Cosman CC and RFK cannula, enable electrode placement of the electrode near target tissue and heating of the target tissue by RF power dissipation of the RF signal output in the target tissue. Temperature monitoring of the target tissue by a temperature sensor in the electrode can control the process. Heat lesions with target tissue temperatures of 60 to 95 degrees Celsius are common. Tissue dies by heating above about 45 degrees Celsius, so this process produces the RF heat lesion. For pain management, RF generator output is also applied to nerves using a type of pulsed RF method, whereby RF output is applied to tissue intermittently such that tissue is exposed to high electrical fields and average tissue temperatures are lower, for example 42 degrees Celsius or less; this is different from the RF pulsing methods for tissue ablation, such as that described in Goldberg et al. (1999) and in embodiments of the present invention, wherein the clinical objective is to heat large volumes of tissue surrounding the active tip to destructive temperatures, including temperatures that induce tissue boiling. High temperatures in pain management pulsed RF are undesired and are only sometimes present over very small regions (eg less than 0.33 mm in radius) near point of high curvature on active electrode tip, as described in an article by E. R. Cosman Jr. and E. R. Cosman Sr. entitled "Electric and thermal field effects in tissue around radiofrequency electrodes" (Pain Medicine 2005; 6(6): 405-424) which is hereby incorporated by reference in full. This is different the temperature profile produced by RF tissue ablation wherein approximately ellipsoidal high-temperature isotherms surround the electrode active tip and spread several millimeters or several centimeters from the active tip, thereby heating a substantially portion of the tissue in contact with the electrode active tip to a destructive temperature. The pain-management pulsed RF method is applied with pulses of RF that have duration in the range less than 50 milliseconds, with the RF level at zero in between pulses, and with pulse repetition rates of 1 to 10 Hz, so that the duration of each period wherein the RF is on is less than 50 milliseconds, and the duration of each period wherein the RF is off is less than 1000 milliseconds; this is different from RF pulsing methods for control of tissue ablation electrodes, such as that described for cooled RF in Goldberg et al. (1999) and in embodiments of the present invention, wherein the duration of each period in which RF is applied at a high level configured to substantially heat the tissue typically greater than 10 seconds and can be as long as the total time of the ablation process, and wherein the duration of each period wherein the RF is applied at a low level configured to allow tissue cooling is typically between 5 and 50 seconds. The pain-management pulsed RF method either adjusts the signal parameters pulse amplitude, pulse rate, and pulse width in response to a measured temperature; or fixes these values; and does not terminate and initiate RF pulses in response to either indications of tissue boiling, indications of tissue cooling, the expected duration of tissue cooling between RF pulses, or the value or variations of a measured impedance, current, voltage, or power. This is different from RF pulsing methods for control of tissue ablation, such as that described for cooled RF in embodiments of the present invention and in Goldberg et al. (1999), wherein the up times are terminated by a rise in impedance, and the down times have a duration configured to allow for the dissipation of high-temperature and high-impedance gas formed around the active electrode tip. The RF pulses in the pain-management method of pulsed RF are configured to reduce tissue heating; whereas the RF pulses in tissue-ablation pulsed RF methods, such as those presented in the present invention, are configured to maximize tissue heating. The durations of low signal level between RF pulses in the pain-management method of pulsed RF are not configured to allow for dissipation of gas bubbles distributed around the electrode active tip; whereas the durations of low signal level between RF pulses in the pulsed-RF methods of the present invention are configured to allow for dissipation of large gas bubbles distributed around the electrode active tip. The level of RF pulses in pain-management pulsed RF are not configured to increase a heat lesion size; whereas the level of RF delivered during the on periods of embodiments of the present invention are configured to increase the size of a heat ablation volume.

A significant difference between non-cooled electrode systems and cooled electrode systems is in the means of controlling the ablation process. For non-cooled electrode systems, the maximum tissue temperature is substantially at or near the surface of the electrode, so measuring the electrode temperature by a temperature sensor in the electrode, one can directly control the ablation process. For a given electrode temperature, size of electrode, and time of heating, you can predict reliably ablation size as described in the papers entitled "Theoretical Aspects of Radiofrequency Lesions and the Dorsal Root Entry Zone," by Cosman, E. R., et al., *Neurosurg* 15:945-950, 1984, and "Bipolar Radiofrequency Lesion Geometry: Implications for Palisade Treatment of Sacroiliac Joint Pain." By E. R. Cosman Jr and C. D. Gonzalez, Pain Practice 2011; 11(1): 3-22, which are herein incorporated by reference in their entireties. For non-cooled electrodes it is also possible to prevent the instability point of boiling of tissue, explosive gas formation, and charring of tissue by direct control of the HF generator signal output so the electrode temperature does not exceed 100° C. as described a monograph entitled "Guide to Radio Frequency Lesion Generation in Neurosurgery" by B. J. Cosman and E. R. Cosman, Radionics, Burlington, Mass., 1974.

A cooled-electrode HF ablation system differs from a non-cooled-electrode HF ablation system in that the maximum tissue temperature is at a distance from the electrode. The maximum tissue temperature around a cooled electrode occurs in a zone around the electrode tip, but at a distance from the electrode tip. The electrode is cooled so the electrode temperature is not typically a direct measure of the maximum tissue temperature, unlike non-cooled electrode systems wherein the maximum tissue temperature can be measured almost directly by means of the non-cooled-electrode's temperature sensor. Cooled-electrode HF ablation using an satellite temperature sensor, such as an extension tip containing a temperature sensor, can be temperature-controlled to prevent tissue boiling; this is different from cooled-electrode HF ablation in which the tissue temperature is not monitored (such as the case wherein the electrode does not contain a temperature sensor, or the case wherein the electrode temperature sensor is within the flow of coolant within the electrode) and the electrode is allowed to raise tissue temperatures into the boiling range.

The use of RF energy in neural tissue for the treatment of pain and functional disorders is well known. A typical nerve ablation protocol includes a first step in which one or more nerve stimulation signal is applied to an RF electrode for guidance of that electrode, and the a second step in which RF energy is applied to the RF electrode to ablate tissue near the electrode active tip. Typical nerve stimulation signals include biphasic electrical pulses delivered at a rate of up to 200 Hz, typically 50 Hz for sensory nerve stimulation and 2 Hz for motor nerve stimulation. Another well-known clinical use of high-frequency energy is the ablation of large tumors; this requires putting large amounts of power from the electrode into the tissue. This will cause the zone of maximum temperature to exceed 100 degrees C. That will cause the tissue to boil and bubbles to form in the zone of maximum temperature. This can be a rapidly explosive process and an unstable process. For tumor ablation performed using a cooled electrode, the temperature measured inside the cooled electrode is not a direct indication of the zone of instability. However, the instability is reflected in other signal output parameters, including, for example, the signal output impedance, power, current, and voltage. The above background references do not teach how to control the cooled HF electrode process when the generator signal output is increased so that the process is pushed into the region on of instability, nor do they show or teach how to maintain and monitor an ablation process that is held close to the instability point for the duration of the process.

U.S. Pat. No. 7,736,357 by Lee et al. (hereinafter "Lee") presents a radiofrequency ablation system wherein RF current from an ablation electrode is switched between two or more ground pads in a repeating sequence wherein only one ground pad is active at a time. One limitation of the prior art in Lee is that it does not provide for simultaneous activation of multiple ground pads at the same time during a switching sequence. Another limitation of Lee is that the peak current at each ground pad is identical and equal to the total current delivered to one or more ablation electrodes. This peak current can be very high, and can limit the total current that can be delivered by the ablation electrodes. Another limitation of the prior art in Lee is that the sequence of switch states is predetermined, alternating sequentially among a number of ground pads. Another limitation of the prior art in Lee is that the sequence of switch states is not based on a measurement of a ground pad parameter. Another limitation of the prior art in Lee is that a sequential ground-pad switching sequence does not generally minimize tissue heating for each ground pad relative to other switching sequences. Another limitation of the prior art in Lee is that a sequential ground-pad switching sequence does not maximize the total ablation current that a configuration of ground pads can carry, across all possible ground-pad switching sequences. Another limitation of the prior art in Lee is that it does not provide a switching method that can control both the total rate of heating in tissue adjacent to two or more ground pads, and the rate of heating in the tissue region adjacent to each one of the said two or more ground pads. In the prior art in Lee, for a given total current I delivered N ground pads by the ablation electrodes, the total average heating power delivered to tissue in contact with the two or more ground pads is proportional to $(I^2 * t_1/t) + \ldots + (I^2 * t_N/t)I^2$, where $t_i$ is the duration of i-th phase of the switching sequence in which only the i-th pad is connected and carrying current, and where $t = t_1 + \ldots + t_N$ is the total duration of one cycle of the switching sequence. Therefore, while the average heating power delivered to the i-th pad (which is proportional to the RMS current $I^2 * t_1/t$ delivered to the pad over the cycle period) can be controlled by adjustment of the duration $t_i$, the total average heating power is invariant variations in the timing of the switching pattern. Another limitation of Lee is that a cyclic switching sequence does not maximize the total current which can be carried by a set of ground pads, where the RMS current each ground pad is held below a safety limit. Another limitation is that the system of Lee does not reduce the number of switching transitions. Another limitation is that the system of Lee does not provide for both switching and independent current-monitoring for each pad.

The papers "Sequential Activation of a Segmented Ground Pad Reduces Skin Heating During Radiofrequency Tumor Ablation: Optimization via Computational Models", IEEE Trans Biomed Eng. 2008 July; 55(7): 1881-9 by D. J. Schutt and D. Haemmerich; "Sequential activation of ground pads reduces skin heating during radiofrequency ablation: Initial in vivo porcine results" Conf Proc IEEE Eng Med Biol Soc. 2009; 1:4287-4290 by D. J. Schutt et al.; and "Sequential Activation of Ground Pads Reduces Skin Heating During Radiofrequency Tumor Ablation: In Vivo Porcine Results" IEEE Trans Biomed Eng 2010 March; 57(3): 746-753 by D. J. Schutt et al. describe switching of power-regulated RF output to three ground pads in known positions relative to each other, wherein each pad includes a temperature sensor, wherein the switching sequence maintains the temperatures at a set level, and wherein the switching produces repeated cycles of the sequence: (1) proximal, middle, and distal ground pads activated; (2) middle and distal ground pads activated; and (3) only distal ground pad activated. One limitation the papers of Schutt et al. is that they do not provide for control the current carried by any one of the ground pads in relative to a target current value or a maximum current value. One limitation the papers of Schutt et al. is that they do not provide for automatic control of the root-mean-squared (RMS) current at each pad over each switching cycle. Another limitation of the papers by Schutt et al. is that integration of temperature sensors into the ground pads is required. One limitation preventing ground pad burns by temperature monitoring is that the temperature sensor may not directly or reliably measure the temperature of heated tissue, for example, in the case where the ground pad is not fully adhered to the skin. Another limitation of the papers by Schutt et al. is that the relative position of the ground pad was known ahead of time and used to set up the switching process manually, rather than automatically by means of a controller based on a measured parameter of a ground pad. Another limitation of the papers by Schutt et al., is that neither the ground-pad switch states (as reflected by the identities of the connected ground pads and disconnected ground pads) in the sequence, nor the order of the switch states in the sequence, was determined by an automatic controller using a measured ground-pad parameter. Another limitation of the papers by Schutt et al., is that the identity and order of switch states is predetermined. Another limitation of the papers by Schutt et al. is that they do not provide for both switching and current monitoring at each pad individually. Another limitation of the papers by Schutt et al. is that ground pad switch was used in conjunction with an ablation electrode output that was set to a constant power, which can lead to variable current density around the electrode active tip as ground pads are connected and disconnected, and thus potentially leading to inconsistent lesion sizes at the ablation site. Another limitation of the papers by Schutt et al. is that they do not provide for both switching and independent current-monitoring for each pad.

U.S. Pat. No. 7,566,332 by Jarrard and Behl presents a radiofrequency ablation system wherein the RF current flowing to each of two or more ground pads from an ablation electrode is balanced by adjusting a limited amount added resistance between the ground pad and the RF power supply. One limitation of adding resistance between a ground pad and the power supply is that generated electrical energy is dissipated in the resistance and does not heat the target tissue, thereby limiting the maximum heating power that the generator can produce. One limitation of the prior art in '322 is that the variety of ground pad configurations to which the system can adapt is limited by the limited amount of resistance that is added to each ground pad line during an ablation procedure.

Another limitation of the prior art is that RF ablation systems configured for nerve ablation do not include means for connection and monitoring of multiple ground pads. This is a significant limitation for energizing multiple nerve ablation electrodes in a single patient at the same time, which can produce high currents in excess of current capacity of a single typical nerve-ablation ground pad.

Another limitation of the prior art on ground pad switching in Lee and Schutt et al. is that they do not provide for the prevention or reduction of electrical stimulation of excitable tissue that can occur due to transient direct-current signals that can arise when a switch opens or closes. Undesired stimulation of excitable tissue can occur at a site remote of the ground pads and ablation electrodes. Undesired stimulation of nerves can occur, and be disturbing to the patient, due to high electric field strengths near the active tip of an RF ablation electrode and transients produced by connection or disconnecting a ground pad from the source of the RF ablation signal.

U.S. Pat. Nos. 6,575,969 and 6,506,189 by Rittman and Cosman, and U.S. Pat. No. 6,241,725 by E. R. Cosman relate to the use of ultrasound imaging data for tissue ablation. In the prior art, ultrasound imaging apparatuses are physically separate from HF ablation generators, and there is no connection between an ultrasound imaging device and a HF ablation generator for unified control of both devices, image and parameter display, and procedure documentation. One limitation the prior art in ultrasound image guidance for tissue ablation is that the physician must use a two sets of controls to operate both the ultrasound imaging device and the HF ablation generator. In one example, the absence of a single user interface for control and monitoring of both ultrasound imaging and ablation readings is a limitation for ultrasound-guided cooled RF tumor ablation using an RF pulsing process that repeatedly induces tissue boiling, because the ultrasound images and the RF generator readings both provide rich information to the operating physician who, as does the correlation of ultrasound features and features of RF generator readings (eg echogenic bubble formation and variations in RF impedance. Another limitation of the prior art is the absence of automated influence of the ablation process using ultrasound imaging data as an input.

The use of RF energy in neural tissue for the treatment of pain and functional disorders is well known. A typical nerve ablation protocol includes a first step in which one or more nerve-stimulation signal configured to induce repeated nerve firing, is applied to an RF electrode for guidance of that electrode to a target position near a near, a second step in which a fluid anesthetic is injected to prevent perception of pain during the nerve ablation, and a third step in which RF energy is applied to the RF electrode to ablate tissue near the electrode active tip. Typical nerve stimulation signals include biphasic electrical pulses delivered at a rate of up to 200 Hz, typically 50 Hz for sensory nerve stimulation, and typically 2 Hz for motor nerve stimulation. One limitation of the prior art is that RF and nerve-stimulation signals are not applied at the same time to a single peripheral nerve. One limitation of the prior art is that RF and nerve-stimulation signals are not applied at the same time to a single peripheral nerve, and firing in that nerve is not monitored at the same time. One limitation of the prior art is that RF and nerve-stimulation signals are not repeatedly interleaved to provide for nerve stimulation throughout an RF ablation process. One limitation of the prior art is the response of a nerve to a stimulation single is not used as a stopping criteria for an RF nerve ablation. Another limitation of the prior art is that an RF generator configured for nerve ablation does not produce nerve stimulation signals that are configured to electrically block the transmission of action potentials within a nerve, such as a high-frequency block signal.

The present invention overcomes the stated disadvantages and other limitations of the prior art.

SUMMARY OF THE INVENTION

The following are examples of embodiments of the systems and methods of the present invention. Further examples and details are given in the Description and Claims sections.

Some embodiments of the present invention include a cooled HF electrode, coolant supply, control system for automatic control of the ablation process, and computer graphic display.

In one exemplary embodiment, the present invention is directed towards systems and methods for ablating tissue in the living body. This can include using a combination of a radiofrequency generator, a graphical display of impedance and generator output level, a controller including an automatic master controller for modulating the radiofrequency generator output level in response to changes in tissue impedance, a coolant pump, multiple ground pads with current monitoring and switching, a cooled radiofrequency electrode system adapted for creating large ablation volumes, an ultrasound imaging system, and a single user interface that provides for control of both the radiofrequency generator and the ultrasound imaging system. In one application, the present invention is directed towards thermal tissue ablation, including ablation of cancerous tumors and nerve ablation for pain management.

In one example of the present invention, at least one of generator signal output parameters from the list of impedance, power, current, and voltage is displayed in real time as a function of a displayed time axis, and variations in the graph of the parameter reflect variations in the generator signal output to maintain the system near the unstable bubble zone around the electrode. One advantage of this is that the clinician gets an instant intuitive visual feeling for the stability of the ablation process.

In another example of the present invention, two or more parameters from the list of impedance, power, current, and voltage are displayed simultaneously and stacked on the same display and versus the same time scale axis. One advantage of this is the clinician gets an instant visual feeling for the relative variation of parameters to access if the ablation process is going properly according to the automatic controller.

In another example of the present invention, generator signal output impedance is displayed with one or more of the output parameters from the list of power, current, and voltage on the same display and versus the same displayed time axis. One advantage of this is that an upward spike in impedance that indicates that the unstable bubble zone is increasing rapidly is accompanied simultaneously with displayed signal output, which should be moderated, either by the user or an automatic controller, to stop the unstable explosive bubble formation according to the controller programming. This joint display of impedance and output level can be of particular importance in controlling a cooled RF electrode by feedback on measured impedance (for example, in the case where the electrode does not measure temperature, or the measured temperature is not representative of the tissue temperature as in the case where the temperature sensor is positioned within the coolant flow within the electrode) when the tissue is repeatedly heated to the point of boiling by the electrode, so the physician can assess, make predictions about, troubleshoot, and make adjustments to an ablation process that can involve multiple phases with variable features depending on electrode geometry and tissue condition. This joint display of impedance and output level can be of particular importance in a method of impedance-based pulsed RF control of cooled RF electrode wherein the pulse signal amplitude can both increase and decrease during the ablation process. This joint display of impedance and output level can be of particular importance in a method of impedance-based pulsed RF control of cooled RF electrode wherein the inter-pulse period can change in duration during the ablation process. This joint display of impedance and output level can be of particular importance in a method of impedance-based pulsed RF control of cooled RF electrode wherein the pulse signal amplitude can both increase and decrease, and the inter-pulse period can change in duration during the ablation process.

In another example of the present invention, the cooled electrode at its distal end has extension tip with indwelling temperature sensor to measure temperature at a distance from the electrode active tip in the region of maximum tissue temperature distal to the electrode active tip, and the maximum tissue temperature being displayed simultaneously on the same display as the measured generator signal output parameters. One advantage of this is that the accessory external temperature measured at the maximum tissue temperature where the bubble zone forms can be used to by the control system to control the ablation process. In another example, the cooled electrode has an extension tip that protrudes from the side of the electrode active tip, wherein the extension tip includes a temperature sensor that measures a temperature at a lateral distance from the main active tip. One advantage of an external temperature sensor at the side of the active tip is that the progress of the lesion along the side of the electrode can be monitored and the lateral extent of the heat lesion can be estimated. In some embodiments, the extension tip is electrically conductive and is a part of the active tip. In some embodiments, the extension tip is not electrically conductive and does not deliver electrical signal output to the tissue. In some embodiments, the extension tip is metallic but is not electrically connected to the generator signal output, and thereby the temperature sensor in the extension tip has a fast thermal response and is not itself generating heat in the tissue; in this embodiment, the thermosensor in the extension tip can include thermal insulation between it and the coolant flowing in the electrode (including in one example, an air gap between the thermosensor and the coolant flow); this has the advantage of more accurate sensing of tissue temperature at a distance from the electrode active tip.

For a cooled electrode system, the prediction of ablation size is less direct than for non-cooled systems because of its intrinsic instability at maximum signal output and the dependence on non-thermal measured parameters, including signal output power, current, voltage, and impedance. The prior references do not show or teach how to predict, nor how to allow the physician to predict, cooled-electrode ablation size in the case that the process is maintained near the instability region described above.

Another significant factor is monitoring the relation of variation of two or more of the signal output parameters including impedance, current, power, and voltage, as well as an external temperature reading if that is available. This is optimally done on a visual display with the graphs of each displayed parameter registered on the same time scale. None of the cited prior references shows or teaches about this aspect of the ablation control and monitoring.

Another objective of this patent is to display the graph of two or more of the parameters from the list of signal output impedance, power, current, and voltage, as well as an external temperature reading if available, on a computer graphic display, the graphs being stacked or superimposed and registered to the same time scale shown on the computer graphic display.

In another aspect, it is important that the clinician has a real time and intuitively clear visual interpretation of the ablation process from its beginning and how the control system and stability of the process is working. The clinician should be able to discriminate different graphs on the computer graphic display in the dim light of an operating room and from a distance, for example by means of color-coding of graphs of different parameters. None of the prior references show or teach these criteria.

Another objective of the present invention is to provide clearly visible and intuitively obvious real-time and histori-cally-complete computer graphic display of the ablation parameters related to the control of the process.

One objective of the present invention is to describe a system to control and monitor the cooled electrode ablation process using a pulsing control method and computer graphic display of one or more of the signal output param-eters power, current, and voltage. Another objective of the present invention is to describe a system and method for prediction of ablation size using a pulse control process executed by the control system, and using computer graphic display of signal output parameters to monitor the stability of the ablation process.

In one example, the control method is adapted to ramp up the signal output power, current, or voltage according to the control method to a desired level, and then turn off and on the signal output triggered by upward impedance spikes and determined by desired durations of on and off times as well as desired output levels during the on times to maintain a steady state of the ablation process near the bubble insta-bility to maximize ablation size, wherein all of this infor-mation is displayed in real time in the graphic displays of impedance, current and/or power. One advantage of this is that it gives an instant intuitive and visual feeling to the clinician about the course of the ablation process and whether it is working in a desired manner. One advantage of this is that the lesion size produced by a cooled ablation probe can be increased by means of automated, impedance-based pulsing of the signal output by a controller and display to the physician of visual information about the actions taken by the controller.

In one example, the amplitude of the pulses of signal output power is increased and decreased during the ablation process in response to measured parameters. In one example, the inter-pulse period of low signal output are increased and decreased during the ablation process in response to measured parameters. One advantage of this is that the pulse amplitudes, pulse duration, inter-pulse dura-tion can be adjusted in response to the conditions of a particular ablation process.

In some embodiments of the present invention, a radiof-requency generator system includes a first setting for the initial pulse output level, a second setting for the maximum pulse output level, and a controller than produces a series of pulses of radiofrequency signal output, each pulse being terminated in response to a measured indication of tissue boiling (such as an impedance rise); the signal output level during the pulses both increasing and decreasing during a single automated ablation process in accordance with the first setting and the second setting; and the output level and duration between pulses being set to a low level configured to allow for tissue cooling.

In one example, the patient has one or more ground pads as reference electrode for carrying return current from the cooled electrode, and the HF generator being adapted to measure the impedance and/or temperature of and/or current to the ground pads and one or more of these quantities being displayed on the computer graphic display in real time and on the same display as the measured generator signal output parameters. One advantage of this is that the ground pads can be monitored for faults that could result in skin burns. Another advantage is the ground pad currents can be regu-lated and/or equalized.

In another example, an RF generator system includes connections for multiple electrodes and multiple ground pads, and radiofrequency ablation can be effected at multiple electrodes at the same time; in this example, the generator provides user controls for activating and deactivating each electrode, changing the settings for each electrode individu-ally or collectively, and selecting the electrical potentials and patterns of switching electrical potentials to each other electrodes to effect radiofrequency ablation configurations including monopolar, bipolar, dual, multipolar, clustered, and sequences thereof; in some embodiments of this example, the system can include a controller that distributes current from the electrodes among the ground pads by sequentially connecting and disconnecting different subsets of the ground pads to source of the electrode current.

In another example, a radiofrequency generator switches current from one or more ablation electrodes among two or more ground pads in a sequence wherein two or ground pads carry current from the ablation electrodes at the same time at some point in the sequence. In another example, a radiofrequency generator maximizes the amount of time during which current is distributed among multiple ground pads in a ground pad switching sequence configured to regulate the current carried by each ground pad. In another example, a radiofrequency generator selects a sequence of ground pad connections that minimizes the current carried by each ground pain for a given, general ground pad configuration. In another example, a radiofrequency genera-tor automatically executes a process that selects a sequence of ground pad switch configurations, and the timing of that sequence, to reduce the current carried by each ground pad, for an arbitrary configuration of two or more ground pads and one or more ablation electrodes. In another example, a radiofrequency generator executes a process comprising selecting a sequence of ground pad switch configurations, and the timing of that sequence, to regulate ground pad heating based on measurement of a parameter related to ground pad heating. One advantage of this aspect, is that the process can adapt to an arbitrary ground pad setup without user input.

One objective of the present invention is to describe a system to reliably limit the heating of tissue in contact with ground pads used to carry return currents during ablation processes. Switching HF signal output among ground pads placed on the skin surface is different from switching HF signal output among ablation electrodes, in part because the former is configured to prevent or limit effects such as tissue heating near the ground pads, and the latter is configured to induce a clinical effect such as heat tissue near ablation electrodes. Generally, the skin heating is influenced by ohmic heating within the tissue volume adjacent to the area of ground pad contact. Ohmic heating is influenced by the local average power density, which is in turn influenced by the RMS current carried by the ground pad. By the principle of current conservation, the RMS current carried by a ground pad from another electrode can be predictive of ohmic heating power dissipated in tissue in close proximity to the ground pad, irrespective of other power losses and voltage drops in the conduction path between the ground pad and the electrode. In one aspect, the present invention is related to the measurement and control of the RMS ground-pad current over time windows that are short relative to the thermal response of tissue in contact with a ground pad, because this kind of RMS ground-pad current is a measurable parameter that relates to the rate of heating and the temperature increases in tissue that is in contact with a ground pad. In one aspect, the present invention relates to measurement of the current at each of two or more ground pads to prevent ground-pad skin burns during RF ablation procedures. In another aspect, the present invention relates to repeatedly connecting and disconnecting each of two or more ground pads during a RF ablation procedure to control the RMS current carried by each pad, and thereby to provide for the delivery of higher output currents to ablation electrodes while preventing skin burns. In another aspect, the present invention relates to avoiding undesired stimulation of excitable tissue as a result of ground pad switching. In another aspect, the present invention relates to maximizing the amount of time that multiple ground pads attached to the system are carrying return currents from ablation probes in order to reduce overall skin heating.

In another aspect, the ablation process, when dealing with very large tumors, can require as much as 200 to 400 watts of power into the body tissues, or more. For a medical RF procedure where return of current from the RF electrode is carried by one or more large area ground pads that are applied to the skin, a risk is that if the ground pad(s) is/are not fixed on the skin properly or is defective, then skin burns can occur. The prior references above do not show or teach solutions to this problem wherein an RF ablation system can adapt to an arbitrary arrangement of ground pads on a patient's skin surface.

Another objective of the present patent is to provide control and safeguards to reduce the chance of skin burns at the ground pads. In another aspect, the present invention relates to avoiding ground pad skin burns produced by a system for RF nerve ablation that produces high output levels, as in the case of multi-electrode RF nerve ablation systems.

In another example, a radiofrequency generator includes controls both for radiofrequency lesioning and for an ultrasound imaging device, so that ultrasound image-guidance for radiofrequency ablation, and the radiofrequency ablation itself, can be controlled from a single console; in a more specific example, the radiofrequency ablation is performed using an cooled RF electrode to which output is delivered using impedance-controlled RF pulses. In another example, ultrasound imaging data can be used as an input to a HF ablation controller and can affect the control of a HF ablation process, such as RF and MW ablation. For example, indicators of tissue changes due to ablation, such as changes related to tissue temperature or the formation of gas bubbles, can be used to control the ablation process, either by an automatic process, by user adjustments, or both. For example, as described in a paper entitled "Ultrasound Monitoring of in Vitro RadioFrequency Ablation by Echo Decorrelation of Imaging" by T. Douglas Mast et al. (J. Ultrasound Med 2008; 27:1685-1697), ultrasound imaging data can provide estimates of tissue temperature in the liver.

In another example, a radiofrequency generator includes a nerve stimulator and multiple ground pad connections. In this example, multiple ground pads can provides for higher total output in nerve ablation procedures. This can provides for ablation of multiple nerves using of multiple electrodes at the same time, nerve ablation using one or more large electrodes, and nerve ablation using one or more cooled electrodes, using standard electrosurgical ground pads.

In another example, a radiofrequency ablation system can produce a nerve stimulation signal and an RF ablation signal at the same time. This can provide for monitoring of nerve stimulation response during the ablation process. This can provide for a termination criteria for a nerve ablation process. This can provide for a means of determining the success of a nerve ablation procedure. This can provide for reduction of pain during a nerve ablation procedure. This can provide for the reduction of pain during a nerve ablation procedure without the direct application of anesthetic to the nerve, thereby allowing for evaluation of the efficacy of the nerve ablation soon after the ablation is complete.

The present invention can be used in numerous organs in the body, including the brain, spine, liver, lung, bone, kidney, and abdominal structures; and for the treatment or partial treatment of cancerous tumors, other pathological target volumes, or other types of tissue target volumes in, for example, nervous tissue, a nerve located within a bone, bone tissue, cardiac tissue, muscle tissue, or other types of bodily tissues.

Other examples of embodiments of the invention are given in the rest of this patent. The details of embodiments of the invention are set forth in the accompanying drawings and description below. Other features, objects, and advantages of the invention will be apparent from the description and drawings and from the claims.

BRIEF DESCRIPTION OF THE DRAWINGS

In the drawings that constitute a part of the specification, embodiments exhibited various forms and features hereof are set forth, specifically.

DETAILED DESCRIPTION OF THE INVENTION

Figure 1A:
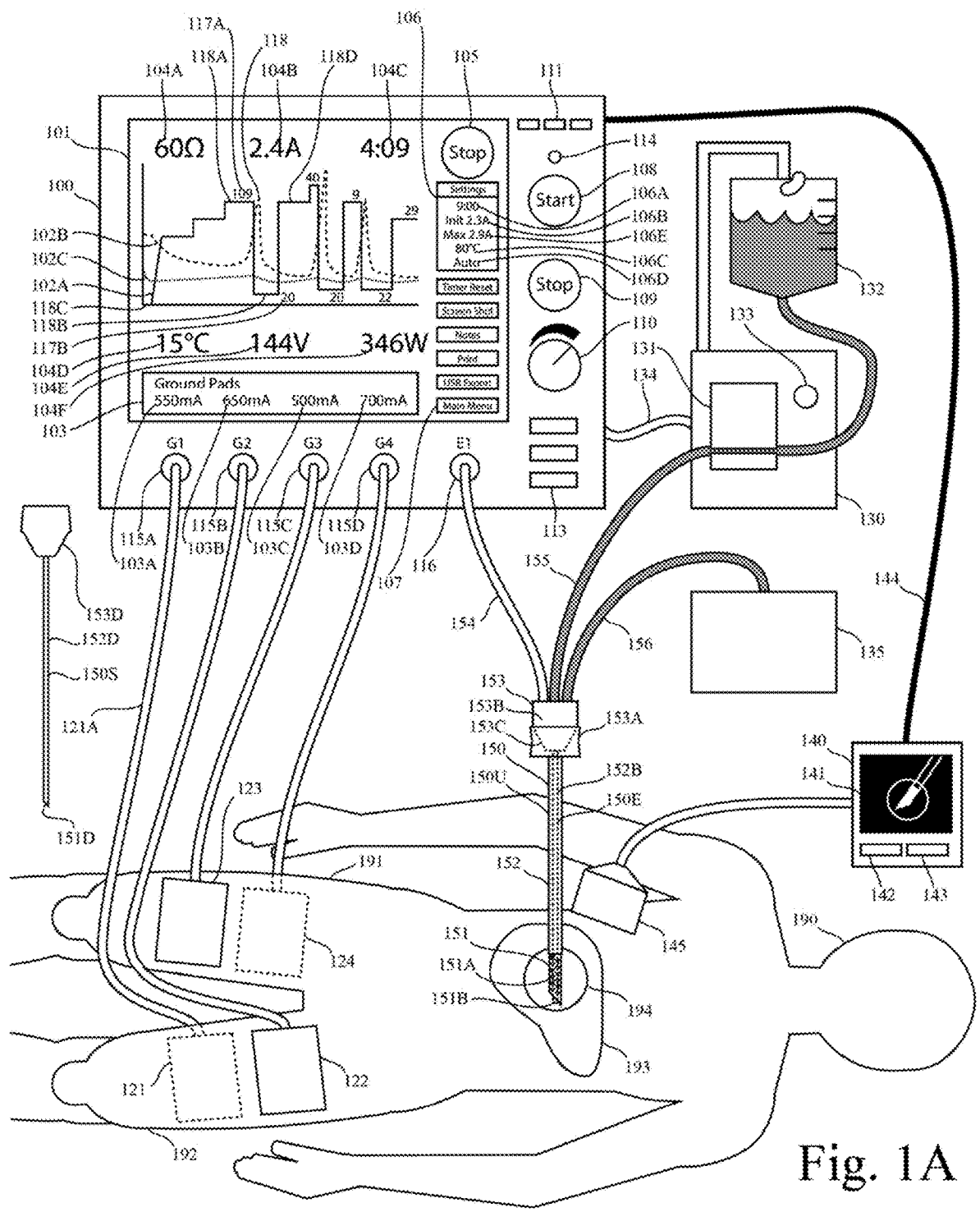
FIG. 1A is a schematic diagram showing a HF electrosurgical system configured for tissue ablation including an internally-cooled ablation probe comprising an internally-cooled electrode inserted into a RF cannula; one or more ground pads each with a current monitoring circuit; a coolant pump; an ultrasound machine; digital display of a HF output level parameters (voltage, current, and power), impedance, ablation probe temperature, and elapsed lesion time; a graphical user interface including graphs of impedance, HF output level, and temperature over time; a pulsing process that alternates between high and low levels of HF output and adjusts the high level of HF output in response to spikes in measured impedance; a HF generator in a front elevation view, including jacks for at least one ground pad; jacks for at least one cooled HF ablation probe; a graphic display including user controls, documentation functions, display of the current carried by each ground pad, and a graphs of ablation probe HF output level, impedance, and temperature plotted on the same time axis in real time; mechanical user controls; jacks for peripheral user interface devices; a jack for printing; a jack for data export; a jack for network connectivity; a link to, and controls for, the ultrasound machine; wherein the graphs report increments and decrements in the HF ablation probe output in response to ablation probe impedance readings, including the drastic reduction of current in response to rapid rises in impedance indicative of boiling tissue around the ablation probe active tip.
Figure 1B:
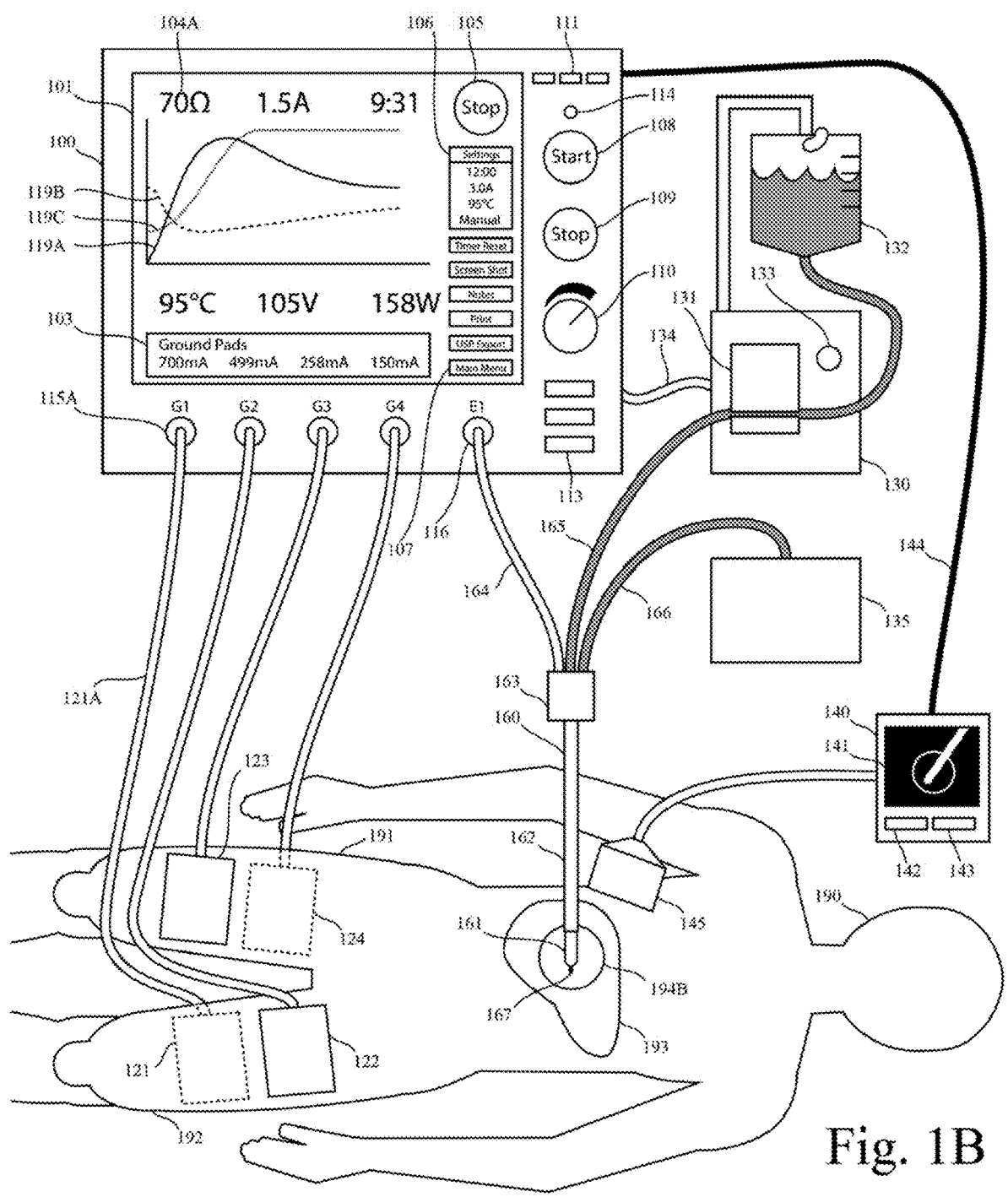
FIG. 1B is a schematic diagram showing a HF electrosurgical system for tissue ablation wherein a cooled HF electrode includes a temperature sensor on a distal extension tip, and a HF generator measures and regulates the temperature from the temperature sensor; wherein the electrical current flowing to each of multiple ground pads is measured, displayed to the user, and automatically controlled; wherein a HF generator includes an operative connection to an ultrasound machine and user controls for that ultrasound machine.
Figure 1C:
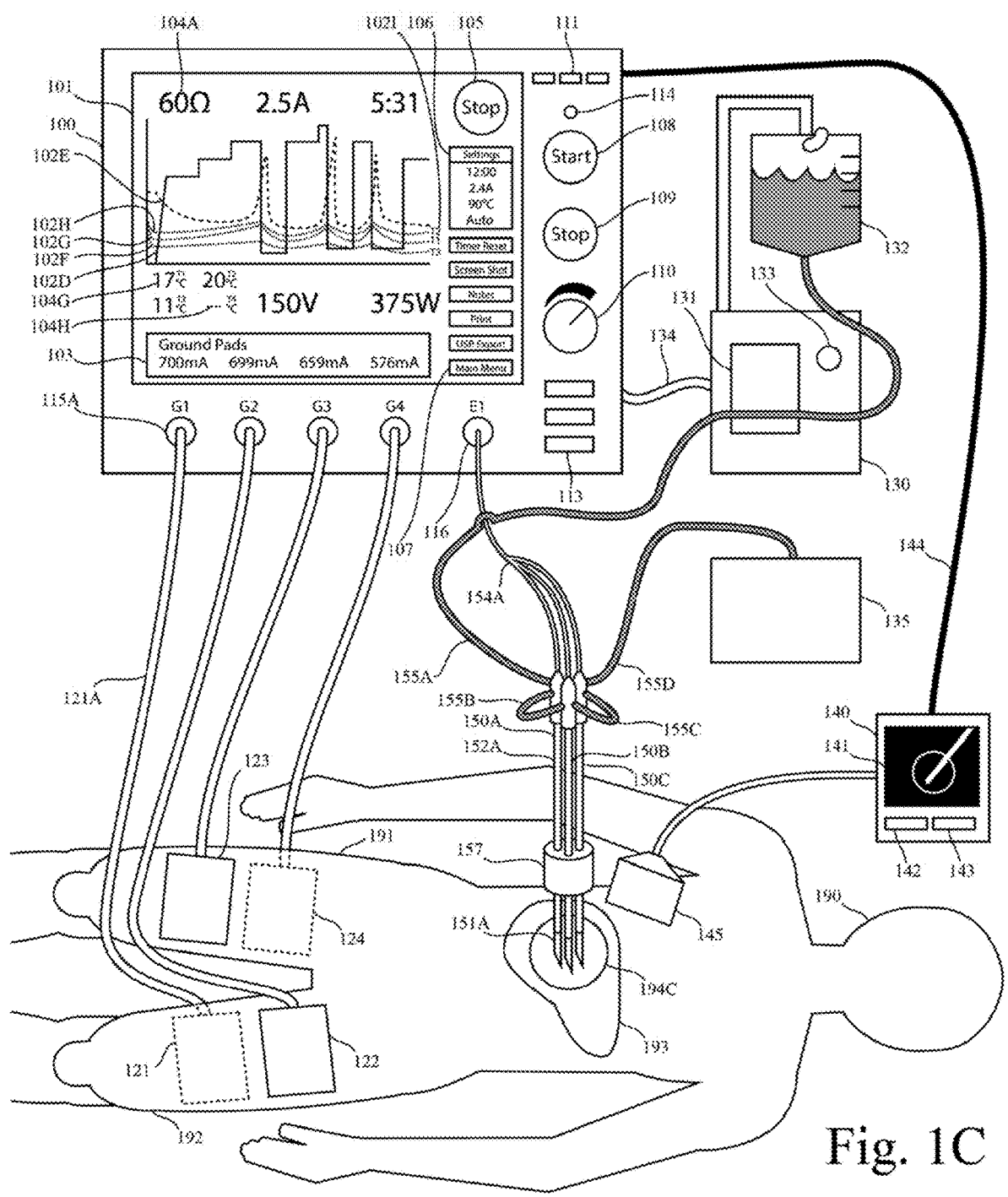
FIG. 1C is a schematic diagram showing a system for HF tissue ablation wherein an internally-cooled cluster of electrodes is attached to signal output of a HF electrical signal generator; wherein each independent shaft of the clustered electrodes includes an active region for transmission of HF signal output to the patient and a temperature sensor positioned within the flow of coolant within the shaft; wherein the electrodes are constrained in a parallel triangular configuration by a guideblock through which the shaft of the electrodes pass; wherein the generator automatically pulses the signal output in response to variations in the impedance encountered by signal output delivered to the electrode cluster that indicate boiling and cooling in tissue heated by the electrode cluster; wherein a graphic display plots on one time axis, in real time, the signal output level delivered to the electrode cluster, the impedance encountered by the signal output to the electrode cluster, and each of the temperatures measured by the electrode cluster; wherein multiple ground pads carry return current from the cluster electrode; wherein the current carried by each ground pad is measured, displayed to the user, and are maintained under a maximum limit; wherein the HF signal generator includes an operative connection to an ultrasound machine and user controls for that ultrasound machine.

FIG. 1 refers collectively to FIG. 1A, FIG. 1B, and FIG. 1C. FIG. 1 presents schematically several embodiments of an apparatus for HF ablation of tissue within a patient 190, in accordance with the present invention. Each of the embodiments in FIG. 1, include a HF generator 100 such as an RF generator, a MW generator, or a RF and MW generator; one or more ground pads 121, 122, 123, 124 applied to the skin surface of patient 190; one or more ablation probes 150, 160, 150A, 150B, 150C, placed within target anatomy, such as liver 193; a coolant pump 130 that is configured to cool one or more of the ablation probes, eg 150; a reservoir 135 for collection of used coolant; and an ultrasound machine 140. The ground pads 121, 122, 123, and 124 can be connected to a reference potential generated by the HF generator 100 to carry return currents from the ablation probe (150 in FIG. 1A, 160 in FIG. 1B) or probes (150A, 50B, 150C in FIG. 1C). In some examples, the ground pads can be omitted when the HF generator 100 is delivering MW energy the ablation probe. The at least one ablation probe can be connected to the HF output 116 of the HF generator 100. The coolant pump 130 can be operably connected to the generator 100 by means of control connection 134, and the activation and rate of coolant flow to an ablation probe can be controlled by the generator 100, for example, in coordination with ablation programs being run by the generator 100. The ultrasound imaging machine 140 includes user controls 142 can be operably connected to the generator 100 by means of control connection 144; controls 113 included in the generator 100 can be used to operate some or all functions of the ultrasound machine 140; and controls 143 included in the ultrasound machine 140 can be used to operate some of all of the function of the generator 100. A data file that includes procedure data both from the RF generator and the ultrasound machine can be produced by the combination of the generator 100 and the ultrasound machine 140; that data file can be saved to internally memory included in the generator 100; that data file can be saved to internal memory including the ultrasound machine 140; and that data file can be exported to an external data repository, such as an external disk or computer, by means of a data connection included in the either the generator 100, the ultrasound machine 140, or both. In some other embodiments, the ultrasound machine 140 and generator 100 can be integrated into a single housing. In some other embodiments, the ultrasound machine 140 and generator 100 can be integrated into a single chassis with a single screen. The generator 100 includes a user interface, including a graphical display 101, which can be a touch screen and includes numerical displays 104A, 104B, 104C, 104D, 104E, 104F, 104G, 104H and graphical displays 102A, 102B, 102C, 102D, 102E, 102F, 102G, 102H, 119A, 119B, 119C of readings and controls. The graphical user interface 101 can graph readings, such as elapsed time, impedance, current, temperature, voltage, and power, as a function of time. In the embodiments shown in FIG. 1, The graphical displays 102A, 102B, 102C, 102D, 102E, 102F, 102G, 102H, 119A, 119B, 119C each plot a parameter on the vertical axis as a function of time on the horizontal axis, and can each be referred to as an (x,y) line plot where y is time and x is a parameters selected from the list: impedance, current, power, voltage, and temperature. Each graphic display of a parameter can be color-coded so they are easy to discriminate from each other on the computer graphic display 101. Each the digital and graphic display of the same reading, can have the same unique color, so that it is easy for the user to associate the digital and graphic display of the same parameter, and to distinguish displays of different parameters. For example, impedance reading 104A can have the same color as graph 102C in FIG. 1A, and that color can be green. The current reading 104B can have the same color as graph 102A in FIG. 1A, and that color can be yellow. The temperature reading 104D can have the same color as graph 102C in FIG. 1A, and that color can be red. Other color assignments can be used. The generator 100 includes one or more controllers for automated and/or semi-automated control of the HF output, including for example, control of the HF output as a function of a measured temperature, impedance, and the past variations of temperature and/or impedance. The generator 100 can include switches, controls, and programmed methods for control of the current delivered to each pad, including the RMS current delivered to a pad over a time period that is short relative to the time-constant of thermal response of the ground pad.

The HF generator 100 can include a lamp 114 that indicates the active delivery of HF energy capable of tissue ablation; a mechanical button 108 by means of which a user, such as a medical doctor or nurse under the direction of a doctor, can turn on the HF ablation output; a mechanical button 109 by means of which a user can turn off the HF ablation output; a mechanical knob 110 by means of which the user can adjust the output level of the HF ablation output, for example the HF current, when the generator 100 is configured to allow for manual adjustment of the output; controls 113 for an ultrasound imaging machine 140; one or more data connections 111, such as USB port or ports, that can each provide for transfer or data and/or control connection with one or more of a computer network, an external hard disk, a computer, a flash drive, a wireless remote control, a wired hand controller, or printer; a jack 116 that provides delivery of HF output to one or more of an RF electrode, a MW antenna, a cluster of RF electrodes, or other type of ablation probes; one or more ground pad jacks 115A, 115B, 115C, 115D for connection to one or more ground pads 121, 122, 123, 124; and a touch screen display 101. In some embodiments, the user can select whether the generator 100 delivers RF output, MW output, or both.

The generator can be capable of producing a high level of power, voltage, and current output, for example, a power output of 0 to 400 W, 100 W, 200 W, 250 W, 300 W, 350 W, 400 W, or more than 400 W; for example, a voltage output level of 100 to 200 Volts-RMS, 100 V-RMS, 120 V-RMS, 140 V-RMS, 160 V-RMS, 180 V-RMS, 200 V-RMS, or more; for example, a current output level of 0-4000 mA-RMS, 500 mA-RMS, 1000 mA-RMS, 1500 mA-RMS, 2000 mA-RMS, 2500 mA-RMS, 3000 mA-RMS, 3500 mA-RMS, 4000 mA-RMS, or more. In some embodiments, the generator 100 is an RF generator capable of producing 400 Watts and 3000 mA-RMS of RF output. An output level of up to 400 W and/or up to 3000 mA-RMS is advantageous for heating cooled RF electrodes with shaft diameters in the range 18-14 gauge and tip lengths in the range 1 to 6 cm, both in single-electrode and in multi-electrode cluster configurations.

The generator 100 can store all measured readings during, before, and after running an ablation program to memory as a procedure record file or files. The record file can be stored in memory internal to the generator and to external memory, such as an external disk attached to data port 111. The procedure record can include averages, maximum, modes, and other statistics of measured readings configured to provide the physician with a meaningful, easy to understand record of a medical ablation procedure. The procedure record can include or be processed to produce graphs and analysis of measured values. The procedure record can include text annotation of the data, including patient information. In some embodiments, the generator can explicitly prevent the storage export of sensitive patient information in the procedure record. The procedure record can include ultrasound, fluoroscopy, CT, MRI, and other imaging data.

In some embodiments, an interface between a HF generator 100 and ultrasound machine 140 via connection 144 can be standardized to allow for interoperability different HF generators and different ultrasound machines. In one example, the manufacturer of the generator 100 can write a specification for data connection 144, and provide a technical specification for the data connection 144 to one or more manufacturers of US machines (such as ultrasound machine 140), whereby each of the said one or more manufacturers of US machines can construct a US machine configured to inter-operate with the generator 100. A method of sales and marketing for a tissue ablation apparatus 100 comprises including an interface 144 in the tissue ablation apparatus 100 and publishing a specification of that interface. This solves the problem of how to integrate tissue ablation technology from a one manufacturer with medical imaging technology from another manufacturer or manufactures. In some examples, the specification can be provided publically. In some examples, the specification can be provided privately. In some examples, the specification can be provided for free. In some examples, the specification can be provided for a price. The specification for the data connection 144 can include pin outs, signal levels and limits, command codes, timing specifications, and other specifications familiar to one skilled in the art of communication and control. The interface 144 can carry multiple type of a data, including data for control of operations of the generator 100, data for control of operations of the US imaging system 140, data representing operation and measurements of the HF electrosurgical apparatus 100, data representing operation and measurements of the US imagining machine 140. For example, the specification can explain how an US machine 140 (or another type of device) can perform one or more of the following functions by means of the connection 144: read the signal output level measurements of the generator 100, read the impedance measurements of the generator 100, read the timer of the generator 100, read the temperature measurements collected by the generator 100, read the settings of the generator 100, read patient and physician data from the generator 100, read the operational state of the generator 100, read images displayed on the screen of the generator 100, enable and disable the signal output of the generator 100, change the settings of the generator 100, change the operational state of the generator 100, send image data from the US machine 140 to the generator 100, send imaging settings to the generator 100, send to the generator 100 operational state information about the US machine 140, allow the generator 100 to control the operational state of the US machine, allow the generator 100 to adjust the settings of the US machine 140, allow the generator 100 to read patient and physician data from the US machine 140. The specification can be used to verify and validate the inter-operation of an US machine 140 and ablation apparatus 100. In some embodiments, the data connection 144 include one of the communication types selected from the list: USB, serial, parallel, RS232, VGA, HDMI, DVI, or a custom communications protocol. In some examples, the communication connection 144 can be uni-directional, such as wherein data is sent from the generator 100 to the US machine 140, or wherein data is sent from the US machine 140 to the generator 100. In some examples, the communication connection 144 can be bi-directional, wherein data is sent back and forth between the electrosurgical system 100 and the ultrasound imaging apparatus 140. In some embodiments, the ultrasound imaging apparatus 140 can be another type of medical imaging apparatus, including, without limitation, a fluoroscopy imaging apparatus, an x-ray imaging machine, an MRI scanner, a CT scanner, a spiral CT scanner, a PET scanner, an optical coherence tomography (OCT) device. In some embodiments, the medical apparatus 100 can be another type of diagnostic or interventional medical device, including, without limitation a RF generator, a MW generator, a laser ablation device, an irreversible electroporation (IRE) ablation apparatus, a cryo-ablation device, an optical coherence tomography (OCT) imaging device.

In another example, the manufacturer of the ultrasound machine 140 can write a specification for data connection 144, and provide a technical specification for the data connection 144 to one or more manufacturers of HF generators (such as generator 100), whereby each of the said one or more manufacturers of HF generators can construct a HF generator configured to inter-operate with the ultrasound machine 140. A method of sales and marketing for a medical imaging apparatus 140 comprises including an interface 144 in the medical imaging apparatus 140 and publishing a specification of that interface. This solves the problem of how to integrate tissue medical imaging technology from a one manufacturer ablation technology from another manufacturer or manufactures. In some examples, the specification can be provided publically. In some examples, the specification can be provided privately. In some examples, the specification can be provided for free. In some examples, the specification can be provided for a price. The specification for the data connection 144 can include pin outs, signal levels and limits, command codes, timing specifications, and other specifications familiar to one skilled in the art of communication and control. The interface 144 can carry multiple type of a data, including data for control of operations of the generator 100, data for control of operations of the US imaging system 140, data representing operation and measurements of the HF electrosurgical apparatus 100, data representing operation and measurements of the US imagining machine 140. For example, the specification can explain how an ablation apparatus 100 (or another type of device) can perform one or more of the following functions by means of the connection 144: read the operational state of the US machine 140, read the measurements of the US machine 140, read the settings of the US machine 140, read patient and physician data from the US machine 140, read the operational state of the US machine 140, read images displayed on the screen of US machine 140, enable and disable the functions of the US machine 140, change the settings of the US machine 140, change the operational state of the US machine 140, send signal output and measurement data from the generator 100 to the US machine 140, send generator settings to the US machine 140, send to the US machine 140 operational state information about the ablation apparatus 100, allow the US machine 140 to control the operational state of the generator 100, allow the US imaging device 140 to adjust the settings of the generator 100, allow the US machine 140 to read patient and physician data from the generator 100. The specification can be used to verify and validate the inter-operation of an US machine 140 and ablation apparatus 100. In some embodiments, the data connection 144 includes one of the communication types selected from the list: USB, serial, parallel, RS232, VGA, HDMI, DVI, or a custom communications protocol. In some examples, the communication connection 144 can be uni-directional, such as wherein data is sent from the generator 100 to the US machine 140, or wherein data is sent from the US machine 140 to the generator 100. In some examples, the communication connection 144 can be bi-directional, wherein data is sent back and forth between the electrosurgical system 100 and the ultrasound imaging apparatus 140. In some embodiments, the ultrasound imaging apparatus 140 can be another type of medical imaging apparatus, including, without limitation, a fluoroscopy imaging apparatus, an x-ray imaging machine, an MRI scanner, a CT scanner, a spiral CT scanner, a PET scanner, an optical coherence tomography (OCT) device. In some embodiments, the medical apparatus 100 can be another type of diagnostic or interventional medical device, including, without limitation a RF generator, a MW generator, a laser ablation device, an irreversible electroporation (IRE) ablation apparatus, a cryo-ablation device, an optical coherence tomography (OCT) imaging device.

Referring now to FIG. 1A, the HF system comprises a HF generator 100 that is adapted to measure the generator signal output parameters including one or more of parameters from the list of impedance, power, current, and voltage. The graphic computer in system 100 is adapted to graphically display in real time these signal output parameters on the graphic display 101. The effects of modulation of the signal output on the measured parameters to stabilize the ablation process when the process is pushed into the limit of an explosive bubble zone can be visualized on the computer graphic display 101. This aspect is shown in more detail in the figures that follow.

In FIG. 1A, the graphical plot of parameters 102A, 102B, 102C gives the clinician a visual, intuitive, and real time update and evaluation of whether the ablation process is proceeding properly and safely. In one example, the graph 102A can represent signal output current. In one example, the graph 102A can represent signal output power. In one example, the graph 102A can represent signal output voltage. The dotted graph 102B represents schematically the output impedance. The upward spikes in impedance, such as spike 118, represent the occurrence of boiling and bubble formation in the tissue around the active or exposed tip of the ablation electrode 150. The bubble zone is the hottest region around the electrode active tip 151 and is located at a distance from the electrode tip 151, which is cooled. This is an unstable situation. If the generator signal output is not reduced, the bubble zone will explosively expand, the impedance spike will shoot up, and the ablation current and power will be reduced dramatically. This unstable situation can be avoided by quick reduction of the generator signal output before the impedance spikes reach too high a level. That impedance level can be a threshold set point in the control system that can be set by the clinician or the manufacturer. That impedance level can be the trigger point to reduce the generator signal output, as illustrated by the reduction from a high level 118A to a low level 118B in graph 102A. In one example, the signal output is reduced to zero for a down time 118B according to the generator controller. In another example, the signal output is reduced or modulated to non-zero value in the down time 118B according to the controller. The down time 118B allows the bubble zone to cool down and the bubbles to dissipate and the impedance to reduce to a baseline value as shown during down time 118B in graph 102B in FIG. 1A. Then the signal output, in one example, can be again brought up to a higher level for another up time, as shown by the level 118D. The ablation heating process resumes during the up time, and the signal output current can pass through the bubble zone and heat the tissue outside it to continue enlarging the ablation size. Then in one example, the signal output level in the up time will heat and grow the bubble zone again so that after an up time duration the impedance will once again become unstable and spike upward. The up time duration depends on the upper signal output level during the up time. In one example, the signal output level will again be turned off for a down time duration according to the control system and programmed methods. The repeating process of up times (eg 118A) and down times (eg 118B) continues according to the automatic controller. The process can, in one example, stabilize to a desired level of signal output level during the up times and a desired repeating durations of up times and down times to produce a desired ablation process and ablation size. In one example, the control system uses the level of impedance spikes (eg 118) and the signal output levels to stabilize the sequences of up times and down times so that the ablation process is uniform and reproducible for a given electrode geometry and tissue impedance. In another aspect the total duration of the ablation process has an effect on the ablation size. This can be a parameter in the controller to predict desired ablation size. The ablation size can be reproducible and predictable by stabilizing the above described control process.

A very important and useful advantage for the clinician is to have an instant and intuitively clear visual check and feedback on the stability and control of the ablation process as it proceeds. One example of how to provide that is to provide a computer graphic real time display of the generator signal output during the procedure. In one example, the graph of only one of the generator signal output parameters, power, current, or voltage, is displayed on the computer graphic display 101. In the example that the displayed parameter is power and/or current, the up times and down times, as well as the stability of the power and/or current level, can visually tell the clinician at a glance if the ablation process is going stably as executed by the controller, or if the ablation process is going wrong. In one example, if the up-time power and/or current is too high, then excessive boiling will occur in the bubble zone. The impedance will be sustained at too high levels, and the power and/or current graphic display 102A will slump, decrease, or otherwise become erratic or unstable. In one example, the displayed output parameter is voltage, and excessive voltage levels during the up time periods will cause impedance 102B to be sustained at too high levels causing the voltage to rise or fall or otherwise behave erratic and not according to smooth desired behavior. In another example, wrong levels of the displayed generator signal output parameter can cause the automatic controller to produce incorrect, erratic, or unstable durations of the up times and/or down times, indicating a deviation from a desired ablation process. These and other examples can be visualized and instantly and intuitively accessed by the clinician by the graphic real time display 102A of one or more of the signal output parameters in the list of power, current, and voltage. This gives the advantage of safety and control.

In one example, the signal output impedance 104A, 102B is measured by the control system. The level and timing of the upward impedance spikes, such as 118, is also measured, and the control system uses that information to determine the timing and/or durations of the up times and down times and/or the levels of the signal output parameters, as the ablation process goes along. In one example, the impedance 102B is not displayed on the computer graphic display, but processing of the impedance information is done within the control system according to the automatic controller. The results of the processing is indirectly manifest in the graphic display of the one or more signal output parameters 102A. Another advantage of the real time display of one or more signal output parameters 102A is that it gives the clinician an instant check of the working of the control system and programmed processes.

In another example the impedance 102B is displayed on the computer graphic display along with the display of the one or more signal output parameters 102A. The graphic displays of impedance 102B and the one or more output parameters 102A can be stacked on each other and/or overlaid relative to the same time scale also displayed on the same computer graphic display 101. This is illustrated in FIG. 1A by the impedance graph 102B. This enables the clinician to see the impedance spikes, such as 118, and see that the level to which they rise is within desired limits according to the automatic controller. One advantage is the clinician can visually evaluate the relation of impedance behavior 102B and behavior of the one or more signal output parameters 102A to see if the control system and control process are functioning properly.

Also shown in FIG. 1A are digital displays of the power 104F, current 104B, voltage 104E, impedance 104A, and elapsed time 104C. In one example, as shown in FIG. 1A, the current to each of the surface ground pads are shown digitally 103A, 103B, 103C, and 103D. In another embodiment, a plot of each of the ground pad currents over time is additionally shown on display 101. For example, element 103 can include a line graph plotting each ground pad current on the vertical axis and time on the horizontal axis; in some embodiments, the horizontal axis can have the same time scale as that of the electrode plots 102A, 102B, 102C. If one or more of the ground pads is lifting off the skin or is otherwise separated, then the graphic display of current for that pad will show an anomaly, for example, as a dip of discontinuity in the graph. In some embodiments, the impedance of each ground pad can be displayed digitally and/or graphically. One advantage of graphic and/or digital displays of ground pad current and/or impedance is that they give the clinician and instant warning of trouble with the equipment to avoid harm to the patient such as skin burns.

FIG. 1A also shows graphic user interface controls, including buttons 105, 106, and 107. In one example, these controls include interaction with the automatic controller and computer graphic control to adjust parameters of the ablation process to suit the clinician needs.

The present invention has the advantage of producing reproducible results in terms of ablation zone size. Visual graphic display of output parameters during the ablation process and seeing that the parameters are stable can indicate to the clinician uniformity of control from one patient to another and one target situation to another. This is significant because the ablation process is a repetition of approaching a unstable boiling condition. Bringing stability to this unstable process and enabling visual conformation is a significant advantage.

Referring to FIG. 1A, FIG. 1A is a schematic drawing showing one example of an arrangement of an apparatus for performing HF ablation of bodily tissue relative to the patient 190, in accordance with some aspects of the present invention. A cooled HF electrode 150 is inserted into the patient body 190 percutaneously. The ablation electrode 150 includes a hub 153 at the electrode proximal end, and an elongated shaft portion with a distal end and a proximal end, wherein the distal end is inserted into the patient body 190 percutaneously, and wherein the shaft portion includes an insulated portion 152 and a tip portion 151. In one example, the shaft portion can comprise rigid metal tubing which is insulated on its outside surface on the insulated portion 152 and uninsulated on active tip portion 151. In another example, the shaft portion is a flexible structure having uninsulated tip portion 151. In another example, the tip portion 151 can comprise an antenna structure for propagating MW energy into body tissue. The electrode is adapted to connect to the HF system 100 by attaching electrode cable 154 to generator jack 116. The HF system 100 comprises a HF generator of HF signal output, a control system with an master controller configured to control the ablation process, and a computer adapted to give a computer graphic display 101 of parameters of the ablation process. Connection 116 is adapted to carry HF power from the HF generator 100 through the electrode tip 151 to produce an ablation volume 194 within a target structure or structures 193 within the body 190. In some examples, target structure 193 can be an organ such as the liver, lung, kidney, brain, nerve, bone, vertebra, uterus, prostate, or a tumor within an organ. As a schematic example in FIG. 1A, a target organ 193 can have a tumor within it, and the operator of the ablation apparatus desires the ablation volume 194 to cover and destroy the tumor.

In the embodiment shown in FIG. 1A, the ablation probe 150 includes an internally-cooled RF electrode 150E inserted into a tissue-piecing RF cannula 150U, wherein the internally-cooled RF electrode 150E includes hub 153B connected to cable 154 and tubes 155 and 156, and internally-cooled shaft 152B with blunt distal end 151B; wherein the cannula 150U includes hub 153A, insulated proximal shaft portion 152, and distal active tip 151; wherein both the electrode 150E and the cannula 150U can be provided sterile-packed to the user. Electrode hub 153B inserts into and engages with cannula hub 153A to form the ablation probe hub 153, and to the set the relative positions of the cooled electrode shaft 152B, cannula shaft 152, and active tip 151, such that the electrode shaft 152B cools the active tip 151, and the electrode distal end 151B is aligned with the bevel of the cannula active tip 151. The thickness and material of the internally-cooled electrode shaft 152B and blunt distal end 151B (eg thin-wall stainless steel hypotube with a thin-wall closed distal end), the thickness and material of the cannula shaft 152 and active tip 151 (eg thin-wall stainless steel hypotube covered by a thin layer of electrical insulation in shaft portion 152), the fluid flow rate through the shaft 152B produced by pump 130 (eg greater than 70 mL/min, or preferably 100 mL/min or greater), and the temperature of the fluid flowing through shaft 152B (eg 0-30° C. or 0-15° C.) are all configured to provide for cooling of the bodily tissue 190, 193 in contact with the active tip 151 to enhance the size of tissue ablated by the ablation probe 150 when energized by generator 100. The engagement surface 153C of electrode hub 153B is shown within cannula hub 153A as a dotted line. In one example electrode hub 153B can be a male luer hub, and cannula hub 153A can be a female luer hub. The electrode shaft 152 is shown as a dotted line within the lumen of the cannula shaft 152 and active tip 151, and the distal end of the electrode shaft 151B is positioned at, or slightly beyond, the hole in the flat sharp bevel at the distal end of the active tip 151. In some examples, the electrode point 151B can be flush with the bevel of the cannula tip 151. In some examples, the electrode point 151B can be aligned with the center of the bevel of the cannula tip 151. In some examples, the curved part of the electrode point 151B can be just distal to the distal-most point of the tip 151 to form a substantially rounded combined active tip to reduce peak electric fields at points of high curvature, and to reduce heat accumulation in tissue just distal to the distal end of the ablation probe 150. The electrode shaft 152B can include a metallic outer surface that touches an inner metallic surface of the cannula shaft 152 and/or active tip 151 to provide RF output signal from the electrode to the active tip 151. The cannula active tip 151 includes echogenic markers 151A configured to produce an enhanced image of the active tip 151 when viewed using ultrasound imaging, as shown on ultrasound display 141. In one example, the echogenic marketers 151A can be depressions in the outer surface of the metallic active tip 151, arrayed around and along the active tip 151, having a substantially flat bottom in the wall of the active tip, and having isosceles triangular cross-section in a plane roughly parallel to the cylindrical outer surface of the tip 151, wherein one altitude of the triangular cross-section is parallel to the long axis of the tip 151 and shaft 152, and wherein the vertex of the triangular cross-section through which the altitude passes is closer to the distal point of the tip 151 than is the base side of the triangular cross-section to which the altitude is perpendicular. In this example, the two distal side faces of each triangular marker provide reflective surfaces for incoming ultrasound waves, the open space within each depression allows ultrasound waves access to the two distal side faces, and the triangular cross-section allows more markers to arranged longitudinally along the active tip relative to depression having a diamond- or square-shaped cross-section of the same width in the cannula circumferential direction. In one example, each of the echogenic markers 151A can have extent of 0.001-0.020 inches the longitudinal direction of tip 151, a 0.001-0.020 inches in circumferential direction of the tip 151, and depth of 0.001-0.006 inches in the tip wall (ie the tip radial direction). In some examples, the triangular cross-section flat-bottom depression can form a corner-cube reflector. In some examples, the echogenic markers 151A can take other forms, such as circular flat-bottom depressions, square flat-bottom depressions, diamond flat-bottom depressions, arbitrary triangular flat-bottom depressions, hemispherical depressions, corner-cube depressions, holes through the side of cannula shaft 151, 152, roughing of the cannula shaft surface, sand-blasting of the cannula shaft surface, knurling of the surface, and combinations of these and other echogenic features in either identical or varied orientations. In some examples, echogenic markers 151A can be included in a metal surface under the electrical insulation of the insulated proximal shaft 152. In some embodiments, other arrangements of echogenic markers 151A can be included on probe 150 to highlight different features and dimensions of the probe 150. In some embodiments, the entirety of the cannula shaft length 151, 152 can include echogenic features. Before insertion of the cannula 150U into the patient tissue 190, a stylet 150S can be inserted to the inner lumen of the cannula shaft 152 and tip 151 (with the electrode 150E removed from the lumen) to close and align with the hole in the distal bevel of the active tip 151 and thereby form a solid bevel tip, wherein the stylet 150S includes a hub 153D, shaft 152D with distal bevel point 151D; this configuration provides for smooth insertion of the cannula 150U into the patient body 190 and organ 193, in part because the cannula 150U and stylet 150S combination includes a sharp, substantially solid bevel, and a smooth, cylindrical outer shaft having substantially the same cross-section along its entire length, without any step discontinuities between the cannula 150U and the stylet 150S outer diameters that could catch onto and thereby displace bodily structures within patient 190 during insertion. The alignment of the stylet 150S and cannula 150U bevels to form a smooth bevel and a smooth outer shaft surface is an advantage of the embodiment of the cannula-electrode ablation probe 150 shown in FIG. 1A. Smooth insertion of an ablation probe can be important to avoid displacing the organ 193, target anatomy such as a tumor, and other bodily structures during insertion of the probe. For example, tissue displacement can be more likely to happen if the target organ 193 is a cirrhotic liver that includes a hepatocellular carcinoma (HCC) tumor, because a cirrhotic liver can more tough and harder to push through than a healthy liver. Avoiding displacement of soft-tissue anatomy, such as an organ 193 such as the liver, can be especially important when using ultrasound guidance in relation to pre-operative three-dimensional (3D) medical images (eg CT, MRI, PET) for placement of the probe 150 because movement of the target anatomy intra-operatively can make the pre-operative imaging less accurate. Displacement of an organ can be more likely to occur if the ablation probe has a changing cross-section along its shaft, such as one that includes catch-points along its outer surface; this can occur when a cannula shaft has a square-cut end from which a thinner stylet protrudes. The ablation probe 150 is directed toward the problem of providing both a lumen for injection of fluids, for a smooth external ablation probe surface, for cooled RF ablation of tissue, and for ultrasound guidance. In the embodiment shown in FIG. 1A, once the cannula is in position in the patient body 190, then the stylet is removed from the cannula inner lumen, and the internally-cooled electrode is inserted into cannula inner lumen to form cooled RF ablation probe 150. The distal end of the electrode 151B is substantially aligned with the distal bevel of cannula tip 151A, and the length of the electrode shaft 152B is substantially the same length as the stylet shaft 152D; this has the advantages that include: the cannula provides a fixed channel within the body 190 into which the stylet and electrode can be exchanged; injections can be introduced into the body through the cannula lumen at the distal end of the active tip 151 for fluid ablation, lesion size enhancement, perfusion ablation, antibiotic infusion, infusion of biologics, and/or anesthesia; the stylet does seed tumor cells to positions distal to the active tip that might not be ablated by the heat lesion that forms around the active tip; and tissue is not mechanically damaged by penetration distal to the active tip. In some embodiments, the ablation probe 150 can be the ablation probe system shown in FIG. 2 of U.S. patent application Ser. No. 13/153,696. In some embodiments, the ablation probe 150 can be the ablation probe system shown in FIGS. 2A, 2B, and 2C of U.S. patent application Ser. No. 14/072,588. In some embodiments, the ablation probe 150 can be the ablation probe system shown in FIG. 2D of U.S. patent application Ser. No. 14/072,588. In some embodiments, the ablation probe 150 can be part of the ablation probe system shown in FIG. 2E of U.S. patent application Ser. No. 14/072,588. In some embodiments, the ablation probe 150 can be part of the ablation probe system shown in FIG. 2F of U.S. patent application Ser. No. 14/072,588. In some embodiments, the ablation probe 150 can be the ablation probe system shown in FIGS. 2I and 2J of U.S. patent application Ser. No. 14/076,113. In some embodiments, the ablation probe 150 can be the ablation probe system shown in FIGS. 2K, 2L, and 2M of U.S. patent application Ser. No. 14/076,113.

Figure 2:
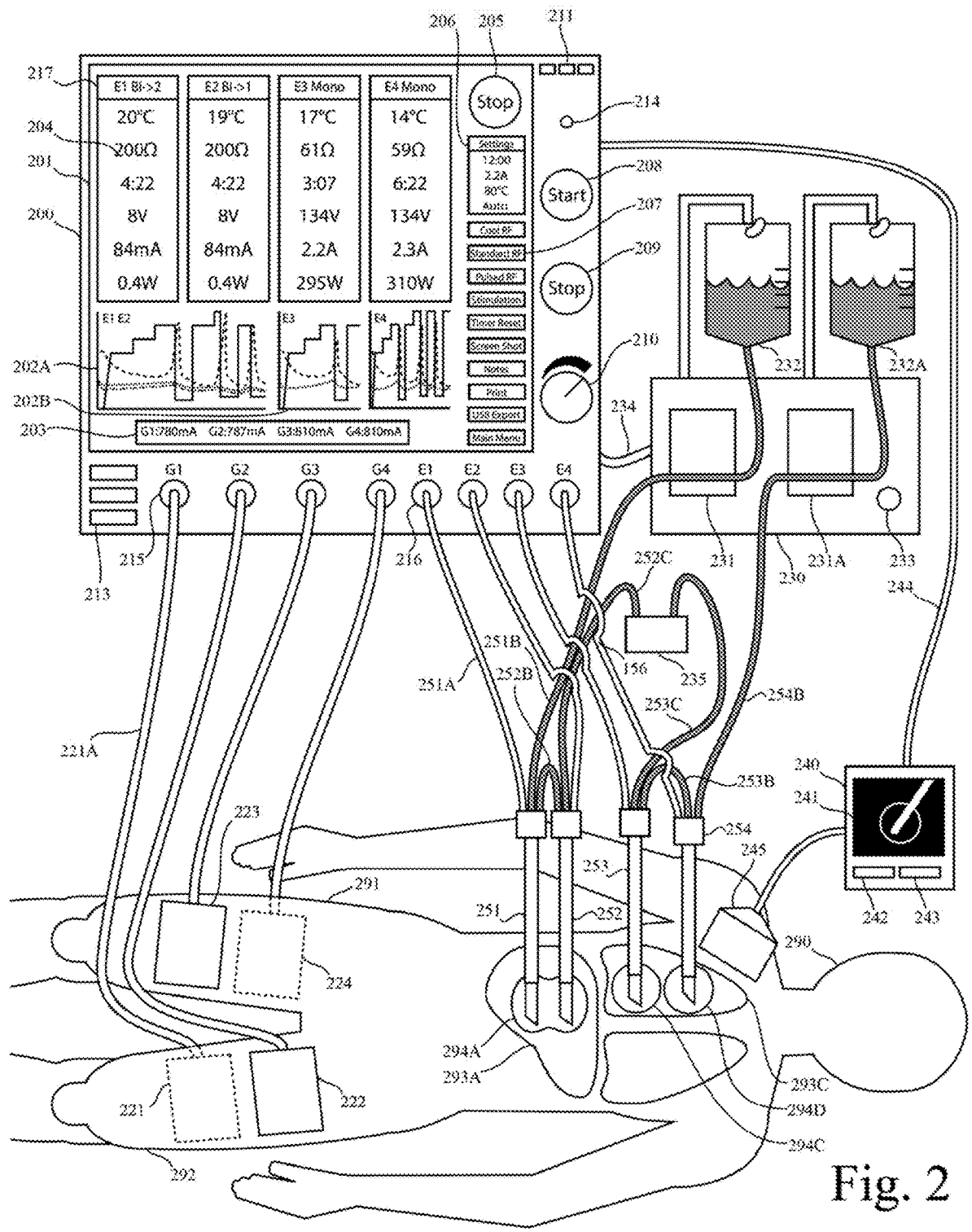
FIG. 2 is a schematic diagram showing a HF system for tissue ablation that includes multiple independent ablation electrodes that are internally-cooled; a radiofrequency generator that can energize the ablation electrodes in a variety of configurations of connection to the generator output potentials, including monpolar, bipolar, and multipolar configurations; graphic plotting of signal output level, impedance, and temperature for each electrode on a time axis in real time; multiple ground pads that carry return currents from the multiple ablation electrodes, wherein the current flowing through each ground pad is measured, displayed to the user, and regulated; and user-controls for, and an operative connection to, an US machine.

The cooled RF ablation probe 150 shown in FIG. 1A, both on its own and as part of the electrosurgical system presented in FIG. 1A, has substantial advantages and simultaneously solves numerous problems of tissue ablation. The combination of a cannula and electrode to form an ablation probe 150 provides a fluid channel for fluid injection into the ablation site, for example, for injection and/or perfusion of an ionic fluid to enhance lesion size, injection of ablation fluid to kill tumor cells, injection of anesthetic to numb pain, and/or injection of antibiotics to prevent infection; this is not provided by solid-tip ablation probes. The stylet and the electrode do not substantially protrude from the hole at the cannula distal end 151; this has advantages that include: the external surface of the combined ablation probe 150 is smooth, without any discontinuities, steps, or other transitions in cross-section size or shape (which can be present when the stylet and/or electrode protrudes from a square cannula distal end, even with the transition is tapered), thus reducing insertion forces and the likelihood of displacing soft tissue and organs during insertion and manipulation (eg when inserting a probe into tough cirrhotic liver to ablate an HCC tumor) and thus potentially making pre-operative three-dimensional (3D) imaging data (eg CT, MRI, PET) less easy to relate to intra-operative anatomy as visualized with ultrasound imaging 141; the electrode 150E is not substantially inserted into bodily tissue, thereby reducing the force applied to the electrode 150E, and thereby avoiding the need for large and/or heavy means to make the electrode 150E more robust (such as a large and/or heavy handle configured for pushing the electrode 150E) which can prevent close spacing of multiple ablation probes (for example, in a cluster configuration, eg 150A, 150B, 150C of FIG. 1C) and which can displace an probe position in bodily tissue either before or during ablation due to torque from the weight of the portion of the probe and hub that remains outside the body; fluids injected to enlarge lesion size (such as saline and other ionic solutions), either before the lesion or during the lesion as an ongoing infusion, are injected at the point of greatest heat around the active tip 151 (ie the distal point of the active tip 151), thereby reducing maximal tissue temperatures and tissue boiling that can limit delivery of RF energy to the tissue 190; fluids injected to kill cancer cells (such as alcohol), anesthetics, steroids, and/or antibiotics can be delivered over the full length of the active tip 151 without advancing the cannula 150U and thus potentially seeding cancer cells to healthy tissue, either by injecting ablation fluid as the cannula 150U is withdrawn from the patient 190 or by the inclusion of side holes along the active tip 151 which can themselves be echogenic; the interface between the tissue and the external surface of the ablation probe 150 does not substantially change when the electrode 150E and stylet 150S are inserted into and removed from the cannula 150U, thereby minimizing tissue movement which can make pre-operative imaging data less useful; the stylet 150S does not penetrate into tissue distal to the distal position of the electrode 150E and cannula active tip 151, thereby reducing the likelihood of movement of cancer cells to the location of healthy tissue that is not ablated by the active tip (a process known as "seeding"). The stylet distal end 151D can be match ground to the distal bevel of the cannula tip 151 to produce a solid, sharp bevel that reduces tissue coring and resistance during probe insertion, thereby reducing the need for a heavy and/or large hub handle which can prevent close spacing of multiple probes in a cluster (eg FIG. 1C) and displace the position of an ablation probe placed in bodily tissue. A single internally-cooled electrode 150E can be used to operate a variety of cannulae like cannula 150U; advantages of this include: a single electrode 150E (which is generally more expensive than a cannula 150U) can operate with a variety of cannula types having different active tip lengths, thereby reducing stocking costs and logistics for physicians relative to the use of integral ablation probes (such as the Radionics Cool-Tip) for which a variety of electrodes having a variety of active tip lengths are kept in supply into order to adapt to clinical needs as an ablation procedure progresses; and multiple cannulae like cannula 150U can be placed at multiple positions in the patient body at low cost and without encumbrance from multiple sets of electrode tubing (eg 155, 156) and cables (eg 154), the multiple cannulae can be visualized relative to each other before lesioning (for example using ultrasound or three-dimensional imaging), and then either lesioning can be performed at each cannula using a single electrode 50E by sequentially moving the electrode 150E among the cannulae (thus keeping cost low), or each of multiple cannula can be energized with one of multiple electrodes. The cooled electrode 150E including a cable 154 and coolant tubes 155, 156 is physically separate from the cannula 150U; the advantage of this configuration include the ability to easily position multiple ablation probes in a variety of locations within the body 190 at the same time (including in a tight cluster configuration, like those shown in FIG. 1C) without the encumbrance of cables and coolant tubes during placement. This advantage can be especially important for use with an RF generator capable of energizing multiple ablation probes at the same time (eg generator 100 as shown FIG. 1C, generator 200 as shown in FIG. 2, generator 700 in FIG. 7, and generator 900 in FIG. 9) and with ultrasound guidance because one hand of physician is generally occupied holding the ultrasound transducer. The electrode distal tip 151B can have a thin-wall and rounded distal end, which increases thermal conduction of heat from the tissue into the internally coolant, and reduced electric field strengths relative to sharp-point electrodes, thereby cooling tissue distal to the ablation probe 150, which is the location where tissue temperatures can be hottest and thus limit lesion size. Echogenic markers 151A of the ablation probe 150 identify the active tip 151 (and can identify other features and dimensions), which can facilitate injection and ablation using ultrasound guidance.

In some embodiments, the ablation probe 150 can be an RF electrode. In some embodiments, the ablation probe 150 can be an MW antenna. In some embodiments, the ablation probe 150 can be an integral, tissue-piercing RF electrode. In some embodiments, the ablation probe 150 can be a cooled-RF electrode 150E that is inserted into a tissue-piercing cannula 150U. In some embodiments, the ablation probe 150 can be one of the ablation probe systems presented in U.S. patent application Ser. No. 13/153,696. In some embodiments, the ablation probe 150 can be one of the ablation probe systems presented in U.S. patent application Ser. No. 14/072,588. In some embodiments, the ablation probe 150 can be one of the ablation probe systems presented in U.S. patent application Ser. No. 14/076,113. In some embodiments, the ablation probe 150 can additionally include an extension tip temperature sensor, such as that shown in FIGS. 2G and 2H of U.S. patent application Ser. No. 14/072,588.

In another example of FIG. 1A, there can be more than one ablation probe similar to 150 inserted into the target organ 193 to create a larger ablation volume 194. In some embodiments, the more than one ablation probe can be connected to the HF generator signal output at the same time; this configuration can be referred to as a cluster configuration. In some embodiments, multiple electrodes energized in a cluster configuration can be position close to each other to produce a single lesion volume; in some embodiments, the single lesion volume can be an enlarged coherent volume, and in some embodiments, the single lesion volume can be not enlarged, but having an irregular shape conforming to target anatomy. In some embodiments, multiple electrodes energized in a cluster configuration can be positioned far from each other to produce multiple lesion volumes. In some embodiments, the more than one ablation probe can be connected to the HF generator signal output non-concurrently; this configuration can be referred to as a multiple-electrode monopolar configuration.

FIG. 1A shows schematically one example of a coolant supply system 130 to cool the active tip portion 151. A reservoir 132, in one example, contains water or saline cooled to a temperature less than body temperature, such as room temperature, approximately 20 deg C., near freezing, less than 10 deg C., or near 0 deg C. Tubing 155 carries the coolant through a peristaltic pump head 131 that pumps the coolant through the electrode 150E, and thus the ablation probe assembly 150. The electrode 150E has an internal channel through which coolant can flow to cool the probe active tip 151 when the electrode 150E is inserted in cannula 150U. The coolant can exit the probe 150 through tubing 156 and dump into the collection reservoir 135. The pump 130 also includes a user control 133 to provide for manual control of pump function. The generator 100 provides an automatic check on the coolant flow into the electrode 150E and ablation electrode 150 when an ablation program is initiated by the user by holding the output level at a low level not expected to heat the electrode tip 151 even in the absence of cooling for an initial period 118C visible on output level graph 102A, and only proceeding with ablation output if the electrode temperature, plotted by dotted line 102C, registers a value below a threshold indicative of proper electrode cooling, such as a temperature below 30 deg C. In some embodiments, the generator 100 does not proceed with ablation heating unless the temperature first registers a value indicative of body temperature, and then drops to a value indicative of coolant flow. In some embodiments, the generator 100 can discontinue the ablation program and signal an error condition to the user, if the coolant-check period 118C persists for longer than the typical time required for coolant to flow from the reservoir 132 to the electrode tip 151, for example 20-45 seconds depending on the pump rate. In some embodiments, the coolant check can be performed on an ongoing basis when ablation generator is being delivered to verify that the coolant flow is sufficient for the ablation output level delivered. In some embodiments, the generator 100 automatically activates the coolant pump via connection 134 when the user initiates an ablation program, for example, by pressing the Start button 108. In some embodiments, for example where connection 134 is absent, the user manually activates by control 133 the coolant pump to suit clinical needs.

The HF system comprises a HF generator 100 that is adapted to measure parameters of the ablation signal output delivered to the ablation probe 150 or probes, including one or more of parameters from the following list: impedance, power, current, voltage, and functions of the time signals of one or more of these parameters. The graphic computer in system 100 is adapted to graphically display simultaneously in real time one or more of these signal output parameters on the graphic display 101. In one example, the graphical display can be one or more signal lines 102A, 102B, or 102C plotted over time, each with the parameter plotted on a vertical axis and time plotted on a horizontal axis. The generator 100 can be capable or modulating the HF output level, including turning the HF output on and off, in response to measured HF signal parameters. In some embodiments, the modulation of the HF signal output can be configured to stabilize the ablation process, for example, to prevent or reverse the effects of boiling tissue around the active tip 151. The computer graphic display 101 can present to the user visual information about the effect of modulating the HF signal output when the ablation process produces tissue boiling and an explosive bubble zone around the active tip 151. This aspect of the present invention is shown in more detail in the figures that follow.

Also shown in FIG. 1A are ground pads 121, 122, 123, 124 which are connected to jacks labeled "G1", "G2", "G3", "G4" of generator 100, respectively. In this example, pad 121 is applied to the posterior side of a muscular portion of left thigh 192, pad 122 is applied to the anterior side of a muscular portion of left thigh 192, pad 124 is applied to the posterior side of a muscular portion of right thigh 191, pad 123 is applied to the anterior side of a muscular portion of right thigh 191. Each ground pad is connected to an individual jack on generator 100 and adapted to carry return HF current from the active tip 151 of cooled HF electrode 150 back to the generator 100. For example, ground pad 121 is attached to jack 115A labeled "G1" via cable 121A. In some embodiments, the jacks G1, G2, G3, and G4 each provide a connection to the generator reference potential. In one example, use of ground pads is relevant when the HF generator delivers an RF signal output to electrode 150. In some embodiments, only one ground pad is used. In some embodiments, two or more ground pads are used. In some embodiments, the number of ground pads used is a function of the HF current expected to be delivered by the ablation program selected by the user and the maximum current capacity of each ground pad under which skin burns can be prevented. The HF generator 100 is adapted to measure the individual current flow though each of the one or more ground pads 121, 122, 123, 124 that are attached to the patient 190. In the embodiment shown in FIG. 1A, the current flowing through each ground pad is displayed to the user by digital displays 103, wherein the individual current displays 103A, 103B, 103C, 103D for the pads connected to jacks G1, G2, G3, and G4 are ordered from left to right on screen 101, in the same order as, and aligned with, their corresponding jacks G1, G2, G3, G4 for easy identification by the user. In another example, the fraction $I_i/I$ of the total current I that is flowing to each pad can be included in display 103, where $I_i$ is the current flowing to pad i=1, 2, 3, 4 and I is the total current flowing from electrode 150; this can give a user a sense of the balance of current flowing to the pads and provide information for correcting improper ground pad adhesion to the skin and/or for rearranging the ground pads on the skin of the patient 190 to produce a more balanced distribution of current among the pads. In some embodiments, the fractional of total current for each pad can be expressed as a percentage of the total current I, or a percentage of the total current relative to a nominal percentage value, such as 100*1/N which represents equal flow of current to each pad, where N is the total number of ground pads, and N=4 in the example shown in FIG. 1A. In another example, the impedance between each ground pad and the ablation electrode 150 can be included in display 103. Display 103 can provide the clinician user has an instant visual feeling if something is wrong with a ground pad. For example, if a ground pad is losing contact with the patient skin or is otherwise defective, then the current and/or impedance related to that ground pad can change abnormally, and the clinician can be warned, thus avoiding possible skin burns. For example, if one ground pad is shielding current flow to another ground pad, such as when one ground pad is placed distal to another ground pad on the limb of the a patient 190, an abnormally low current can be displayed to the user and the generator can warn the user about the suboptimal ground pad arrangement. In some embodiments, graphical display of the individual ground pad currents, fractional currents, impedances, or some functions thereof can be including in display 103; the graphical display can be updated in real-time and can take the form of the one or more of the following: an analog meter, an indicator on a graduated scale, an indicator on a graduated dial, a bar graph, a bar chart, a graphic equalizer, a line graph over time, a plot of points (x,y) on x-axis and y-axis where x is a function of impedance and y is function of time, a plot as a function of a time axis, or another type of real-time graphical display. A graph of the ground pad current that includes past and present values, such as a line plot on a time axis, can show ground pad anomalies and trends that can indicate suboptimal or dangerous situations to the clinician, and the chance of observation of an anomaly is increased since clinician can observe the signature of that anomaly in the graphical history at any time after the anomaly occurs, not just when the anomaly is occurring. For example, if one or more of the ground pads is lifting off the skin or is otherwise separated, then the graphic display for that pad will show an anomaly, such as a dip in a current graph or a spike in an impedance graph. For example, if there is progressive heating at the ground pad, the impedance graph can show a trend, such as a downward trend. One advantage of a graphic and/or numerical display of a ground pad current and/or impedance is that it gives the clinician and instant warning of trouble with the equipment to avoid harm to the patient such as skin burns. Independently current monitoring of multiple ground pads by generator 100 provides the advantage that very high levels of ablation current can be delivered to an ablation probe 150 or probes and distributed among multiple skin locations on the patient 190, thus minimizing resistive heating current at any one skin location and preventing ground pad skin burns.

In some embodiments, the generator 100 can include more than four ground pad jacks each with individual current monitoring. For example, the number of ground pad jacks can be a number selected from the list 1, 2, 3, 4, 5, 6, 7, 8, 9 10, a number more than 10. One advantage of a generator 100 including more than one ground pad jack is that higher currents can be delivered to the ablation electrode or electrodes 150, particularly when multiple electrodes are energized at the same time. Another advantage of a generator 100 including more than one ground pad jack is that smaller ground pads can be safely used with the generator and skin burns can be prevented. One advantage of individual current monitoring of each ground pad is that imbalances in the current distribution, for example due to shielding of one ground pad by another, can be detected by the generator 100 and/or user, flagged to the user by the generator 100, and the user can be prompted to reposition the ground pads to avoid skin burns.

In some embodiments, the generator 100 can include a switch between the reference potential and each ground pad jack G1, G2, G3, G4; a current measurement for each ground pad jack G1, G2, G3, G4; and an automatic controller that varies the distribution of current among the ground pads connected to the ground pad jacks in order to control the average current flowing to each pad. For example, by these mechanisms, the current flowing through each pad can be equalized. For example, by these mechanisms, the current flowing to each pad can be held below the upper limit for each pad, above which a ground pad burn would be more likely. In one example, a repeating sequence of ground pad connections can be effected automatically by the generator 100 wherein only one ground pad is connected to generator potentials at a time; such a sequence can be referred to as a sequential sequence. In another example, the generator 100 can produce a repeating sequence of ground pad connections, which can be referred to as a "nested simultaneous" sequence, wherein each sequence includes up to N+1 steps; wherein in the first step, all ground pads are connected to the generator reference potential; in each subsequent step, the highest-current pad that was active in the previous step is disconnected from the reference potential; in the Nth step only one ground pad is connected to the reference potential; and in the (N+1)-th step no ground pad is connected to the reference potential; wherein the duration of each step in each sequence is adjusted so that the root-mean-square (RMS) current for each pad over the duration of the sequence does not exceed an upper bound; and wherein N is the number of ground pads. In a more specific example, each sequence of the said repeating sequence only includes the steps subsequent to the i-th step if the RMS current over the entire sequence would exceed the upper bound if those subsequent steps were not included, where i can take values 1, 2, . . . , N. In another example, the generator 100 can reduce the total HF current output so that the RMS current at each ground pad is less than the upper bound and the (N+1)th step can be excluded. One example of one sequence in a "nested simultaneous" sequence of ground pad connections can be G1, G2, G3, G4 connected for 0.5 second in step 1 wherein G1 carries the most current; G1 disconnected and G2, G3, G4 connected for 0.25 seconds in step 2 wherein G2 carries the most current; G1 and G2 disconnected and G3 and G4 connected for 0.1 seconds in step 3 wherein G3 carries the most current; G1, G2, and G3 disconnected and G4 connected for 0.1 seconds in step 4; all ground pads disconnected for 0.05 in step 5; wherein the RMS current of each ground pad is equal to the upper bound 900 milliamps RMS (mA-RMS); wherein RMS current is evaluated over the 1 second duration that includes steps 1 through 5. One advantage of a nested simultaneous sequence of ground pad connections that controls the RMS current flowing to each pad is that the amount of ground pad switching can be reduced relative to a sequentially switching sequence in which only one ground pad is connected to the reference potential at any one time. One advantage of a nested simultaneous sequence of ground pad connections that controls the RMS current flowing to each pad is that a higher total current can be carried by the ground pads than in a repeated switching pattern in which only one ground pad is connected to the generator 100 at the same time.

In some alternative embodiments, two or more of the ground pads 121, 122, 123, 124 can be combined into a single skin-contacting pad structure such that each of the two or more ground pads make up some of the area of the said single skin-contacting pad structure and is electrically isolated from the other of the two or more ground pads. In some embodiments wherein two or more ground pads are combined into a single skin-contacting pad structure, the said structure can have a single cable that include a separate wire for connecting each constituent ground pad to the generator independently.

In some embodiments of generator 100, as shown in FIG. 1A, the electrode output is regulated by its current value. The use of current-regulation for the electrode output is an important for the use of a ground-pad switching process. For a regulated electrode current, tissue heating near in the electrode is invariant to the positive number of ground pads that are connected and disconnected from the generator power supply unless a limit of the power supply is reached, because even though changes in the ground pad connections can affect the overall impedance between the electrode and the generator reference potential, the current density (and therefore the power density and the rate of tissue heating) near the electrode is regulated. In contrast, in some embodiments, for an electrode output that is regulated by voltage or power, the voltage drop and power loss in tissue near the electrode (which are responsible for tissue heating there) can change depending on magnitude of impedance at points far from the electrode along the circuit path, because the magnitude of those distant impedances can affect the proportions of the total voltage drop and power loss (which is regulated) that occurs far away from the electrode and near the electrode. Connecting and disconnecting ground pads from the generator reference potential can affect the impedance between the electrode and the reference potential at locations that are distant from the electrode, thus affecting the rate of heat near the electrode and the size of the ablation zone. In one aspect the present invention relates to RF ablation system, such as generator 100, that includes controller that regulates the ablation electrode current and changes the number of ground pads carrying current from the ablation electrode.

FIG. 1A also shows an ultrasound machine 140 examining by means of transducer 145 the patient body 190 and the particular region around the target organ 193 into which the electrode tip 151 is placed. The ultrasound imaging device 140 includes ultrasound controls 142 and RF generator controls 143. The ultrasound machine 140 is adapted to display the ultrasound image on ultrasound display 141. In one embodiment of the invention, the ablation probe includes echogenic markings on its tip 151 so that the tip portion is visually enhanced in the ultrasound display 141 relative to the target organ 193 and any pathology in the organ such as a tumor. In one example, the echogenic markings can comprise indentations in the surface of the probe tip portion 151 that are adapted to give enhanced ultrasound reflections. In some embodiments, the electrode shaft 152 can include echogenic markers that enhance shaft visibility in ultrasound imaging of the shaft. In the example shown in FIG. 1A, the electrode shaft 152 is visible on the ultrasound display 141 is the shaft of the ablation probe 150 and bubbles formed in the tissue around the tip 151. It is advantageous that the physician can monitor and/or adjust the ablation process from the same console using both visual imaging, such as that from ultrasound imaging, and a real-time display of measured HF parameters, such as plotted time series of impedance and current. In some embodiments, the ultrasound image can be displayed on the graphic display 101 or the generator 100; one advantage of this configuration is that the doctor can easily monitor and control the ablation process by imaging and generator readings at the same time. In some embodiments, generator readings can be displayed on the graphic display 141 or the ultrasound machine 140; one advantage of this configuration is that the doctor can easily monitor and control the ablation process by imaging and generator readings at the same time.

FIG. 1A shows in a schematic drawing one example of a computer graphic display 101 of the system 100. The graphic display 101 includes digital readings displays 104A, 104B, 104C, 104D, 104E, 104F of measured parameters, including the electrode impedance 104A in units ohms (a), the electrode current 104B in units RMS Amps (A), the elapsed lesion time 104C in minutes and seconds formatted MM:SS, the electrode temperature 104D in units degrees Celcius (° C.), the electrode Voltage 104E in units RMS Volts (V), and the electrode power 104F in units Watts (W). The graphic display 101 includes digital readings 103A, 103B, 103C, 103D of measured current for each ground pad in units RMS milliamps (mA). The graphic display 101 includes a start/stop toggle button 105 with which the user can turn the ablation output on and off. The graphic display includes controls 106 for adjusting and displaying the settings 106A, 106B, 106C, 106D, 106E and other controls, such as the "Main Menu" button 107, that provide for user-operated functions such as resetting the ablation time ("Timer Reset"), saving a screen shot image of the screen to generator memory ("Screen Shot"), printing a record of the procedure to a printer if attached to a data jack 111 ("Print"), export of procedure data to an external USB disk if connected to a data jack 111 ("USB Export"), adding text notes to procedure data ("Notes"), transitioning to other screens and menus ("Main Menu"). The graphic display 101 includes one or more line plots 102A, 102B, 102C of measured parameters, including one or more of the parameters displayed digitally as a function of time. The solid graph 102A can represent schematically one of the measured generator signal output parameters from the list of power, current, and voltage. The dashed-line graph 102B schematically represents the measured impedance of the ablation probe 150, for example, in the case where an RF signal is applied between the electrode active tip 151 and one or more of the ground pads 121, 122, 123, 124, the measured impedance can be the impedance between the active tip 151 and the energized ground pads 121, 122, 123, 124. The dotted graph 102C can schematically represent the temperature measured from the indwelling temperature sensor is inside the ablation probe tip portion 151, essentially representing the temperature of the coolant inside the tip portion 151 of the ablation probe 150. The graphic display 101 and the line graphs 102A, 102B, 102C give the clinician a visual, intuitive, and real-time update and evaluation of whether the ablation process is progressing properly and safely. In one example, the graph 102A can represent signal output current. In one example, the graph 102A can represent signal output power. In one example, the graph 102A can represent signal output voltage. In one example, the graph 102A can represent the characteristic of the HF signal output that is being automatically regulated by the automatic control system of the generator 100.

The dashed graph 102B represents schematically the output impedance. The upward spikes, such as 118, represent the occurrence of substantial boiling and bubble formation in the tissue around the active and/or exposed tip 151 of the electrode 150. The bubble zone is the hottest region and is located at a distance from the electrode tip 151 which is cooled. The presence of a bubble zone around the active tip 151 represents an unstable situation. If the generator signal output is not reduced, a bubble zone will explosively expand, the impedance will rapidly increase, and the ablation current and ohmic heating power will be reduced dramatically, for example, in the case of RF ablation. This unstable situation can be avoided or reversed by reduction of the generator HF signal output when the impedance spikes upward 118. The generator 100 can be configured to automatically reduce the output level when the impedance exceeds an upper limit, which can be set by the user physician or by the factory, and which can be an absolute value or a value relative to previously measured impedance values, such as a global or local minimum among past impedance measurements during the present ablation routine. In one example, the upper limit can be 10 ohms above the minimum impedance during the present up time period. As shown in FIG. 1A, the HF output level signal 102A steps down from high values 118A to much lower values 118B when the impedance signal 102B spikes upward. In one example, the signal output is reduced or modulated to non-zero values 118B configured to allow for tissue cooling in the "down time" (also referred to as "off time") according to the control process. In another example, the signal output is reduced to zero for a "down time" (also referred to as "off time" or "off period") according to the control process. The down time 118B allows the tissue to cool down and the bubble zone to dissipate, as reflected by the impedance 102B reducing to a baseline value after spike 118. In some cases, the impedance can continue to rise for a short duration after the beginning of a down time due to the response time of the controller or a lag in the ablation process. After the down time, the ablation heating process can resume with another "up time" (also referred to as "on time" or "on period") by increasing the signal output to a higher level configured to heat tissue around the electrode active tip 151, such as the output level immediately before the down time, or to a level somewhat below the output level immediately before the down time if, for example, the previous up time was less than some lower bound indicating too much output is being delivered to the tissue. During this up time, the signal output level can again heat the tissue and grow the bubble zone, so that after an up time duration, which depends on the signal output level and the state of the tissue around the active tip 151, the impedance will once again become unstable and spike upward, prompting the generator 100 to initiate another down time cooling period with low output level. The repeating process of up times and down times, one embodiment of which is shown by 102A and 102B, continues according to the control process programmed into generator 100. The repeating process of up times and down times can maintain the impedance within a desired range. In embodiments wherein a lower impedance-rise threshold is used, boiling can be more limited, so a shorter down-time duration can be used, and the repeating process of up times and down times can maintain the impedance near to, at a desired level. In some embodiments, the repeating process of up times and down times can stabilize to a desired level of signal output level during the up times, a desired duration of up times, and a desired duration of down times to produce a desired ablation process and ablation size. In some embodiments, the control system included in generator 100 uses the level of impedance spikes and the signal output levels to stabilize the sequences of up times and down times so that the ablation process is uniform and reproducible for a given electrode geometry and tissue impedance. The repeating alternation between up time 118A and down time 118B, the adjustment of the down time duration, adjustment of the down time output level, and the adjustment of the up time output level can proceed by automatic control by the generator 100. By multiple alternations of up and down time, and adjustment of the signal output level in response to parameters indicative of the ablation process, a high level of signal output current can heat tissue beyond high-impedance bubble zones and enlarge the ablation size. In some embodiments, tissue boiling can be detected by a drop in current for a known or fixed applied voltage. In some embodiments, tissue boiling can be detected by a drop in power for a known or fixed applied voltage.

The generator display 101 includes a numerical display of the duration of each up time and down time, such as 117A and 117B, each positioned on the output level graph 102A near the location of its corresponding up time or down time level. On display 101, numerical display 117A presents the time duration of up time 118A in seconds units as "109", and numerical display 117B presents the time duration of down time 118B in seconds units as "20". The graph 102A includes four instances of up times and duration labels "109", "40", "9", and "29" in seconds units, and three instances of down times and a duration labels "20", "20", and "22" in seconds units, wherein the duration label for each up time or down time appears near its end point on the output level graph 102A. In some embodiments, the up time and down time durations can be displayed in a different arrangement, such as a list. In some embodiments, other parameters associated with an up time or a down time can be displayed, including for example, the average output level during an up time or down time, the RMS current during an up time or down time, the RMS voltage during an up time or down time, the average power level during an up time or down time. Digital presentation of parameters related to each up time and down time provide important information to the user physician about the proper progress of the ablation progress. The combination of numerical and graphical presentation of parameters related to each up time and down time provide important information to the user physician about the proper progression of the ablation process.

The generator 100 can include an automatic controller that uses one or more measurement parameters as input for regulation of the output level, including for example the measured electrode impedance, current, power, voltage, and temperature. The generator 100 can include an automatic controller that includes one or more methods for regulating the output level during the up times, including, for example, regulation of the output level as a function of the timing of impedance spikes in response to variations in the output level, and regulation of the output level to control the electrode temperature to a set point. In some embodiments, the generator 100 can include an automatic controller that includes both said one or more methods for regulating the output level during the up times, and a method of alternating up time and down time in response to impedance spikes. For example, for embodiments in which the indwelling temperature sensor of the electrode 150 is positioned in the coolant flow and therefore effectively measures the coolant temperature, the output level during the up times can be regulated to fix a parameter of the output level, such as current, voltage or power, and alternation of up time and down time in response to impedance spikes can be the primary means of feedback control of the output level in response to unmeasured temperature changes in the tissue. In another example, for embodiments in which the temperature measurement more directly measures the maximum tissue temperature (for example, in the case where the cooled electrode includes an temperature-sensing extension tip that extends distal or lateral to the active tip 151, or in the case where an separate remote temperature probe is positioned near the electrode active tip 151), the output level can be regulated to hold the measured temperature at or near a set value, and the alternation of up time and down time in response to impedance spikes can be used to dissipate bubble zones that can form either because the temperature set value is intentionally set to produce tissue boiling, or because inaccuracies in the temperature measurement lead to undesired tissue boiling even though the temperature set value is set to a value expected to prevent tissue boiling.

The solid graph line 102A represents the HF output level delivered to the electrode. The graph 102A shows a sequence of plateaus and steps which can represent a sequence in which the generator 100 automatically regulates the output level to hold the output level at or near a sequence of set levels for a parameter of the output signal, such as the current, power, or voltage. For example, the output level graph 102A within up time 118A can reflect the output set level stepping from an initial value of 2.3 Amps, to 2.4 Amps after 30 seconds, and then to 2.5 Amps after another seconds; and after this, within the down time 118B, the output level graph 102A can represent the output level being regulated at or near a level of 100 mA. For each instance of up time, the output level increases in steps of 100 mA after each 30 seconds of elapsed up-time duration. One advantage of slowly increasing the output level while ablation energy is being delivered to the tissue is that the duration of the up time as an indication of the tissue's ability to carry more tissue-heating current without boiling rapidly and thereby interrupting tissue heating. For each instance of up time, the initial output level of the up time is 100 mA less than the final output level of the previous instance of up time if the total duration of the previous up time is less than 10 seconds or if the duration of the final output-level step of the previous up time is less than 10 seconds; otherwise, the initial output level for each instance of up time is equal to the final output level of the last instance of up time. In some embodiments, a threshold duration other than 10 seconds (eg a value selected form the range 0-30 seconds or more) can be used in relation to the final output-level step of the previous up time to determine whether the next up time starts at the same level or a lower level than the previous up time ended. One advantage of decreasing the initial output level of the next up time when the previous up time's duration is too short is that a short up time duration is an indication of the tissue's inability to carry the output level of previous up time without rapidly boiling, and thereby interrupting heating. The duration of the initial down time is 20 seconds. The duration of subsequent instances of down time are increased by 2 seconds relative to the duration of the previous instance of down time when the total duration of the prior instance of up time is less than 10 seconds. In some embodiments, a threshold duration other than 10 seconds (eg a value selected form the range 0-30 seconds or more) can be used in relation to the duration of the previous up time to determine whether the down time duration is increased. One advantage of increasing the duration of the down time as function of the up time duration is that a short up time can indicate that a longer cooling time is required before the next up time in order to more completely dissipate the bubble zone to allow for continued tissue heating. One advantage of increasing the duration of the down time as the total elapsed lesion time increases is that total lesion time is correlated with larger lesion size, larger bubble zone size, and thus a longer required duration of cooling for complete bubble zone dissipation between up times to allow for continued tissue heating. One advantage of increasing and decreasing the output level in response to the duration of up time, when the duration of the up time is influenced by increases in the measured impedance indicative of tissue boiling around the active tip 151, is that, even without direct tissue temperature measurements, the output level can be adjusted to tissue conditions around the active tip, which conditions can vary in an unpredictable manner as a function of tissue type, blood flow, tumor type, disease state, tissue inhomogeneity, patient variability, and other factors. One advantage of increasing and decreasing the output level in response to the duration of up time, when the duration of the up time is influenced by increases in the measured impedance that are indicative of tissue boiling around the active tip 151, is that the output level can be increased to a high a level as possible to increase lesion size, while preventing excessively rapid heating that can hinder the progression of heat lesion size, for instance due to irreversible changes such as tissue charring, or rapid boiling. In some embodiments, the parameters of the up time and down time pulsing process can be adjustable or selectable by the user, wherein the parameters can include the impedance threshold for terminating an up time, the duration of the downtime, the rate of increase of the output level during an up time, the up time duration below which the output level of the next up time is reduced, the up time duration below which the duration of the subsequent down time is increased, other parameters described herein, and other parameters.

Settings panel 106 presents one example of user settable parameters ("settings") that influence the behavior of the ablation controller included in generator 100 to suit clinician user needs. The settings include a set time 106A, an initial current 106B, a maximum current 106E, a set temperature 106C, and a mode 106D setting, which in FIG. 1A take values 9:00 minutes, 2.3 Amps, 80 deg C., and "automatic", respectively. The set time 106A determines the amount of time an ablation program will be run before the generator 100 automatically shuts it off, and in some embodiments, it can take values in the range 0-30 minutes or more, in one-second increments. The total duration of the ablation process has an effect on ablation size, and proper selection of the total duration of an ablation process is an important factor for producing reproducible and predicable heat lesions. In some other embodiments, the stopping criteria for the ablation process can be that a one or more of the quantifies in the following list exceeds a threshold value: total ablation program running time (ie set time 106A), total duration of up time, time-integrated power, time-integrated squared RMS current, total energy deposition into the tissue, the baseline impedance value, a temperature measured at a distance from the active tip 151, an indication of tissue heating within some volume, an imaging parameter. The initial current setting 106B, displayed in units Amps (A) which is equal to 1000 milliamps (mA), determines the target the output level for the beginning of the first "up time", and in some embodiments, it can takes values between 0-3000 mA (RMS) or more, in 1 mA or 10 mA increments. In FIG. 1A, after the output is turned on and an initial coolant test period 118C, the output level 102A is rapidly ramped to this level, and then the output level is increased and decreased in response to measured impedance to maximize the output level current without excessively, sub-optimally heating the tissue. In some embodiments, it is advantageous to select a starting output level that is likely to be below the minimum maximal output level for the electrode tip size 151 and the target anatomy 193 conditions in order to prevent an initial overheating of the tissue that could limit the ultimate lesion size, and to allow for calibration of the output level to the tissue conditions which cannot be precisely predicted. In some embodiments, it is desirable to allow the user to set a maximum output level, such as a maximum current, voltage, or power, to prevent overheating of the tissue. The maximum current setting 106E, displayed in units Amps (A) which is equal to 1000 milliamps (mA), determines the maximum target output level for all "up time" during the ablation program. The setting 106E allows the user to limit the maximum output level during an "up time", for example, to prevent too rapid heating which can limit lesion size, or to provide for additional safety in case where is there a problem with feedback control of the "up time" output level. In some embodiments, the maximum current 106E can takes values between 0-3000 mA (RMS) or more, in 1 mA or 10 mA increments. The set temperature 106C determines the measured temperature value that the generator 100 will try to achieve by regulation of the output level, unless the output level is limited by another control objective, such as that of the initial current or that of impedance control. In some embodiments, the set temperature can take values in the range 0-100 deg C. or more, in 1 deg C. increments. Regulation of the measured temperature can be important to prevent excessive tissue heating in the case of coolant flow failure. Regulation of the measured temperature can be important when a temperature measured remote of the active tip 151 is used to regulate lesion progression. The mode setting 106D allows the user to select among automatic output control using the other user-selectable parameters (setting value "Auto"), and manual output control by means of the manual control knob 110, which can be a potentiometer, a rotary encoder, an encoder, an on-screen slider, or another device for selecting a value, such as quantized or real values, within a range of valves (setting value "Manual"). It is advantageous to allow for both automatic and manual control of the output level so that the clinician user can select automatic control when an automatic implementation of the control process can outperform a human controller, and can select manual control when the ablation is not proceeding in a manner consistent with programmed processes. In some embodiments, the mode setting 106D can provide additional settings to the user, such as impedance control, fixed current control, fixed power control, fixed voltage control, manual control with an automatic temperature limit, manual control with an automatic output level limit. In some embodiments, the generator 100 can regulate the voltage in steps, and the initial voltage can be in the range 0-200 V-RMS or more, in 1 V increments. In some embodiments, the generator 100 can regulate the power in steps, and the initial power can be in the range 0-400 W or more, in 1 W increments.

In the embodiment presented in FIG. 1A, all settings shown in settings panel 106 can be active at the same time. This embodiment allows the user to select cooled-probe non-temperature control by turning on the coolant pump (for example by means on control 133 or an on-screen 101 button) when using a cooled electrode 150 for which the temperature sensor is absent or immersed in intra-probe coolant, and select non-cooled-probe temperature control by turning off the coolant pump for the same probe. One advantage of this configuration is the ability to rapidly switch from cooled RF ablation mode to non-cooled track coagulation mode after a cooled-RF heat lesion is generated in a tumor and the physician desired to coagulate the needle track of the cooled-RF probe. Another advantage of the setting configuration presented in 106, is that the same settings can be used both for an internally-cooled probe whose temperature sensor is positioned within the coolant flow, and for an internally-cooled probe whose temperature sensory is positioned at a distance from the coolant flow (such as the extension tip electrode 160 in FIG. 1B), since both a temperature setting and a current setting are active at the same time. Another advantage of the setting configuration 106 is that if either temperature or impedance feedback is not functioning properly, the other feedback setting can still provide control and safety.

A very important and useful advantage for the clinician user is to have an instant and intuitively clear visual check and feedback on the stability and control of the ablation process as it proceeds, particularly for impedance-controlled pulsing processes, of which one embodiment is presented in FIG. 1A. This intuitive visual feedback is provided, in one example, by a computer-graphic real time display of the generator signal output 102A during the procedure. This intuitive visual feedback is provided, in one example, by a computer-graphic real time display of the generator signal output 102A and impedance 102B during the procedure. This intuitive visual feedback is provided, in one example, by a computer-graphic real time display of the generator signal output 102A, impedance 102B, and temperature 102C during the procedure. For embodiments in which the displayed output level parameter is power and/or current, the up times and down times and the stability of the power and/or current level can visually indicate the clinician at a glance if the ablation process is going stably according to the automatic process, or if the ablation process is suboptimal, for example, the tissue is being overheated locally and instances of boiling are occurring too rapidly (as indicated by impedance rises in response to the output level) to optimally heat tissue beyond a high-impedance bubble zone. One example of a scenario in which a graphical display can provide information about a suboptimal ablation process involves the up-time power and/or current being too high, leading to excessive boiling around the active tip 151, the rapid and/or sustained formation of a high-impedance bubble zone, and a slump, a decrease, erratic variations, or other otherwise unstable variations displayed is the line graph of output current and/or power 102A. In another example scenario wherein the displayed output parameter is voltage, excessive voltage levels during the up time periods can cause the tissue to boil and impedance to be elevated in a sustained and/or frequent manner that prevents growth in lesions size and can lead to erratic controller behavior which can be detected by the user as erroneous by observation of the line plot of the voltage over time. Another example of a scenario in which graphical plot of the generator output level over time can help the user clinician troubleshoot a problematic ablation process is where incorrect output levels, output settings that are inappropriate for the ablation probe and tissue conditions, controller malfunction, and/or controller mismatch to tissue conditions produce incorrect, erratic, or unstable variations in the graphical plot of the generator signal output level and/or the up times and downtimes observable in that graphical plot. In another example, the graphs can show that the output level is too low; this can be indicated by the absence of an impedance spike after a sustained delivery of an output level, such as a constant voltage, constant current, or constant power. A too low output level can occur due to initial selection of the output level at a too low value for the probe size and tissue conditions. A too low output level can occur due to a too large reduction in the output level after an impedance spike; therefore, monitoring of a too low output level can be important throughout an ablation process. These and other example scenarios can be visualized and instantly and intuitively accessed by the clinician by the graphic real time display of one or more of the signal output parameters in the list of power, current, and voltage. These and other example scenarios can be visualized and instantly and intuitively accessed by the clinician by the graphic real time display of impedance and one or more of the signal output parameters in the list of power, current, and voltage, in real time, on the same axis. This gives the advantage of safety and control.

In other embodiments, two or more of the parameters impedance, voltage, current, and power can be plotted on the same time axis, in real time, for an ablation electrode output; this can provide the similar information to plotting impedance and one or more of voltage, current, and power, in real time on the same time axis. For example, for a control process in which a constant voltage is delivered, a drop in the current or the power can indicate a boiling condition. This instant visual feedback to the user is adventurous for the user to monitor the stability and efficacy of a pulsing ablation process by means of an internally-cooled HF probe, such as a cooled RF electrode, wherein the tissue repeated produces tissue boiling. This instant visual feedback is also important for non-cooled HF ablation processes to detect undesired boiling conditions.

In other embodiments, only a signal output level parameter, such as voltage, current, and power is plotted in real time. For example, if current and/or power is the sole plotted parameter, a drop in the plotted parameter can indicate a boiling condition that has produced such high impedance that the HF electrical supply is not able to deliver the desired plotted level. This does not provide as sensitive and rapid an indication of the ablation process as plotting two or more of the parameters voltage, current, power, and impedance on the same time axis in real time. Though this does not provide as rich information as the time-registered plotting of two or more of the parameters voltage, current, power, and impedance, it can provide some information about the ablation process, particularly for cooled HF ablation processes that intentionally produce tissue boiling, in accordance with aspects of the present invention.

In some embodiments, the control system measures the impedance between the electrode 150 and ground pads 121, 122, 123, 124. In some embodiments, the control system measures the level and timing of upward impedance spikes, as well as the level and timing of the post-spike decrease and stabilization of the impedance, and the control system uses that information to adjust the ablation process as it progresses, such as adjusting the timing and/or durations of the up-time phases and down-times phases, and/or the levels of the signal output during these phases. In some embodiments, the impedance is not displayed on the computer graphic display, but the processing of the impedance information is done within the control system according to its programming, and the results of the processing is indirectly manifest in the graphic display of the one or more signal output parameters, such as 102A. In some other embodiments, including that presented in FIG. 1A, the impedance is displayed on a computer graphic display, eg 102B, and this display can be an important for the clinical user to assess the efficiency, effectiveness, and safety of the ablation process. For example, graphical plotting of the impedance 102B can demonstrate irregularity, erraticness, and non-smoothness indicative of unstable lesion formation and improper placement of the probe. In some embodiments, the simultaneous graphical display of impedance 102B and the signal output level 102A provides the clinical user with an immediate sense of the progress of the ablation process, the correctness or incorrectness of the ablation control process relative to the tissue conditions, the tissue reaction to the applied HF output, and the relative timing and amplitude of impedance spikes relative to output level variations such as up times and down times. The graphic displays of impedance 102B and the one or more output parameters 102A can be stacked on each other, overlaid relative to the same time scale, or presented on the same two instances of the same time axis, either on the same computer graphic display 101 or on multiple displays. One advantage of graphical displays 102A and 102B is that the clinician can user them to visually evaluate the relation of impedance behavior and behavior of the one or more signal output parameters to see if the control system is functioning properly.

In some embodiments, a temperature is measured by the generator 100, such as the temperature of a temperature sensor integrated into the electrode 150E, and thus into the assembly probe 150, when the electrode 150E is inserted into cannula 150U. In some cases, the temperature signal can be measured by the generator 100 and used as an input to the ablation control process, but not displayed graphically to the user, for example, on screen 101. In some other embodiments, the electrode temperature can be displayed graphically, as shown for example by line plot 102C in FIG. 1A, on the same time axis as the output level graph 102A and the impedance graph 102B. One advantage of displaying the temperature graphically 102C in sync with the output level 102A, is that the temperature response of the electrode 150, the coolant flowing through the electrode, and/or the tissue near the electrode active tip 151 can be intuitively assessed by the user during the ablation process. For example, when the temperature sensor of electrode 150 is in the coolant flow path, variations in the temperature graph indicates to the user the effectiveness of the electrode cooling. For example, if the temperature were to rise substantially during the up times of the ablation process, the user would be prompted to evaluate the coolant flow rate and check for any flow blockages, electrode malfunction, or electrode misconstruction. In the example shown in FIG. 1A, graph 102C shows moderate increases in temperature during the up times due to the coolant being heated by elevated tissue temperatures around the active tip 151, and decreases temperature during the downtimes due to dissipation of temperature in the tissue around the active tip 151.

One general advantage of a graphical display of the output level 102A, the impedance 102B, and/or the temperature 102C that displays the history of one or more of these values during the ablation process is that the user can observe variations in these values over time, and has access to a documentation of past irregularities that might otherwise be missed if the user does not happen to look at a digital display 104A, 104B, 104C, 104D, 104E, 104F of an irregular value at the moment the irregularity occurs; this is particularly important for automated processes that alternate between states, such as up times and down times, since the operating conditions of the generator 100 and ablation process can change discontinuously and/or rapidly. Another advantage of dynamics graphs of the output level 102A, the impedance 102B, and/or the temperature 102C over time is that the clinician can use it to perform an instant check on the proper operation of the control system and ablation process over the entirety of the preceding duration of the ablation process.

In some embodiments, the signal output level, such as the level graphed by line plot 102A, can be displayed as voltage, current, power, RMS voltage, RMS current, RMS power, duty cycle, duty cycle of a set output level, time-averaged voltage, time-averaged current, time-averaged power, RMS voltage over a time window, RMS current over a time window, RMS power over a time window, or mathematical functions of these values, where a mathematical function can be, for example, addition, subtraction, multiplication, an average, an average over a time window, the root mean squared value over a time window, squaring, cubing, square root, logarithm, and combinations of these mathematical functions.

In some embodiments of the system shown in FIG. 1A, one of the user settings "initial current" 106B or "maximum current" 106E (which are one example of settings that control the output level of the beginning of the initial pulse, and the maximum output level of all pulses, respectively, in a cooled-RF system and method for impedance-based pulsed control of the ablation process) can be omitted. For example, in FIG. 1B and FIG. 1C, only one current setting is available to the user. In some embodiments wherein one of the user settings "initial current" 106B or "maximum current" 106E is omitted, the value of the omitted setting can be automatically determined by the control system relative the value of the remaining displayed user setting. For example, if the user selects 1900 mA for the "initial current" setting 106B and setting 106E is not available for user selection, the controller can automatically set a control variable for the "maximum current" to be some amount higher than the "initial current" user setting value 106B, such 2500 mA, a difference of 600 mA. Similarly, for example, if the user selects 2300 mA for the "maximum current" setting 106E and setting 106B is not available for user selection, the controller can automatically set a control variable for the "initial current" to be some amount lower than the "maximum current" user setting value 106E, such 1800 mA. The controller can set the relative value for a maximum current or an initial current setting relative a user-selected value for initial current or maximum current, respectively, by adding or subtracting a predetermined value from the user-selected value (such as a value in the range 100 mA to 800 mA, 600 mA, a value less than 100 mA, a value greater than 800 mA), by multiplying the user-selected value by a fraction (such as a value in the range 0.8-1.2, a values less than 0.8, a value greater than 1.2), or another method for selecting relative values to suit clinical needs. In some embodiments wherein the maximum current is not user-settable, the maximum current can be set to the maximum current output level for the generator. In some embodiments, the initial output level and the maximum output level can be parameterized by voltage, power, current, or another measurement of output level. In some embodiments, a minimum output level (such as a current level) can be included as a user setting.

Referring now to FIG. 1B, FIG. 1B is a schematic drawing showing one example of an arrangement of an apparatus for performing HF ablation of bodily tissue of patient 190, in accordance with some aspects of the present invention. In some embodiments, the apparatus of FIG. 1B can be another configuration of the apparatus of FIG. 1A, wherein electrode 150 is replaced by electrode 160 and the generator settings 106 take different values. Electrode 160 includes an extension tip 167 that houses a temperature sensor configured to monitor tissue temperature distal to the active tip 161 of the electrode 160, close to or at the location of maximum tissue temperature. The generator settings 106 include a set temperature value of 95° C. The combination of the extension tip 167 temperature sensor and the set temperature are configured to hold the maximum tissue temperature just below the boiling point in order to maximize heat lesion size and to prevent tissue boiling. The generator control system is adapted to measure the extended temperature from sensor 167, and to display the extended temperature 119C on the computer graphic display 101 together with other signal output parameters in the list of power, current 199A, voltage, and impedance 119B. The control system is can be adapted to use the extended temperature 167 as a feedback parameter in the ablation process. In one example, the extended temperature can be a check that the boiling bubble zone, or potential boiling bubble zone, is in the desired range of temperature and time duration. By displaying the extended temperature 119C along with the other output parameters 119A and 119B, the clinician can have visual check and confirmation of the ablation process.

Electrode 160 is connected to generator electrode jack 116 via cable 164 that carries HF output to the electrode 160. Coolant, such as chilled saline or water, is pumped through tube 165 into the electrode 160, flows through the electrode shaft to cool the active tip 161, and out from the electrode through tube 166 and into collection container 135. Electrode 160 includes a hub 163 at the electrode proximal end, an elongated shaft including an insulated portion 162 at the shaft proximal end and a conductive active tip 161 at the shaft distal end, an extension tip 167 extending distal to the distal end of the active tip 161, wherein the extension tip 167 includes a temperature sensor at a distance from distal end of the active tip 161, wherein the distance between the extension tip temperature sensor 167 and the distal end of active tip 161 can be a value in the range 0.1 mm to 10 mm (or value adapted to locate the temperature sensor at the most likely location of maximum tissue temperature), wherein the insulated portion 162 prevents outflow of the generator's HF output signal, and wherein active tip 161 allows outflow of the generator's HF output signal to the bodily tissue of organ 193 of body 190 and thereby generates heat lesion 194B. In some embodiments, the temperature sensor can be at the distal end of the extension tip 167. In some embodiments, electrode 160 is introduced into bodily tissue by means of an introducer cannula that can be tissue-piercing or that can be configured to be tissue-piercing by means of a sharp-point stylet. In some embodiments, the introducer cannula can have sharp bevel at its distal, and a removable stylet with match-ground distal bevel, to reduce insertion forces when the cannula is inserted into patient tissue 190. In some embodiments, the distal extension tip 167 can be electrically uninsulated so that it does produces HF heating of the tissue by itself, and measures the temperature of the tissue at a distance D from the end of the active tip 161. In some embodiments, the distal extension tip 167 can be electrically insulated so that the extension tip 167 does not produce HF heating of the tissue by itself, and thus less influences the temperature of the tissue at a distance D from the end of the active tip. The distance D can be predetermined so that sensor is located in the hottest part of the tissue during ablation. Alternatively, the distance D can be adjustable by the user if the extension tip is configured to slide relative to the active tip 161. In some embodiments, the extension tip can be slidably mounted to the active tip 161, perhaps via other elements of the electrode 160, such as a clamp in the electrode hub 163, so that the user can measure temperature at multiple locations distal to the tip 161 by sliding the extension tip 167 relative to the active tip 161. In some embodiments, the extension tip can be fixedly mounted to the active tip 161. In some embodiments, the distal extension tip 167 can comprise a stainless steel tube, a temperature sensor at the distal point of the tube (for example, formed by welding a constantan wire within the stainless steel tube to the distal end of the stainless steel tube), electrical insulation (which can comprise a plastic coating or sheath along the tube, and glue covering wire connections at the tube proximal end) covering all but the distal point of the tube; wherein the tube proximal end is positioned within an inner lumen of the electrode shaft 162 and tip 161 (for example, the lumen can be formed by a pipe within the shaft 162 and tip 161 that is welded to the distal end of the pipe that forms the outer surface of the tip 161, between both of which pipes, the coolant fluid flows and is contained), the tube position is fixed relative to the active tip 161 by a thermally-insulative element at a proximal location within the electrode 160 (for example, by glue within the electrode hub 163), and the extension tip 167 is thereby thermally, electrically, and physically separated from both the active tip 161 and the coolant flow within the electrode shaft 162 and tip 161, both by a physical gap (ie the space between inner surface of the lumen and the outer surface of the tube electrical insulation) and the electrical insulation covering the tube; and wherein the wires connecting to the extension tip temperature sensor to the generator 100 are electrically isolated from the HF output wires in the electrode 160, cables 164, and generator 100; so that the extension tip 167 does itself produce HF heating of the tissue, and the extension tip 167 measures temperature of the tissue at a distance D from the end of the active tip 161 with a fast thermal response due to the metallic temperature sensor that is integral with the outer surface of the distal end of the extension tip 167 and that is in direct contact with bodily tissue 190. In some embodiments, the distal extension tip 167 can comprise a stainless steel tube, a temperature sensor at the distal point of the tube (for example, formed by welding a constantan wire within the stainless steel tube to the distal end of the stainless steel tube), electrical insulation (which can comprise a plastic coating or sheath along the tube, and glue covering wire connections at the tube proximal end) entirely covering all parts of the extension tip 167 that emerge from the tip 161 and thus directly contact tissue 190; wherein the tube proximal end is positioned within an inner lumen of the electrode shaft 162 and tip 161 (for example, the lumen can be formed a pipe within the shaft 162 and tip 161 that is welded to the distal end of the pipe forming the outer surface of the tip 161, between both of which pipes, coolant fluid flows and is contained), the tube position is fixed relative to the active tip 161 by a thermally-insulative element at more proximal location in the electrode 160 (for example, by glue within the electrode hub 163), and the extension tip 167 is thereby thermally and physically separated from both the active tip 161 and the coolant flow within the electrode shaft 162 and tip 161, both by a physical gap (ie the space between inner surface of the lumen and the outer surface of the tube electrical insulation) and the electrical insulation covering the tube; and wherein tube can either be electrically insulated or not electrically insulated within the electrode 160 and cable 164 from the HF output delivered to the active tip 161 by generator 100; so that the extension tip 167 does itself produce HF heating of the tissue because its outer surface is electrically insulated, and the extension tip 167 measures temperature of the tissue distance D from the end of the active tip 161.

In the example presented in FIG. 1B settings panel 106 includes a set time of 12 minutes, a set current of 3 Amps, a set temperature of 95° C., and manual control mode. In some embodiments, these settings can take values in the ranges described in relation to FIG. 1A. In some embodiments, the set temperature for an electrode 160 with a temperature-sensing extension tip, it is advantageous to select a set temperature sufficiently below boiling to avoid boiling across an expected variety of typical tissue conditions. For example, the set temperature can be in the range 40-90 deg C., 40 deg C., 50 deg C., 60 deg C., 70 deg C., 80 deg C., 45 deg C., 55 deg C., 65 deg C., 75 deg C., 85 deg C., or 90 deg C. The HF current output delivered to electrode 160 is plotted over time by solid line 119A. The electrode impedance is plotted by dashed line 119B on the same time axis. The electrode temperature, measured by the temperature sensor included in the extension tip 167, is plotted by dotted line 119C on the same time axis. The graphed values 119A, 119B, 19C were generated by the following process that involved both manual and automatic control functions. After the user started with ablation program, since the control mode is set to "Manual", the user increased the HF output current by turning the control knob 110 counter clockwise to a sufficient level to heat the tissue around the active tip 161. Before the output level reached the current limit of 3.0 Amps, the generator automatically adjusted the output level 119A to ramp the measured temperature 119C up to the set temperature value 95° C. over approximately 2 minutes. A slow ramp up to the set temperature, for example wherein the ramp to full temperature occurs over 1 to 3 minutes, has the advantage of preventing tissue boiling due to a lag in the measured temperature response, particularly for large active tips 161. Once the temperature 119C reaches the set temperature value, the generator 100 controller automatically adjusts the HF output level 119A to maintain the measured temperature 119C at the set temperature setting value. During the heating process, the impedance 119B first decreases in value as the tissue around the active tip 161 heats up, and then rises slowly and smoothly as irreversible tissue changes occur and micro bubbles form around the active tip 161. In another embodiment, the control mode can be set to "Auto" with the other settings 106 taking the same values as shown in FIG. 1B, and temperature-controlled ablation can proceed without user interaction via the control knob 110. One advantage of a generator 100 that can control an ablation process by measurement of tissue temperature remote of the active tip 161, such as by means of an extension tip 167 or side-outlet temperature sensor, is that tissue heating can be sustained without interruptions and/or "down times" (as in FIG. 1A). In some embodiments, the temperature control configuration presented in FIG. 1B can produce substantial tissue boiling and impedance spikes, such as 118 in FIG. 1A. In that case, if the control mode of generator 100 is set to "Auto", the generator can use the impedance-controlled up-time/down-time pulsing process presented in FIG. 1A in coordination with the temperature-control process presented in FIG. 1B, wherein the output level during the up time is modulated to maintain the measured temperature at or near the set temperature setting value. One advantage of a controller that includes both a temperature-control controller and an impedance-based pulsing controller is that direct temperature measures can be used to control the ablation process, and output pulsing can be used to dissipate high-impedance bubble zones that can form when temperature control fails, for example, because the temperature sensor is not located at the exact location of maximum tissue temperature or because the temperature-control controller's programming is not well matched to particular tissue conditions.

Referring to FIG. 1C, FIG. 1C is a schematic drawing showing one example of an arrangement of an apparatus for performing HF ablation of bodily tissue of patient 190, in accordance with some aspects of the present invention. In some embodiments, the apparatus of FIG. 1C can be another configuration of the apparatus of FIG. 1A, wherein electrode 150 is replaced by three ablation electrodes 150A, 150B, 150C arranged in cluster, and the generator settings 106 take different values. In the embodiment shown in FIG. 1C, each of the ablation probes 150A, 150B, and 150C are integral tissue-piercing RF electrodes. Electrodes 150A, 150B, 150C are connected to HF output jack 116 by splitter cable 154A which carries HF output to each electrode. In the embodiment shown in FIG. 1C, the same HF output signal is applied to all electrodes 150A, 150B, 150C, each of which include a temperature sensor that is positioned within that electrode's active tip. Return current from the electrodes 150A, 150B, 150C are carried by ground pads 121, 122, 123, 124. This can be referred to as a "monopolar cluster" configuration. The inflow and outflow tubes of the electrodes 150A, 150B, 150C are connected in series, and coolant is pumped through tube 155A into electrode 150A; out from electrode 150A, through tube 1558, and into electrode 150B; out from electrode 150B, through tube 155C, and into electrode 150C; and out from electrode 150C, through tube 155D, and into the waste container 135. The electrodes are held in a triangular arrangement by guideblock 157, wherein the electrode shafts are substantially parallel and the electrodes are equidistant from each other. The guideblock 157 can be a solid block (or another type of rigid structure) that includes holes through which, or slots into which, the electrodes shafts can slide. The guideblock 157 can include multiple sets of holes to allow for different parallel electrode spacings, such as 5 mm, 10 mm, 15 mm, 20 mm, 25 mm, and 30 mm. In some embodiments, the block 157 can be one of the guideblocks presented in relation to FIG. 25, 26, 27, 28. One advantage of heating tissue with a cluster of closely-spaced electrodes is that a larger heat lesion zone 194C can be generated, for instance, to destroy a large tumor in a large organ 193 such as the liver, lung, or kidney. Another advantage of the a guideblock 157 is that two or more electrodes inserted into the same body 190 can mechanically support each other to prevent movement due to electrode weight outside the body 190. Another advantage of a guideblock 157 is that two or more lesions can be created sequentially to produce a total lesion zone of an irregular shape. In some embodiments, the guideblock can allow for unequal parallel electrode spacings, such as three electrodes with inter-electrode spacings 10 mm, 15 mm, and 15 mm. In some embodiments, wherein the number of electrodes is 4, a square or quadrangular parallel-electrode guideblock can be used. In some embodiments, a guideblock can accommodate two or more electrode arranged in an arbitrary parallel-shaft configuration. In some embodiments, a guideblock can provide for surrounding one of more electrode by three or more electrodes, wherein all electrodes are parallel. In some embodiments a guideblock can provide for non-parallel electrode arrangements. In some embodiments, a non-parallel-electrode guideblock can be configured to provide for avoidance of sensitive or impenetrable bodily structures like the rib that can prevent some parallel-electrode configurations. In some embodiments, a guideblock can provide for the non-parallel placement of multiple electrode active tips are location within the body in an arrangement that is configured to produce a uniform ablation volume around the multiple active tips. In some embodiments, guideblock 157 can have guide holes whose inner diameter is large relative to electrodes 150A, 150B, and 150C so that the electrodes are inserted by the physician in a non-predetermined configuration, and the physician can adjust the relative position and alignment of electrodes to adapt to anatomical constraints.

The settings panel 106 shows that the set time is set to 12:00 minutes, the initial current to 2.4 Amps, the set temperature to 90 deg C., and control mode set to Automatic. Because the temperature sensors of electrodes 150A, 150B, 150C are positioned within the coolant flow within the electrode active tips, the output level is not limited by the requirement of hold the measured temperatures at or below 90 deg C., and the generator operates in an pulsing impedance-control mode, analogous to that of FIG. 1A. Correspondingly, the output level goes through multiple cycles of high-output up times and low-output down times as shown by current graph 102D; the impedance goes through multiple cycles of spikes and returns to baseline as shown by impedance graph 102E; and the electrode temperatures 102F, 102G, 102H rise and fall moderately during up times and down times, respectively.

Referring to FIG. 1C, the graphic display 101 shows four digital temperature readings 104G labeled "T1", "T2", "T3", and "T4", which replace the single digital temperature reading 104D shown in FIG. 1A. The generator 100 automatically changes the digital and graphical temperature-reading displays when the number of temperature readings detected on the pins of 116 changes, reflecting a change in the number of temperature-sensing electrodes 150A, 150B, 150C attached to jack 116 by splitter cable 154A. The splitter cable 154A can include markers by which the user can match an electrode 150A, 150B, 150C to a temperature reading label "T1", "T2", "T3", and "T4". In the example shown in FIG. 1C, temperature readings T1, T2, T3 come from electrodes 150A, 150B, 150C, respectively. In some embodiments, the number of temperature readings can be equal to the number of detected temperatures. In some embodiments, changes in the number of displayed temperature readings can be prompted by one or more of the list: user selection of settings values, jumper pins in adaptor cable 154A, circuitry in adaptor cable 154A, circuitry in each electrode 150A, 150B, 150C, and other mechanisms. The fourth temperature display 104H, labeled "T4" indicates the absence of a fourth temperature reading by means of the "--" indicator. In some embodiments, a fourth electrode analogous to electrode 150A can be attached to jack 116 with a four-electrode splitter cable. The display screen 101 includes graphical display of the generator output level as solid line 102D, the impedance between the generator reference potential and HF output as dashed line 102E, the temperature of electrode 150A as dotted line 102G labeled "T1", the temperature of electrode 150B as dotted line 102H labeled "T2", and the temperature of electrode 150A as dotted line 102F labeled "T3". Labels "T1", "T2" 102I, "T3" appear on the screen next to the right end of temperature graphs 102G, 102H, 102F to identify the graphs to the user. Label 102I reads "T2" and labels line 102H.

Paragraph B: The impedance 104A and 102E, current 102D, voltage, and power displays pertain to the HF current flowing between the electrodes 150A, 150B, 150C and ground pads 121, 122, 123, 124 that are attached to generator potentials, where the electrodes 150A, 150B, 150C can be connected and disconnected from the HF output potential, and the ground pads 121, 122, 123, 124 can be connected and disconnected from the reference potential. In the example presented in FIG. 1C, the electrodes 150A, 150B, 150C are uniformly connected to the HF output signal, and the ground pads 121, 122, 123, 124 are connected to the reference potential in a repeating switching pattern configured to maintain the RMS current of each ground pad below at maximum of 700 mA, which is the maximum safe current rating for each pad, in this example. Generally, ground pad heating is influenced by the RMS current averaged over time windows that are short relative to the thermal response time constant of the ground pad, for example time windows up to 5-10 seconds, or up to 30 seconds, or longer for some ground pads. For a HF signal, such as a 500 kHz RF signal, the RMS current over a time window W with duration |W| much longer the HF signal's carrier is the square root of the integral of $I^2(t)$ with respect to time t over time window W, where I(t) is the RMS Current over the period of the carrier of the HF signal; that is $((1/|W|)*\int_W I^2(t)*dt)^{1/2}$. For a 500 kHz RF signal, the carrier can be a sinusoidal signal with period 2 microseconds. In the example shown in FIG. 1C, for the total electrode current 2500 mA=2.5 A, the individual ground pad currents 700 mA, 699 mA, 659 mA, 576 mA for pads G1 121, G2 122, G3 123, G4 124, respectively, can be achieved to within single-digit precision by a first pattern of switched ground pad connections, which can be classified as a "nested simultaneous" switching pattern. In the first step of the first pattern, jacks G1, G2, G3, G4 are connected to the generator reference potential for 4.35 seconds, and return current flows to the jacks' respective pads in proportions 0.3, 0.28, 0.22, 0.2, respectively. In the second step of the pattern, jacks G2, G3, G4 are connected to the generator reference potential for 0.31 seconds, and return current flows to the jacks' respective pads in proportions 0.4, 0.33, 0.27, respectively. In the third step of the pattern, jacks G3, G4 are connected to the generator reference potential for 0.34 seconds, and return current flows to the jacks' respective pads in proportions 0.55, 0.45, respectively. The duration of the pattern is 5 seconds. The RMS current for jack/pad G1 over the pattern duration can be computed sqrt((4.35/5)* (2500*0.3)^2)=699.55 mA. The RMS current for jack/pad G2 over the pattern duration can be computed sqrt((4.35/5) *(2500*0.28)^2+(0.31/5)*(2500*0.4)^2)=698.78 mA. The RMS current for jack/pad G3 over the pattern duration can be computed sqrt((4.35/5)*(2500*0.22)^2+(0.31/5)* (2500*0.33)^2+(0.34/5)*(2500*0.55)^2)=658.74 mA. The RMS current for jack/pad G4 over the pattern duration can be computed sqrt((4.35/5)*(2500*0.2)^2+(0.31/5)* (2500*0.27)^2+(0.34/5)*(2500*0.45) ^2)=576.03 mA. One advantage of this first example of a "nested simultaneous" switching pattern for four ground pads is that only three switching steps are used to maintain the ground pad currents at or below their maximum rating. One advantage of reducing the number of ground pad switching steps is that it can increases the maximum power that the generator can deliver to the electrode by reducing switching transition times, it can reduce wear and tear on the ground pad switches, it can reduce switching noise, and it can reduce impedance variations due to changes in the ground pad connection configuration. One advantage of maximizing the number of active ground pads in a switching pattern is that the peak current to any one pad is minimized since the total current is distributed across a maximum number of pads. The precision with which the ground pad currents can be controlled can be limited by the maximum switching speed, the minimum possible duration of a step in a switching pattern, the speed with which the total electrode current can be adjusted, and other factors. In another example, a second nested-simultaneous switching pattern can be used to equalize the RMS-average ground pad currents, so that each ground pad carries 682 mA+/−2 mA over the sequence of ground-pad connection states in the pattern. In this second pattern, the total current 2500 mA and the proportion of current flow to each pad is the same as in the first three steps of the first pattern described above, and a fourth step is added in which only jack G4 is connected to the generator reference potential and all the return current flows to the G4's pad 124. The durations of steps 1 through 4 of the second pattern are 4.15 seconds, 0.3 seconds, 0.46 seconds, and 0.09 seconds, respectively. The total time of the pattern is 5 seconds. The RMS current for jack/pad G1 can be computed sqrt((4.15/5)*(2500*0.3)^2)=683.28 mA. The RMS current for jack/pad G2 over the pattern duration can be computed sqrt((4.15/5)*(2500*0.28)^2+(0.30/5)*(2500*0.4)^2)=683.15 mA. The RMS current for jack/pad G3 over the pattern duration can be computed sqrt((4.15/5)*(2500*0.22)^2+(0.30/5)*(2500*0.33)^2+(0.46/5)*(2500*0.55)^2)=682.53 mA. The RMS current for jack/pad G4 over the pattern duration can be computed sqrt((4.15/5)*(2500*0.2)^2+(0.30/5)*(2500*0.27)^2+(0.46/5)*(2500*0.45)^2+(0.09/5)*(2500*1.00)^2)=681.01 mA. One advantage of the second example of a nested-simultaneous switching is pattern is that current is evenly distributed across the ground pads on average. One advantage of both the first and second examples of a nested-simultaneous switching is pattern is that the RMS current for each ground pad over the duration of the switching pattern can be less than that produced by a sequential switching pattern wherein only one ground pad is active at a time. For example, for a total current flow of 2500 mA and a sequential switching pattern in which each of four pads/jacks G1, G2, G3, G4 is connected to the generator reference potential for 1.25 seconds with all other pads disconnected, the RMS current over the total 5 second pattern is sqrt((1.25/5)*(2500*1.0)^2)=1250 mA. In the preceding examples, switching ground pad connections between subsequent pattern steps is assumed to be instantaneous. In practice, in some embodiments, non-zero switching time can be used. When non-zero switching time is used, the total switching pattern duration can be increased to include the switching time and/or the step durations can be reduced to remove the switching time. In some embodiments, the HF output is disabled during the time when a ground-pad switch is opening or closing. This produces a non-zero switching time, and it advantageously avoids high-current arcing within the switches and the production of non-zero-mean transients in the electrical signal. Because switching can take up to several milliseconds, and because ground pads can carry high currents from an ablation electrode, non-zero-mean signal transients can produce undesired nerve-stimulation effects on the patient in some cases. In the prior art of Lee, it is suggested this can be avoid by timing ground pad switches with zero-crossing of the RF. One limitation of this approach is that hundreds of zero crossings will occur during even one millisecond of switch transition time (eg a 500,000 Hz RF signal has period of 0.002 milliseconds). Another limitation is that the switching signal must be synchronized with accuracy on the order of one microsecond. In Lee, it is suggested that stimulation of excitable tissue can be avoid during ground pad switching by the application of a high-pass filter. One limitation of this approach is that for the very high output levels characteristic of tissue ablation, a high pass filter may not reduce stimulating transients to below a level capable of stimulation. In one aspect of the present invention, a RF ablation generator turns off the RF output during changes to the state of ground pad switches. This has the advantage of completely removing stimulating transients due to ground pad switching. This has the advantage of enabling the use of higher ablation output levels both by switching ground pad connections to limit ground pad heating, and by avoiding simulative effects of ground pad switching.

In some embodiments, the electrodes 150A, 150B, 150C are connected to the pump 130 in a parallel configuration. This has the advantage all electrodes received coolant at the same temperature. This contrasts a serial coolant flow configuration, such as that shown in FIG. 1C, wherein a downstream electrode, eg 150B, is cooled by coolant that is somewhat heated after having already flowed through one or upstream electrodes, eg 150A. One advantage of a serial configuration is simplicity of setup since a single pump tube can be used to carry water to and from the cluster of multiple electrodes 150A, 150B, 150C.

In some embodiments, the cluster electrodes 150A, 150B, 150C can be inserted into the tissue without the use of a guideblock. In some embodiments, cluster electrodes can be inserted in a non-parallel configuration and an ellipsoidal or pseudo-ellipsoidal lesion zone can form around the cluster of non-parallel active tip as long as the tips are sufficiently close, for example 5-15 mm apart, because thermal conduction tends to smooth irregularities and/or non-convexities in the heating pattern around the active tips. In some embodiments, guideblock 157 provides electrode holes and/or slots that allow for non-equidistant spacing of multiple electrodes; this has the advantage of allowing the insertion of electrodes around bony structures such as the ribs that might block an equidistant electrode configuration, while at the same time constraining the active tips of the electrodes to be in a known geometrical configuration, such as a parallel-shaft isosceles-triangle configuration, a parallel-shaft arbitrary triangular configuration, a parallel-shaft quadrangular configuration, a non-parallel shaft triangular or quadrangular configuration in which the active tips will be in non-parallel but sufficiently close proximity to create a convex heat lesion when inserted to a predetermined depth beyond the guideblock, and other configurations.

In some embodiments, a different HF output signal is conducted to each cluster electrode 150A, 150B, 150C, wherein the HF output signals can differ, for example, in their amplitudes or in their patterns of connection and disconnection from generator output potentials.

In some embodiments, the generator 100 only measures the temperature of one of the clustered electrodes 150A, 150B, 150C. In some embodiments, each of the electrode 150A, 150B, and 150C can include extension tips, like that of ablation electrode 160 in FIG. 1B, and the generator can maintain all electrode temperatures below the set temperature value, for example, by adjusting the output level to maintain the maximum of all electrode temperatures at or below the set temperature value.

In some embodiments, the one or more ablation probes 150, 150A, 150B, 50C, 160 are non-internally-cooled probes, such as a non-cooled MW antenna, a standard non-cooled RF electrode, or a non-cooled RF electrode inserted into an RF cannula. In some embodiments, the generator 100 can be configured for nerve ablation, for example for functional neurosurgical procedure and/or for pain management procedures. In some embodiments, the generator 100 can include a nerve stimulator. In some embodiments, ablation probes 150, 150A, 150B, 150C, 160 are perfusion electrodes from which fluid is pumped into the tissue around the active tip to enhance heat lesions size. In some embodiments, a cooled RF electrode also includes outlets in or near its active tip configured for perfusion of fluid into the tissue; the perfused fluid can include some of the cooling fluid, or the perfusion fluid can be another fluid, or both. In some embodiments, a perfusion RF electrode can output into the tissue all the cooling fluid supplied to it by a pump. In some embodiments, a perfusion RF electrode can output into the tissue a portion of the cooling fluid supplied to it by pump, and can circulate back up the shaft and into a output tube another portion of the cooling fluid supplied to it by the pump. In some embodiments, ablation probes 150, 150A, 150B, 150C, 160, can each be any one ore the following: cooled RF electrode, a cooled RF electrode inside an RF cannula, cooled RF electrode with extension-tip temperature sensor, cooled RF electrode with lateral temperature sensor, cooled RF electrode temperature sensory on outer surface proximal to the active tip, perfusion RF electrode, cool-wet RF electrode, single-prong cooled RF electrode, multi-prong cooled RF electrode, cooled cluster RF electrode, a cooled RF cluster electrode with two electrode shafts, a cooled RF cluster electrode with three electrode shafts, a cooled RF cluster electrode with four electrode shafts, a cooled RF cluster electrode more than four electrode shafts, multiple RF electrodes of any of the aforementioned types, cooled MW ablation antenna, multiple cooled MW ablation antennae, a cluster MW antenna, and other type of HF ablation probes. In some embodiments, a cluster RF electrode can have a number of shafts selected from the list: 2, 3, 4, 5, 6, 7, 8, 9, 10, more than 10.

The present invention, as shown in one embodiment in FIG. 1, has the advantages of producing reproducible and predicable size of ablation zone, and presenting measurements to the user to maintain efficacy and safety during HF heat ablation. The visual graphic display of output (eg current, voltage, or power) and tissue parameters (eg impedance) during the ablation process allows the user to correlate clinical outcomes, both positive and negative, with behaviors displayed by the displayed parameters, so that the user can improve his or her ability to interpret the parameters and adjust the ablation setup in future cases. This is a particularly significant advantage in the case of HF ablation using an internally-cooled electrode 150 (which, in one example, can be cooled RF ablation), because the ablation process involves repeatedly approaching unstable boiling tissue conditions. To bring stability to this unstable process and to enable visual conformation is a significant advantage. Another advantage of the embodiment presented in FIG. 1 is the ability for the same generator 100 to operate in a variety of configurations to suit clinical needs, wherein the configurations differ in the types and number of ablation probes, types of parameters controlled, and the parameter values of automated ablation controllers.

Referring now to FIG. 2, one embodiment of a multielectrode ablation system is presented in a schematic drawing in accordance with several aspects of the present invention. Many elements of the system in FIG. 2 are analogous to elements of the system presented in FIG. 1, and the system in FIG. 2 presents additional functionality including performing tissue ablation on multiple electrodes at the same time with independent measurements, digital displays of measurements, graphical displays of measurements, and settings; and energizing multiple electrodes and ground pads at the same time or in arbitrary sequences of connection to different generator potentials such that current flows between electrodes and either other electrodes or ground pads either at the same time or at different times. Generator 200 is configured as an RF generator as shown in FIG. 2, and in other configurations and similar embodiments can be a MW generator, a hybrid RF and MW generator, or another kind of HF generator for tissue ablation. Generator 200 is connected to four ground pads 221, 222, 223, 224 placed on the skin surface of patient 290; four internally-cooled treatment electrodes 251, 252, 253, 254 that are placed in the bodily tissue of patient 290; coolant pump 230 that includes two pump heads 231, 231A; and ultrasound imaging machine 240 by means of which the internal anatomy of patient 290 can be visualized. Ground pads 221, 222, 223, 224 are connected to generator jacks 215 labeled "G1", "G2", "G3", "G4", respectively. Ground pad 221 is connected to jack G1 by cable 221A. Ablation electrodes 251, 252, 253, 254 are connected to generator electrode jacks 216 labeled "E1", "E2", "E3", "E4", respectively. Electrode 251 is connected to jack E1 by cable 251A. Ultrasound imaging machine 240 includes ultrasound transducer 245 which can display images of the internal anatomy of patient 290 and electrodes 251, 252, 253, 254 within that anatomy on display 241; controls 242; and generator controls 243 by means of which a user can operate the generator 200 via data connection 244. Coolant pump 230 includes user control 233 and two pump heads 231, 231A connected to coolant reservoirs 232, 232A, respectively, wherein the coolant can be a fluid such as sterile water or sterile saline solution. Pump head 231 pumps coolant from reservoir 232 through tube 251B into electrode 251 to cool the electrode's active tip, and then out through tube 252B into electrode 252 to cool that electrode's active tip, and then out through tube 252C into collection container 235. Pump head 231A pumps coolant from reservoir 232A through tube 254B into electrode 254 to cool the electrode's active tip, and then out through tube 253B into electrode 253 to cool that electrode's active tip, and then out through tube 253C into collection container 235. One advantage of this configuration is that two fluid pump heads can cool four cooled ablation probes. Generator 200 includes touch screen 201; ultrasound machine controls 213 by means of which the user can control ultrasound machine 240 via data connection 244; four ground pad jacks 215; four ablation probe jacks 216; a control knob 210; a button 209 to disable and/or discontinue delivery of ablation energy to the electrodes; a button 208 to enable delivery of ablation energy to one or more electrode jacks 216 and electrodes attached to those jacks; a lamp 214 indicating active delivery of ablation energy to jack 216; data ports 211 which can provide for export of data, printing of data, input of data, input of control signals from remote controllers, and other data input and output. The touch screen 201 includes a toggle button 205 for activating and deactivating delivery of ablation energy to attached electrodes 251, 252, 253, 254; a settings panel 206 for display and user-adjustment of generator settings such as the set time, set current, set temperature, and other parameters of ablation programs included in generator 200; and control buttons 207 for selecting cooled RF ablation mode, selecting standard RF (aka coagulation) lesioning mode, selecting pulsed RF lesion mode of the variety familiar to one skilled in the art of spinal nerve ablation and pain treatment, selecting nerve stimulation mode, resetting the lesion program timer, saving an image of the screen to memory, entering procedure notes to stored procedure data, printing stored procedure data, exporting stored procedure data to an external disk, and changing the screen display to main menu screen. In some embodiments, including other operating modes of generator 200, settings panel 206 can allow the user to select different settings for each electrode E1, E2, E3, E4. In some embodiments, the settings in panel 206 can take values in the ranges described in relation to settings 106A, 106B, 106C, 106D, 106E. The display screen 201 includes display 203 which displays an individual current for each ground pad attached to ground pad jacks G1, G2, G3, and G4. All ground pad jacks, and their attached ground pads, can be connected to the generator reference potential at the same time, or can be connected and disconnected from the generator reference potential to limit, equalize, or otherwise control the average current flow through each pad. The display 201 includes an individual mode selection button 217, individual set of digital displays 204, and individual graphical displays 202A, 202B for each electrode jack E1, E2, E3, E4 and each electrode 251, 252, 253, 254 attached to those jacks, respectively. The mode-selection control 217 for electrode jack E1 and electrode 251 provides controls, for example by means of a drop-down menu, for activating and deactivating jack E1, selecting electrode-specific settings for electrode 251, and selecting the pattern of connections between jack E1 and generator output potentials. Control 217 displays "E1 Bi→2" indicating that the control and displays below it correspond to the electrode attached to jack E1 and that electrode E1 and electrode E2 are energized in a bipolar (also known as "dual") configuration, wherein current flows between electrodes E1 and E2. The control display for electrode E2 reads "E2 Bi→1" also indicating a bipolar configuration between electrode jacks E2 and E1. The control for electrode E3 reads "E3 Mono" indicating that electrode E3 is energized in a monopolar configuration wherein return currents from electrode E3 are carried by one or more of the ground pad jacks. The control for electrode E4 reads "E4 Mono" indicating that electrode jack E4 is energized in monopolar configuration. In another embodiment, the control 217 for electrode E1 can read "E1 Cluster→E2,E3" indicating that electrodes E1, E2, E3 are connected to the same HF output signal and energized as a monopolar cluster, referenced to one or more ground pads.

In some embodiments, groups of electrodes are energized non-concurrently, so that only one group is connected to and energized by a generator power supply at any one time, and groups are energized repeatedly and sequentially; for example, for the case depicted in FIG. 2, the generator can first drives RF current between E1 and E2 with E3, E4, and ground pads disconnected; then drive RF current between E3 and one or more ground pads with E1, E2, and E4 disconnected; then drive RF current between E4 and one or more ground pads with E1, E2, and E3 disconnected; and then continue sequentially delivering RF signal output to each of the groups bipolar pair E1-E2, monopolar output E3, and monopolar output E4. For a generator setting configuration wherein E1 and E2 are energized in a "cluster" configuration, in one step of a non-concurrent activation sequence, the generator connects E1 and E2 to the same electrical potential and current flows from both E1 and E2 to one or more ground pads, with E3 and E4 disconnected. In some embodiments, one electrode can appear in more than one group. One advantage of a non-concurrent activation sequence is that currents do not flow between electrodes of different groups and the pattern of RF current flow and heating patterns between electrodes can be controlled.

In some other embodiments, electrode groups are activated at the same time. This has the advantage of simplicity, and RF heating patterns are not affected if electrodes in different groups are spaced far enough away from each other.

In some other embodiments, electrodes in different groups are connected to different, isolated RF power supplies. This had the advantage of not requiring temporal sequencing of electrode group activation.

Digital displays 204 present measurements specific to electrode E1 251: temperature, impedance, lesion time, voltage, current, and power (from top to bottom). A similar set of digital displays is included on display 201 for each other electrode jacks, organized and ordered from left to right in the same organization and order as jacks E1, E2, E3, and E4. Underneath the controls and digital displays for electrodes E1 and E2 is a plot 202A of measured readings as a function of the lesion time for outputs E1 and E2. Graphical plot 202A is labeled "E1 E2" and includes a single solid line for the current, a single dashed line for impedance, a dotted line for the temperature of electrode E1, and a dash-dot line for the temperature for electrode E2. Since electrodes E1 and E2 are energized in a bipolar configuration, the HF current flowing through jack E1 is the same as the current flowing through jack E2, and thus a single current measurement for both is sufficient information about the output level for both electrodes. Similarly, there is only one impedance between jacks E1 and E2 since there is only one voltage applied between the jacks and only one current flows between the jacks. Graph 202A shows that an impedance-controlled pulsing process, similar to that presented in FIG. 1A, is applied to electrodes E1 and E2 by generator 200. This configuration generates a bipolar heat lesion 294A connecting and surrounding the active tips of electrodes 251 and 252 within organ 293A. Below the control for electrode E3 labeled "E3 Mono" are digital displays of temperature, impedance, lesion time, voltage, current, and power for electrode 253, and a time graph 202B of current (solid line), impedance (dashed line), and temperature (dotted line) for electrode 253, which indicates that generator 200 is using an impedance-controlled pulsing process to control the monopolar ablation zone 294C around the active tip of electrode 253 within organ 293C. Electrode 4 has analogous digital and graphical displays monitoring its ablation progress displayed under its control labeled "E4 Mono". Electrode E4 254 is positioned at a different location within the same organ 293C as electrode E3 253 is positioned in order to target two spatially-separate targets, such as two tumors. In the example shown in FIG. 2, the user activated bipolar output E1-E2, monopolar output E3, and monopolar output E4 at different times using their respective output controls 217, and thus the elapsed lesion times for outputs E1-E2, E3, and E4 are different. Features presented in FIG. 1, such as display of up and down times, ground pad switching and control, multiple operating and control modes, and other features, can be combined with the embodiments presented in FIG. 2. One advantage of the ablation system presented in FIG. 2 is that multiple ablation probes can be independently energized, monitored, and controlled by the same generator 200. The generator 200 includes graphical displays of multiple ablation processes 202A, 202B; this display is important for monitoring multiple ablation processes because the history of each ablation process, including anomalies, can be assessed rapidly by the user physician, even when that assessment occurs after an anomaly of other important event occurs. In some embodiments of the system presented in FIG. 2, the number of ground pads can be one or more. In some embodiments, the number of ground pads can be a number selected from the list: 1, 2, 3, 4, 5, 6, 7, 8, 9, 10, a number greater than 10. In some embodiments of the system presented in FIG. 2, the number of electrode can be two or more. In some embodiments, the number of electrodes can be a number selected from the list: 1, 2, 3, 4, 5, 6, 7, 8, 9, 10, a number greater than 10. In some embodiments, each of the treatment electrodes 251, 252, 253, 254 can be any one of the following: non-cooled RF electrode, non-cooled RF electrode in an RF cannula, cooled RF electrode, a cooled RF electrode inside an RF cannula, a cooled RF electrode with extension-tip temperature sensor, cooled RF electrode with lateral temperature sensor, cooled RF electrode temperature sensory on outer surface proximal to the active tip, perfusion RF electrode, cool-wet RF electrode, single-prong cooled RF electrode, multi-prong cooled RF electrode, cooled cluster RF electrode, a cooled RF cluster electrode with two electrode shafts, a cooled RF cluster electrode with three electrode shafts, a cooled RF cluster electrode with four electrode shafts, a cooled RF cluster electrode more than four electrode shafts, multiple RF electrodes of any of the aforementioned types, non-cooled MW antenna, cooled MW ablation antenna, multiple cooled MW ablation antennae, a cluster MW antenna, and other type of HF ablation probes.

Figure 3:
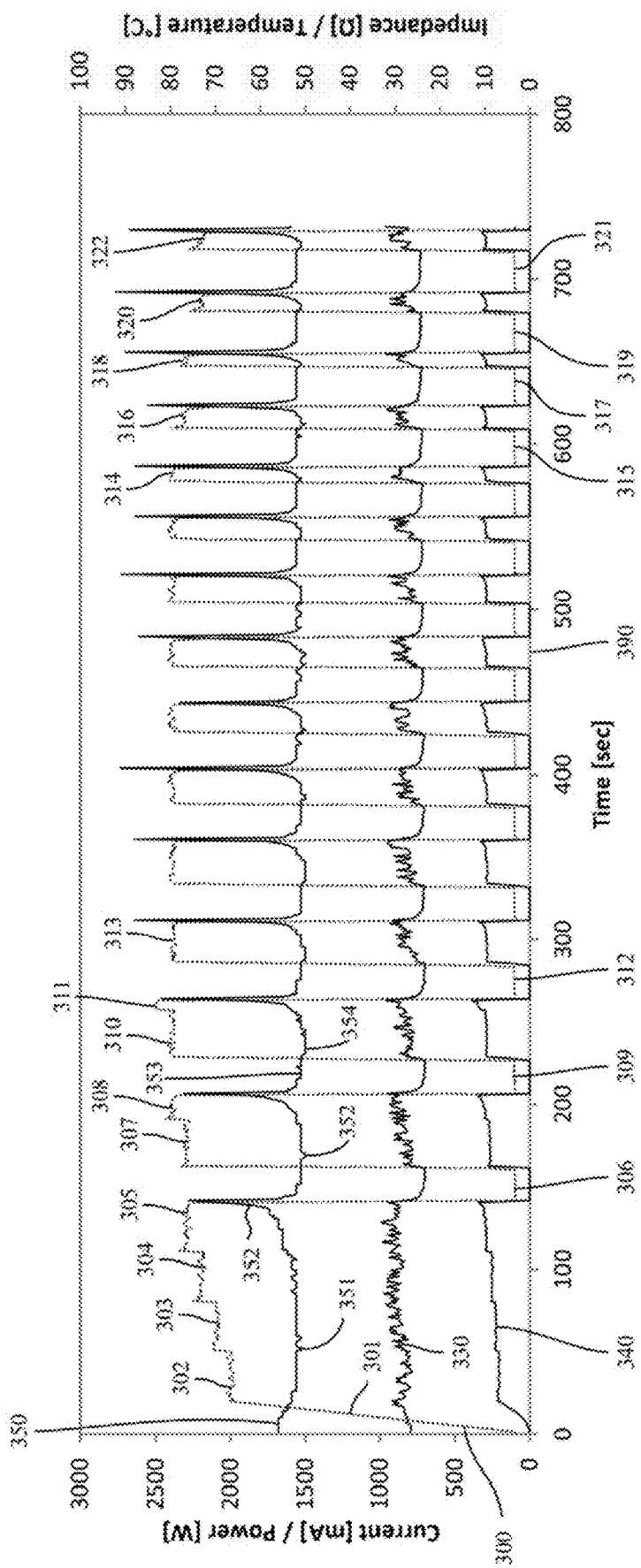
FIG. 3 is a schematic diagram of a real-time graphical display of parameters of a cooled-RF tissue ablation process that is controlled by an RF pulsing method whereby the RF signal alternates between a high level configured to substantially heat the tissue, and a low level configured to allow for cooling of heated tissue; whereby after an initial high level RF signal is set, the high signal level both increases and decreases; and whereby the duration of periods varies in which a low level is delivered, based in part on measured parameters of the ablation process.

Referring to FIG. 3, one example of a graphic display of measured RF ablation parameters during one example of a HF ablation using a cooled RF system and control method in accordance with several aspects the present invention. In some embodiments, the graphs shown in FIG. 3 can be generated and displayed by the systems presented in FIG. 1A, FIG. 1C, FIG. 2, FIG. 6, FIG. 7, FIG. 8, FIG. 9, and FIG. 10. For example, the plots shown in FIG. 3 can be a specific example of graph 202B on screen 201 in FIG. 2 with the addition of a power graph 340.

In one example, the graphs in FIG. 3 can be measurements from tissue ablation using an electrode system in which a 17-gauge cooled RF electrode inserted into a 15-gauge RF cannula with 5 cm active tip at its distal end, wherein the electrode distal end aligned with the cannula distal. The cannula active tip is energized by the electrode and is positioned percutaneously within a large tumor in the patient's otherwise healthy liver, wherein the tumor is a colorectal metastasis whose width is 4.5 cm to 5.5 cm. The electrode temperature sensor is positioned near the electrode distal end, within the internal coolant flow path. The electrode is cooled by chilled saline. The electrode is energized by the RF generator in a monopolar configuration wherein return currents are carried by by four large-area ground pads placed on the anterior and posterior aspects of both thighs of the patient. The resulting lesion volume is 5 cm to 6 cm in width and completely covers and destroys the tumor in a predictable and stable manner by means of aspects of the present invention.

The computer graphic display in FIG. 3 includes line graphs of the electrode current 300 in units milliAmps (mA), electrode impedance 350 in units Ohms (Ω), electrode temperature 330 in units of degrees Centigrade (° C.), and electrode power 340 in units Watts (W). The vertical scale for current and power is shown on the left, and the vertical scale for impedance and temperature is shown on the right side. The temperature graph 330 monitors the temperature of the coolant flowing inside the electrode active tip and provides an indication that the cooling process and coolant system are functioning properly. All the line graphs 300, 350, 330, 340 are stacked, overlapped, and registered to the same time scale 390, and can be easily visually compared.

In the example presented in FIG. 3, the control system ramps up the current 300 step-wise, increasing 100 milli-Ampere (mA) every 30 seconds, starting from 2000 mA, which is conservatively below the equilibrium output level for the electrode and tissue. By 2400 mA in phase 305, the impedance begins to spike upward 352. The automatic control system triggers on impedance spikes and reduces the current for the down-time duration that is determined by the automatic controller, such as in phase 306. The automatic controller times the down time according, raises the signal output current to a level to start an up time phase (such as step 307), and possibly adjusts the high output current further until the next impedance spike, at which point the automatic controller reduces the current substantially for the next down time. The process of sequences of up times and down times continues for the duration of the ablation process. The automatic controller and control system are adapted to adjust the level of generator signal output current and the duration of up times and down times so that the sequence settles to a stable process. In the example shown in FIG. 3, the current level stabilizes to about 2400 mA during the on times, and the durations of the on times and off times settle stabilize at about 20 seconds each. The clinician user can select the total duration of the ablation program based on the control-method type, the of the generator signal output current, the chosen electrode active tip size, the size of the target structure, and the size of the desired ablation zone. In the example shown in FIG. 3, the clinician can know from clinical experience that about 12 minutes is sufficient time to cover and destroy the target tumor, given the control-method type, output current level, and electrode type.

In the example presented in FIG. 3, the controller regulates the output current. In another example, the controller regulates power. In another example, the controller regulates voltage. In one example, the controller regulates the ablation process by monitoring the impedance and uses that to control the modulation of at least one of the output parameters in the list of power, current, and voltage. The example of FIG. 3 illustrates how the present invention enables a stable, controlled, and reproducible ablation process that has real time visual confirmation.

The following description of the FIG. 3 includes several examples of ablation processes, steps, and branch points that can produce the graphs presented in FIG. 3. The generator begins the ablation process at time zero (0) on time axis 390. The generator quickly ramps 301 the output level at a rate of 100 mA/sec, up to the initial current level 2000 mA, which is conservatively below the equilibrium current value for the known electrode type, geometry, and size, and for the known conditions of the tissue around electrode active tip. During the initial ramp 301, the power 340 increases to approximately 200 W, the impedance 350 begins to drop as tissue adjacent to the electrode active tip heats up, and the measured temperature increases moderately by 5-10 deg C. as heat is conducted from heated tissue into the coolant. After ramp 301, the generator increments the set current by a step of 100 mA after every 30 seconds of elapsed time. The set current goes from 2000 mA in step 302, to 2100 mA in step 303, to 2200 mA in step 304, to 2300 mA in step 305. Correspondingly, the power goes from 200 W to 330 W. The step increment 100 mA and the step time 30 seconds are controller parameters configured to slowly increase the output level to determine a maximal, stable output level for the ablation process. Phases 302, 303, 304, and 305 are collectively the first "up time" of the ablation. The generator controller executes this schedule of current steps in all up times longer than 30 seconds, for example up time 307, 308; and up time 310, 311. One advantage of adjusting the up-time output level in steps is that sufficient time elapses after each adjustment of the output level for the system to respond to that level, and if the response is unfavorable, the change can be reversed or moderated by a step decrement (described below). In some embodiments, the step size can be a value in the range 0-200 mA or more. In some embodiments, the elapsed up-time before a step increase can be a value in the range 0-120 sec or longer. In some embodiments, the up-time output level can be increased in a continuous, smooth, linear, concave-up, or concave-down ramp, and the ramp rate can be in the range 0-10 mA/sec. In some embodiments, the ramp rate can be configured to allow for discrimination of the maximum ablation current level that the tissue can carry without boiling too rapidly. In some embodiments the up-time output level can be increase in a ramp after a delay, wherein the delay can be a value in the range 0-120 sec or longer.

The first up time is terminated in phase 305 when the impedance 350 spikes upward, rising more than 20 Ohms above its minimum value 351 from the initial ramp phase 301 and the first up time. The impedance-increase threshold of 20 Ohms is one example of a criteria for detecting boiling in the tissue around the electrode active tip. This criteria for terminating an up time based on impedance spike is applied throughout the ablation process in FIG. 3. In some examples, the impedance threshold for up-time termination can be in the range 0-50 ohms. In some examples, the impedance threshold for up-time termination can be greater than 50 ohms. In some examples, the impedance threshold for up-time termination can be an absolute impedance value. In some examples, the impedance threshold for up-time termination be A*Zmin, where Zmin is the minimum impedance from the last up time, and A is a number greater than 100%, such as 105%, 110%, 115%, 120%, or another number.

After step 305, the generator controller decreases the output to a low level 306 configured to allow for tissue cooling and the dissipation of the bubbles around the electrode active tip. This is the first down time 306 of the ablation session. During this down time, the current is approximately 100 mA and the power is approximately 0.5 Watts. The generator controller initializes the down-Ill time duration at 20 seconds, and increments the down-time duration by 2 seconds whenever the preceding up-time duration is less than 10 seconds to allow for more cooling time in subsequent down times. The initial down-time duration 20 seconds is configured to provide for sufficient cooling after impedance spikes in the initial phase of tissue heating. The down-time increment 2 seconds is configured to allow for more cooling time as the lesion size grows. The minimum up-time duration 10 second is a threshold configured to identify whether insufficient cooling occurred during the preceding down time. In the example of FIG. 3, the duration of initial down time 306 is seconds because the preceding up time 302, 303, 304, 305 is greater than 20 seconds. Similarly, every down time before down time 315 has duration 20 seconds because all up times until up time 314 are longer than 10 seconds. Because up time 314 is shorter than 10 seconds, the subsequent down times 315. Because up time 316 exceeds 10 seconds, down time 317 also lasts 22 seconds. Because up time 318 is shorter than 10 seconds, the subsequent down times 319 lasts 24 seconds. Because up time 320 exceeds 10 seconds, down tune 321 also lasts 24 seconds.

In the example presented in FIG. 3, the generator determines the starting set current for an up-time based on the duration of the final set-current step in the previous up-time. If that duration is at least 10 seconds, the up-time starts with the same set current as the end of the previous up-time, as illustrated by steps 305 and 307 wherein step 305 has duration greater than 10 seconds, and wherein both step 305 and 307 have set current 2300 mA. However, if that duration is less than 10 seconds, the up-time starts with a set current that is 100 mA less than the set current at the end of the previous up-time, as illustrated by steps 311 and 313, wherein step 311 has duration less than 10 seconds, and wherein the set current of step 311 and 313 differ by 100 mA. Steps 314 and 316 are another example of a set current decrement, wherein step 314 has duration less than 10 seconds, the subsequent up time 316 has a set current 100 mA less than that of step 314. The minimum step time seconds is a duration configured to identify whether an output level can be used to heat tissue stably without too-rapid boiling. The step decrement 100A is a value configured to reduce the generator output when tissue boiling occurs too rapidly, and thus to determine a stable output level for the ablation process.

In the example presented in FIG. 3, the generator controller adjusts the output level, up time durations, and down time durations to achieve stable values for tissue ablation. For example, for every up-time between the including 313 and 314, the up-time set current is 2400 mA, the up-time durations are between 10 and 30 seconds, the down-time set currents are 100 mA, and the down-time durations are 20 seconds. The achievement of stable, maximal ablation parameters provides for a high degree of tissue heating without producing high-impedance boiling too frequently, which might otherwise hinder lesion size growth.

For the example in FIG. 3, the set time is 12:00 minutes, so the ablation program is automatically discontinued by the generator at 720 seconds. This lesion time can be configured by the user to produce a maximal and reproducible lesion size. The total time of the ablation program can be determined as a function of the electrode geometry, electrode type, electrode tip length, tissue type, disease type, target ablation size, tumor size, tissue condition, output level, control method type, and other factors. The set time can be a function of the active tip length of the electrode. The set time can be a value selected from the range 0-30 minutes. In some embodiments, the stopping criteria for the ablation process can include a criteria based on one or more of the following parameters: the total energy delivered to the tissue, the total aggregate up-time duration, and other parameters, the time-integrated power, the time-integrated squared RMS current. For example, the diminishing output level, diminishing up-time durations, and increasing down-time durations over steps 314, 315, 316, 317, 318, 319, 320, 321, and 322 are an indication of diminishing heating power and a diminishing rate of lesion size increase; thus, in some embodiments, these factors can be used by an automatic controller and/or user to determine a stop time for the ablation program.

In the example presented in FIG. 3, the control system starts with an ablation output level 302 that is conservatively below the equilibrium value. This provides the advantage of avoiding overheating the tissue and inducing irreversible or slowly-reversible tissue changes that can prevent, hinder, or slow the formation of a large lesion around a cooled electrode tip. The control system then increases the output level to increase lesion size, but does so at a rate slow enough for the tissue to respond measurably to the elevated output level. This has the advantage of providing sufficient time for the control system to calibrate to changing thermal dynamics while raising the output level, without too frequently boiling the tissue and thus interrupting lesion growth. The system can produce sufficiently high output levels to maximize lesion size for larger RF electrodes, which can create larger RF heat lesions when properly powered. The control system interrupts tissue heating in response to tissue boiling, as indicated by large impedance rises, to provide for tissue cooling and the dissipation of high-impedance bubbles that hinder lesion growth. This allows tissue heating and lesion-size growth to continue even after excessive current has been driven into the tissue. Throughout the ablation process, the control system adjusts the ablation output level in response to the magnitude and timing of impedance changes relative to heating phases and cooling phases. Ablation output levels (during "up times") are reduced if previous output levels lead to tissue boiling too quickly for sufficient tissue heating to occur beyond the bubble zone. This has the advantage of calibrating to the output level that the tissue can sustain without rapid boiling, which can change as the ablation process evolves and the lesion size increases. The adjustment of the ablation level up and down in response to the timing of impedance spikes to find a stable output level for ablation has the advantage of delivering the an optimal amount of heating power into the tissue: high enough to increase lesion size, but not so high as to frequently interrupt lesion growth with high-impedance tissue boiling. The control system adjusts the duration of cooling phases ("down times") in response to the timing of impedance changes. Cooling-time duration is increased if the duration of the previous ablation phase was too brief to produce efficient lesion size growth and/or if the duration of the previous ablation phase indicates that additional time is required to dissipate high-impedance bubbles around the active tip. This has the advantage of increasing the cooling time in response to rapid tissue boiling and the overall lesion time, both of which can be indicative of lesion size and bubble zone size. The control system is adapted to adjust the level of generator signal output current and the duration of up-times and down-times so that the sequence of ablation and cooling settles down to a stable desired process. The example of FIG. 3 illustrates how the present invention enables a stable, controlled, and reproducible ablation process with real-time visual confirmation.

In the example shown in FIG. 3, the controller regulates the output current. In another example, the controller regulates power. In another example, the controller regulates voltage. In one example, the controller regulates the ablation process by monitoring the impedance and uses that to control the modulation of at least one of the output parameters in the list of power, current, and voltage. In some embodiments, the initial current can be a value selected from the range 500 mA to 3000 mA. In some embodiments, the initial current can be a value less than 700 mA. In some embodiments, the initial current can be greater than 3000 mA. In some embodiments, the initial current can selected as a function of the cooled electrode active tip length, for example, 500 mA for a 1 cm tip, 1000 mA for a 2 cm tip, 1400 mA for a 3 cm tip, 1800 mA for a 4 cm tip, 2000 mA for a 5 cm tip. For example, the initial current can be selected as 2200 mA for a cluster of three parallel cooled RF electrode, each with a tip exposure between 3 and 4 cm, and equally spaced by 1 to 2 cm.

In some embodiments, as in the embodiment of FIG. 3, the size of the step increments and decrements can each be configured to determine a generator output level, eg ablation current, that the tissue around the electrode active tip can sustain to maximum the heat lesion size. In some embodiments, as in the embodiment of FIG. 3, step decrements and step increments are the same amplitude. In some embodiments, the step decrements are smaller than the step increments to provide for greater precision in determining a stable output level for ablation. For example, the step decrement can be 50 mA and the step increment can be 100 mA. In some embodiments, the step increments are smaller than the step increments. In some embodiments, the step increment can be a value selected from the range 0-200 mA. In some embodiments, the step decrement can be a value selected from the range 0-200 mA. In some embodiments, the step increments and decrements can be greater than 200 mA. In some embodiments, the step increments and decrements can change during the ablation process, for example, reducing in size to refine optimization of the output level. In some embodiments, the step decrements can be inversely proportional to the duration of the preceding up-time and/or the preceding up-time step increments; one advantage of this is that the output level can be refined more precisely if the preceding output level was sustained for a longer period without boiling. In some embodiments, the step time for output level increments can be a value selected from the range 0-2 minutes. In some embodiments, the step time can be longer than 2 minutes. In some embodiments, the output level can be increased during the up time in a manner different from step increments, such as a constant-rate ramp, a concave ramp, a convex ramp, or a combination of different ramp shapes. For example, the output level can be ramped at a rate of mA/sec after 60 seconds of elapsed up time. For embodiments wherein the output level is increased as a ramp, the size of the step decrement can be influenced by a parameter of the ramp, such as the rate of the ramp, or the amount of output level increase during a final duration of the ramp.

In some embodiments, the initial down-time duration can be a value selected from the range 0-40 seconds. In some embodiments, the initial down time can be a value greater than 40 seconds. In some embodiments, the down-time duration increment can be a value selected from the range 0-seconds. In some embodiments, the down-time duration increment can be a value greater than 10 seconds. In some embodiments, the down time can be set and adjusted by the generator control by a different method than the one shown in FIG. 3. For example, the down time can be a function of the preceding up-time duration, for example, proportional to the preceding up-time duration. For example, the down time can increase in a predetermined schedule as an increasing function of one or more of the values selected from the following list: total elapsed time, number of up-time pulses, total elapsed up-time duration, and other parameters. For example, the duration of the down time can be incremented by the down-time duration increment after every up time. For example, the down time can be affected by the dynamics of the impedance signal 350. For example, the down time can be affected by the dynamics of the impedance signal 350 during the down time. For example, during the down time, the generator can monitor the impedance signal for a large drop from an elevated value, followed by a stabilizing impedance signal. This impedance "cooling pattern" can be observed following every impedance spike in signal 350 of FIG. 3, and can be indicative of the size of the heat lesion, the extent of the bubble zone, and therefore the cooling time required before the next up time should be optimally initiated. In one example, the generator can prevent termination of the down time until the impedance cooling pattern is detected. In one example, the generator can prevent termination of a down-time period until both the impedance cooling pattern is detected and the minimum down-time duration has elapsed. In one example, the generator controller can determine the duration of each down time as the sum of (1) the time it takes for the impedance cooling pattern to be detected, and (2) an additional duration that can be either fixed or a variable function of measured ablation parameters. One advantage of a non-zero output level during the down time, such as shown by downtime 306 in FIG. 3, is that it provides for continued impedance measurement 350.

The parameters of the control process presented in one specific example in FIG. 3 can vary depending on the specific clinical situation. Selection of parameters can include consideration of target size, electrode geometry, durations of up-times and down-times, generator signal output parameters, total duration of HF exposure and other factor in order to optimize to stability of the process and desired clinical outcome.

Figure 4:
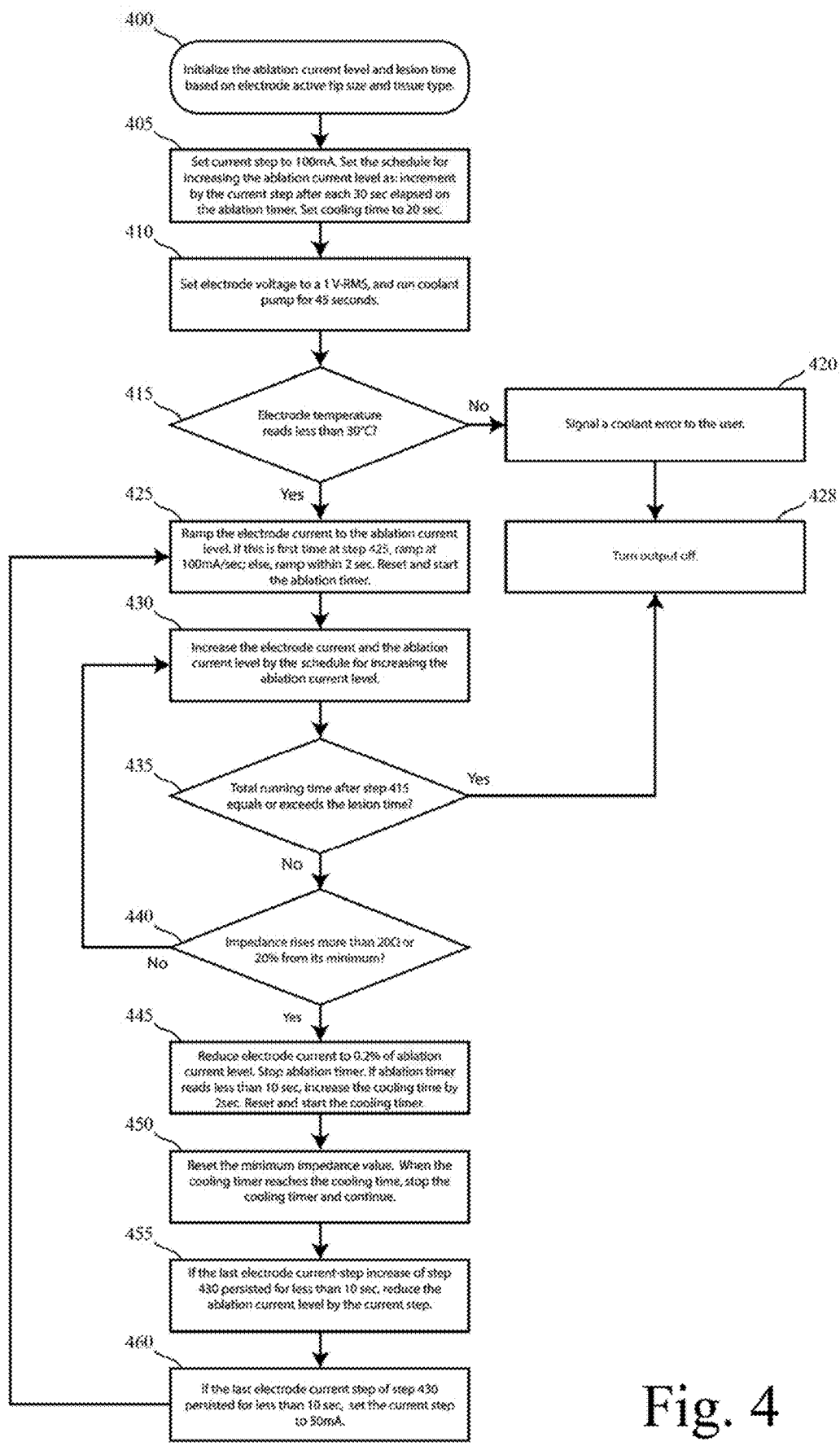
FIG. 4 is a flow chart that shows a method of tissue ablation by means of a fluid cooled RF electrode, wherein RF is delivered in high-current pulses that are terminated tissue boiling indicated by a rise in impedance; wherein the inter-pulse duration of low signal output between pulses can increase during ablation process based on measurements of the ablation process; wherein the amplitude of the high-current pulses are both increased and decreased during the ablation process in response to measured parameters of the ablation process, and configured to stabilize the pulse amplitude, pulse duration, and inter-pulse duration, and to maximize the volume of ablated tissue; wherein the size of increases and decreases in the amplitude of high-current pulses being varied during the ablation process.

Referring now to FIG. 4, one embodiment of a pulsing method for impedance-based control of a cooled-RF ablation electrode is presented as flow chart in accordance with several aspects of the present invention. In some embodiments, the method in FIG. 4 can executed by the generator systems presented in FIG. 1 and FIG. 2. In some embodiments, the ablation measurements presented in FIG. 3 can be produced by a method similar to that presented in FIG. 4 with the following modifications: (1) The coolant tests in steps 405, 410, 415, and 420 are either omitted, or occur before time zero on axis 390 of FIG. 3; and (2) step 460, in which the output current step size is adjusted, is omitted, and step 455 transitions directly to step 425.

In initial step 400, the method begins by initializing with parameters that can be user-selectable. The lesion time (also referred to as "set time") is typically in the range 2-20 minutes, but can be any non-zero value. The initial ablation current (also referred to as the "initial set current" for the up time) can be any non-zero current up to the maximum current output level of the generator, typically in the range 500-2500 mA. In some embodiments, a user-selectable maximum current can be included as well. In step 405, parameters are initialized that may vary during the ablation session, including the step size for set-current increments and decrements, and the step time for set-current increments. In some embodiments, a maximum set current can also be set in step 405, and that maximum set current can be user-selectable, factory set, set by the generator as a function of the initial set current, or a combination of these. In some embodiments, the step size can be a value in the range 0-200 mA or more. In some embodiments, each step can be a step in Power and the step size can be a value in the range 0-50 Watts or more. In some embodiments, each step can be a step in Voltage and the step size can be a value in the range 0-50 Volts or more. In some embodiments, each step can be in units of some measurement of the signal output level. In some embodiments, the elapsed up-time before a step increase can be a value in the range 0-120 sec or longer. In some embodiments, the step size and duration can be configured to allow for optimization of a stable output level for given electrode geometry and construction and tissue conditions. One advantage of controlling the current of the RF output level is that, for a given electrode active tip geometry, a set current can regularize the current density around the active tip across different ground pad placements relative to the electrode position in the body; in contrast, a set voltage or set power, the local heating power near the active tip will vary with the position of the ground pad(s) on the body due to different degrees of ohmic voltage/power drops in the tissue between the ablation electrode active tip and the ground pad(s). Another advantage of controlling the current of the RF output level delivered to a monopolar ablation electrode is that control and monitoring of ground pad currents is simplified by having a controlled total ground pad current (which is equal to the electrode current in a monopolar configuration). In step 410, the generator output is set to a very low level that provides for impedance measurement, and that is configured not to raise the electrode temperature, even in the absence of coolant flow. The pump runs for sufficient time for electrode coolant to flow from the coolant reservoir into the electrode. In some embodiments, the duration in step 410 can be a value in the range 5-60 seconds, or a value larger than 60 seconds for very long coolant tubes and/or very slow pump speed. In step 415, the generator checks whether the electrode is properly cooled. If there is a problem with the coolant or coolant flow, the temperature will read a value close to the tissue temperature in which the electrode is placed, a coolant error 420 will be signaled to the user, and the ablation program terminated 428. If the temperature in step 415 is below 30 deg C., then the ablation phase of the program begins in step 425. In some embodiments, step 410 and 415 and combined so that the process proceeds with step 425 as soon as the temperature is in a range indicating successful cooling (less than 30 deg C.) within the maximum pump time (45 seconds), and otherwise signals an error 420. On the first visit to step 425, the output level is rapidly ramped up to the initial ablation current level at a rate of approximately 100 mA/sec. An example of this is illustrated by ramp 301 to initial ablation-current level 2000 mA in FIG. 3. An instance of "up time" begins as the process transitions from step 425 to 430. In step 430, the output level is incremented by approximately 50 mA or 100 mA (depending on the present value of the "current step", which is set in steps 405 and 460) after every 30 seconds of the time elapsed since the end of step 425, which is the elapsed duration of the present "up time". One example of this process is illustrated by the RF current curve 300 as it increases through steps 302, 303, 304, and 305 in FIG. 3. Step 435 is a check on the total ablation program duration, which terminates the ablation program 428 after the ablation phase of the program has operated for at least the duration of the "lesion time" setting. In some embodiments, other termination criteria can be included in step 435, such as the criteria that one of the following quantities exceeds a specified threshold: the total heating energy delivered in units Joules, the sum of the durations of all up-times, the number of up-time pulses; one advantage of using these quantities in the termination criteria is that they relate to the aggregate signal output delivered to the tissue. In some embodiments, the termination criteria of step 435 can include the criteria that one of the following quantities is less than a specified threshold: the duration of the down time (for methods in which the down time increases), the current level during the up time (for processes that can decrease the current level during the up times), the average current over the latest up time and down time (for processes that can decrease the current level during the up times); one advantage of including these kinds of criteria is that they can reflect a decrease in the heating power delivered by the generator, and thus, a decrease in the amount of lesion size growth for the additional ablation time investment. In some embodiments, a termination criterion in step 435 can be influenced by a decline in the output level, a decline in the average output level, and/or an increase in the down time duration; one advantage of these factors for influencing a termination criteria is that can indicate a decrease in the efficiency of the ablation process and thus, diminishing returns in lesion size growth for continued ablation. Step 440 is a check on the termination criteria for the present up-time phase. If an impedance spike is detected in step 440, the process proceeds to step 445 thus starting a down-time phase. If an impedance spike is not detected in step 440, the up time continues. The cycle of steps 430, 435, and 440 can correspond to one instance of "up time" (which can also be a referred to as an "on period" or "up period" or "on time" or "pulse") in which the RF signal level is configured to heat tissue and increase the volume of heated tissue by means of the ablation electrode. In step 445, the output level is reduced from the level of the preceding up time to a low level configured to provide for tissue cooling and bubble zone dissipation. In step 445, the programmed duration of the down time, which can be referred to as the "cooling time", is increased if the duration of the preceding up time is less than 10 seconds, a duration configured to indicate that additional cooling time is required between ablation pulses (which are also known as "up times", "on times", "up periods", or "on periods"). The cooling time was initialized in step 405. By means of step 445, the cooling time increases with the number of short "up times". This has the advantage that the cooling time is adjusted in response to evolving tissue conditions throughout the ablation process. An example of this adjustment of the cooling time is illustrated by the down time 315 and down time 319 in FIG. 3. In some embodiments of step 445, the cooling time duration can be increased or decreased as a function of one or more of the following parameters: the duration of the final output-level step of the previous up time, the duration of the previous up time (measured here by the "ablation timer"). In some embodiments of the step 445, the change in the cooling time is inversely proportional to the duration of up time (measured by the value on the "ablation timer"). In some embodiments of step 445, the duration 10 sec can be a different value, for example, a value selected from the range 0-30 sec or longer. In step 450, the generator controller allows the cooling time to elapse. In step 455, it is determined whether the target current for the next up-time will be equal to, or lower than, the target current of the previous up-time, based on the duration of the final current step of the previous up-time. An example of this downward adjustment is illustrated by the current measurement 300 in FIG. 3. In some embodiments of step 455, the ablation current level can be increased or decreased as a function of one or more of the following parameters: the duration of the final output-level step of the previous up time, the duration of the previous up time. In some embodiments of the step 455, the change in the ablation current level is proportional to the duration of the last electrode current-step increase. In some embodiments of step 455, the duration 10 sec can be a different value, for example, a value selected from the range 0-30 sec or longer. In step 460, it is determined whether to reduce the magnitude of subsequent upward and downward changes in the output current, based on the duration of the final current step of the previous up-time, which can indicate rapid boiling in response to the last output-level adjustment. Step 460 is one example of a process configured to increase the precision with which the output level is adjusted when there is an indication that the size of the last adjustment was too large. In some embodiments of step 460, the step increments and decrements can be changed independently. In some embodiments of step 460, an adjustment to the frequency with which current-step increments are made during step 430. In some embodiments of step 460, amplitude of the current step can be proportional to the duration of the last up time. In some embodiments of step 460, the time "10 sec" can be a different value, such as a value in the range 0-30 seconds or longer. In some embodiments of step 460, the current step value "50 mA" can be a different value, such as any value less than the present current step value. In some embodiments of step 460, the current step value "50 mA" can be a different value, such as a value greater than the present current step value, but less than a maximum current step, such as a value of 200 mA or more. In some embodiments of step 460, the current step value can increase or decrease from its previous value as a function of a measurement of an ablation parameter. After step 460, in step 425, the generator controller steps the output level to approximately the target current level for ablation, thus ending the "down time" and starting the next "up time" in step 430. Steps 445, 450, 455, and 460 can represent one instance of "down time", which is an example of a period in which the controller configures the RF level to allow for cooling of heated tissue and/or dissipation of gas formed in the tissue due to heating during the preceding "up time".

One advantage of the impedance-based RF pulsing method for cooled RF ablation presented in FIG. 4 is that the ablation output level, the duration of ablation pulses (which can be referred to as "up times" or "on periods"), and the duration of inter-pulse cooling periods (which can be referred as a "down times" or "off periods") are adjusted in response to measured system parameters. One advantage of the cooled-RF ablation program presented in FIG. 4 is that output level during high-intensity ablation pulses is adjusted both upward and downward to maximize the degree and duration of tissue heating throughout the ablation process, without overheating tissue close to the electrode active tip into the boiling range too frequently. In some embodiments, automated checks for the program's termination criteria, eg step 435, for checks on system performance, and for error conditions typical of RF lesioning systems (such as open circuit, short circuit, temperature signal loss, and over temperature limit conditions) can be inserted throughout the method presented in FIG. 4 to ensure timely reaction to these conditions. For example, a check on the total running time of the method can be included between step 445 and 450. It is understood that the order of some steps, such as 405 and 410, can be changed without affecting the essential method. It is understood that some steps can be combined without affecting essential method. It is understood that some omitted without affecting the essential method. It is understood that additional controller behaviors can be include in the method presented in FIG. 4, for example, temperature control. In some embodiments, the parameters of the method presented in FIG. 4 can take values in the ranges presented in the text describing FIG. 3.

Figure 5:
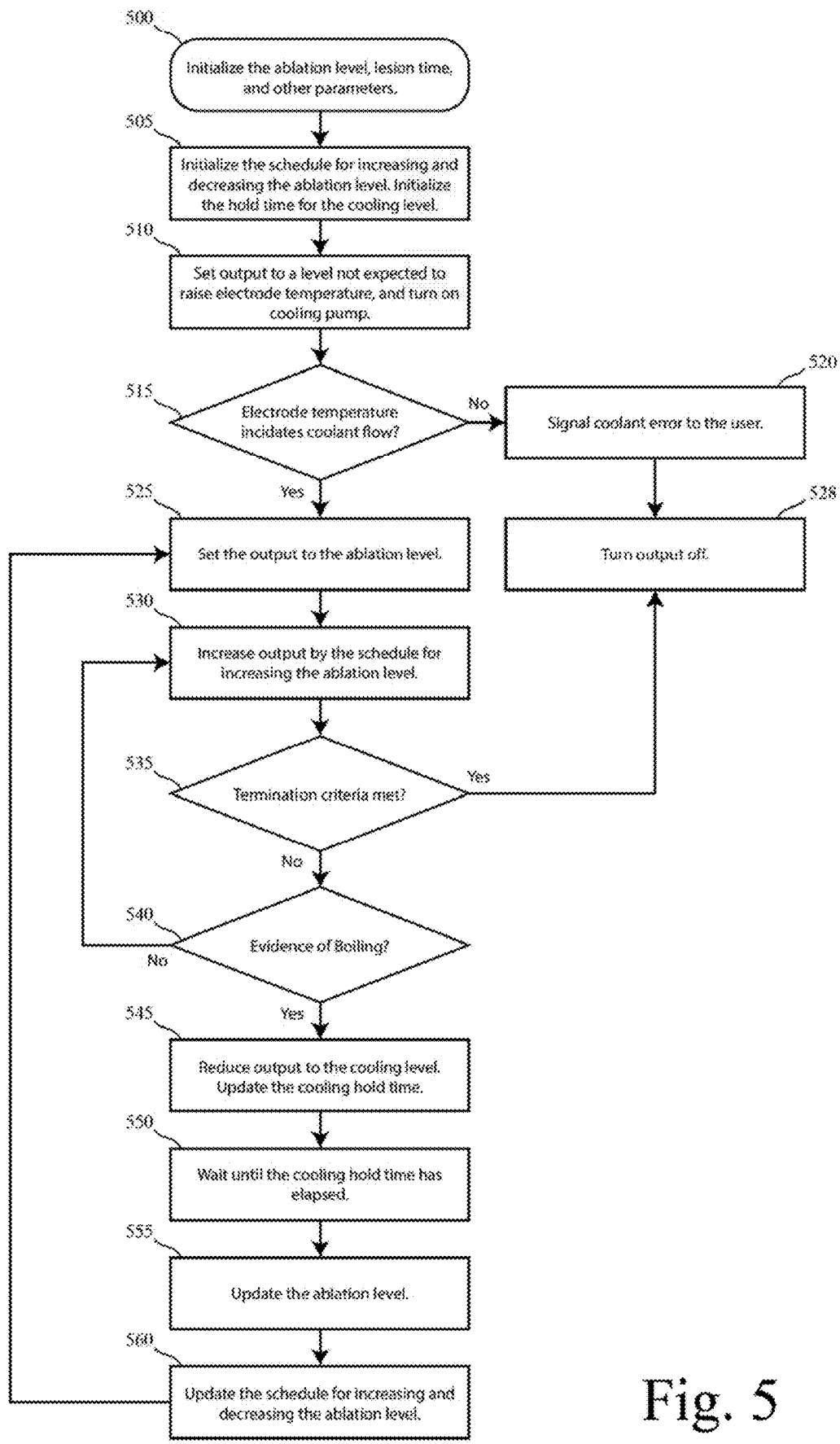
FIG. 5 is a flow chart that shows a method of tissue ablation by means of a high-frequency, internally-cooled ablation probe comprising: testing the function of the cooling system by measuring the electrode temperature when coolant is flowing and the signal output level is low; setting the signal output to a high level configured to ablate, and then further increasing the signal output level based on the tissue response to the signal output; reducing the high signal output level to a low signal output level if boiling is detected in the tissue to allow for cooling of heated tissue over a cooling duration; varying the cooling duration during the ablation process in response to measured parameters of the ablation process; increasing and/or decreasing the high signal output level in response to measured parameters of the ablation process; alternating the signal output between the high output level and the low output level until a termination criteria is reached.

Referring now to FIG. 5, one embodiment of a method for tissue ablation using an internally-cooled HF ablation probe is presented as a flow chart. The method in FIG. 5 can be one example of one control process automatically executed by the generator presented in FIG. 1, and in the generator presented in FIG. 2. The method in FIG. 4 can be a specific embodiment of the method presented in FIG. 5. The process that produced the ablation data in FIG. 3 can be a specific embodiment of the process presented in FIG. 5. In some examples, the ablation probe can be an RF electrode. In some examples, the ablation probe can be a MW antenna.

In step 500, parameters that influence the ablation process are set. These parameters can include target output level, initial output level, maximum output level, minimum output level, duration of the ablation program, parameters related to the timing of processes, parameters that characterize the target tissue, parameters that characterize the ablation probe, ablation probe type, tissue type, desired lesion size. One or of these parameters can be selected by the user. One of more of these parameters can be set by the factory. One or more of these parameters can be selected user selection of a preset configuration of settings, for example, as user-customizable preset. In Step 505, parameters are set that may vary during the ablation process, for example, in response to values measured during the ablation process.

In Step 510 and 515, the operation of the coolant system is checked. If the checks indicate insufficient coolant operation, a user error is prompted in step 520, and the ablation program is discontinued in step 528. In embodiment presented in FIG. 5, the coolant system is checked by holding the output at zero or a very low level, operating the coolant system pump, and checking for desired cooling of the ablation probe. In some embodiments, other checks of the cooling system can be included in the steps 510 and 515, such as checking the flow rate coolant flow, checking the coolant temperature directly, and checking that the ablation probe temperature does not rise substantially when the ablation probe is energized at levels capable of heating the tissue. In some embodiments, checks on coolant operation, such as steps 505 and 510, can be performed either intermittently or continuously throughout the ablation processes. For example, the controller can check that the ablation probe temperature does not exceed an absolute upper limit or an upper limit relative to a baseline value, either throughout the ablation process, during up time, during down times, or at other times during the ablation process.

Step 535 performs one or more checks of termination criteria for the ablation program, and if one is successful, the ablation process is terminated in step 528. One example of a check of a termination criterion is checking that one of the following quantities exceeds its respective termination threshold: elapsed program time, elapsed time delivering output levels capable of heating tissue, total heating energy delivered to the tissue, time-integrated power delivered to the tissue, time-integrated current delivered to the tissue, the duration of the down time, an increase in the down time duration, a decrease in the ablation output level, an indicator of lesion size, an indicator of the bubble zone size, the time it takes for the impedance to return to a baseline value after an impedance spike. One example of a check of a termination criterion is checking if one of the following quantities is less than its respective termination threshold: an average output level, an RMS output level, the output level during an up time, the output level averaged over the most recent up time and down time, a moving average of the output level, the duration of the up time.

Steps 525, 530, 540 implement the "up times" (which can also be referred to as "up periods", "on periods", or "on times", or "pulses") of the ablation process, wherein signal output is delivered to the ablation probe at a level or levels that are capable of producing tissue ablation, heating tissue, and increasing the size of the ablation volume. In one example, when step 525 is executed for the first time, the initial output can be set to a level configured to be conservatively below the expected steady-state output level for the present ablation probe and tissue configuration. For example, the initial output level can be set in steps 500 and/or 505 by either a user, factory settings, or both. In another example, during the first execution of step 525, the output level can be configured to be equal to the steady-state ablation output level. In another example, during the first execution of step 525, the output level can configured to be greater than to the steady-state ablation output level. In step 530, the output level is increased. For example, in step 530, the output level increase can be configured to raise the output level slowly to determine a steady output level for the majority of the ablation process. For example, in step 530, the output level can be increased to adjust an erroneously low initial output level, which in one example, can be due to a user error in selection of settings values in step 500. In step 530, the increase in ablation output level can be configured to test the tissue response to higher output levels. In some embodiments of step 530, the output level is not increased, but rather held at a constant value. In step 540, the HF generator controller checks for evidence of boiling in heated tissue. If boiling is not detected, the output level is maintained at levels capable of tissue ablation in step 530. If boiling is not detected, then the generator output level is reduced in step 545 to halt the boiling and to allow for tissue cooling and dissipation of high-impedance gas formed due to boiling. In some embodiments of 540, boiling is detected by the impedance rising above an impedance threshold. In some embodiments that impedance threshold can be an predetermined impedance value, an impedance value computed relative to a statistic of impedance measured during the ablation program, an impedance value that is a function of the initial impedance, an impedance value that is a function of the minimum impedance measured during the ablation program, an impedance value that is a function of the minimum impedance measured during the present up time, an impedance value that is determined based on the electrode type, an impedance value that is determined based on tissue characteristics, and other impedance values. In some embodiments of 540, boiling can be detected as a function of one or more of the following measurements: voltage, current, power, impedance, temperature. In some embodiments of 540, boiling can be detected by measurement of an electrical signal (such as an impedance, voltage, current, or power measurement) that is different from the electrical signal that is producing the tissue ablation; for example, this can be another electrical signal applied to the ablation electrode, or it can be an electrical signal applied to another probe or probes in or near the tissue being heated by the ablation electrode. In some embodiments of 540, boiling can be detected by means of one or more temperature measurements, which can either taken from a sensor within an ablation probe, or from sensor that is nearby an ablation probe. In some embodiments of 540, boiling can be detected by means of one or more temperature measurements distributed around the ablation probe. In some embodiments of 540, boiling can be detected by the efficiency of radiative power transmission into the tissue. In some embodiments, such as an embodiment in which the electrode voltage is regulated, boiling can be detected by a drop in electrode power. In some embodiments, such as an embodiment in which the electrode voltage is regulated, boiling can be detected by a drop in electrode current. In some embodiments, boiling can be detected by an indication of the volume and/or density of vapor formed in the tissue around the ablation probe due to tissue heating. The test for boiling in step 540 is one example of criteria for ending an "up time" in response to an indication that the size of the volume of ablated tissue cannot be substantially increased by continued application of a high signal output level to the ablation electrode, because boiling or an almost boiling condition in some of all of the tissue around an electrode active tip can produce a high impedance that prevents substantial tissue heating beyond the location of boiling.

In steps 545 and 550, the generator controller reduces the output level a period of time (the "cooling time", which can also be referred to as the "down time", "off time", "off period", "down time", "down period", "inter-pulse time", or "inter-pulse period") to allow for the reversal of tissue boiling detected in step 540. The output level set in step 540 can be a predetermined value, a fraction of the ablation output level, a value determined by measurement of the present tissue to provide for cooling, zero, a small value, a value less than 1 Watt, or another value. The period of time during which the tissue cools can be a predetermined value, a fixed value, a computed value, a value that increases as the ablation process proceeds, a value that is affected by measurement during an ablation phase (ie "up time"), a value that is affected measurements during a cooling phase (ie "down time"), a value that is affected measurements collected during step 545, a value that is proportional to the preceding up time. The cooling time can be configured to produce a stable ablation process. The cooling time can be configured to the particular time required for cooling of the heated tissue. The cooling time can be configured to provide for dissipation of vapor formed due to tissue heating. The cooling time and the level of RF signal during the cooling time can provide for cooling of heated tissue to a degree configured to allow for further increase in the volume of heated tissue in the subsequent ablation phase ("up time"). In some embodiments, the cooling time can be increased, decreased, or both increased and decreased in response to measured parameters, for example, the measured duration of previous up times and down times. In some embodiments, the cooling time can be increased and/or decreased over the course of the ablation process to determine a stable value of the cooling time and/or other output signal characteristics. In some embodiments, the down time can be influenced by a temperature measurement at distance from the electrode active tip. In some embodiments, the down time can be influenced by ultrasound data.

In 555 and 560, the generator controller adjusts the ablation output level which will be delivered to the ablation probe in step 525, and the schedule by which the ablation output level is varied during in step 530. For example, in step 555 the ablation output level can be reduced in response to measured parameters during the preceding ablation process. For example, in step 555, the ablation output level can be reduced to prevent rapid tissue boiling. For example, in step 555, the ablation output level can be reduced to produce a stable ablation output level. For example, in step 555, the ablation output level can be reduced to maximize lesion size. For example, in step 555, the ablation output level can be reduced to more rapidly increase lesion size. For example, in step 555, the ablation output level can increased by a degree influenced by the duration of the immediately preceding up time. For example, in step 555, the ablation output level can increased by a degree that increase as the duration of the preceding up time increases. For example, in step 555, the ablation output level can increased if the preceding up time exceeded a threshold; in one example, the threshold can be configured to a value that indicates the rate of heating during the preceding up time was too low. For example, in step 560 one or of the following parameters can be changed either for the output-level increase in step 530, for the output-level decreases in step 545, or both: the amplitude of change, the rate of change, the frequency with which changes are made. For example, in step 560 stepped changes in the output level can be increased or decreased as a function of measured ablation parameters.

The steps 525, 530, 540, and cycles thereof can produce one instance of "up time" in an ablation process. The steps 545 and 550 produce one instance of "down time" in an ablation process. In one example, the ablation program in FIG. 5 alternates between up times and down times, adjusts the ablation output level upward and downward, adjusts the down time duration upward and downward, for the purpose of determining stable output signal for tissue ablation. In one example, the ablation program in FIG. 5 alternates between up times and down times, adjusts the ablation output level upward and downward, adjusts the down time duration upward and downward, for the purpose of maximizing heat lesion size. In one example, the ablation program in FIG. 5 alternates between up times and down times, adjusts the ablation output level upward and downward, adjusts the down time duration upward and downward, for the purpose of increasing the speed for heat lesion formation. In one example, the ablation program in FIG. 5 alternates between up times and down times, adjusts the ablation output level upward and downward, adjusts the down time duration upward and downward, for the purpose of ablating a target bodily structure, such as a tumor.

In some embodiments of the RF pulsing method shown in FIG. 5, the signal level during the on periods are held constant by instances of step 530, and increased by instances of step 555 by an amount influenced by the duration of a preceding on period. In some embodiments of the pulsing method shown in FIG. 5, the signal level during the on periods is increased during instance of step 530 as a function of the duration of the present on period, and not increased by instance of step 555. In some embodiments of the pulsing method shown in FIG. 5, the signal level during the on periods are increased during instance of step 530 as a function of the duration of the present on period, and increased by instances of step 555 by an amount influenced by the duration of a preceding on period.

In some embodiments, the method of FIG. 5 can be applied to a non-cooled ablation probe, such as an ablation probe that does not include a temperature sensor, a non-cooled ablation probe by means of which it is desired to maximize the heat lesion around the ablation probe, a non-cooled RF electrode, a non-cooled and non-temperature-monitoring RF electrode, a non-cooled MW antenna, or a non-cooled and non-temperature-monitoring MW antenna. In such embodiments, steps 510, 515, 520 can be omitted, because they relate to the flow of coolant within the ablation probe. Note that, for both internally-cooled and non-internally-cooled HF ablation probes, tissue heated by a HF ablation probe will cool passively when the applied HF signal output is lowered sufficiently (eg turned off) due to the cooler surrounding tissue.

One advantage of the method presented in FIG. 5 is that the ablation output level is adjusted both upward and downward in response to evidence of tissue boiling to produce a maximal, stable HF ablation process. One advantage of the method presented in FIG. 5 is that the size of the ablation zone can be maximized. One advantage of the method presented in FIG. 5 is that the ablation output level is adjusted both upward and downward to calibrate to particular tissue conditions and ablation probe type. One advantage of the method presented in FIG. 5 is that the duration of inter-pulse cooling periods are adjusted in response to measurements of the ablation process. One advantage of the method presented in FIG. 5 is that HF signal level during on periods, the duration of on periods, and the duration of off periods are adjusted to increase the volume of heated tissue maximally by approaching or exceeding the boiling temperatures within heated tissue throughout the ablation process. One advantage of the method presented in FIG. 5 is that HF heating energy is delivered in high-intensity pulses to increase heat lesion size and avoid the hindering effect of tissue boiling. It is understood that some steps in the flow chart of FIG. 5 can be rearranged, combined, omitted, or added without affecting one or aspects of the present invention embodied in FIG. 5. It is understood that error checks, user notification steps, and termination criteria checks can be added to the method in FIG. 5. It is understood that additional controller behaviors can be included in the method presented in FIG. 5, for example, temperature control.

Figure 6:
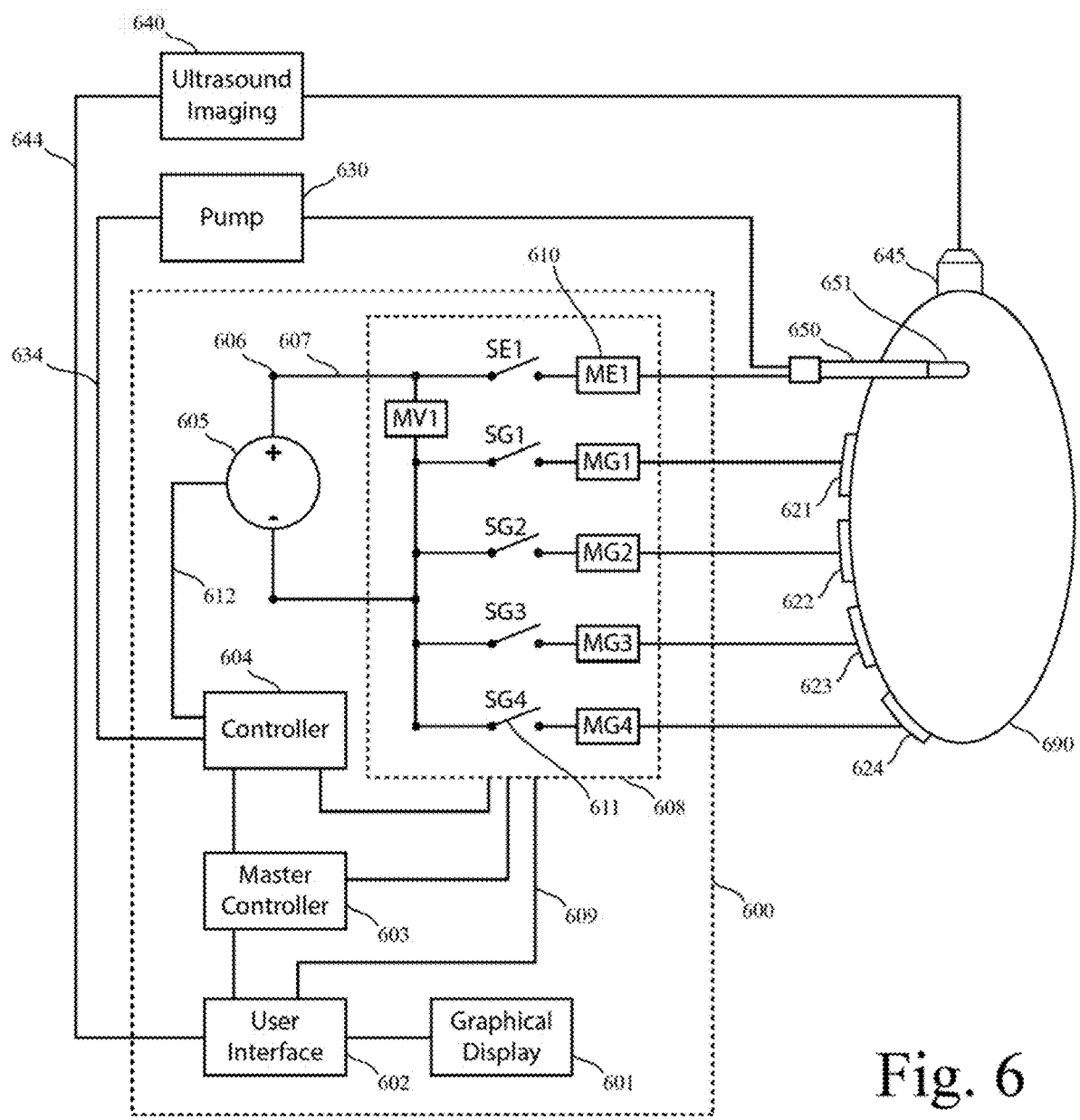
FIG. 6 is a schematic diagram showing a circuit for a HF tumor ablation system including a HF power supply; a measurement circuit for the HF output level; a connection for at least one HF electrode including a switch and measurement circuit for electrode current and temperature; connections for one or more ground pads each connection including a switch and a measurement circuit for ground pad current; a coolant pump connected to the at least one electrode and including a measurement of coolant flow; a master controller capable of computing the power supply output level, switch positions, and coolant flow rate in response to measured values and their history including HF output voltage, HF output power, impedance, electrode current, ground pad current, coolant flow, user interface state, user input, and functions of these values and other values; a controller configured to adjust the power supply output level, switch positions, and coolant pump output level; a user interface; a graphical display including numerical, digital, analog, and/or graphical displays of measured and computed values, and user-interface elements.

Referring now to FIG. 6, one embodiment of a HF ablation system is presented as in a block diagram, in accordance with several aspects of the present invention. The system presented in FIG. 6 can be one embodiment of the system presented in FIG. 1. The system presented in FIG. 6 is one example of a system that can generate the ablation processes and measurements presented in FIG. 3. In some embodiments, the master controller 603 can execute the process presented in FIG. 4. In some embodiments, the master controller 603 can execute the process presented in FIG. 5. In some embodiments, FIG. 6 presents one example of a system for tissue ablation that includes a radiofrequency signal generator 605, a user interface 602, an ablation electrode 650, and at least two ground pads 621, 622, 623, 624; wherein current from the radiofrequency signal 605 generator can flow between the electrode 650 and each ground pad if the electrode and the ground pad are in contact with the same living body 690; wherein the system measures the current flowing through each ground pad (by means of measurement devices MG1, MG2, MG3, MG4). In some embodiments, the user interface 602 or its graphical display 601 can include a display of a parameter of the current of a ground pad.

The generator 600 is connected to one or more cooled ablation probes 650 inserted into patient body 690. The coolant pump 630 can be connected to the generator controller 604 via control line 634, and can supply coolant to the ablation probe 650. The generator 600 can monitor and control the coolant pump 630 via connection 634. The ultrasound imaging device 640 can be connected to the generator user interface 602 via control line 644, and to transducer 645 which can image the electrode 650 in body 690. In some embodiments, the ultrasound machine can interface with the generator controller. Ablation probe 650 has active tip 651.

Controller 604 is connected to HF power supply 605, master controller 603, probe and ground pad interface 608, user interface 602. In some embodiments, the user interface can include display and interface elements that are familiar one skilled in the art, including non-graphical user-interface elements. The user interface 602 is connected to graphical display 601. Graphical display 601 can be a display monitor or a touch screen display. Graphical display 601 can present ablation parameters and measurements graphically to the user, such as the graphs 102A, 102B, 102C, 102D, 102E, 102F, 102G, 102H, 119A, 119B, 119C in FIG. 1, or the graphs presented in FIG. 3. The interface element 608 can provide measurements of the HF output delivered to the ablation probe 650 and of temperatures and other signals sensed by the ablation probe 608. The combination the HF supply 605, controller 604, master controller 603, probe measurement and interface element 608, user interface 602, and graphical display 601 provides for automatic control of the ablation process and for graphic display of parameters, for example as described in FIG. 1, FIG. 2, FIG. 3, FIG. 4, and FIG. 5. The user interface 602 and graphical display 601 provide a graphical user interface. The master controller 603 connects to the control computer 604 to control its functions, to the graphic user interface 601, 601 to allow the user to see and/or to adjust the controller settings; and to the probe interface element 608 to monitor and control interface to the ablation probe 608 and ground pads 621, 622, 623, 624. In some embodiments, the ultrasound imaging machine 640 and the controller 604 can be connected, and the controller 604 can adjust the ablation process automatically based on data from the ultrasound machine, such as estimates of tissue temperature, estimates of lesion size, and estimates of lesion size based on hyperechoic bubbles.

FIG. 6 shows, in one example, an electrode and ground pad interface 608 which is connected to the HF supply 605, the computer controller 604, and the graphical user interface 601 and 602. The element 608 connects to electrode 650 and ground pads 621, 622, 623, 624. The element provides measurements of the signal output delivered to the electrode 650 and to each of the ground pads 621, 622, 623, 624, as well as measurement of the electrode temperature or temperatures. The interface 608 includes switches 611 labeled SG1, SG2, SG3, SG4 that can connect and disconnect the one or more ground pads 621, 622, 623, 624 from the generator supply 605. The switches 611 can connect and disconnect each ground pad from supply 605 as clinically desired and/or to control the current flowing to each pad. The switches 611 can be closed to create an electrical circuit through the patent between the electrode 650 and one or more ground pads 621, 622, 623, 624. The interface 608 includes switch SE1 that can connect and disconnect the one or more electrode 650 from the generator supply 605. The switch SE1 can turn electrode 650 on and off during pulsing sequences. The control line 612 can also be used to enable and disable the power supply 605 to turn the electrode 650 on and off during pulsing sequences. In some embodiments, an active circuit element can be put in series with each ground pad switch, such as SG1, wherein the active circuit element produces an adjustable resistance that can be adjusted by the controller to change the distribution of current among the connected ground pads. Measurement element MV1 can be a high-impedance voltage measurement device that measures the output potential generated by supply 605. ME1 610 can be a low-impedance measurement device through which HF signals from supply 605 flow to electrode 650. ME1 can measure the current flowing to electrode 650 and the one or more temperatures measured by electrode 650. Measurement elements MG1, MG2, MG3, and MG4 connect to ground pads 621, 622, 623, and 624, respectively, and each can be a low-impedance device through which HF current flows to the connected ground pad, and by which ground-pad-specific current can be measured. The voltage and current measurements from MV1 and ME1 respectively can be used to compute an impedance and power for electrode 650. The measurements from MV1, ME1, MG1, MG2 MG3, and MG4 can be used to compute voltages, current, powers, and impedance related to each or any of the electrodes 650 and ground pads 621, 622, 623, 624. The controller 604 and master controller 603 can use measurements from interface element 608 to control generator output. Measurements from element 608 can be displayed by user interface 601 and graphical display 601. The interface element 608 and its component switches 611 and measurement devices 610 can be controlled by the controller 604, master controller 603, and user interface 602.

When electrode 650 and ground pad 621 are in contact with living body 690, electrode switch SE1 is closed, ground pad switch SG1 is closed, and power supply 605 is active, then electrical current can flow between the electrode 650 and ground pad 621 through living body 690; however, when the switch SG1 is open, current from supply 605 is prevented from flowing through ground pad 621. When electrode 650 and ground pad 622 are in contact with living body 690, electrode switch SE1 is closed, ground pad switch SG2 is closed, and power supply 605 is active, then electrical current can flow between the electrode 650 and ground pad 622 through living body 690; however, when the switch SG2 is open, current from supply 605 is prevented from flowing through ground pad 622. When electrode 650 and ground pad 623 are in contact with living body 690, electrode switch SE1 is closed, ground pad switch SG3 is closed, and power supply 605 is active, then electrical current can flow between the electrode 650 and ground pad 623 through living body 690; however, when the switch SG3 is open, current from supply 605 is prevented from flowing through ground pad 623. When electrode 650 and ground pad 624 are in contact with living body 690, electrode switch SE1 is closed, ground pad switch SG4 is closed, and power supply 605 is active, then electrical current can flow between the electrode 650 and ground pad 624 through living body 690; however, when the switch SG4 is open, current from supply 605 is prevented from flowing through ground pad 624. It is understood that when a switch (such as SG1, SG2, SG3, or SG4) is open some de minimus amount of current from the power supply 605 can flow through its attached ground pad (such as 621, 622, 623, 624, respectively) due to, for example, capacitive and inductive coupling among the many ground pads, electrodes, cables, wires, and other electrical circuit elements in the system; in this case, it can still be said that current from the power supply 605 does not substantially flow through the ground pad (such as 621, 622, 623, 624, respectively).

The generator 600 can provide a jack to connect each electrode 650 and ground pad 621, 622, 623, 624 to their respective output lines. Jacks E1, G1, G2, and G3 in FIG. 1A are one example of such jacks. In some embodiments, the order of the measurement element and the switch can be reverses along the output line leading to the attached electrode or ground pad; for example, switch SE1 can be positioned between electrode 650 and measurement device ME1.

In some embodiments, the generator chassis 600 can include the pump 630. In some embodiments, the generator chassis 600 can include the ultrasound imaging unit 640. In some embodiments, elements contained in housing 600 as shown in FIG. 6 can be housed in two or more physically separate classes. In some embodiments, ultrasound imaging data from ultrasound machine 640 is displayed on graphical display 601. In some embodiments, the ultrasound imaging device can be controlled using generator user interface 602, including with input from the generator graphical display 601, master controller 603, and/or controller 604. In some embodiments, the ultrasound machine 640 can control and/or display data from generator 100 via data connection 644. In some embodiments, the user interface 602 can generate a data file for an ablation session. In some embodiments, the user interface 602 can generator a data file that contains both ultrasound and HF ablation data.

In some embodiments, the HF supply 605 can be a HF voltage source. In some embodiments the power supply 605 can be an RF power supply. In some embodiments the power supply 605 can be an MW power supply. The power supply 605 can be enabled and disabled by controller 604 via control connection 612. The output level of the power supply 605 can be adjusted by the controller 604 by means of control connection 612. In some embodiments, power supply 850 can generate additional RF and stimulation potentials. In some embodiments, the power supply can include multiple electrical sources which are electrically isolated from each other. In some embodiments, current flows between a first electrode and ground pad pair connected to generator 800, and current flows between a second electrode and ground pad pair connected to generator 800, and the first pair and the second pair are electrically-isolated from each other.

In some embodiments, power supply 850 can include an electrical supply that produces a direct current (DC) potential. The DC supply can be active at the same time as the RF supply and thereby add a direct-current offset to the RF signal. For example, the cathode of the DC supply can be connected to an electrode, and the anode of the DC supply can be connected to one or more ground pads, to implement bimodal electric tissue ablation (BETA) which is theorized to increase hydration of tissue near the electrode, slow tissue desiccation, and thereby increase lesion size. In some examples, the DC supply can supply a constant DC voltage. In some examples, the DC supply can supply a constant DC current. In some examples, the DC supply can supply a constant DC power. One advantage of performing BETA with a constant DC current is that the effect of the DC signal at the electrode is not affected by voltage drops and power losses remote of the electrode (such as in the impedance between the skin surface and the ground pad) in the circuit between the anode and cathode of the DC supply.

In some embodiments, the ablation probe 650 is an MW antenna and the ground pads 621, 622, 623, 624 can be omitted. In some embodiments, the ablation probe 650 can be an RF electrode. In some embodiments, the ablation probe 650 can be multi-prong RF electrode. In some embodiments, the ablation probe 650 can be a cluster RF electrode, wherein the electrode includes multiple independent shafts with each an active tip. In some embodiments, the ablation probe 650 can be multiple RF electrodes connected to the generator output using a splitter cable. In embodiments wherein multiple electrodes are connected to measurement element ME1, ME1 can monitor the temperature signal for each electrode. In some embodiments, the generator output signal line 607 is split into a multiplicity of lines, each of which contains a switch SE1 and measurement element ME1 configured to conduct current to, measure the current flowing to, and measure the temperature from one of a multiplicity of electrodes 650; this provides for independent switching, measurement, and control of the output signal to multiple electrodes. For example, this can be used to independently pulse the generator output to each of multiple electrode 650.

Figure 7:
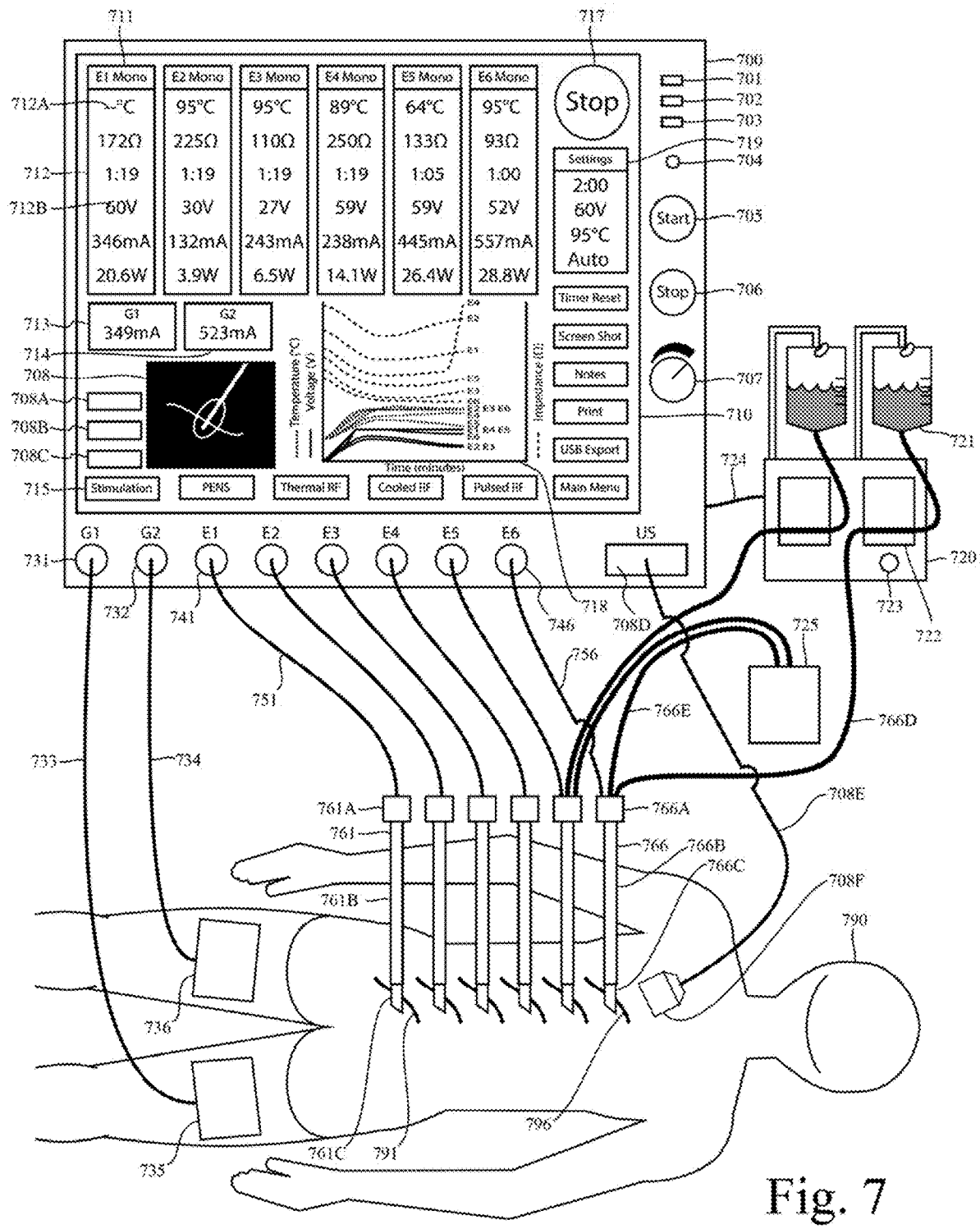
FIG. 7 is a schematic diagram showing a system for high-frequency tissue ablation that includes multiple cooled and non-cooled electrodes that heat tissue at the same time; multiple ground pads that carry current from the electrodes; an integrated nerve stimulator; a graphical display that includes a plot of output level, impedance, and temperature for each electrode on one time axis; an integrated ultrasound imaging apparatus; display of US imaging data; controls for the an integrated ultrasound imaging apparatus.

Referring now to FIG. 7, one embodiment of a HF system for tissue ablation is presented as a schematic drawing in accordance with several aspects of the present invention. In some embodiments, the HF system can perform RF tissue ablation. In some embodiments, the HF system can perform MW tissue ablation. In one aspect, FIG. 7 presents one example of a tissue ablation system 700 that includes a HF generator and an ultrasound imaging machine in a single chassis. In one aspect, the HF generator 700 one example of a HF generator is configured for both ultrasound imaging and tissue ablation. In one aspect, the generator 700 presents one example of a generator that can perform ultrasound imaging and that can produce both a HF signals for ablation, and nerve stimulation signal for electrical stimulation of nerves. In one aspect, HF generator 700 presents one example of a HF generator that includes a display of ultrasound imaging data 708 and of HF ablation parameters 712, 718. In one aspect, FIG. 7 presents one example of a system 700 for HF tissue ablation that includes one or more cooled HF probes, a real-time graphical display of measured parameters 718, a controller that implements a method for impedance-based control of the one or more cooled HF probes, a controller that implements temperature control of one or more cooled HF probes, a controller that implements voltage control of one or more cooled HF probes, a controller that implements current control of one or more cooled HF probes, a controller that implements power control of one or more cooled HF probes, and a graphic display of ultrasound imaging data 708. In one aspect, FIG. 7 presents one example of a system 700 for HF tissue ablation that includes a graphic display on which impedance (dashed line)

and HF signal output level (solid line; eg current, voltage, power) are plotting in real time on the same time axis 718 for each of at least one generator ablation-probe outputs (eg ablation electrodes); in the example of FIG. 7, the signal output level plotted in voltage (solid line). In one aspect, FIG. 7 presents one example of a system 700 for HF tissue ablation that includes a graphic display on which impedance (dashed line), HF signal output level (solid line), and temperature (dotted line) are plotted in real time on the same time axis 718 for each of multiple ablation electrodes, which can include cooled electrodes, cooled electrode with extension-tip temperature monitor, standard electrodes, non-cooled electrodes, non-temperature-sensing electrodes, non-temperature-sensing and non-cooled electrodes. In one aspect, the generator 700 is one example of a generator that includes an RF signal generator and a nerve stimulation signal generator, and that can connect to two or more reference ground pads 735, 736. In one aspect, the generator 700 is one example of a generator that includes an RF signal generator and a nerve-stimulation signal generator, that can perform RF ablation at one or more ablation probes at the same time, that can connect to two or more ground pads to carry return current from the one or more ablation probes, and that can measure the current flowing through each of two or more reference ground pads.

The system 700 includes data ports 701, 702, 703 that provide for input and output of data including procedure data, ultrasound data, ablation data, and control signals; a lamp 704 that indicates active electrode output; a mechanical button 705 that activates electrode output; a mechanical button 706 that deactivates electrode output; a display touch screen 710; ground pad jacks 731, 732 labeled "G1", "G2", that connect to ground pads 735, 736 via cables 733, 744, respectively, wherein ground pads 735 and 736 are placed on the skin surface of patient 790; six electrode jacks labeled "E1", "E2", "E3", "E4", "E5", and "E6", for example 741 and 746, that each connect to an electrode, such as electrode 761 and 766; ultrasound jack 708D labeled "US" that connects to ultrasound transducer 708F via cable 708E; and pump control and measurement connection 724 that connects to coolant pump 720. Standard electrode 761 is connected to jack 741 via cable 751, and includes a proximal hub 761A, an insulated shaft 761B, and an active tip 761C, wherein the active tip 761C is placed near target nerve 791 in patient body 790. Internally-cooled electrode 766 is connected to jack 746 via cable 756, and includes a proximal hub 766A, an insulated shaft 766B, and an active tip 766C, wherein the active tip 766C is placed near target nerve 796 in patient body 790. In one example, electrode 766 can include a temperature-measuring extension tip. Coolant from fluid reservoir 721 is pumped by pump head 722 of pump 720 through tubing 766D, into electrode 766 to cool active tip 766C, through tubing 766E, and into collection container 725. In FIG. 7, each electrode targets a nerve, such as a spinal nerve carrying painful impulses. In other embodiments, one or more of the electrodes, or all the electrodes, can target tumors, such as tumors in the liver, kidney, lung, or another organ or bone. In some embodiments, electrodes can target different type of bodily structures. In some embodiments, all the electrodes can be cooled electrodes. In some embodiments, an electrode can be of one type selected from the list: a standard RF electrode, an electrode placed within an RF cannula, a temperature-sensing electrode, a cooled electrode, a cooled electrode including an extension-tip temperature sensor, a multi-tined electrode, a side-output electrode, and other types of RF electrodes known to one skilled in the art. In the following description, electrodes and ground pads can be referred to by their respective jack label, such as "E6" for electrode 766. Pump 720 includes user control 723, two pump heads such as head 722, and two fluid reservoirs such as fluid bag 721.

The graphic display 710 includes a control for each electrode, such as control button 711 for electrode E1, with which the electrode can be activated and deactivated, and with which the output polarity and other electrode-specific settings can be changed by the user; digital measurement displays for each electrode, such as displays 712, including temperature, impedance, elapsed lesion time, voltage, current, and power; a digital measurement display for each ground pad current, such as display 713; graphical measurement displays for electrode and/or ground pad readings, such as graph 718 of the temperatures, impedances, and voltages of all electrodes plotted on the same time axis in real-time and matching the digital displays of those measurements in each electrode panel (eg 712); ultrasound controls 708A, 708B, 708C for control of the ultrasound system; ultrasound image display 708 for display of ultrasound imaging data collected by transducer 708E; RF generator controls, such as button 715, for timer reset, taking screen shots, entering clinical notes, printing procedure data, exporting procedure data, transitioning to a menu screen, and selection among various output control modes, including sensory and motor nerve stimulation, peripheral electrical nerve stimulation (PENS), standard RF, cooled RF, and pulsed RF as used in the field of RF pain management; a control and display for ablation program settings 719; and a toggle button for activating and deactivating electrode output 717. The graphical display 718 includes a label for each plotted line to identify the electrode for which the line plots a measurement. In some embodiments, the graphs 718 can include a reading for the output level of the each electrode, such as current, voltage, or power. In some embodiments, the graph 718 can include a line for the impedance for each electrode. In some embodiments, the graph 718 can include a line for the temperature for each electrode. Real-time plotting on the same time axis of impedance and HF signal output level for each electrode can be important for non-temperature-sensing electrodes, for example E1 in FIG. 7 (as indicated by the "--" indicator for "no temperature reading" 712A), because the real-time graphic display can provide a clear indication of tissue boiling, such as by means of a rapid increase in impedance, such as shown in one example by the impedance line plot for electrode E4 on graphical plots 718. Real-time plotting on the same time axis of impedance and HF signal output level for each electrode can be important for a cooled RF electrode with a temperature-sensing extension tip because the extension tip may not measure the maximum tissue temperature, and the impedance signal relative to the signal output level can provide an indication that the maximum tissue temperature is in the boiling range. Real-time plotting on the same time axis of impedance and HF signal output level for each electrode can be important for all electrode types to provide a signal to the physician of boiling, for example, in the case where a temperature sensor is malfunctioning and the temperature reading is not accurate. In some embodiments, the real-time graphical plots for each electrode can be positioned on an individual axis for each electrode, for example axes that are stacked side by side, for example aligned with each electrode display panel (eg 712 for electrode E1). The settings panel 719 includes settings for total lesion time, voltage, temperature, and a selection for automatic/manual control. These can take a variety of settings values. In some embodiments, the lesion time, temperature, and mode settings can take values in the ranges described in relation to settings 106A, 106C, 106D, respectively. In some embodiments, the voltage setting can take a value in the range 0-200 V-RMS or higher. In the example shown in FIG. 7, for each of electrodes E2, E3, and E6, the voltage is below the set value 60V because the output level is limited by the set temperature 95 deg C. which the temperature sensor has reached. In the example shown in FIG. 7, for each of electrodes E1, E4, and E5, the voltage is limited at the voltage set value 60V (to within the limits of control and measurement accuracy) because E1 is a non-temperature-sensing electrode (as indicated by the temperature sensor open-circuit indicator "--" 712A) and for E4 and E5, the temperature sensor is below the set value 95 deg C. Examples of non-temperature-sensing electrodes include the Cosman CR "pole" needle, the Cotop CXE "pole" needle, a deep-brain-stimulation (DBS) electrode contact on which a neurosurgeon performs an RF heat lesion before removal of the DBS electrode, a non-temperature-sensing spring-coil epidural electrode, a temperature-sensing RF electrode whose temperature sensor is broken, and other RF electrode types. Plotting of impedance and output level on the same time axis 718 can be important for RF ablation non-temperature-sensing electrodes, because the impedance signal gives the physician visual feedback about boiling around the electrode active tip, which the physician wants to avoid in some cases, such as in lesioning of nervous tissue, lesioning in the brain, creating a lesion of uniform size with gas venting, and other cases. In other embodiments of generator 700, different settings and settings values can be included. In some embodiments, the settings for each electrode can be set independently of other electrodes. The elapsed time readings for each electrode, as displayed by 1:19 for electrode E1 in panel 712, indicate the same values for electrodes E1. E2, E3, and E4 because they were energized at the same time, and a different value for each of E5 and E6 because these electrode were activated by the user at a different times. The graphical user interface 710 provides for simultaneous or staggered activation of the electrode outputs, using control buttons such as 711.

Each electrode control button both identifies, and provides a means for changing, the "polarity" its corresponding electrode output. In some embodiments, the generator 700 can create any pattern of connections, and sequences of connection patterns, between generator potentials and the electrodes and ground pads. For example, some groups of electrodes can be energized in a bipolar or multipolar manner, wherein the electrodes reciprocally carry returns currents for each other. For example, some electrodes can be energized in a monopolar manner, wherein one or more ground pads carries return currents from the electrodes. In this way, the generator can create a wide variety of heating patterns to suit clinical needs. In some embodiments, the generator can include an automatic controller for ground pad switching to distribute and/or control current among multiple pads, such as the ground-pad switching methods presented in FIG. 1, FIG. 12, FIG. 14, FIG. 15, FIG. 17, FIG. 19, FIG. 20, FIG. 21, FIG. 22, and FIG. 23. In some embodiments, the parameter of the ground pad current displayed to the user is the same parameter that the ground pad switching is configured to control.

In some embodiments, the generator 700 can include a different number of electrode jacks and corresponding electrode-specific displays and controls than the number shown in FIG. 7. In some embodiments, the generator 700 can energize a number of electrodes selected from the list: 1, 2, 3, 4, 5, 6, 7, 8, 9, 10, a number more than 10. In some embodiments, the number of electrodes that can be connected to each electrode jack is more than one. In some embodiments, the generator 700 can include a different number of ground pad jacks and corresponding ground-pad current-measurement displays than the number shown in FIG. 7. In some embodiments, generator 700 can connect to, and measure current from each of, a number of electrodes, wherein the number can be selected from the list: 1, 2, 3, 4, 5, 6, 7, 8, 9, 10, a number more than 10. In some embodiments, multiple ground pads can be connected to the same jack by means of a single cable and the current flowing through each pad can be measured by the generator 700; this can have the advantage of simplifying cable organization for configurations with multiple ground pads. In some embodiments, more than one ground pad can be combined into a single ground pad structure.

In some embodiments, the generator 700 can omit the nerve stimulator. In some embodiments, the generator 700 can be configured for tumor ablation. In some embodiments, the generator 700 can be configured for nerve ablation. In some embodiments, the generator 700 can be configured for surgical coagulation. In some embodiments, the generator 700 can be configured for multiple medical applications. In some embodiments, the generator 700 can execute one or more of the tissue ablation method presented in FIG. 1, FIG. 2, FIG. 3, FIG. 4, FIG. 5, and FIG. 6. In some embodiments, the generator 700 can include one or more of the graphical displays presented in FIG. 1, FIG. 2, FIG. 3, FIG. 4, FIG. 5, and FIG. 6. In some embodiments, the system 700 can operate in multiple modes to accommodate different type of electrodes and clinical objectives. In some embodiments, generator 700 can a variety of ablation control methods by means of which multiple types of electrodes can be controlled; for example, a conventional electrode, a non-temperature-sensing electrode, an internally-cooled electrode wherein a temperature sensor is positioned within the coolant flow within the active tip, an internally-cooled electrodes including a temperature-sensing extension tip.

In some embodiments, the ultrasound machine of system 700 can be placed in a separate chassis from the RF generator, and the ultrasound chassis and generator chassis can exchange data via a connection, such as a cable. One example of a separated RF machine and ultrasound machine is presented in FIG. 1. In some embodiments, the ultrasound machine is produced by a first manufacturer, and the HF generator is produced by a second manufacturer. In some embodiments, the RF generator simply displays ultrasound data, such as images, from a physically separate US machine. In some embodiments, the ultrasound machine simply displays readings from a physically separate RF generator. In some embodiments, the transmission of data between an ultrasound machine and an RF generator is only in one direction. In some embodiments, the transmission of data between an ultrasound machine and an RF generator is only in both directions.

One advantage of a system that includes both a tissue-ablation system and an ultrasound-imaging system is that the physician can easily control both processes from the same console. One advantage of a system that includes both heat-lesioning and ultrasound-imaging functions is that the physician can easily use ultrasound imaging to guide and monitor the ablation process, such as by visualization of lesion formation relative to target structures in the body. Lesion formation can be visualized by bubbles around the electrode tip. One advantage of a system that includes both tissue-ablation and ultrasound-imaging functions is that the system can produce a single data record that includes an imaging record and an ablation-data record of the ablation process. For ablation of multiple electrodes at the same time, display of US image data and electrode readings on the same screen has the important advantage of that a large amount of data can monitored by the physician without having to turn his or her attention to a different console, which could perturb the physician's handling of the ultrasound transducer. This is a great advantage when many outputs are controlled at the same time. This can be a great advantage when an impedance-based control method is executed for each electrode, wherein execution of the method can produce rapid changes in electrode readings.

The application of a nerve-stimulation signal to an ablation electrode can provide for safe and effective nerve ablation, for example, to avoid ablation of a nerve which should be preserved, and to improve targetry of nerves targeted for ablation. The application of a sensory-nerve stimulation signal to an ablation electrode can be used to guide the electrode a position favorable to ablation of a target nerve, for example a nerve carrying undesired and/or painful signals. The application of a motor-nerve stimulation signal to an ablation electrode can be used to indicate that the electrode is too close to a nerve carrying a desirable motor function, and that the motor nerve may be damaged during ablation. Ground pad burns are an undesirable complication of tissue ablation, including nerve ablation. The risk of ground pad burns can increase as the generator output level increases. The risk of ground pad burns can increase as the total electrode current output increases. Ground pad current is an important indicator of safe ground pad usage and ground pad heating, as described in the electrosurgical safety standard ANSI/AAMI/IEC 60601-2-2:2009. Ground pad current influences the current density and rate of ohmic heating of tissue is contact with the ground pad. In some embodiments, the safe use of each of multiple ground pads can be ascertained by other measurements, such as direct temperature measurement, voltage measurement, power measurement. The risk of ground pads burns can increase with the number of electrodes energized in the same ablation session. It can be desirable to ablate multiple nerves at the same time to treat chronic pain. It can be desirable that a nerve ablation generator can perform nerve ablation using one more electrodes at the same time, wherein the number of electrodes can be a number selected from the list: 1, 2, 3, 4, 5, 6, 7, 8, 9, 10, a number greater than 10. The use of multiple ground pads can reduce the likelihood of a ground pad burn, because electrode current is distributed to multiple ground pads. The use of independent monitoring of the current flowing through each of multiple ground pad can reduce the likelihood a ground pad burn, because the current flowing to each pad can be monitored, for example, by the generator 700 and/or the generator user. Individual ground pad current monitoring can be used to detect improper ground pad placement. Individual ground pad current monitoring can be used to detect unequal current distribution among multiple ground pads, such as in the case that a first ground pad shields a second ground pad from electrode current so that more electrode current flows to the first pad than the second pad.

An RF generator that includes a nerve stimulator, multiple ground pad connections, and individual current measurement for each ground pad connection provides three important safety features for high-current RF ablation of nerves. The combination of the nerve stimulation, multiple ground pads, and individual ground-pad current monitoring provides important safety features for multi-electrode RF ablation of nervous tissue. An RF generator that includes connections for multiple electrodes, connections for multiple ground pads, and nerve stimulator provides for the safe and effective ablation of multiple nerves at the same time. The importance of these safety features increases as the number of electrode increases, as the size of the electrodes increase, and as the number of cooled RF electrodes increases, because each of these factors can increase the total return current that ground pads carry. The use of multiple ground pads, and the use of multiple ground pads with independent current measurement and/or control, can be advantageous for spinal nerve ablation, for example, because heating multiple electrodes can require more total current than the maximum current rating of one typical electrosurgical ground, because heating multiple cooled RF electrodes can require more current than the typical current rating of an electrosurgical ground pad, because electrosurgical ground pads have a maximum current rating, and because 1 to 8 or more electrodes can be used in the same procedure. For example, a typical electrosurgical ground pad for nerve ablation conforms to the ANSI/AAMI/IEC 60601-2-2:2009 standard and can be limited to carrying 700 mA for 60 seconds, and heating multiple large electrodes of 18 gauge and 16 gauge to a temperature in the range 80-90 deg C. can require more than 700 mA on average over longer than 60 seconds. In the example show in FIG. 7, the total ground-pad current from six electrodes is 872 mA, distributed between two pads G1 and G2. For example, the use of multiple ground pads can be important to ensure ground pad current is below the maximum value when the number of electrodes energized at the same time is greater than four (4). One advantage of system for tissue ablation that includes an RF generator, a nerve stimulator, two or more ground pad connections, and individual current measurement for each ground pad connection is that nerve ablation can be performed with the safety of nerve-stimulation guidance and the safety of multiple ground pads. This has the important advantage of improving the efficiency, efficacy, and safety of nerve ablation, particularly multi-electrode nerve ablation.

Figure 8:
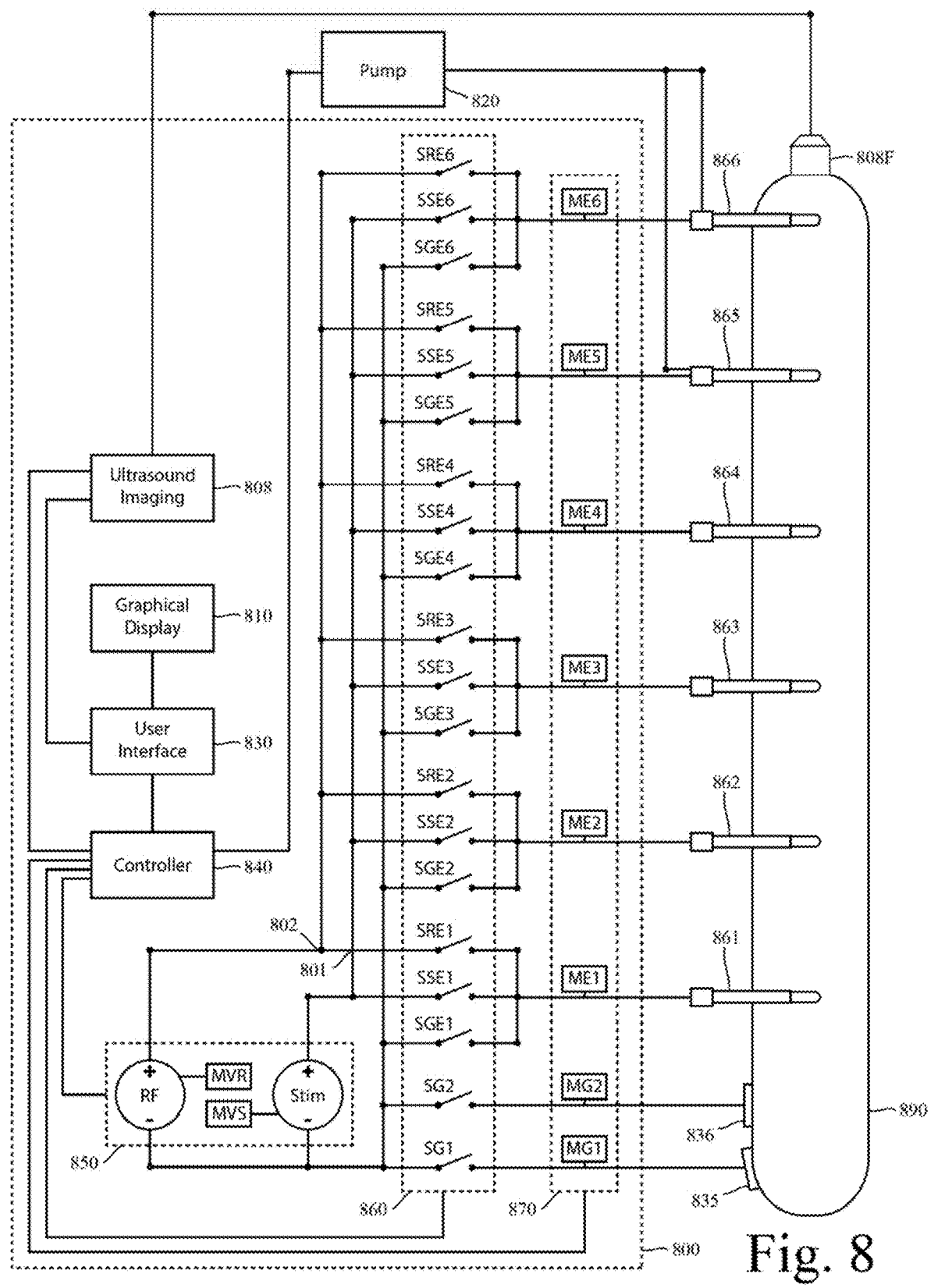
FIG. 8 is a schematic diagram showing a circuit for an RF generator that includes a RF power supply with a measurement circuit; a nerve stimulation signal generator with a measurement circuit; connections to multiple cooled electrodes and multiple non-cooled electrodes wherein each connection includes a measurement circuit for electrode current and temperature, a switch configured to connect and disconnect the electrode from the reference potential, a switch configured to connect and disconnect the electrode from the nerve-stimulation potential, a switch configured to connect and disconnect the electrode from the RF potential; connections to multiple ground pads wherein each connection includes a measurement circuit for the ground pad and a switch configured to connect and disconnect the ground pad from the reference potential; a coolant pump that delivers coolant to the cooled electrodes; an ultrasound imaging machine; a controller that can measure and control the RF supply, stimulation signal generator, the switches, electrode current and temperature, ground pad current, coolant pump output level, and ultrasound imaging parameters in response to system programming and user input from the user interface; a user interface configured for monitoring and control of stimulation, tissue ablation, coolant pump, and ultrasound imaging machine; a graphical display configured to display parameters and data for stimulation, tissue ablation, and ultrasound imaging processes.

Referring now to FIG. 8, one embodiment of a system for HF tissue ablation is presented as a block diagram in accordance with several aspects of the present invention. In one aspect, FIG. 8 presents one example of a HF ablation system that includes an HF generator and an imaging device in the same chassis. In one aspect, FIG. 8 presents one example of an RF generator that includes a nerve stimulator, multiple ground pad connections, and individual current measurement for each ground pad connection. In one aspect, FIG. 8 presents one example of an RF ablation system that provides for switching of among multiple ground pads. In one aspect, FIG. 8 presents one example of an RF generator configured to generate RF and stimulation signals at the same time. In one aspect, FIG. 8 presents on example of an RF generator that provides for connection and disconnection of each of multiple electrodes to either an RF potential stimulation potential, reference potential, or no generator potential, and for sequences of these connections and disconnections.

In some embodiments, the system in FIG. 8 can be one example of the internal construction of the system presented in FIG. 7. In some embodiments, the system in FIG. 8 can be one example of the internal construction of the system presented in FIG. 9. In some embodiments, the system in FIG. 8 can be one example of the internal construction of the system presented in FIG. 10. Some embodiments of the system in FIG. 8 wherein the number of electrodes and ground pads are different than shown in FIG. 8 and wherein the ultrasound machine 808 is outside the chassis 800 can one example of the internal construction of the system presented FIG. 1 and of the system presented in FIG. 2. In some embodiments, the ablation control methods presented in FIG. 1, FIG. 2, FIG. 3, FIG. 4, and FIG. 5 can be included in controller 840.

In FIG. 8, connection lines that cross over each other, such as at position 801 where two wires cross each other, are not connected. Generator 800 includes controller 840 configured for measurement and automatic control of generator output, electrode switching, ground pad switching, pump output, and user interface input; user interface 830 configured for user monitoring and control of RF, stimulation, and ultrasound functions; graphical display 810 of RF, stimulation, and ultrasound readings and settings; ultrasound imaging device 808 connected to transducer 808F; power supply 850 that includes an RF source labeled "RF", a nerve-stimulation source labeled "Stim", a measurement device MVR for the RF source, and a measurement device MVS for the Stim source; switching unit 860 which can connect and disconnect electrodes and ground pads from electrical potentials generated by power supply 850; measurement unit 870 including a measurement element for each of one or more electrodes ME1, ME2, ME3, ME4, ME5, ME6, and a measurement element for each of one or more ground pads MG1, MG2, wherein each measurement element is configured to measure the current and temperature (if a temperature sensor is included in the attached device) of its attached electrode 861, 862, 863, 864, 865, 866 and ground pad 835, 836; and connection to pump 820 for measurement and control of pump functions. In some alternative embodiments, measurement unit 870 can include a single measurement element, such as ME1, that is switched sequentially to each of multiple electrodes and/or ground pads, whereby individual current and/or temperature measurement can be performed that is independent of the pattern and timing of connections of the ground pads to the generator supplies 850. In some alternative embodiments, the current for each of N ground pads can be measured by directly measuring the current flowing though (N−1) of the ground pads, and subtracting the sum of those values from the total current flow from one or more treatment electrodes to the N ground pads at the same time, by means of the principle of current conservation.

Electrodes 861, 862, 863, 864, 865, 866 are inserted into body 890. Cooled electrodes 865 and 866 are connected to coolant output of pump 820. In some embodiments, each electrode 861, 862, 863, 864, 865, 866 can be any type of RF electrode, including non-cooled electrode and cooled electrodes. Ground pads 835, 836 are placed on the surface of body 890. The graphical display 810 can be a touch screen. The graphical display 810 can be a non-touch-screen display. The graphical display can display measurements digitally and graphically. User interface 830 can save RF, stimulation, and ultrasound procedure data to an internal disk and/or an external disk. Ultrasound transducer 808F can be positioned at the surface of body 890 and configured to image the internal anatomy of body 890, including, for example a heat lesion within body 890. RF power supply "RF" is configured to produce an RF signal capable of heating the electrodes 861, 862, 863, 864, 865, 866 within body 890. Measurement element MVR can measure the voltage, current, and power delivered by the RF source. The radiofrequency signal generator "RF" can generate a sinusoidal voltage across its "+" and "−" poles, with frequency in the radiofrequency range. In some embodiments, the RF source can generate an RF signal with amplitude in the range 0-200 V-RMS. Stimulation supply "Stim" is configured to generate a nerve stimulation signal across its "+" and "−" poles, such as a waveform including biphasic square pulses. In some embodiments, stimulation source "Stim" can produce stimulation signals to evoke sensory and motor response, such as signals that include biphasic pulses with pulse-repetition rates in the range 0-200 Hz, for example 50 Hz and 2 Hz. In some embodiments, the stimulation signal generator "Stim" can produce a stimulation signal that is configured to block nerve conduction, such as a signal that includes biphasic pulses in the range 1 kHz-50 kHz.

The "−" pole of each of RF and Stim sources are tied together and this can be the generator reference output pole/potential. The "+" pole of the RF output is the RF signal output pole/potential. The "−" pole of the RF output is the stimulation signal output pole/potential. Switching unit 860 can connect and disconnect each of one or more electrodes to the RF output pole, the stimulation output pole, and the reference output pole. For example, electrode 861 can be connected to and disconnected from the RF output pole, the stimulation output pole, and the reference output pole by switches SRE1, SSE1, and SGE1, respectively. Switching unit 860 can connect and disconnect each of one or more ground pads to the reference output pole. For example, ground pad 835 can be connected to and disconnected from the reference output pole by switch SG1. In some embodiments, generator 800 can provide jacks that can each be connected to either an electrode or a ground pad, and that can be connected to any system pole. The switches in unit 860 can be mechanical switches or other devices for changing the resistance and/or impedance of the connection between the power supply 850 and the electrode or ground pads jacks.

Controller 840 is connected to power supply and measurement unit 850, switching unit 860, measurement units 870, pump 820, ultrasound machine 808, user interface 830, and graphical display via user interface 830. The controller 840 can execute a tissue ablation method by means of these connections. The controller can process measurement from the power supply 850 and the electrode and ground pad measurements 870. The controller 840 can combine measurements to produce other measurements, such as an impedance combined from the quotient of a voltage and current. The controller 840 can use a measurement as input to a control process. The controller 840 can display measurements and other values on the user interface and/or graphical display. The controller 820 can enable and disable the coolant output of pump 820, adjust the output level of coolant pump 820, and use signals from pump 820 as input to control processes. The controller 840 can change the operation mode of the ultrasound machine 808. The controller 840 can adjust the ablation process using measurements from the ultrasound machine 808, such as an estimate of tissue temperature, an estimate of heat lesion size, an estimate of lesion size based on imaging of bubbles. The controller 840 can enable and disable the output of the RF source, adjust the amplitude of the RF source signal, and measure the RF voltage, current, and power measured by MVR. The controller 840 can enable and disable the Stim source, adjust the timing of stimulation pulses, adjust the frequency of stimulation pulses, adjust the pulse width of stimulation pulses, adjust the amplitude of stimulation pulses, and measure the stimulation pulse voltage and current measured by MVS. The controller 840 can operate the switches in unit 860 and produce a sequence of switching states. A sequence of switching states can be configured for one or more of the following purposes: to create a spatial pattern of heating in the tissue, to stimulate a nerve and ablate a nerve at the same time, to stimulate a nerve and ablate tissue at the same time, to regulate the ground pad currents, ablate tissue, to modify nerve function, to control the output delivered to an electrode, to control a temperature, to suit a clinical need, and other purposes. The controller 840 can energize the electrodes in a variety of polarities and patterns thereof, including "monopolar simultaneous" or "cluster" wherein multiple electrodes are coupled to the same HF output potential signal and referenced to one or more ground pads; "monopolar sequential" wherein each of one or more electrodes is connected to an output pole at a different time, and is referenced to one or more ground pads; "bipolar" or "dual" wherein one or more electrodes are referenced to each one or more other electrodes; and sequential combinations of these are other polarity configurations wherein the generator automatically switches between different polarities. In some embodiments, the controller can automatically reduce or turn off the radiofrequency signal output from the RF supply when connecting and/or disconnecting an ablation electrode and/or ground pad in order to avoid undesired stimulation of nerve and other excitable tissue due to transient DC signal components that can arrive from changing the position of a switch 860. For example, in some embodiments including two ablation electrodes and one ground pad, wherein the controller alternately switches RF current between the two electrodes (a "bipolar" configuration), between the first electrode and the ground pad (a first "monopolar" configuration), and then the second electrode and the ground pad (a second "monopolar" configuration), the controller disables the RF power supply while the switches are changing position between sequential configurations. In one example operating mode, the controller 840 alternates the delivery of an RF and stimulation signal so that tissue, such as a nerve, is ablated at the same time as a nerve is stimulated, and so that electrical current does not flow between the RF and Stim power supplies. This can have the advantage of monitoring the response of a nerve ablation by monitoring the stimulation response of nerve. In some embodiments, the alternating RF and stimulation signals can be delivered to the same electrode. In some embodiments, the alternating RF and stimulation signals can each be delivered to a different electrode; this can provide for ablation of a nerve at a first position, stimulation of the nerve at another position, and monitoring the nerve's response to the stimulation at a third position, wherein the second and third positions are configured to be on opposite sides of the first position, and wherein the monitoring can be measurement of action potentials conducted by the nerve, or can be observation of a bodily response produced by the nerve, such as a motor or sensory response.

In some embodiments, the system in FIG. 8 can include the pump 820 within chassis 800. In some embodiments, system 800 can be connected to another imaging device, such as an x-ray machine, fluoroscopy machine, CT scanner, MRI scanner, spiral CT scanner, intraoperative MRI scanner, OCT scanner, laparoscopic scope machine, endoscopic scope machine, video camera. In some embodiments, another imaging device can be included in chassis 800. In some embodiments, the ultrasound machine 808 can be omitted. In some embodiments, the generator 800 can include one or more ground pad connections each with independent switching and measurement. In some embodiments, the generator 800 can include one or more electrode connections each with independently switching and measurement.

Figure 9:
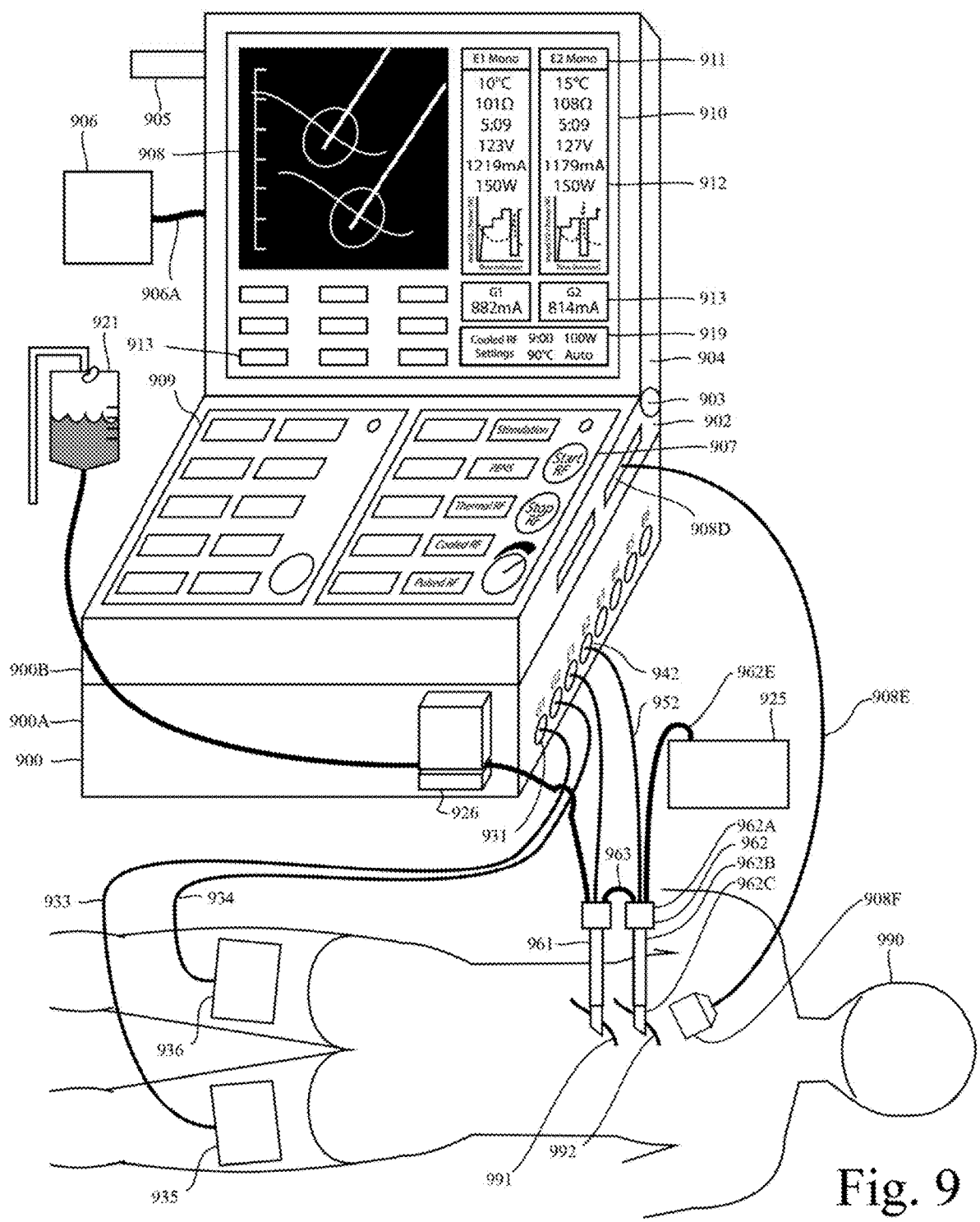
FIG. 9 is a schematic diagram that shows a medical system that includes an ultrasound imaging device and a high-frequency electrosurgical generator that are both contained in the same chassis, and that are both controlled by a single user interface console.

Referring now to FIG. 9, one embodiment of a HF system for tissue ablation is presented as a schematic drawing, in accordance with several aspects of the present invention. In one aspect, FIG. 9 presents one example of an integrated system for HF ablation and ultrasound imaging. FIG. 9 presents one example of an integrated system for impedance-based pulsing control of RF ablation and ultrasound imaging for one or more cooled RF electrodes. In one aspect, FIG. 9 presents one example of an ultrasound machine that controls a HF generator for tissue ablation. In one aspect, FIG. 9 presents one example of a system for RF ablation of nerves that includes two or more ground pad jacks, and current measurement for each ground pad attached to a ground pad jack. In one aspect, FIG. 9 presents one example of a system for HF ablation that includes a graph of signal output level and impedance plotted on the same time axis for each of one or more HF electrodes.

System 900 is configured to ablate target tissue 991, 992 in living body 990 by means of one or more ablation probes 961, 962; to image the living body 990 by means of ultrasound transducer 908F; and to provide a single-console user interface with which a physician can monitor and control both the ablation process and the ultrasound imaging process. System 900 includes a bottom part 900A and a top part 900B. Bottom part 900A includes an integrated peristaltic pump 926 that pumps coolant from supply 921 to one or more electrodes 961, 962; one or more ground-pad jacks 931 configured to connect one or more ground pads 935, 936 to a system reference potential; and one or more electrode jacks 942 configured to connect one or more electrodes 961, 962 to an RF output. Top part 900B includes a base 902; upper section 904; hinge 903; one or more ultrasound transducer jacks 908D configured to attached to one or more ultrasound transducers 908F; ultrasound imaging controls 909; RF generator controls 907; display screen 910; a connection port configured to export RF and ultrasound procedure data to USB drive 905; and a connection port configured to export RF and ultrasound procedure data to external computer 906 via connection 906A, which can be a computer network in one example. Display screen 910 can be a touch screen monitor. Display 910 includes ultrasound controls 913; graphic display of ultrasound imaging data 908; RF controls 911; display 912 of digital and graphical readings for each of the one or more electrodes 961, 962 attached to the system 900; display 913 of current for each of the one or more ground pads 935, 936 connected to the system 900; display of RF settings values 919. The settings 919 include a set time, set power, set temperature, and mode settings. In some embodiments, the set time, set temperature, and mode settings can take values in the ranges described in relation to settings 106A, 106C, 106D, respectively. In some embodiments, the power setting can take a value in the range 0-400 Watts or more. In some embodiments, the power setting can be the initial power set level. In some embodiment, the power setting can be a maximum power set level. In some embodiments, the power setting can be the set power level. Coolant from fluid bag 921 is pumped by pump head 926 through electrodes 961 and 962 in series and into container 925. In the example presented in FIG. 9, the system 900 includes two ground pad jacks 931, and six electrode jacks 942.

In some embodiments, system 900 can be an integrated ultrasound and RF system, wherein top 900A and bottom 900B are inseparably connected, for example composing a single chassis. In some embodiments, top 900A and bottom 900B are physically separate and connected by a data connection such as a cable, or a jack and plug. In some embodiments, bottom part 900A is an RF generator that includes a coolant pump, one or more ground pad jacks, and one or more electrode jacks. In some embodiments, top part 900B is a laptop-style ultrasound machine that includes a connection to RF generator 900A, and user controls and displays for RF generator 900A. In some embodiments, the interface between RF generator 900A and ultrasound machine 900B is a standardized interface that allows one or more ultrasound system to operably connected to one or more RF generator, wherein the ultrasound machine and RF machine can either produced by the same manufacturer, or different manufacturer. In some embodiments, generator 900A is a "black box" HF generator including connections for control and measure, and configured for integration into ultrasound systems.

In the operating mode shown in FIG. 9, the RF signal output delivered to each internally-cooled electrode alternates between and high power level and a low power level based on a measured impedance and controller parameter. In some examples, the controller for each electrode can automatically execute one of the methods presented in relation to FIGS. 1A, 1C, 3, 4, and 5. One advantage of the system presented in FIG. 9 is that ultrasound images and RF signal output readings are displayed on the same screen, wherein RF signal output and cooled-RF electrode readings can increase and decrease rapidly and repeatedly, so that the physician can easily monitor and correlate imaging information and electrode measurements. In some other examples, the controller for each electrode can execute one of the methods presented in relation to FIG. 1B. In some examples, other control methods can be used.

In some embodiments, ground pad currents are not displayed to the user, but are an input to the automatic control system of the ablation system 900. The automatic control system can check that the current values are within safety limits, prompt the user if one or more of the current measures is outside allowed limits, prompt the user if the ground pad currents are unbalanced, adjust the current flowing to one or more pads, and/or balance the current among one or more pads.

In some embodiments, system 900 can include a MW generator. In some embodiments, the one or more ablation probes 961, 962 can be MW antennae; the system 900 can include a MW generator; the one or more ground-pad jacks 931 can be omitted; and the one or more ground pads 935, 936 can be omitted. In some embodiments, system 900 can omit an RF generator.

Figure 10:
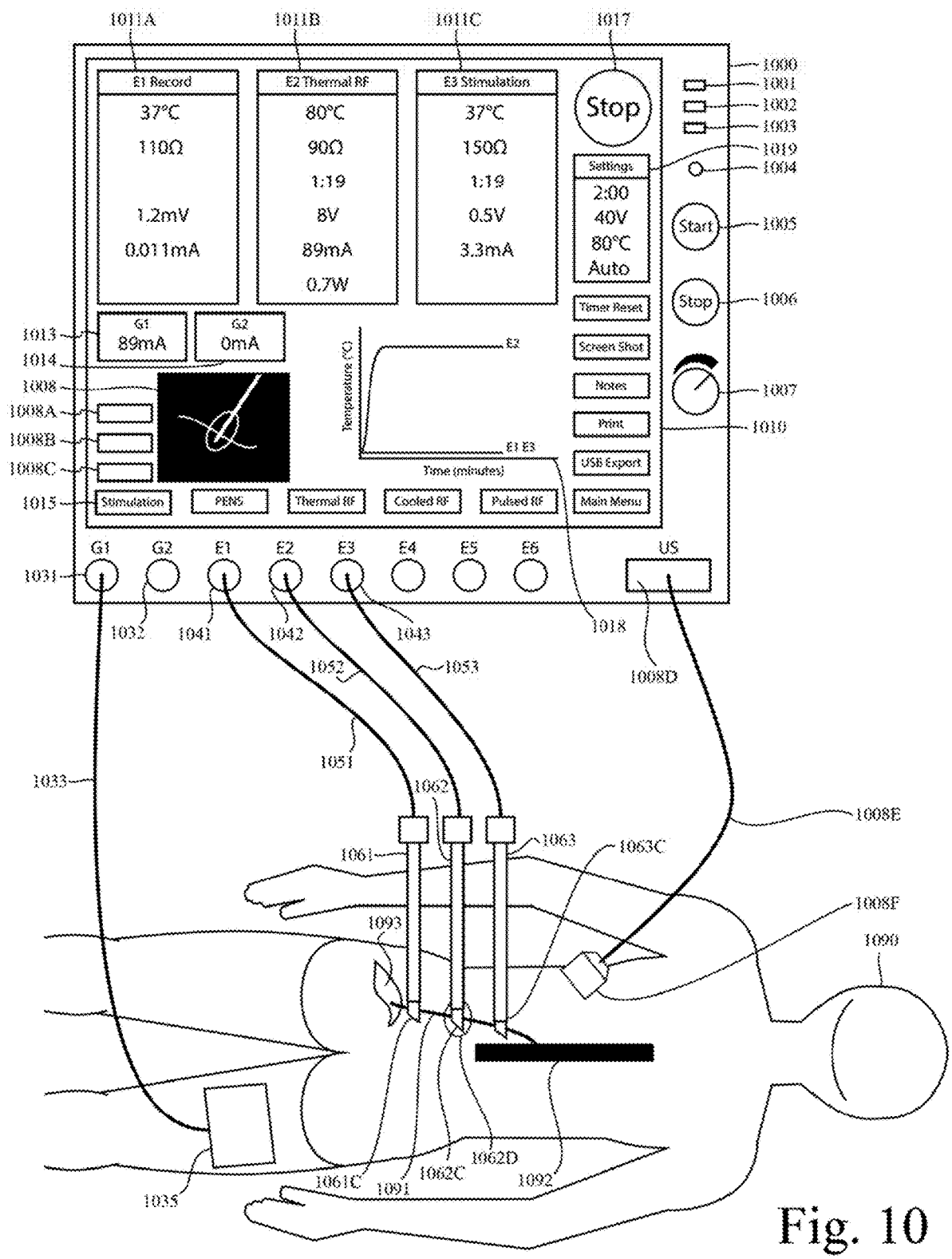
FIG. 10 is a schematic diagram showing a medical system configured to stimulate a nerve, record from a nerve, and ablate tissue at the same time.

Referring now to FIG. 10, several embodiments of a HF system for tissue ablation is presented as a schematic drawing, in accordance with several aspects of the present invention. The text describing FIG. 10 also presents several methods of HF tissue ablation in accordance with several aspects of the present invention. In one aspect, FIG. 10 presents one example of an integrated system 1000 for HF ablation and medical imaging. In one aspect, FIG. 10 presents one example of an integrated system 1000 for HF ablation and image-guidance for HF ablation. In one aspect, FIG. 10 presents one example of a system for nerve ablation 1000 that includes a HF generator, a nerve stimulator, a nerve monitor, and an ultrasound machine. In one aspect, FIG. 10 presents one example of a system that can stimulate a nerve and ablate a nerve at the same time. In one aspect, FIG. 10 presents one example of a system that can stimulate a nerve while the nerve is being ablated. In one aspect, FIG. 10 presents one example of a system that can ablate a nerve and block perception of the nerve ablation by application of electrical signal that blocks action potential transmission to a location between the site of nerve ablation and the central nervous system. In one aspect, the system 1000 has the important feature that it provides a single console for image guidance of the placement of stimulation, ablation, and recording electrodes at precise desired locations relative to one or more nerves for the purpose of stimulation-based monitoring of a nerve ablation process.

In one embodiment, the generator 1000 in FIG. 10 can be another operating mode of the generator 700 in FIG. 7. In some embodiments, the internal circuitry of generator 1000 in FIG. 10 can be represented by the block diagram in FIG. 8. Recording electrode 1061, RF ablation electrode 1062, and stimulation electrode 1063 are connected to generator jacks 1041 ("E1"), 1042 ("E2"), and 1043 ("E3"), respectively. Measurements for electrode 1061, 1062, and 1063 are displayed digitally in panels 1011A, 1011B, and 1011C, respectively. The generator 1000 is configured to perform the following functions on an ongoing basis during an ablation program: (1) record nerve signals from electrode 1061 connected to jack E1; (2) deliver an RF signal to electrode 1062 connected to jack E2, wherein the RF signal is configured to heat the tissue around the electrode active tip 1062C; and (3) deliver a nerve stimulation signal to electrode 1063 connected to jack E3. Measurements for electrode 1061, 1062, 1063 are displayed graphically on plot 1018. Ultrasound data 1008 is displayed from transducer 1008E which can be used to image an electrode in relation to soft and hard tissue, including a target nerve, such as nerve 1091 in body 1090. Electrodes 1061, 1062, 1063 can include ultrasound-visible features, such as a echogenic markers, configured to allow identification of each electrode's active tip. In the example configuration shown in FIG. 10, the active tip 1063C of stimulation electrode 1063 is placed at a proximal location along peripheral nerve 1091, which branches off spinal cord 1092. The active tip 1062C of ablation electrode 1062 is placed at location along peripheral nerve 1091 that is distal to the position of stimulation electrode 1063. The measurement contact or contacts 1061C of measurement electrode 1061 is placed at location along peripheral nerve 1091 that is distal to the position of RF electrode 1062. Ground pad 1035 carries return currents from the RF ablation electrode 1062 and the stimulation electrode 1063. In some embodiments, recording electrode 1061 can be electrically referenced to ground pad 1035. In some embodiments, recording electrode 1061 can be a bipolar electrode with its own electrical reference, isolated electrically and/or temporally from RF and stimulation output potentials.

The configuration of electrodes 1061, 1062, 1063 along nerve 1091 can provide for a method of monitoring of the success or failure of interrupting of nerve 1091 by RF heating 1062D around RF electrode tip 1062C as the nerve is being heated. When RF heating is successful at the position of tip 1062C, the firing of nerve 1091 due to stimulation by electrode 1063, for example by means of a sensory-nerve stimulation signal and/or motor-nerve stimulation signal applied to electrode 1063, can be blocked by heat lesion 1062D and no longer detected by recording electrode 1063. The measured discontinuation of a stimulated response can be a condition for stopping the nerve ablation process heating. The measured discontinuation of a stimulated response can be a condition for accepting the nerve ablation as complete. In one method, when the firing of nerve 1091 due to stimulation by electrode 1063 is no longer detected, the RF ablation of nerve 1091 can be discontinued, either automatically by the generator controller or by decision of the user physician. In another method for preventing desired damage to motor nerve fibers near the site of tissue ablation, a motor-nerve stimulation signal can be delivered by output E3 through electrode 1063, a physician and/or the generator can monitor the transmission of action potential along motor fibers of nerve 1091 through the position of delivery of RF (include pain-management-type pulsed RF) at tip 1062C either by means of recording electrode 1061 or the contraction of a muscle 1093 innervated by nerve 1091, and the physician and/or generator can discontinue the ablation process if undesired damage to motor fibers of nerve 1091 is indicated by a decrease in transmission of action potentials generated by electrode 1063 through the site of RF application. In another method for preventing undesired damage to a nerve fiber, the ablation 1062D not intended to damage nerve 1091, but rather to ablate tissue nearby nerve 1091, and stimulation by electrode 1063 is used to monitor undesired damage to nerve 1091 using sensory-nerve stimulation, motor-nerve stimulation, or both. In another method for monitoring the successful ablation or modulation of sensory-nerve fibers and preventing the ablation of motor-nerve fiber, generator 1000 is configured to deliver through electrode 1063 an electrical signal configured to stimulated both sensory and motor nerve fibers of nerve 1091 during delivery of a high-frequency signal (such as an RF or pulsed RF signal) through electrode 1062 to nerve 1091. In some embodiments, recording electrode 1061 can be placed within muscle 1093, and output E1 or generator 1000 can be configured for recording the electrical activity muscle 1093 evoked by stimulation by electrode 1063. In some embodiments, the location of electrode 1061 and the location of electrode 1063 can be switched, so that stimulating electrode 1063 is distal to the ablation electrode 1062 along the nerve 1091, and the recording electrode 1061 is proximal to the ablation electrode 1062 along nerve 1091. Generator 1000 provides both digital and graphical displays of the stimulation, ablation, and recording processes. This can be important data for the physician to assess the ablation process.

In another embodiment, recording electrode 1061 can be omitted, and the blockage of stimulated nerve signals can be monitored by a physiological and/or physical response, such as the contraction of a muscle 1093. In some examples, nerve 1091 can be a medical branch nerve innervating a multifidus muscle 1093 in the spine. In some embodiments, the recording electrode 1061 can be omitted, the stimulation electrode 1063 can be placed distal to the ablation electrode 1062 along the nerve 1091, the blockage of stimulation nerve signals can be monitored by patient perception of stimulated nerve signals; for example, this could be performed if the electrode 1062 produces a pain-management-type pulsed RF signal with control temperature at or below 45 deg C. In some embodiments, the recording electrode 1061 can be placed proximal to the ablation probe 1062 along a nerve 1091, and the stimulating electrode 1063 can be placed distal to the ablation probe 1062 along a nerve 1091, and the progress of the ablation process can be monitored by changes in measured stimulation action potentials propagating the distal to proximal along the nerve. In some embodiments, the stimulation electrode can be omitted, and the stimulation of action potentials can be produced by a physical and/or physiological process, such touching or moving a body part, or by an existing pain process. In some embodiments, a stimulation signal and an RF ablation signal can be delivered to the same electrode. In some embodiments, a stimulation signal and an RF ablation signal can be delivered to each of one or more RF electrodes.

In another example, the configuration presented in FIG. 10 can be used to block the patient's perception of painful sensations during nerve ablation without direct application of anesthetic to the nerve. In this example, the recording electrode E1 can be omitted, and structure 1093 can represent a painful facet joint in the spine of patient 1090 that is innervated by medial branch nerve 1091. Generator 1000 can deliver to electrode 1063 a stimulation signal capable of temporarily blocking signal conduction in nerve 1091 at the same time that nerve 1091 is being ablated due to RF signals delivered to electrode 1062. Pain signals generated by heating at the location of active tip 1062C can be blocked by nerve-blocking stimulation signals applied by electrode 1063C at a location proximal location along the nerve 1091. Direct application of anesthetic to nerve 1091 to block pain signals due to nerve heating can be omitted. After the ablation and stimulation signals are turned off, the stimulation block ceases to have an effect, and the patient can quickly assess whether painful sensations from joint 1093 were blocked by heat lesion 1062D, by contrasting pain before and after the ablation. The patient can be instructed to distinguish pre-procedure pain from pain induced due to the nerve injury. In this example, a first electrode E3 configured to produce an electrical conduction block, is placed proximal to a second ablation E2 electrode along a sensory nerve, and operation of the first and second electrodes reversibly blocks pain sensations produced by nerve ablation at the second electrode E2 without the use of anesthetic. This has the advantage that the result of an attempt at nerve ablation (namely that painful or undesired signals are blocked in the target nerve) can be evaluated immediately afterward, because direct application of anesthetic to the target nerve can be avoided without producing excessive patient discomfort. In one example, the nerve-blocking stimulation signal can be a high-frequency stimulation configured to produce a high-frequency conduction block. In one example, nerve-blocking stimulation signal can be a biphasic signal as described in Rosenblueth A, Reboul J. The Blocking and Deblocking Effects of Alternating Currents on Nerve. Am J Physiol. 1939; 125(2):251-264. High frequency alternating current with fundamental frequency in the range 2-50 kHz can produce a nerve block. In another embodiment, a nerve-blocking stimulation signal and an RF ablation signal can be applied to the same electrode to reduce pain during RF ablation. In one method, a stimulation configured to block nerve signal conduction is applied to a nerve that is being subjected to an ablation process, such an RF ablation process, wherein the application of the stimulation signal is configured to block the patient's sensation of the ablation process.

In another example, the configuration presented in FIG. 10 can further include a fourth electrode attached to jack E4 and having an active tip that is positioned along nerve 1091 between the active tip 1063C of electrode 1063 and the spinal cord 1092; generator 1000 can be configured to deliver a first nerve stimulation signal to jack E3 configured to produce repeated nerve firing, and to deliver a second nerve stimulation signal to jack E4 configured to block nerve signal transmission; and the system can be one example of a system performing a method comprising simultaneously ablating a nerve; blocking perception of pain from the nerve ablation by delivery of a nerve-stimulation signal that blocks transmission to the central nervous system action potentials induced by the nerve ablation; and monitoring the progress of the nerve ablation by applying a nerve-stimulation signal configured to induce repeated nerve firing, and either recording stimulated action potentials or observing a physiologic effect of stimulated action potentials. The said method can further comprise the step of evaluating the effectiveness of an action-potential-blocking nerve-stimulation signal applied to the nerve, by applying a nerve-stimulation signal to a location along the nerve that is distal to the location of application of the action-potential-blocking nerve-stimulation signal. One advantage using an electrical signal to block perception of the nerve ablation in this method, instead of injection of an anesthetic, is that injection of an anesthetic can spread undesirable to the location of the application of the nerve-stimulation signal configured to induce repeated nerve firing, and block said firing, thereby preventing monitoring of the progress of the nerve ablation.

In the examples presented in FIG. 10, stimulation, RF, and measurement phases of generator output and measurement can be sequenced cyclically throughout the ablation process so that they do not overlap in time. This has the advantage that the stimulation, RF, or measurement functions are not disturbed by the presence of other electrical signals and potentials. This can be important to protect sensitive measurement circuitry from stimulation and RF output, and to protect sensitive stimulation circuitry from high-voltage RF output. In some embodiments, the RF, stimulation, and measurement phases can be delivered at the same. In some embodiments, the RF ablation signal is delivered by a first electrode by a first electrical signal generator, the stimulation signal is delivered by a second electrode by a second electrical signal generator, the first electrode and the second electrode are electrically isolated except for their contact with the same patients, and the first and second electrical signal generators are electrical isolated to prevent substantial current from flowing between the first electrode and the second electrode. In some embodiments, the stimulation signal is generated by first generator unit, the RF ablation signal is generated by a second generator unit, and the first generator unit and the second generator unit are physically separate units.

Figure 11:
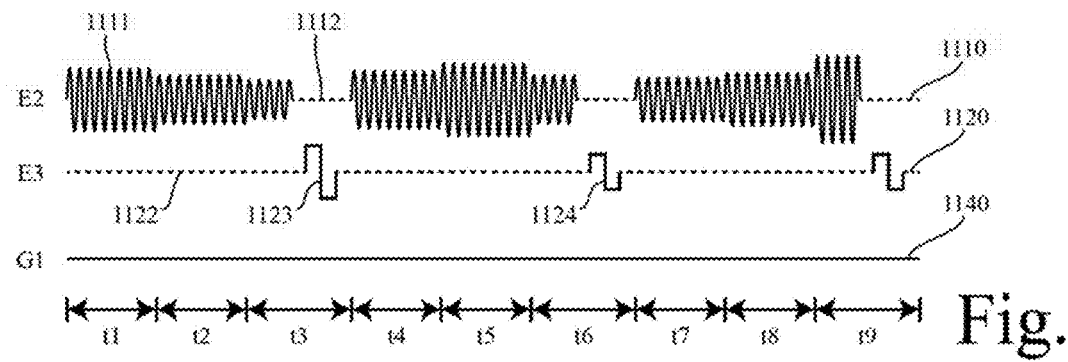
FIG. 11 is a schematic diagram showing the output signal delivered to two electrodes energized by the same system, wherein the first electrode is energized with a high-frequency signal configured to ablate tissue in contact with the first electrode, the second electrode is energized with a nerve stimulation signal, the high-frequency signal and the nerve stimulation signal are not delivered at the same time, and return current from the electrodes is carried by a ground pad.

Referring now to FIGS. 11, 12, 13, 14, 15, 16, 17, and 18, several examples of output signals produced by RF generator systems are presented in schematic graphs as a function of time, in accordance with several aspects of the present invention. The horizontal axis represents time. The vertical axis represents a signal output voltage. Each signal is presented on the same time scale. Each signal is labeled on the left by generator output jack, eg "E1" and "G1", by which the signal is delivered to the electrode or ground pad attached to the jack. A signal labelled "Ex" where "x" is a number is the output signal for an electrode jack and the connected electrode. A signal labelled "Gx" where "x" is a number is the output signal for ground pad jack and the connected ground pad. Within each signal, (such as signals 1110, 1120, and 1140 in FIG. 1), a solid line (such as lines 1111, 1123, and 1140 in FIG. 11) shows the output signal delivered to the corresponding electrode or ground pad by the generator, for example via a closed switch connected to a generator output pole (such as the "+" or "−" pole of the RF supply or the Stim supply in FIG. 8). Within the each signal, a dotted line (such as line 1122 in FIG. 11) indicates that the jack, and its connected electrode or ground pad, is disconnected from all generator output poles, for example via an open switch. A sinusoidal line, such as 1111 in FIG. 11 represents an RF signal. In some embodiments, the RF signal, such as 1111, can be generated by an RF supply, such as the RF source of power supply 850 in FIG. 8. In some embodiments, the frequency RF signal represented by a sinusoidal line, such as 1111, is higher or lower than it appears schematically in these schematic figures. A biphasic square pulse, such as pulse 1123 in FIG. 11, represents a stimulation signal. In some embodiments, a schematic biphasic square pulse can represent a single biphasic pulse.

In some embodiments, a schematic biphasic square pulse can represent a sequence of biphasic square pulses, such as a signal configured to produce a high-frequency electrical nerve block. In some embodiments, a stimulation signal, such as 1123, can be generated by a stimulation signal generator, such as the Stim source of power supply 850 in FIG. 8. A flat line, such as lines 1140 in FIG. 11, represents a constant electrical potential. In some cases, a schematic constant electrical potential can be the potential of the "−" output pole of RF source and Stim source in power supply 850 of FIG. 8. In some embodiments, return currents from the electrode signals shown in each figure are carried by the ground pads whose signals are represented in the same figure. In some embodiments, the electrode signals can represent a measurement of electrical signal output other than voltage, such as current or power. In the schematic representations of signal outputs presented in these figures, instances in which signal output is switched from one output to another are depicted as occurring instantaneously. In practice these transitions can take a non-zero time. In some embodiments, wherein the controller forces switching of an output signal from one electrode to another, or from one ground pad to another, the controller can deactivate the output signal (for example by disabling the RF oscillator of the RF power supply), then open or close one or more switches, and then reactivate the output signal. The duration for which an output signal is disabled to allow for switching can be configured to cover the entire duration of the change in switch configuration. This can remove signal transients that can have an undesired and/or confounding stimulation effect on nerves and other excitable bodily tissue. For some switches the transition time can be a number in the range 2-30 milliseconds; in other cases the switch transition time can be shorter than 2 milliseconds or longer than 30 milliseconds. In one aspect, the present invention relates to a system and method wherein generator signal output is turned off while a switch that connects an electrode to a generator power supply is opened or closed. In one aspect, the present invention relates to a system and method wherein the generator signal output is turned off while a switch that connects a ground pad to a generator power supply is opened or closed. In some embodiments, the RF signal of one electrode is generated by a different RF supply than the RF supply generating the RF signal of another electrode. In these embodiments, the controller can ensure that the two RF supplies are not active at the same time, and/or add a time gap between the sequential activation of the two supplies in which neither supply is active, to avoid simulative switching transients.

Referring now to FIG. 11, one example of delivery of a nerve stimulation signal to a first electrode while RF ablation is performed by a second electrode is presented in schematic graphs, in accordance with several aspects of the present invention. In some embodiments, the signals presented in FIG. 11 can be from a time slice of the signals delivered to jacks E2, E3, and G1 by generator 1000 in FIG. 10. In some embodiments, the signals presented in FIG. 11 can be produced by any one of the systems presented in FIGS. 2, 7, 8, 9, and 10.

In example of FIG. 11, signal 1110 is delivered to electrode E2 and is configured to generate a heat lesion around the active tip of electrode E2. Signal 1120 is delivered to electrode E3 and is configured to a stimulate a nerve in proximity to the active tip of electrode E3. Signal 1140 is delivered to ground pad G1 and is a constant reference potential. Time intervals t1, t2, t3, t4, t5, t6, t7, t8, and t9 can represent the periods over which the generator of signals E2, E3, and E4 updates the characteristics of the signals in response to measurement parameters. For example, the amplitude of the RF ablation signal 1110 is adjusted during each time interval where it is delivered to electrode E2. This adjustment can be configured to control the electrode temperature, voltage, current, power, impedance, or another parameter. For example, the amplitude of the stimulation pulse 1123 and 1124 changes. For example, this change can be in response to user adjustment of the stimulation output level. The duration of the time intervals can be configured to suit control objectives. The duration of the time intervals can be equal or time-varying. The duration of the time intervals can be configured to allow for temporal interleaving of RF and stimulation signals. The duration of the time intervals can be configured to produce a desired repetition rate for stimulation pulses. The duration of each time interval can be in less than 1 second. The duration of each time interval can be one-third of the period of the stimulation signal 1120, wherein biphasic pulses are delivered at a rate in the range 0-50 Hz. The ground pad G1 is constantly connected to the generator reference potential over the time window shown in FIG. 11. When an RF signal such as 1111 is delivered to electrode E2, electrode E3 has a high impedance to generator potentials, as shown by dotted line 1122 in one example. In some embodiments, the high impedance can be produced by opening a switch between electrode E3 and the generator power supply. When a stimulation signal such as 1123 is delivered to electrode E3, electrode E2 has a high impedance to generator potentials. In some embodiments, the high impedance can be produced by opening a switch between electrode E2 and the generator power supply. In this way, RF ablation output and stimulation output are not applied at the same time. This has the important advantage that current does not flow between electrodes E1 and E2, which can damage the stimulation source and/or affect the desired nerve stimulation configuration. In some embodiments, a stimulation signal is applied to a first electrode, and an RF ablation signal is applied to a second electrode, at the same.

Figure 12:
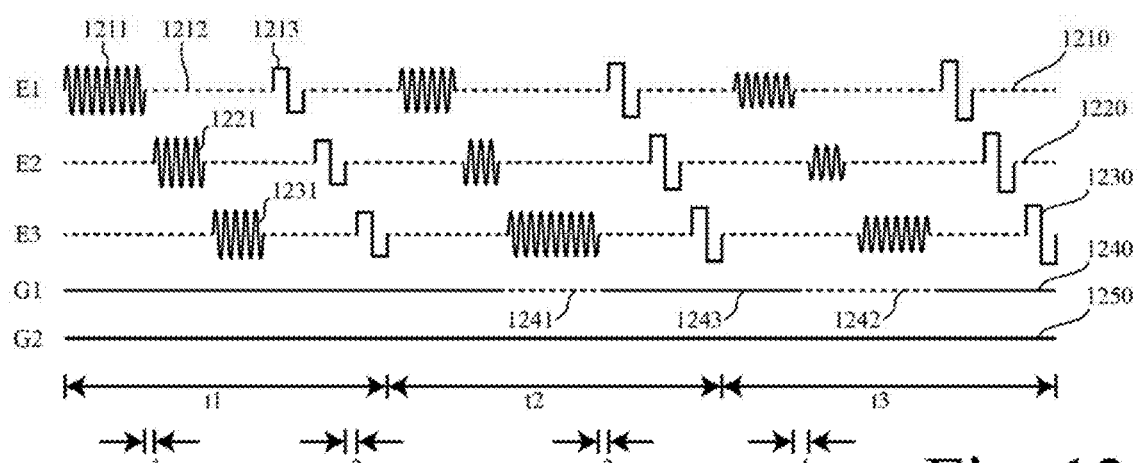
FIG. 12 is a schematic diagram showing the electrical signal applied to each of multiple electrodes energized in a monopolar configuration, wherein a high-frequency ablation signal and a stimulation signal are applied to each electrode, current from the electrodes are carried by multiple ground pads, the ground pads connected and disconnected from the generator reference potential in order to control a ground-pad current, no electrode is energized at the same time, and the high-frequency ablation signal source and the stimulation source are turned off during changes in the electrode and ground pad switch states.

Referring now to FIG. 12, one example of the delivery of a nerve stimulation signal and an RF-ablation signal to the same electrode during a single ablation session is presented in schematic graphs, in accordance with several aspects of the present invention. In one aspect, FIG. 12 presents one example of simultaneous nerve ablation and nerve stimulation by means of one or more electrodes. In some embodiments, the signals presented in FIG. 12 can be from a time slice of the signals delivered to jacks E1, E2, E3, G1, and G4 by generator 700 in one possible operating mode of generator 700. In some embodiments, the signals presented in FIG. 11 can be produced by any one of the systems presented in FIGS. 2, 7, 8, 9, and 10.

Each of the signals 1210, 1220, 1230 delivered to electrodes E1, E2, E3, respectively, includes a repeating sequence of an RF-ablation signal (eg 1211), a disconnection (eg 1212), and a stimulation signal (eg 1213). Three repetitions of this sequence is shown in FIG. 12, one in each of the time intervals t1, t2, and t3. In some embodiments, the duration of each time interval can be in the range 20-1000 milliseconds. The amplitude and duration of each RF pulse for each RF electrode can be adjusted to meet a clinical objective, such as control of temperature for each electrode, or for control of power, RMS current, or RMS voltage averaged over each interval t1, t2, t3, for each electrode. In some embodiments, the duration of each time interval can be longer than 1000 milliseconds. By means of this sequence, a nerve in proximity to the active tip of each electrode is both ablated and stimulated at the same time. In one example, the stimulation signal can be used to induce an electrical block. In one example, the stimulation signal can be used to evoke nerve firing. The three sequences 1210, 1220, 1230 are timed so that no output signal is delivered to more than one electrode at the same time. This prevents current from flowing between electrodes and confounding clinical objectives. In other embodiments, stimulation and RF-ablation signals are applied to the same electrode at the same time, or to multiple electrodes at the same time.

Return currents from each electrode E1, E2, E3 are carried by ground pads G1, G2. Ground pad G2 is constantly energized over the time window shown in FIG. 11, as indicated by signal 1250. Ground pad G1 is intermittently disconnected from the generator potentials in periods 1241 and 1242 of time intervals t2 and t3. In some embodiments, the generator automatically, intermittently disconnects ground pad G1 to equalize the electrical current flowing to each pad G1, G2. This is one example of ground-pad current control. In some embodiments, the one or more ground pads G1, G2 are constantly connected to generator reference potential.

The plots for electrodes E1, E2, and E3 include "dead periods" of positive duration in which output is not delivered to any electrode, such as period s1, s2, s3, and s4. These dead periods appear between each instance where signal output switch from one electrode to another, as in the sequence where RF 1211 is delivered to electrode E1, and then RF 1221 is applied to electrode E2, and then RF 1231 is applied to electrode E3, and then stimulation 1213 is applied to electrode E1, and so forth. In some embodiments, the electrical supply or supplies producing the signal or signals being switched between electrodes (either by opening and closing a switch or switches, or by enabling and disabling an electrical supply or supplies) are disabled for a non-zero duration by an automatic controller to produce a dead period for the purpose of avoiding the production of an unintended simulative transient. In some embodiments, the electrical supply or supplies delivering output to an electrode are disabled to produce a dead period of sufficient time to allow the supply or supplies to be connected or disconnected from a ground pad, to avoid producing an unintended simulative transient. In some embodiments, the RF supply or supplies producing RF bursts 1211 and 1221 are disabled to produce dead period s1 to avoid undesired switching transients when the switch connecting E1 to the RF supply is opened and the switch connecting E2 to the RF supply is closed. In some embodiments, the stimulation supply or supplies producing stimulation signals on E2 and E3 immediately before and after dead period s2 are disabled during dead period s2 to avoid undesired switching transients when the switch connecting E2 to the stimulation supply is opened and the switch connecting E3 to the stimulation supply is closed. In some embodiments, during dead period s3, the RF supply that is connected to electrode E3 immediately before dead period s3, and the simulation supply that is connected to electrode E1 immediately after dead period s3 are both disabled to avoid undesired switching transients when the switch connecting E3 to the RF supply is opened and the switch connecting E1 to the stimulation supply is closed. In some embodiments, the power supply or supplies connected to ground pad G1 in phase 1243 are disabled during dead period s3 to avoid undesired switching transients when the switch connecting ground pad G1 to a reference potential is opened to go from a disconnected state 1241 to a connected state 1243. In some embodiments, the power supply or supplies connected to ground pad G1 in phase 1243 are disabled during dead period s4 to avoid undesired switching transients when the switch connecting ground pad G1 to a reference potential is opened to go from a connected state 1243 to a disconnected state 1242.

Referring now to FIGS. 13, 14, 15, 16, 17, and 18, several examples of sequences of electrode switch states for two or more electrodes are presented in schematic diagrams, in accordance with several aspects of the present invention. The electrode signals presented in these figures are examples of signals that can be generated by embodiments of generators 200, 700, 800, 900, and 1000 during all or part of an ablation process. In some embodiments, the switching patterns presented are repeated throughout an ablation process. In each of the examples presented, at least three electrodes are connected to the generator that produces the presented signals E1, E2, and E3. The switching patterns presented can be generalized to configurations including two or more electrodes. The duration of each time intervals t1, t2, t3 can be either the same or different, either pre-determined or not pre-determined, and either fixed or variable suit clinical needs. The duration of each time interval t1, t2, t3 can short relative to tissue responses so that the signals' effects closely approximate the effects of a smooth signal. In some embodiments, the RF pulse duration and amplitude of each signal can be adjusted to meet a clinical objective such as control of temperature for each electrode, or for control of power, RMS current, or RMS voltage averaged over each interval t1, t2, t3, for each electrode. In some embodiments, time periods t1, t2, and t3 can represent control-update periods at the end of each of which RF pulse durations, amplitudes, and orders are updated. In some embodiments, the time schedule by which electrodes are switched is predetermined. In some embodiments, the time schedule by which electrodes are switched is not predetermined. In some embodiments, the time schedule by which electrodes are switched can vary, for example in response to measured parameters. In some embodiments, in accordance with one aspect of the present invention, the RF source can be disabled during switching to prevent non-zero-mean voltage transients that can produce undesired stimulation of nerves, muscles, and other excitable tissue. This can advantageously prevent undesired patient discomfort, sensations, and/or muscle contractions during the ablation process. Without removal of such simulative switching transients in multi-electrode configurations, undesired stimulation of excitable tissue can occur in scenarios where multiple electrodes are placed near nerves for the purpose of nerve ablation, in scenarios where multiple large cooled-RF electrodes cause high currents to flow through the body, and in other scenarios. In one aspect of the present invention, disabling the RF output during switch transitions (opening and/or closing), switching transients during multi-electrode cooled-RF tumor ablation wherein the output is switched among multiple electrodes, can prevent undesired stimulation of excitable tissue, such as muscles, sensory nerve fibers, motor fibers. In some embodiments, the signals can be produced by a single RF voltage source. In some embodiments, the signals can be produced by more than one RF voltage source.

Figure 13:
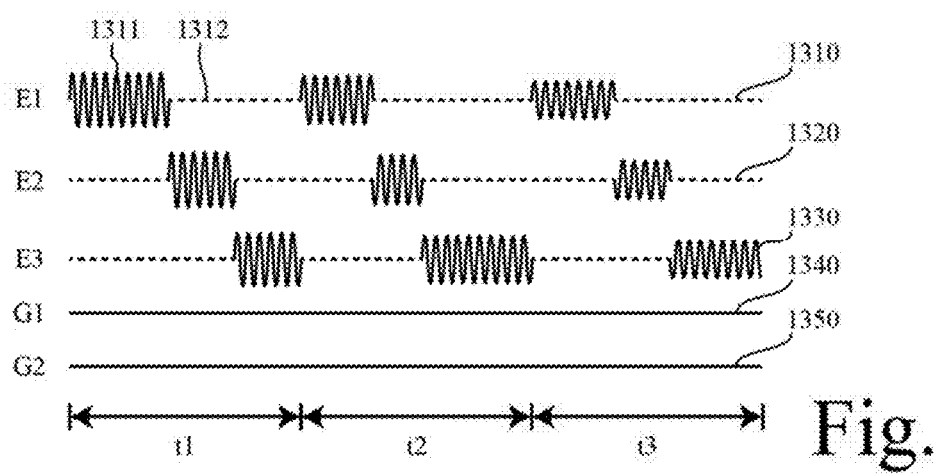
FIG. 13 is a schematic diagram showing the electrical signal applied to each of multiple electrodes energized in a monopolar configuration, wherein an RF ablation signal is applied to each electrode, current from the electrodes are carried by multiple ground pads, the ground pads are constantly a generator reference potential, and no electrode is energized at the same time.
Figure 14:
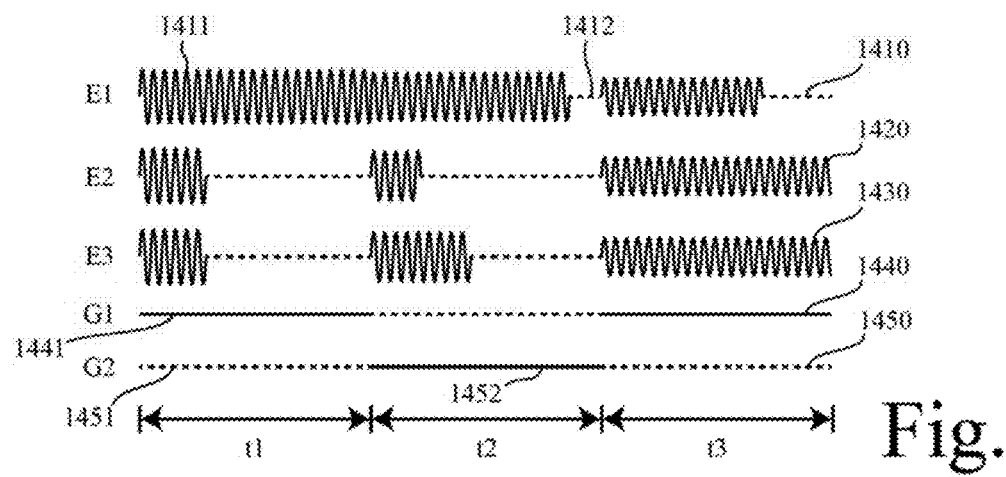
FIG. 14 is a schematic diagram showing the electrical signal applied to each of multiple electrodes energized in a monopolar configuration, wherein an RF ablation signal is applied to each electrode, current from the electrodes are carried by multiple ground pads, electrodes are energized at the same time, and current from the electrodes is carried by the ground pads alternately such that no ground pad carries current at the same time.
Figure 15:
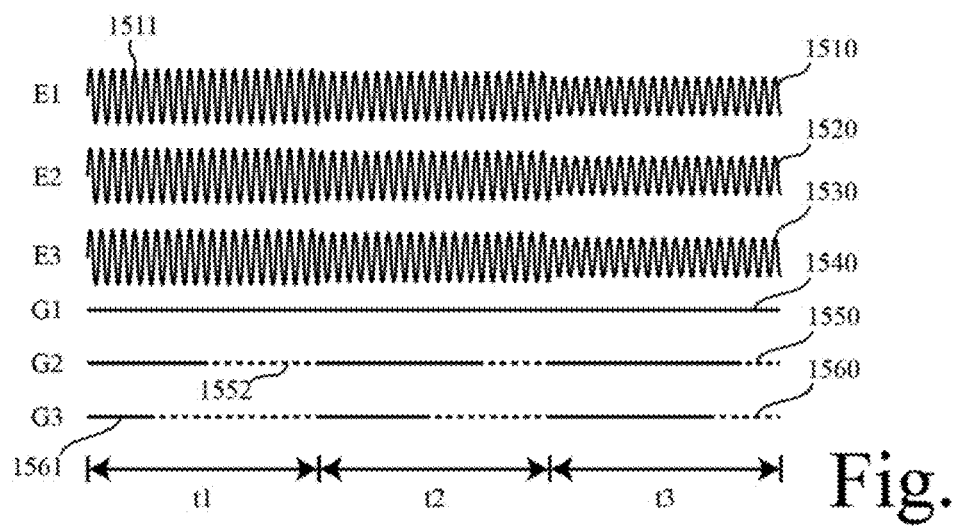
FIG. 15 is a schematic diagram showing the electrical signal applied to each of multiple electrodes energized in a monopolar configuration, wherein an single RF ablation signal is applied to multiple electrode at the same time, current from the electrodes are carried by multiple ground pads, and current from the electrodes is carried by the ground pads in a nested-simultaneous switching pattern.
Figure 16:
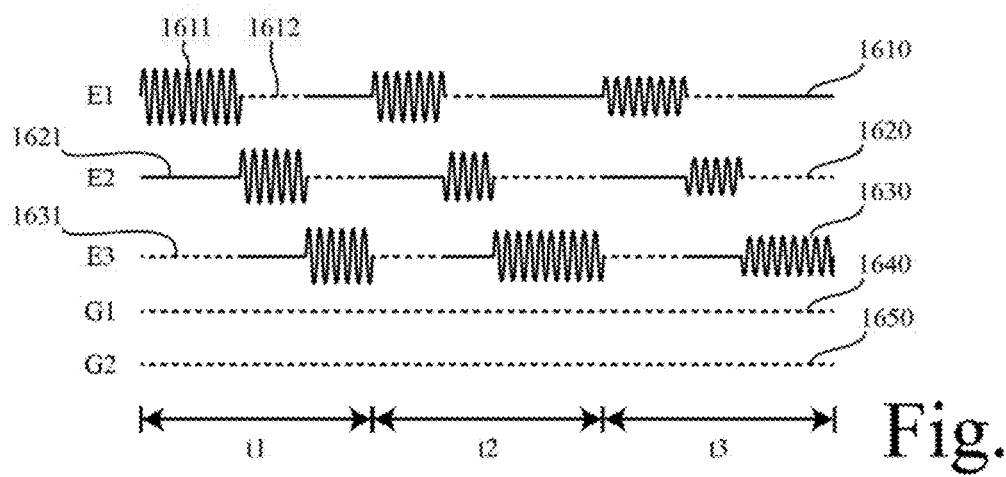
FIG. 16 is a schematic diagram showing the electrical signal applied to each of multiple electrodes energized in a sequential bipolar configuration, wherein at any given time, two electrodes carry return currents from the other without the use of a ground pad.
Figure 17:
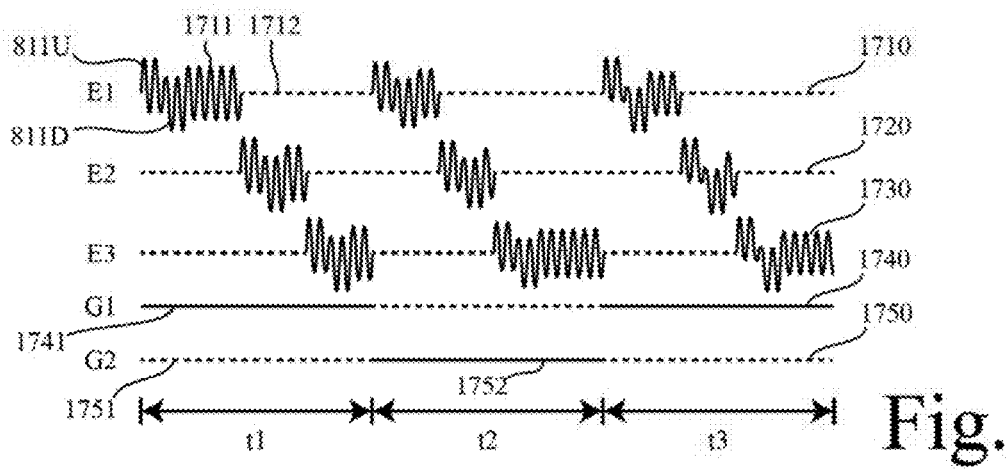
FIG. 17 is a schematic diagram showing the electrical signal applied to each of multiple electrodes energized in a sequential monopolar configuration wherein only one electrode is energized at a time and a ground pad carries return current from the electrode, and wherein and RF signal and a stimulation signal is applied to an electrode at the same time.
Figure 18:
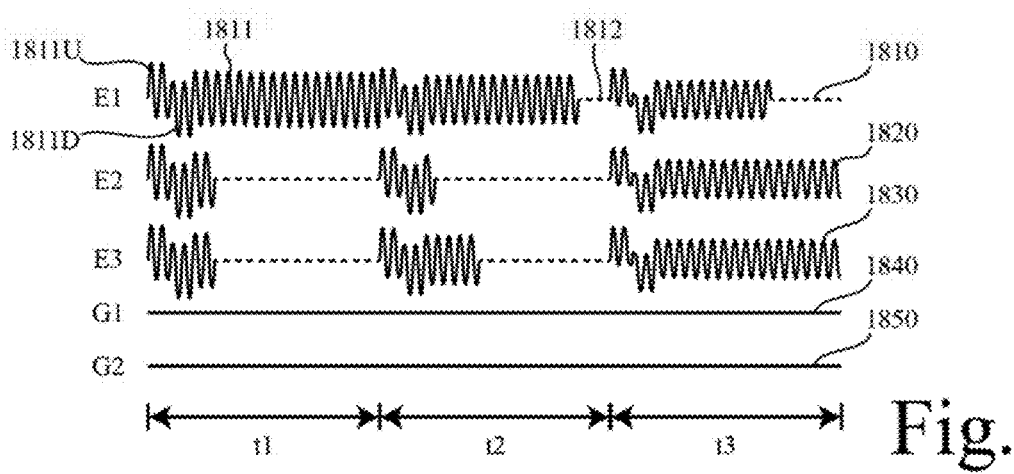
FIG. 18 is a schematic diagram showing the electrical signal applied to each of multiple electrodes energized in a monopolar configuration wherein more than one electrode is energized at the same time multiple ground pads carry return current from the electrodes, and wherein and RF signal and a stimulation signal is applied to an electrode at the same time.

FIG. 13 presents one example of a monopolar non-concurrent switching pattern, wherein one or more ground pads carry return currents from each electrode, and wherein no two electrodes are energized at the same time. FIG. 14 presents one example of a monopolar concurrent switching pattern, wherein one or more ground pads carry return currents from each electrode, and wherein one or more electrode are energized at the same time; this kind of pattern can be used to energize a cluster of electrode with individual control of the output to each electrode, for example to control each electrode's temperature or impedance. FIG. 15 presents one example of a monopolar concurrent pattern, wherein one or more ground pads carry return currents from each electrode, and wherein all electrodes are energized at the same time; this kind of pattern can be used for cluster ablation. FIG. 16 presents one example of a bipolar (or "dual") non-concurrent switching pattern, wherein ground pads are not used, wherein electrodes carry return current for each other, and wherein pairs of electrode are energized at different, non-overlapping times. In each time period t1, t2, t3, first current flows between electrodes E1 and E2, then current flows between electrodes E2 and E3, and then current flows between electrodes E3 and E1. In other embodiments of bipolar non-concurrent switching patterns, more than one electrode can carry return currents from one or more electrode, and order and composition of energized groups of electrode can change. FIG. 17 presents one example of a monopolar non-concurrent switching pattern in which stimulation pulses are delivered at the same time as RF is delivered. In this example, one a biphasic square stimulation pulse is added to each burst of RF delivered to each electrode. FIG. 18 presents one example of a monopolar concurrent switching pattern in which stimulation pulses are delivered at the same time as RF is delivered. In this example, one a biphasic square stimulation pulse is added to each burst of RF delivered to each electrode. In some embodiments, a sequence of electrode switch states can include one or more of the patterns presented in FIGS. 13 through 18.

Referring now to FIGS. 13, 14, 15, 16, 17, and 18, several examples of sequences of ground-pad switch states for two or more ground pads are presented in schematic diagrams, in accordance with several aspects of the present invention. The ground-pads signal presented in these figures are examples of signals that can be generated by embodiments of generators 100, 200, 700, 800, 900, and 1000 during all or part of an ablation process. In some embodiments, the switching patterns presented are repeated throughout an ablation process. In each of the examples presented, at least ground pads are connected to the generator that produces the presented signals G1, G2 and, in some figures, G3. The switching patterns presented can be generalized to configurations including two or more ground pads. The duration of each time intervals t1, t2, t3 can be either the same or different, either pre-determined or not pre-determined, and either fixed or variable suit clinical needs. The duration of each time interval t1, t2, t3 can short relative to tissue responses so that the signals' effects closely approximate the effects of a smooth signal. In some embodiments, the durations of connection and disconnection between each ground pad and a generator potential can be varied to meet a clinical objective such as control of temperature for each ground pad, or for control of power, RMS current, or RMS voltage averaged over each interval t1, t2, t3, or over a number of intervals, for each ground pad. In some embodiments, time periods t1, t2, and t3 can represent control-update periods at the end of each of which ground-connection order and duration are updated. In some embodiments, the time schedule by which ground pads are switched is predetermined. In some embodiments, the time schedule by which ground pads are switched is not predetermined. In some embodiments, the time schedule by which ground pads are switched can vary, for example in response to measured parameters. In some embodiments, the RF source can be turned off during switching to prevent non-zero-mean voltage transients that can produce undesired nerve or muscle stimulation. In some embodiments, the signals can be produced by a single RF voltage source. In some embodiments, the signals can be produced by more than one RF voltage source.

FIG. 13 and FIG. 18 each presents one example in which one or more ground pads are constantly connected to a generator reference potential. FIG. 16 presents one example in which one or more ground pads are constantly disconnected from all generator potentials.

FIG. 14 and FIG. 17 each presents one example a non-concurrent switching pattern, wherein no two ground pads are energized at the same time. In some embodiments of non-concurrent ground pad switching patterns, the switching time schedule is predetermined. In some embodiments of non-current ground pad switching patterns, the switching time schedule is not predetermined. In some embodiments of non-current ground pad switching patterns, the switching time schedule can be variable, for example changing in response to measured parameters during an ablation process.

FIG. 15 presents one example a nested-simultaneous switching pattern wherein ground pads are turned off in an order, and then turned back on in the opposite order. The last ground pad to be turned off is the first ground pad to be turned back on. A given ground pad is not turned back on until all ground pads that were turned off after the given ground pad have been turned back on. In some embodiments, two or more ground pads can turn off at the same time. In some embodiments, two or more ground pads can turn on at the same time. In some embodiments of nested-simultaneous switching, the order in which ground pads are turned off and on is fixed. In embodiments of nested-simultaneous ground-pad switching wherein the order in which ground pads are turned off and on is fixed, there do not exist any two time instants in the switching sequence for which, in the first instant, a first ground pad is connected and a second ground pad is disconnected, and, in the second instant, the first ground pad is disconnected and the second ground pad is connected. In some embodiments of nested simultaneous switching, the order in which the ground pads are turned off can vary across switching cycles. For example, in one time interval the ground pads are shut off in the order G3, G2, G1, and in another time interval, the ground pads are shut off in the order G3, G1, G2. In some embodiments of nested-simultaneous ground pad switching patterns, the switching time schedule is predetermined. In some embodiments of nested-simultaneous ground pad switching patterns, the switching time schedule is not predetermined. In some embodiments of nested-simultaneous ground pad switching patterns, the switching time schedule can be variable, for example changing in response to measured parameters. In some embodiments of nested-simultaneous ground pad switching patterns, the switching time schedule is not predetermined, but is fixed based on measured parameters.

FIGS. 1, 2, 6, 7, 8, 9 and 10 each present examples of an ablation system wherein two or more ground pads can carry return currents from one or more ablation electrodes, wherein a switch between each ground pad and a generator potential (eg the reference potential) can be opened and closed to disconnect and connect the ground pad, respectively, wherein a sequence of ground-pad switch states can be produced by an automated controller, and wherein the current at each ground pad can be measured. A ground pad does not carry substantial current from any electrode when it is disconnected from all generator potentials, as in the case, for example, where all switches between a ground pad and generator potentials are open. A ground pad can be called "active" when it is connected to a generator potential by a closed switch or another substantially low-impedance connection. A ground pad can be called "inactive" when it is disconnected from all generator potentials by an open switch or another high-impedance connection.

Referring now to FIGS. 19, 20, 21, 22, and 23, several embodiments of methods for control of tissue heating by two or more ground pads are presented as flow charts, in accordance with several aspects of the present invention. In one aspect, these embodiments relate to the control of ground pad current by ground-pad switching. In one aspect, these embodiments relate to the control of ground pad temperature by ground-pad switching. In one aspect, these embodiments relate to the control of a parameter that depends on the ground-pad current by ground-pad switching, examples of such a parameter include, but are not limited to, the temperature of the ground pad, a temperature measured at the ground pad, the current carried by the ground pad, the RMS current carried by the ground pad over a time period, a moving average of the current carried by the ground pad, the heating power dissipated in tissue near the ground pad, the impedance between the ground pad an ablation electrode. In one aspect, these embodiments relate to reduction of ground-pad current. In one aspect, these embodiments relate to the reduction of ground-pad temperature. In one aspect, these embodiments relate to regulation of a parameter related to ground-pad current and/or ground pad heating. In some embodiment, the ground pads carry RF current.

Paragraph A: Given the total ablation current I produced by one or more ablation electrodes when at least one ground pad is active, a sequence of ground-pad switch states for N ground pads, and the current flowing through each ground pad during the duration of the sequence, can be characterized as follows, wherein that the total current I has approximately constant over the duration of the sequence. For embodiments in which the RF current is delivered to the one or more ablation electrodes, the total current I can be the RMS value of the RF current over the period of the RF carrier wave (eg 2 milliseconds for a 500 kHz RF signal). The sequence has M steps, wherein for step j=1, . . . , M, the switch state can be described by indicator variable $q_{ij}=1$ if ground pad i=1, . . . , N is active, and otherwise $q_{ij}=0$. There are $2^N$ possible switch states. Variable $p_{ij}$ is the proportion of the total current I that flows to pad i during step j, and has the constraints $0 \le p_{ij} \le 1$ and $p_{1j}+ \ldots +p_{Nj}=1$, for all i,j. Variable $p_{ij}=0$ if $q_{ij}=0$, and otherwise its value is affected by the bodily system, the placement of the ablation electrode, and the placement of it and other active ground pads in step j. The duration of step j is $t_j \ge 0$. The duty cycle for step j is $d_j=t_j/t$, where $t=t_1+ \ldots +t_M+t_S$ is the total sequence duration, and where $t_S \ge 0$ is optional switching time during which no electrode output is produced. The duty cycle has constraints $0 \le d_j \le 1$ and $d_1+ \ldots +d_M=1$, for all j. The current flowing to pad i in step j is $I_{ij}=I*p_{ij}$ and can have a maximum peak current constraint $I_{ij} \le I_{i,max}$, for all i,j in some examples. The RMS current flowing through pad i over the total duration of the sequence is $I_{i,RMS}=I*(d_1*p_{i1}^2+ \ldots +d_M*p_{iM}^2)^{1/2}$ and can have a maximum RMS current constraint $I_{i,RMS} \le I_{i,maxRMS}$ for all i. In some embodiments wherein the total current varies more generally over the sequence duration, the current flowing to pad i in step j is $I_{ij}=I_j*p_{ij}$, and the RMS current flowing through pad i over the total duration of the sequence is $I_{i,RMS}=(d_1*I_1^2*p_{i1}^2+ \ldots +d_M*I_M^2*p_{1M}^2)^{1/2}$, where $I_j$ is the total RMS electrode current is over step j. One advantage of an ablation method in which changes in the electrode output level are synchronized to changes in the state of ground pad switches is that measurement and optimization of parameters related to ground pad heating can be facilitated. One important advantage of these equations is that they describe parameters that are important influences on ground pad heating. One advantage of a ground-pad control system that measures the current flowing to each ground pad in two or more ground-pad switch configurations is that these equations can be used to adjust a ground pad switching sequence to optimize one or more parameters related to ground pad heating, without prior knowledge of the arrangement of the ground pads on the patient body. For embodiments in which it is desired to control the current over time intervals throughout an ablation process, these equations can be used for each time interval (which can be referred to as a "time window") to determine a ground pad switch sequence configured to control the current over the time interval, including control of the maximum current over the time interval, or control the average RMS current over each time interval; examples of time intervals include a sliding time window, a moving time window, regular time intervals, time intervals formed by partitioning the duration of an ablation process, time intervals that are short relative to the thermal response of the ground pads, time intervals whose durations are less and 1 second, time intervals whose durations are less than 5 seconds, time intervals whose durations are less than 10 seconds, time intervals whose durations are less than 15 seconds, time intervals whose durations are less than 20 seconds, time intervals whose durations are less than 30 seconds, time interval whose durations are greater than 30 seconds. Another advantage of a ground-pad control system that measures the current flowing to each ground pad in two or more ground-pad switch configurations is that these equations can be used to adjust the identity of the switch states, the order of the switch states, and/or the timing of switch states of a ground pad switching sequence to program a controller to automatically optimize one or more parameters that are influenced by an average current (such as an RMS current) delivered to one or more of two or more ground pads, based on measurements of the current flowing through each ground pad, without manually programming the physical arrangement of the ground pads into the controller. Another advantage of a ground-pad control system that measures the current flowing to each ground pad in two or more ground-pad switch configurations is that these equations can be used in the programming of an automatic controller of a system for tissue ablation to equalize current distribution among all ground pads, using measurement of ground pad currents. In one example, by measurement of all ground-pad current portions $p_{ij}$ for a given switching sequence $\{q_{ij}\}$, the above equations can be used by the automatic controller of an ablation system to determine whether RMS ground-pad currents can be equalized (meaning $I_{i,RMS}=I_{k,RMS}$ for all i,k) for some selection of step times $t_1, \ldots, t_M$, and if so, then to determine the value of the equalized RMS currents $I_{i,RMS}$. Furthermore, these equations can be used by a RF-generator controller to select automatically the sequence $\{q_{ij}\}$ among all possible sequences that produces the smallest equalized RMS currents $I_{i,RMS}$. One advantage of a ground-pad switching process that produces a nested-simultaneous sequence of ground-pad connections by activating all pads in the first step, and deactivating the highest-current pad in each subsequent step until only one pad is active in the final step, is that the process can executed by the automatic controller of an RF ablation system to equalize RMS ground-pad currents for a variety of ground pad configurations, because it produces a full-rank lower-triangular matrix $[I_j^{2}*p_{ij}^{2}]$ for which $I_{RMS}=(d_1*I_i^{2}*p_{i1}^{2}+ \ldots +d_M*I_M^{2}*p_{1M}^{2})^{1/2}$ can be solved for some value $I_{RMS}$ with $0 \leq d_j \leq 1$ and $d_1+ \ldots +d_M=1$, for all j, for variety of ground pad configurations, where the ground pads have been labeled such that ground pad i is deactivated in the (i+1)-th step without loss of generality.

Figure 19:
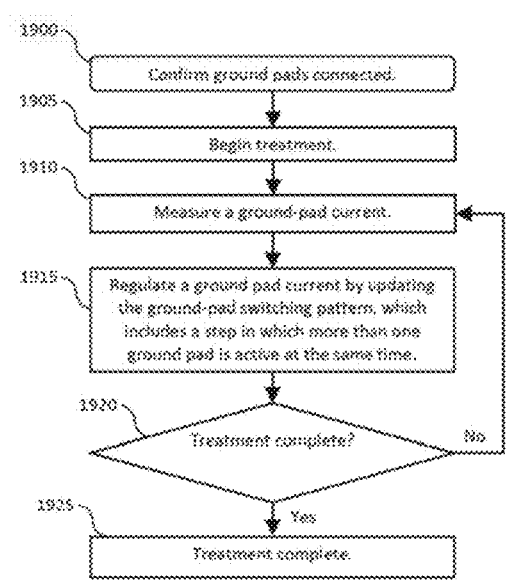
FIG. 19 is a flow chart that shows a method for regulating the electrosurgical current flowing through at least two ground pads comprising: switching the current among subsets of the ground pads; adjusting the pattern in which current is switched among subsets of the ground pads; wherein more than one ground pad each carry a portion of the current at the same time.

Referring now to FIG. 19, one embodiment of a method for control of tissue heating by two or more ground pads is presented as a flow chart, in accordance with several aspects of the present invention. In one aspect, FIG. 19 relates to a ground-pad switching sequence configured to regulate a measured ground-pad current, wherein more than one ground pad is connected to a power supply (such as a radiofrequency signal generator) at same time. In one aspect, FIG. 19 relates to a ground-pad switching sequence which is configured to regulate the RMS current of each of two or more ground pads, and in which more than one ground pad is connected to an electrical signal generator at same time. In the first step 1900, it is confirmed that all ground pads are connected. In one embodiment, this can be confirmed by detecting a non-zero current on each ground pad when the electrode is conducting a current. In one embodiment, the generator can activate only one ground pad at a time, and confirm that both the electrode and the ground pad conduct the same non-zero current. In step 1905, an ablation program is started and the controller starts producing a ground-pad switching pattern, which can be a single sequence of ground pad switch states, or a sequence of repeated ground pad switch states. A switching pattern for a ground pad can be produced by alternately opening and closing a switch that connects the ground pad to the output pole of an electrical power supply. The switching pattern can include a time period in which only one ground pad is active. The switching pattern can include a time period in which two or more ground pads are active at the same time. The switching pattern can include a time period in which all ground pads are connected. The switching pattern can include a subsequence of ground-pad switch states that is repeated at regular time intervals, wherein in each subsequence, the duration of each configuration of ground-pad switch states is adjustable to meet an objective, such as control of a time average of the current flowing through a ground pad over the duration of each subsequence. Generally, a "time average" or "time-average" of a value is the average of the value with respect to time over a time interval or time intervals. The switching pattern can include a sequence of at least two steps, wherein during each step, a subset (meaning "a set each of whose elements is an element of an inclusive set") of the ground pads is connected to an electrical signal generator, and ground pads not included in the subset, if any, are disconnected from the electrical signal generator; and wherein subset of a first step includes at least one element that is not contained in the subset of a second step. The switching pattern can include a sequence of at least two steps, wherein during each step, a subset of the ground pads is connected to an electrical signal generator, and the remaining ground pads are, if any, are disconnected from the electrical signal generator; and wherein ground pads connected in a first step are different from the ground pads connected in a second step. The switching pattern can include a sequence of at least two steps, wherein during each step, the controller selects which ground pads are connected to a power supply and which ground pads are disconnected from the power supply; and wherein at least one of the ground pads connected in a first step is not connected in a second step. Note that "all of the ground pads" is one example of "a subset of ground pads". In step 1910, the generator can measure one or more individual ground-pad currents during each of the one or more ground-pad-switch configurations in the pattern. In some embodiments of step 1910, the generator can measure one or more of the following: a ground-pad temperature, a ground-pad current, a ground-pad voltage, a ground-pad power, a measurement of tissue heating near a ground pad. In some embodiments of step 1910, the current flowing collectively to a group of ground pads can be measured. In step 1915, the generator adjusts the ground-pad switching pattern. One or more aspects of the pattern can be varied by a controller for the purpose of regulating a measured ground pad current, wherein the aspects can include the identity of the switch states included in the pattern, the order of the switch states included in the pattern, and the duration of each switch state included in the a pattern. One or more these aspects can be predetermined. One or more these aspects can be fixed. One or more these aspects can be determined in response to a measurement, and then fixed afterwards. The switching pattern can be varied to minimize the number of changes in ground-pad switch states in response to a measurement of ground pad current. The switching pattern can be varied to minimize the number of active ground pads. The switching patterns can be a sequential switching pattern. The switching pattern can be a nested-simultaneous switching pattern. The switching pattern can be a nested-simultaneous switching pattern wherein a higher-current pad is inactivated before a lower-current pad. In some embodiments, the generator controller can include an automatic solver for equations of Paragraph A in order to automatically regulate the current flowing through each of two or more ground pads based on measurements of the current flowing through each of said two or more ground pads; wherein automatic solvers can be programmed using algebraic, closed-form, iterative, or other methods for solving to linear and non-linear equations that are familiar to one skilled in the art of linear algebra, optimization, search, and computer algorithms. Regulating a measured ground pad current can include one or more of the following: holding one or some or all ground-pad currents below a limit, holding one or some or all RMS ground-pad currents over a sliding time window below a limit, holding one or some or all ground-pad peak currents below a limit, minimizing one or some or all ground-pad currents, minimizing one or some or all RMS ground-pad currents over a moving time window, minimizing one or some or all peak ground-pad currents, equalizing one or some or all ground-pad currents, equalizing one or some or all RMS ground-pad currents over a moving time window, reducing the number of ground-pad switch changes, increasing the number of active ground pads, minimizing one or some or all peak ground-pad currents, regulating a parameter that is a influenced by a ground pad current, regulating a temperature for one or some or all ground pads, regulating a power for one or some or all ground pads, regulating a voltage for one or some or all ground pads, regulating the ablation electrode output level, and regulating the current, voltage, power, output level of one or more ablation electrodes, wherein "holding below a limit", "minimizing", and "equalizing" can be performed in relation to a time window, moving time window, or to the entirety of the ablation program. In some embodiments, the duration of the time window for regulation of a current is configured to be short relative to the time-constant of tissue heating due to current density at or near a ground pad. A "sliding" or "moving" time window can be a time window that at any given moment (such as the present time, or the moment at which a moving average is assessed), the time window includes a time segment starting at the given moment minus the duration of the time window, and finishing at the given moment. An average over a moving time window can be referred to as a "moving average". An RMS average over a moving time window can be referred to a "RMS moving average", and is one example of a moving average. For embodiments in which the ground-pad switching pattern includes a repeated sequence of ground pad switch states, the moving average of a parameter being controlled (such as the RMS moving average of ground pad current) by the switching pattern can be computed over each repetition of the sequence; this is one example of a moving average that is synchronized to the switching sequence. In step 1920, if the ablation program is complete, the process terminates in step 1925, but if the ablation program is not yet complete, the process returns to the measurement step 1910 to continue updating the switching pattern in step 1915. The frequency with which the switching pattern is adjusted by repeated visits to step 1915 can be configured to provide for regulating a measured ground pad current. For example, the time intervals between visits to step 1915 and adjustments of the switch pattern in each visit to step 1915 can be configured to be short relative to the speed of the thermal response of a ground pad whose current is being regulated. For example, the time intervals between adjustments of the switching pattern in step 1915 can be less than 1 second, less than 2 seconds, less than 5 seconds, less than 10 seconds, less than 15 seconds, less than 20 seconds, less than 30 seconds, or greater than 30 seconds. For example, the time intervals between adjustments of the switching pattern in visits to step 1915 can be synchronized to the time intervals over which the average of a ground-pad current (such as the RMS value of the ground-pad current) is measured for the purpose of regulating that average. For example, the measurement and adjustment time intervals can be identical. For example, a whole number of the measurement time intervals make up on adjustment time interval.

In some embodiments of measurement step 1910, one or some or all active ground-pad currents can be measured during an exploratory switch configuration, and those measurements can be used to optimize the switching sequence. For example, an exploratory switch configuration can be brief and configured to have limited effect on regulated parameters. For example, an exploratory switch configuration can be produced during the down time of an ablation electrode control program, wherein the total current is too small to increase any ground pad temperature. For example, all possible switch configurations can be explored during a down time in order to perform a global optimization of the switching sequence.

Figure 20:
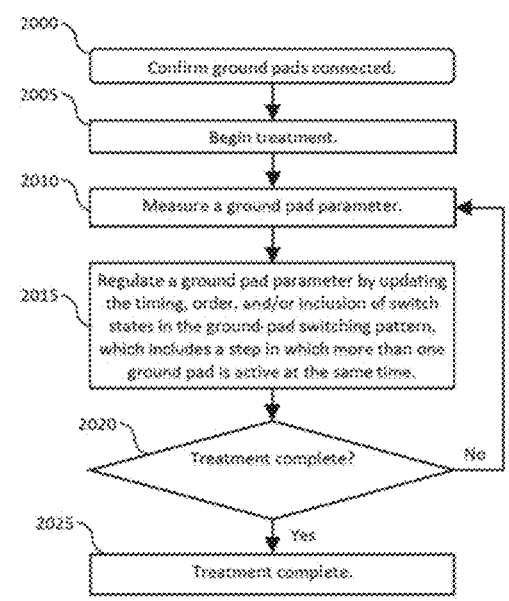
FIG. 20 is a flow chart that shows a method for regulating a parameter of at least one of at least two electrosurgical ground pads comprising: switching the current among subsets of the ground pads in a pattern having a timing and order of switch states; adjusting timing, order, and/or inclusion of switch states in the pattern; wherein the pattern includes at least one switch state in which a first ground pad carries a first portion of the current, and a second ground pad carries a second portion of the current, at the same time.

Referring now to FIG. 20, one embodiment of a method for control of tissue heating by two or more ground pads is presented as a flow chart, in accordance with several aspects of the present invention. In some embodiments, a ground-pad parameter can be one or more parameters selected from the list: temperature, current, voltage, power. Some embodiments of the method presented in FIG. 19 can be an embodiment of the method presented in FIG. 20. In step 2000, system can confirm that the ground pads are connected, for example by checking a ground-pad contact current, checking that current flows to the ground pad, or checking that the ground pad produces a temperature measurement. In step 2005, an ablation electrode produces output, for example for tissue ablation, the generator controller switches return currents from the electrode to two or more ground pads in a switching pattern. In step 2010, a parameter for one or more ground pads is measured, wherein the parameter can be one or more of the items selected from the list: temperature, current, voltage, power. In step 2015, the automatic controller updates the switching pattern in response to one or more ground pad measurements. The updating process can include both adjustment of timing of the switch configurations of the pattern, as well as the switch configurations included in the pattern. In step 2020, it is checked whether the electrode ablation program is complete. If so, the ground pad switching pattern stops in Step 2025, and otherwise the process repeats in step 2010.

In one embodiment of the method of FIG. 20, measured ground pad temperatures are regulated in a fully automatic process that can adapt to a variety of ground pad setups, including setups that differ in the number of ground pads and the arrangement of ground pads on the patient body. In this example, each ground pad includes a temperature sensor. In step 2005, all ground pads are active. In measurement step 2010, the temperature each ground pad is measured. In step 2015, cycle period is set, which can be a fixed value or a value that is varied in response to measurements. For each ground pad, the controller uses a feedback controller (such as a PID controller, bang bang controller, or another standard controller) to update the proportion of time during the upcoming cycle period that the ground pad is active in order to regulate the ground pad temperature. For example, the temperature can be held at a value below a temperature capable of inducing thermal tissue damage, such as 43 deg C. In some embodiments, the controller can additionally use a measurement of the electrode output level (voltage, current, and/or power) as an input to the feedback controller. In some embodiments, the controller can additionally use a measurement of the ground pad current as an input to the feedback controller. In some embodiments, additional measurements can be made at various times throughout the cycle in step 2015. The generator then generates a switching pattern during the cycle period wherein each ground pad is connected for the proportion of time determined by its feedback controller. In one embodiment, each cycle starts with all ground pads active, and each ground pad turns off at the time specified by its individual feedback controller. This forces ground pads to be active at the same time, which advantageously reduces ground pad heating by distributing current to multiple pads at the same time. If all ground pads reach their control value, there will be a time period in a cycle during which no ground pad is attached and therefore no current flows out of the ablation electrode output. This condition can be allowed to persist, or it can prompt a user warning or error condition. In some embodiments, in some cases, if the overlapping pattern will produce a period in which no ground pads are active, the controller can shift the active times for the ground pads to ensure one ground pad is connected at all time.

Figure 21:
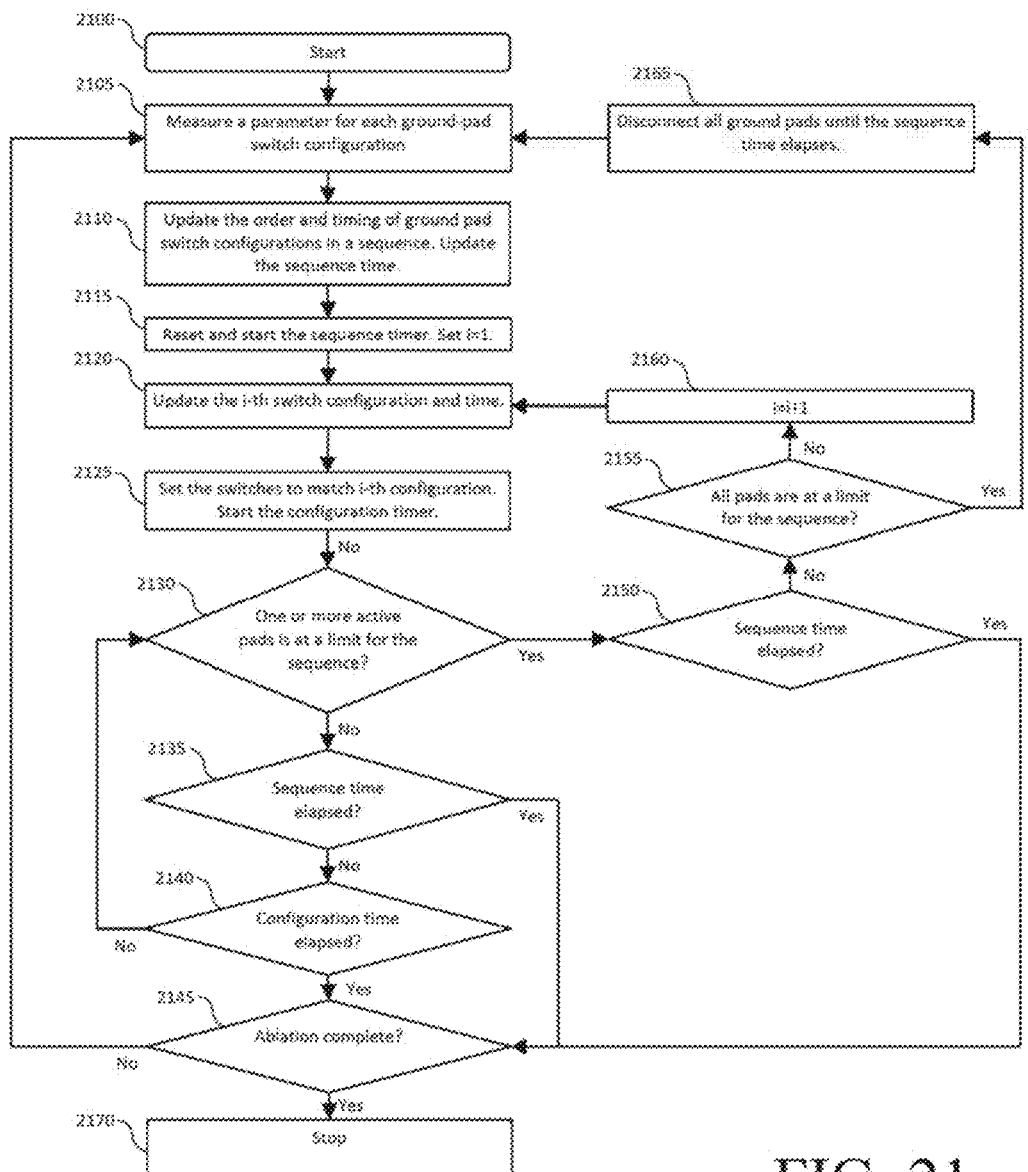
FIG. 21 is a flow chart that shows a method for regulating a parameter of each of at least two ground pads carrying return current from at least one ablation electrode connected to a current source, comprising: producing a sequence of switch configurations, in each configuration of which some or all ground pads are connected to the current source, and the other ground pads are disconnected from the current source; measuring a parameter for each ground pad in each configuration; updating the order and timing of the switch configurations based on the measurements.

Referring now to FIG. 21, one embodiment of a method for limitation of tissue heating by two or more ground pads is presented as a flow chart, in accordance with several aspects of the present invention. The method presented in FIG. 21 can be an embodiment of the method presented in FIG. 20. The ablation process starts in step 2100. In one aspect, the method presented in FIG. 20 is a ground-pad switching method that includes optimization of a switching sequence and timing that is computed either before a switching sequence is executed (step 2110), or while a switching sequence is ongoing (step 2120), or both. Computation in step 2110 can provide for global optimization of sequences parameters. Computation in step 2120 can provide for optimization of sequence parameters as additional, refined, or updated measurements are made during execution of the switching sequence. In some embodiments, the measurements in step 2105 are omitted, only performed conditionally, or only performed only as needed for either step 2110 or for step 2120 or for both. In some embodiments, measurements in step 2105 are performed only once, only at the on the initial visit to step 2105, only intermittently, only during ablation program down times, only when measured parameters differ substantially from those previously used to optimize sequence parameters, or only when needed for subsequent update of switching parameter in step 2110. In some embodiments, the update in step 2110 is omitted or only performed conditionally. In some embodiments, the update in step 2120 is omitted or only performed conditionally. In some embodiments, some parameters of a switch sequence can be fixed in the first visit to step 2110, and other parameters are updated by step 2120 throughout the ablation program. For example, in some embodiments, on the first visit to step 2110 the identity and order of switch configurations to be included in all subsequent sequences can be fixed, and step 2120 only determines the timing for each pre-set configuration. Step 2115 is the start of a switching sequence of switch states. Operations 2115, 2120, 2125, 2130, 2135, 2140, 2145, 2150, 2155, and 2160 produce the switching sequence. Each repetition of these steps produces another switching sequence. A switching sequence can include a step in which two or more ground pads are active at the same time. The switching sequence can include a step in which only one ground pad is connected. The ground-pad currents during the switching sequence can be described by the equations in Paragraph A. Step 2130 can provide for an process that changes switch configurations when a limit is reached, such as, for example, when a ground pad reaches the RMS current limit for the expected sequence duration. This can provide for minimization of the number of switch changes. This can provide for maximization of time spent in a desired configuration, such as a configuration in which more ground pads are active so that current is more distributed among pads. Step 2150 checks whether the sequence duration has reached its set value at the same time as a ground pad limit was detected in step 2130. Step 2155 checks whether all pads are at a limit. If not, the sequence advances to the next switch configuration in step 2160. If so, the all ground pads are disconnected in step 2165 to prevent them from exceeding the limit. Step 2165 will discontinue the flow of current through ablation electrodes that is configured to be carried by a ground pad, and thus reaching step 2165 can be an indication that the electrode current is too high to be carried by the existing ground pad configuration. The generator can warn the user about this situation, reduce the electrode output level, and/or discontinue the ablation program. In one example, step 2155 can check whether all ground pads have already carried so much current during the sequence that they would exceed their RMS current limit were any pad to continue being active for during the remainder of the sequence duration. Step 2135 provides for termination of a switching sequence based on a set value for the sequence duration. This can provide for returning to desired configurations at the beginning of the sequence that were temporarily discontinued due to a ground pad exceeding a limit. Step 2140 can provide for limiting the duration of a configuration to a desired value, for example, to regulate a measured value. For example, a sequence of configurations and durations can be computed in step 2110 or 2120 to equalize the RMS current of all ground pads over the sequence duration. Step 2145 checks if the ablation process is complete. If the ablation process is complete, the process stops in Step 2170. If the ablation process is not complete, the ground-pad control process continues in Step 2105.

Figure 22:
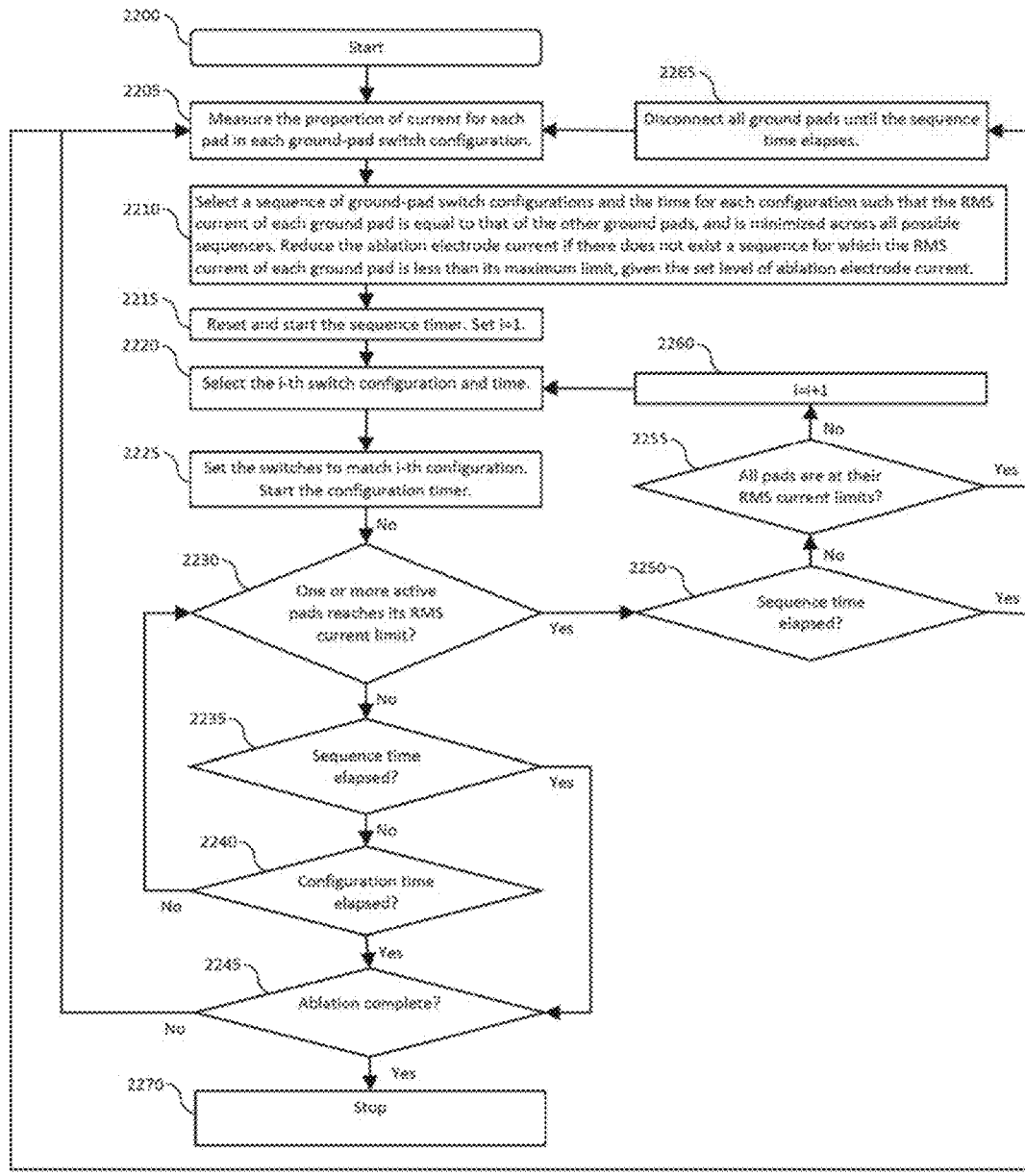
FIG. 22 is a flow chart that shows a method for equalizing and reducing the current flowing through each of at least two ground pads carrying return current from at least one ablation electrode connected to a current source, comprising: producing a sequence of switch configurations, in each configuration of which some or all ground pads are connected to the current source, and the other ground pads are disconnected from the current source; measuring the current flowing through each ground pad in each configuration; updating the order and timing of the switch configurations to equalize the RMS currents flowing through each ground pad based on the measurements.

Referring now to FIG. 22, one embodiment of a method for limitation of tissue heating by two or more ground pads is presented as a flow chart in accordance with several aspects of the present invention. The method presented in FIG. 22 can be an embodiment of the method presented in FIG. 21 wherein the RMS current carried by each ground pad is equalized and minimized by measurement of the current flowing through each ground pad in each of multiple switch configurations. In some embodiments, the identity and order of the switch configurations is updated only intermittently, and otherwise fixed through multiple sequence cycles, in each of which the timing of the sequence steps are updated to equalize the RMS ground pad currents. In some embodiments, the identity and order of the switch configurations is updated only once (for instance at an initial time when the output level is very low, before the ablation electrode output voltage is raised to level configured to ablate tissue at the ablation site), and otherwise fixed through multiple sequence cycles, in each of which the timing of the sequence steps are updated to equalize the RMS ground pad currents. The ablation process starts in step 2200. In the first visit to step 2205, when the electrode current is at a low level not expected to heat any ground pad even if it is the only active pad, the current is measured for each ground pad in all $2^N$ switch configurations, where N is the number of ground pads. In some embodiments, this step is only repeated if measured currents vary substantially during the lesion process. In first visit to step 2210, using the data from step 2205 and equations from Paragraph A, the space of all configuration sequences is searched to determine the sequence order and timing that produces the minimum balanced distribution of RMS current among the ground pads over a time window. If no such configuration exists because the electrode output level is too high, the electrode current is reduced to a level that the ground pad currents can carry. In some embodiments, the user can be notified that the number of ground pads must be increased to meet the demands of the ablation program. In some embodiments, because the space of all ground-pad switching sequences can be very large, the search over sequences can be limited to sequences that are likely to produce an optimal or near optimal balanced value, and redundant or degenerate sequences can be omitted. For example, given the four-ground-pad setup described in Paragraph B, the process in step 2210 can select between the "second nested-simultaneous switching pattern" and the "sequential switching pattern" on the basis of the equalized ground-pad RMS current that each pattern produces by means on the calculations described in Paragraph B. In subsequent visits to step 2210, in some embodiments, if the ground pad currents in each configuration have not changed substantially since the first visit to step 2210, only the timing of the sequence of configurations is updated as a function of the electrode current, and the electrode current is reduced if the ground pad RMS current capacity is exceeded. No computation is done in step 2220, only selection of sequence parameters determined in step 2210. Steps 2230 and 2255 provide a failsafe against over-current conditions due to variations in actual current distribution from sequence to sequence. Step 2240 implements the switching sequence timing in accordance with the configuration times determined in step 2210. Step 2245 checks if the ablation process is complete. If the ablation process is complete, the process stops in Step 2270. If the ablation process is not complete, the ground-pad-control process continues in Step 2205.

Figure 23:
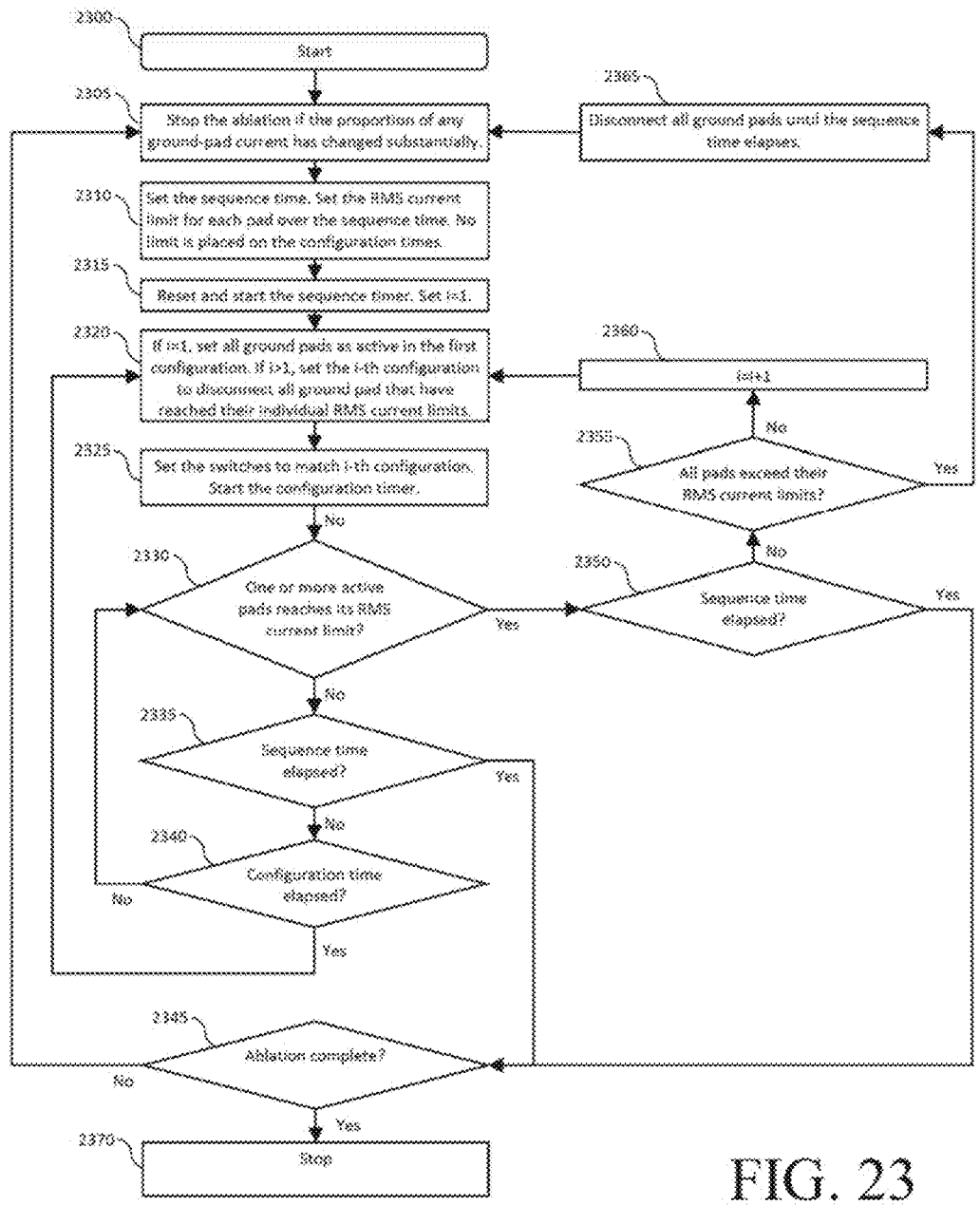
FIG. 23 is a flow chart that shows a method for holding below a limit the current flowing through each of at least two ground pads carrying return current from at least one ablation electrode connected to a current source, and for increasing the amount of time when more ground pads carry current at the same time, comprising: producing a sequence of switch configurations, in each configuration of which some or all ground pads are connected to the current source, and some ground pads are disconnected from the current source; measuring the current flowing through each ground pad in each configuration; disconnecting a ground pad when its measured RMS current reaches the limit.

Referring now to FIG. 23, one embodiment of a method for limitation of tissue heating by two or more ground pads is presented as a flow chart, in accordance with several aspects of the present invention. The method presented in FIG. 23 can be an embodiment of the method presented in FIG. 21 wherein the method is configured maximize the time in which more ground pads are active at the same time. The ablation process starts in step 2300. Step 2305 presents an example of a check on ground-pad skin adhesion wherein if a previously measured current changes substantially an error condition is produced. In step 2310, the sequence time is set, which in some embodiments, can be set to be fast relative to the time constant of ground pad heating dynamics. An RMS current limit is set for each ground pad. In some embodiments, including for example wherein the all ground pads are identical, this can be the same value for all ground pads. No limit is placed on the time for which each switch configuration is active during the sequence; this means that each configuration time is set to be effectively infinite so that step 2340 always follows it's "No" branch. Step 2315 starts a new ground-pad switching sequence. In the first visit to steps 2320 and 2325 in each sequence, all ground pads are connected. This configuration is maintained by steps 2330, 2335, and 2340 until either (1) the RMS current for a ground pad over the entirety of the switching sequence time (including both the time that has already elapsed during the present sequence and any future remaining time for the present sequence) is presently equal to its RMS current limit and will exceed that limit if any additional current is delivery to that ground pad during the remaining sequence time, or (2) the sequence time has elapsed. In case (2), step 2305 follows step 2335, the present switching sequence ends, and the next switching sequence begins. If case (1), step 2350 follows step 2330. Step 2350 proceeds to the next switching sequence if the present sequence time has elapsed. Step 2355 checks whether all ground pads must be deactivated. If so, all ground pads are held inactive in step 2365 until the sequence time has elapsed to prevent an over-RMS-current condition on some or all pads. If not, the sequence advances to the second switch configuration, for which steps 2320 and 2325 turn off the ground pad(s) that reached their RMS current limits during the first switch-configuration period, and the cycle will repeat. In each successive cycle wherein one or more ground pads reach the RMS current limit, the number of active ground pads is decreased. This continues until the sequence time elapses (step 2335 or 2350) or all ground pads are inactivated (steps 2355 and 2365), after which the next sequence begins with all ground pads active. By this method, during each sequence period, no ground pad substantially exceeds its RMS current limit. The method gives preference is given to ground pad switch configurations with more active ground pads. This can advantageously reduce the RMS ground pad currents by distributing current across multiple ground pads at the same time (even in cases wherein the distribution of currents is small due to the arrangement of ground pads, such as in the case where ground pads are placed along the length of a limb). In some embodiments of the method in FIG. 23, the controller can be configured to fix the i-th switch configuration after the first time it is set; in that case, this method will produce a nested-simultaneous sequence throughout the ablation process. In some embodiments, of the method in FIG. 23, the controller can compute the configuration time the i-th configuration in step 2320 based on previously measured distribution of ground-pad currents for the i-th configuration (such as, for example, by using equations of Paragraph A), and then use the configuration time as a limit in step 2340. Step 2345 checks if the ablation process is complete. If the ablation process is complete, the process stops in Step 2370.

If the ablation process is not complete, the ground-pad-control-process continues in Step 2305.

Referring now to FIGS. 19, 20, 21, 22, and 23, in some embodiments, a check for completion of the ablation program (eg 2145, 2245, or 2345) can be inserted at any location in the flow chart. In some embodiments, a check for ground pad connection and skin adhesion (for instance by observation of a change in the proportions of current distribution for a given switch configuration) can be inserted at any location in the flow chart. In some embodiments, a check for ground pad connection and skin adhesion can be omitted. In some embodiments, a controller implementing the ground pad switching method can access and use the state of the electrode output and/or the ablation-control controller.

Figure 24:
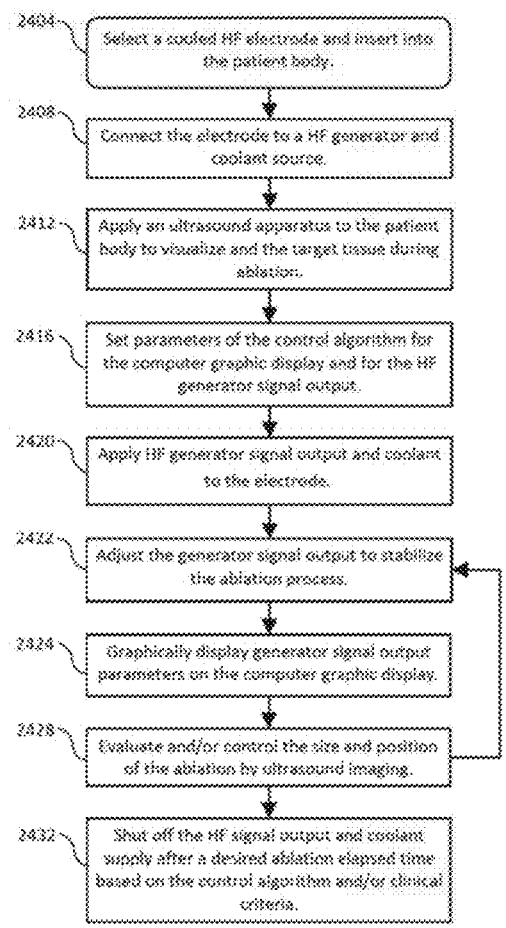
FIG. 24 is a flow chart that shows a method for control of a HF ablation process using an internally-cooled HF electrode, an automated controller, ultrasound imaging of the ablation process, and a real-time graphic display HF signal output parameters.

Referring now to FIG. 24, one embodiment of a method for HF tissue ablation is presented as a flow chart, in accordance with several aspects of the present invention. In one aspect, this method relates to the control of a HF ablation process using an internally-cooled HF electrode by means of an automated controller, graphic display of HF signal output parameters, and ultrasound imaging. In some embodiments, the FIG. 24 is a method for control of a HF ablation process using an internally-cooled HF electrode, an automated controller, ultrasound imaging comprising viewing the controlling both the ablation process parameters and ultrasound images of the ablation site on same control console. In some embodiments, the method can be performed using any one of the systems presented in FIGS. 1, 2, 6, 7, 8, 9, and 10. The method starts in step 2404 wherein an internally-cooled HF electrode is selected. The type and/or the size of the electrode can be selected. The electrode can be one of the following: In some embodiments, ablation probes 150, 150A, 150B, 150C, 160, can each be any one ore the following: cooled RF electrode, a cooled RF electrode inside an RF cannula, a cooled RF electrode with extension-tip temperature sensor, cooled RF electrode with lateral temperature sensor, cooled RF electrode temperature sensory on outer surface proximal to the active tip, perfusion RF electrode, cool-wet RF electrode, single-prong cooled RF electrode, multi-prong cooled RF electrode, cooled cluster RF electrode, a cooled RF cluster electrode with two electrode shafts, a cooled RF cluster electrode with three electrode shafts, a cooled RF cluster electrode with four electrode shafts, a cooled RF cluster electrode more than four electrode shafts, multiple RF electrodes of any of the aforementioned types, cooled MW ablation antenna, multiple cooled MW ablation antennae, a cluster MW antenna, and other type of HF ablation probes. Selectable parameters of the size of the electrode can include the active tip length, the active tip diameter, the prong geometry, the number of prongs, and other geometric and dimensional parameters. The electrode size can be selected as a function of one or more of the following parameters and data: the size of the target tissue volume, the size of a target tumor, the target tissue type, the type of a target tumor, the type of tissue surrounding or nearby a target tumor, imaging data of the target tissue, ultrasound imaging of the target tissue, intraoperative imaging data, preoperative image data. The electrode can be selected by the physician to fulfill a clinical objective. A computer system included in a HF generator can automatically recommend and/or select the electrode based on measured on provided parameters and/or measured data. For an RF electrode, one or more reference ground pads are applied to the patient skin to carry return current from the electrode. The number and type of ground pad(s) can be selected based on the electrode type, electrode size, target tissue characteristic, maximum expected generator output level, desired heat lesion size, and other parameters. In step 2408, the electrode is connected to the HF generator configured to deliver a HF electrical signal to the electrode, such as an RF generator or a MW generator. The electrode is connected to a coolant source, such a peristaltic pump delivering a fluid or a cryogenic coolant source. If present, the ground pads can be connected to the generator reference jacks. In step 2412, an ultrasound imaging apparatus is applied to the patient body and configured to image the target tissue in relation to the HF electrode. In step 2416, parameters of the controller for the computer graphic display of the generator and generator signal output are set. Some or all of these parameters can be set by the physician. Some or all of these parameters can be set by the generator controller based on one or more of the following: measurements, input provided by the physician, imaging data, ultrasound imaging data, the electrode type, the electrode size, the target tissue size, target tissue type, target tumor size, target tumor type, tissue type nearby the target tumor, the desired treatment time, the number of ground pads, ground pad characteristics, clinical objectives, and other factors. The computer graphic display can be adjusted depending on any or all of the aforementioned measurements, factors, and data, including the electrode type and size. The computer graphic display can display ablation parameters digitally and graphically, including parameters of the HF signal output, parameters of the electrode such as temperature and current, parameters of the ground pads such as temperature and current. Graphical display of the appropriate parameters can be an important factor for safe, effective, and efficient HF ablation. One advantage of graphical display of parameters in the form of a graph over time is that the physician can easily and quickly observe the stability or instability of the ablation process, error conditions that are transient or persistent, and other parameters of the ablation process. In one example, graphical display is important for monitoring of an ablation process that includes tissue boiling. In step 2420, the ablation process is initiated and HF signal output from the generator is delivered to the tissue by the electrode. In step 2422, the generator adjusts the electrode signal output to stabilize the ablation process. For this purpose, the generator can measure and/or regulate one or more of the following: electrode voltage, electrode current, electrode power, electrode temperature, electrode polarity, multi-electrode switching pattern, temperature probe measurement, ultrasound image data, measurements of heat lesion size, ultrasound image of bubble zone, ultrasound-derived temperature measurements. In step 2422, for an RF generator and electrode with two or more ground pads, the generator can adjust the ground pad configuration to regulate and/or limit ground-pad heating and/or fulfill another clinical objective. In some embodiments, the generator can open and close switches that connect each ground pad to the ground reference potential in a pattern over time that is configured to regulate the average current distribution among the ground pads, regulate measured ground pad temperatures, and/or reduce ground pad heating. In some embodiments, the generator can adjust a variable resistor in series with each ground pad to regulate current distribution across ground pads. In step 2424, the generator displays parameters of the generator signal output on the computer graphic display of the generator. Graphical plots of ablation parameters and ground pad parameters can be displayed over time to provide the physician with clear and rapidly understandable information about the ablation process. The graphical display can show rapid changes in the generator operating mode in response to measured parameters, such as transitions between up-time and down-times due to impedance spikes during a cooled HF ablation process. The graphical display can show intermittent irregularities in electrode and ground pad parameters that can be viewed and interpreted after they occur. The graphical history of such displays provides important context to the present and ongoing measured throughout the ablation process. In step 2428, ultrasound imaging data is presented to the physician to monitor the ablation process. For example, the physician can monitor the development of a bubble zone around a HF electrode, and observe its variations and their correlation to signal output variations. In some embodiments, the ultrasound data can influence the ablation process either by a manual process or an automatic process. For example, the physician can adjust controller parameters in response to measured ultrasound data. For example, the controller can automatically process ultrasound data by image processing techniques to assess lesion size, the rate of lesion size growth, maximum temperatures. For automated feedback, it is advantageous to have an ultrasound image either from a fixed location relative to anatomy, or registered to patient anatomy by a transducer position and orientation tracking system. The ablation monitoring and control process 2422, 2424, 2428 can repeat throughout the ablation process, until in step 2432, the HF output signal is shut off when the ablation process has operated for a desired amount of time. In some embodiments, the ablation time can be a preset value, for example based on the electrode type, a clinical objective, target tissue characteristics, desired lesion size, and other factors before the ablation process was started. In some embodiments, the ablation time can be determined by measurement of the progress of the ablation process, for example based on measurement of lesions size, measurements of HF signal parameters, timing parameters of the ablation control process, total delivered energy, the degree of decline in delivery energy during the ablation process, a measured temperature, a tissue temperature at a location distant from the electrode, and other parameters. In some embodiments, the ablation control processes of steps 2420, 2422, 2424, and 2428 can include one or more of the methods for control of HF ablation presented in FIGS. 3, 4, 5, 11, 12, 13, 14, 15, 16, 17, 18, 19, 20, 21, 22, and 23.

Figure 25:
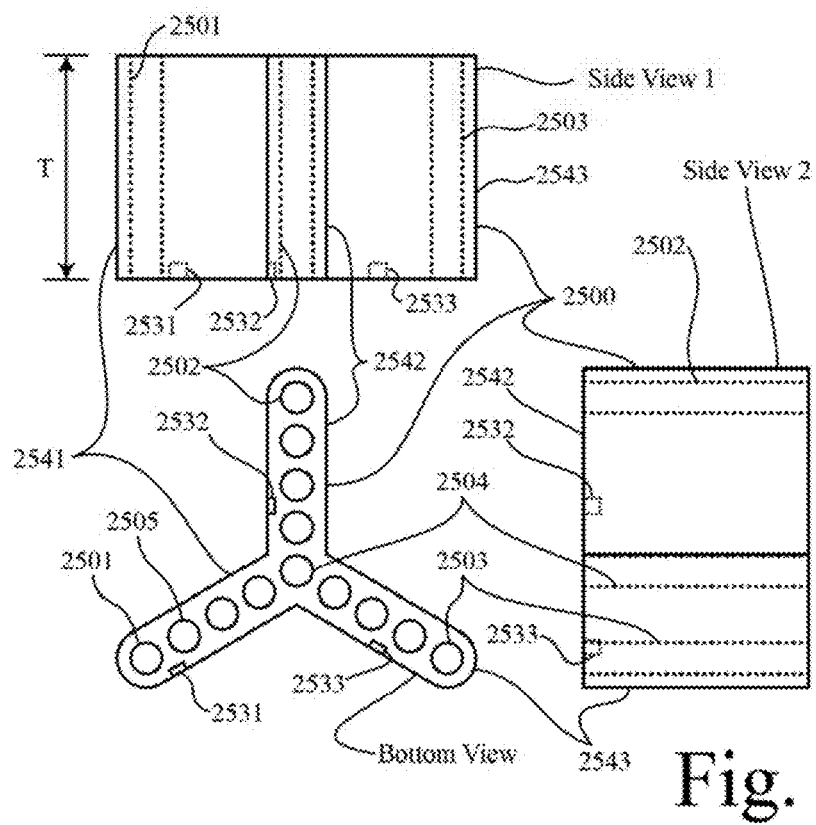
FIG. 25 is a schematic diagram showing, in three perpendicular views, an ablation-probe guideblock including a cross-section having three branches, at least one guidehole on each branch, and fiducial markers for determination of guideblock position and orientation relative to anatomy in a medical image; wherein the guideholes are parallel holes through the guideblock; wherein the guideblock can be used to guide two or more ablation probes, through two or more guideholes, into a body, in parallel, and in a linear, triangular, isosceles triangular, equilateral triangular, or another type of configuration to influence the shape of one or more ablation regions, to adapt to anatomical restriction, and/or to a suit clinical need; and wherein the guideblock has thin walls around the guideholes to reduce guideblock weight, to allow an ultrasound transducer to be positioned close to the shafts of the ablation probes at the surface of the body.

Referring now to FIG. 25, one embodiment of a guideblock 2500 for alignment of two or more ablation probes within a body is presented as a schematic diagram showing three perpendicular external views of the guideblock, in accordance with several aspects of the present invention. The guideblock 2500 is shown in a bottom view labeled "Bottom View", a first side view labeled "Side View 1", and a second second view "Side View 2". The guideblock 2500 includes thirteen guideholes, such as 2501, 2502, 2503, 2504, and 2505, which are mutually parallel, and each of which goes completely through the top-to-bottom thickness T of the guideblock and is configured to allow passage of an elongated HF ablation probe, such as an RF electrode or cannula, through the guideblock thickness T with sufficiently close clearance (for example, in the range 0.001-0.004 inches) to hold parallel multiple probes each passing through one of multiple guideholes as the probes are inserted into a body (for example 190 in FIG. 1) for the purpose of tissue ablation. In some embodiments, the guidehole diameter is increased to increase the clearance between the ablation probe and the guidehole (for example, greater than 0.004 inches) to allow the physician more flexibility in orienting and positioning the ablation probe, so that the position of the ablation is less restricted by the block 2500; in these embodiments, the ablation probes are inserted in a non-predetermined configuration. In FIG. 25, each guidehole (eg 2501) is configured to admit and align a 15-gauge ablation probe shaft. In other embodiments, each guideholes (eg 2501) can be sized to admit and align probes with a shaft diameter selected from the range 23 to 10 gauge. In FIG. 25, the thickness T is 15 mm. In other embodiments, the thickness T of the guideblock can be in the range 1 to 30 mm or more. In other embodiments, a lesser thickness T can be used to reduce guideblock size, to allow for deeper probe penetration in tissue, and/or to allow for more physician flexibility in orienting ablation probes passing through the guideholes (eg 2501) since a thinner block can be less restrictive of probe orientation and probes can be inserted in a non-predetermined configuration. A physician may desire more flexibility in probe orientation to suit clinical needs, target a variety of anatomical structures with the ablation probes, to shape or extend the lesion zone or zone, and/or to avoid anatomical hindrances through which ablation probe should not or cannot pass, such as delicate structures or hard structures like the ribs. In other embodiments, the thickness T can be increased to more constrain the orientation of ablation probes. All of the guideholes are shown in the Bottom View. Only the guideholes 2501, 2502, 2503 are shown in Side View 1, each through hole shown as a pair of parallel dashed lines going through the thickness T of the block 2500. Only the guideholes 2502, 2503, 2504 are shown in Side View 2, each through hole shown as a pair of parallel dashed lines going through the thickness T of the block 2500; one of the dashed lines for hole 2504 overlapping the solid line of another feature of the guideblock 2500. The guideblock 2500 provides for alignment of between two and thirteen (inclusive) ablation probes and/or satellite temperature sensors in a variety of parallel-probe configurations. For example, three ablation probes can be inserted through holes 2501, 2502, 2503 (one probe in each hole) to produce a parallel, equilateral-triangle configuration, wherein the inter-electrode spacing is 20 mm. For example, three ablation probes can be inserted through holes 2501, 2502, 2505 (one probe in each hole) to produce a parallel, isosceles-triangle configuration. Block 2500 provides for placement of three ablation probes in a parallel, equilateral-triangle configuration having electrode spacing of either 5, 10, 15, or 20 mm. Block 2500 provides for placement of three ablation probes in equilateral, isosceles, or arbitrary triangular configurations. Block 2500 provides for placement of two to four ablation probes in a parallel-shaft, linear arrangement. Block 2500 provides for placement of a first probe in the central hole 2504, and one or more ablation probes arrayed around the first probe, for example in holes 2501, 2502, 2503. Block 2500 can provide for placement of an ablation probe in the central hole 2504, and one or more satellite temperature probes arrayed around the ablation probe at a variety of distances to monitor and/or control the growth of an ablation zone produced by the ablation probe. Block 2500 has the advantage that multiple electrodes can be constrained in a parallel configuration with known spacing in the body to produce a single enlarged heating zone by energizing multiple probes at the same time. Block 2500 has the advantage of allowing the physician to move an ablation probe between nearby holes (separated by 2-3 mm) to make fine adjustments to the geometry of the ablation zone or to avoid anatomical structures blocking placement of an ablation probe from a desired bodily location. Block 2500 has the advantage that multiple electrodes can be inserted in a geometric arrangement to create multiple separate lesions in a desired arrangement, for example by inserting electrodes into more distant guide holes, or by inserting electrodes to different depths. The guideblock 2500 further includes fiducial markers 2531, 2532, 2533 inserted into the bottom surface of the block 2500, having a known geometric arrangement, and visible in at least one medical imaging type (such as CT, MRI, PET, x-ray, and/or fluoroscopy). The markers 2531, 2532, 2533 are arranged in a triangle for which no two sides have the same length, so that when the markers are imaged in three-dimensions (such as by CT, MRI, or PET) the location and orientation of the block 2500 can be unambiguously determined in relation to patient anatomy, and the known geometry of the block 2500 and ablation probe can be used to plan ablation probe placement in patient anatomy. In some embodiments of block 2500, additional fiducial markers can be included throughout the block to improve localization accuracy and robustness. The fiducials 2531, 2532, 2533 are visible in the Bottom View. The fiducials 2531, 2532, 2533 are shown as dotted line within the block 2500 in the Side View 1. Only fiducials 2532 and 2533 are shown as dotted line within the block 2500 in the Side View 2. In planes parallel to the bottom of the block 2500, the guideblock cross-section has three branches 2541, 2542, 2543, each containing several guideholes. The guideblock 2500 includes thin walls around each of the guideholes. This guideblock geometry has the advantage that an ultrasound transducer can be brought close to each ablation probe during insertion, and the orientation of the ultrasound transducer can be adjusted by the physician within minimal interference from the block 2500 in order to improve surgical guidance; this is an advantage of use of guideblock 2500 with the electrosurgical systems presented in relation to FIGS. 1, 2, 6, 7, 8, 9 and 10. In one aspect, the guideblock 2500 is directed toward the problem of aligning multiple ablation probes in a body using ultrasound guidance, providing for clear ultrasound views during placement of the ablation probes, and allowing for fine adjustment of ablation probe spacing to adapt to anatomical constraints and clinical objectives during an ablation procedure. In one aspect, the guideblock 2500 is directed toward the problem of aligning multiple ablation probes in a body in a non-predetermined configuration using ultrasound guidance, providing for clear ultrasound views during placement of the ablation probes, and allowing for fine adjustment of ablation probe spacing to adapt to anatomical constraints and clinical objectives during an ablation procedure. In some embodiments, each guideholes can have one of a variety of sizes within block 2500 so that each hole is specialized to admit one of a variety of probe types, such as thinner guide needles, ablation probes of different types, and satellite temperature probes. In some embodiments, the guideblock 2500 cross-section can have a different number of branches, such as number selected from the list 4, 5, 6, 7, 8. For example, a four-branch guideblock can be used to produce square or rectangular probe configurations. In some embodiments, the guideblock 2500 can include non-parallel holes. In some embodiments, the guideholes of block 2500 can be arranged with different spacings, for example, to provide for an equilateral triangular configuration with 12 mm interprobe spacing. In alternative embodiments, the guideholes of block 2500 can include side openings that provide for removal of the guideblock from the ablation probes the ablation probes are inserted into the body. For example, in one embodiment, each guidehole except the central hole 2504 can be a curved slot following a circular path, wherein the circle is centered at the center of central hole 2504, and the circle is parallel to the bottom surface of the block 2500; in this example, after three probes are inserted into bodily tissue through three holes each on a different branch of the alternative block, the alternative block 2500 can be rotated around the central axis of the central hole 2504, one end of the alternative block 2500 can be lifted up, and the block 2500 removed by lateral movement between the probes, providing that the block thickness T is less than the interprobe spacing. In some embodiments, the guideblock 2500 can be adapted to allow for its removal from ablation probes having hubs and having been inserted through the block 2500 and into bodily tissue, without removing the probes from the bodily tissue, by building the block 2500 with multiple parts that can be broken apart thereby opening the guideholes of the block.

In some alternative embodiments, the guideblock 2500 can have a cylindrical shape with guidehole therethrough (similar to the block 157 in FIG. 1C), having a circular cross-section, rather than a branched cross-section as shown in FIG. 25. In some alternative embodiments, the guideblock 2500 can have a different shape, including one of the following selected from the list: cylindrical, rectangular volume, cubic, ellipsoidal cylinder, and solid with triangular cross-section and uniform thickness. In some embodiments, the central hole 2504 can be omitted from block 2500. In some embodiments, different arrangements of holes can be included in block 2500.

Figure 26:
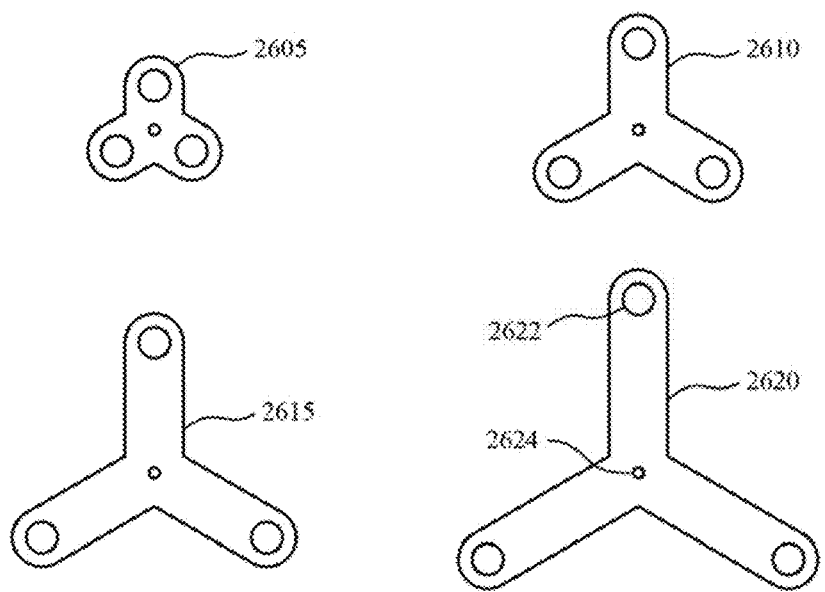
FIG. 26 is a schematic diagram showing a set of ablation-probe guideblocks, each including a cross-section having three branches, an ablation-probe guidehole at the peripheral end of each branch, a central alignment hole parallel to the ablation-probe guideholes; wherein the central axes of the guideholes of each guideblock are holes through the guideblock that are parallel to each other; wherein each guideblock can be used to guide two or more ablation probes, through two or more guideholes, into a body, in parallel, and in either a two-probe linear, or a three-probe equilateral triangular configuration; wherein the set of guideblocks provides for a variety of spacings between ablation-probes.

Referring now to FIG. 26, one embodiment of a set of guideblocks 2605, 2610, 2615, 2620 is presented as a schematic diagram in an external view from the top of the guideblocks, in accordance with several aspects of the present invention. Each guideblock 2605, 2610, 2615, 2620 has similar construction and side views as the block 2500 in FIG. 25. Each block 2605, 2610, 2615, 2620 includes a central guide-needle hole (for example 2624 in block 2620) through the top-to-bottom thickness of the block, and three, equally-spaced, parallel, ablation-probe guideholes through the top-to-bottom block thickness (for example 2622 in block 2620), each guidehole being positioned at the distal end of a branch of the block cross-section. The central guide-needle hole can be used to provisionally align the guideblock in anatomy using a guide-needle that is thinner than the ablation probe, such as a 28-20 gauge needle. Block 2605 can used to align three ablation probes in a body, in parallel, and in an equilateral triangular configuration with 5 mm probe spacing. Block 2610 can used to align three ablation probes in a body, in parallel, and in an equilateral triangular configuration with 10 mm probe spacing. Block 2615 can used to align three ablation probes in a body, in parallel, and in an equilateral triangular configuration with 15 mm probe spacing. Block 2620 can used to align three ablation probes in a body, in parallel, and in an equilateral triangular configuration with 20 mm probe spacing. In some embodiments, the set of guideblocks can include guideblocks that provide for equilateral triangular configuration with different spacings, for example as spacing in the range 5-30 mm or more. In some embodiments, the set can include guideblocks that provide for other triangular, rectangular, and/or non-parallel electrode configurations. The set of guideblocks 2605, 2610, 2615, 2620 allows a physician to adapt inter-electrode spacing during the procedure to suit clinical needs and to conform to anatomical constraints, and at the same time, use a guideblock that has minimal material around the desired guideholes to allow for minimal obstruction of the insertion site by the guideblock. This can be important when using ultrasound to guide ablation probe insertion (for example, as shown in FIGS. 1, 2, 6, 7, 8, 9 and 10) because probe-placement can be facilitated and improve by bringing the ultrasound transducer close to the point of insertion of the probe into the patient skin surface in a percutaneous procedure, or into the organ surface in an open surgical procedure, and by adjusting the orientation and position of the ultrasound transducer around the ablation probe to view a variety of anatomical structures in a variety of planes around the ablation probe shaft and active tip. In one aspect, the set of guideblocks 2605, 2610, 2615, 2620 is directed toward the problem of aligning multiple ablation probes in a body using ultrasound guidance, providing for clear ultrasound views during placement of the ablation probes, and allowing for adjustment of ablation probe spacing to adapt to anatomical constraints and clinical objectives. The set of guideblocks 2605, 2610, 2615, 2620 can be provided in a single sterile package, or in separate sterile packages, or can be autoclavable. In some embodiments, the cross-sectional area of the portion of the guideblock branches that are more central to the guideholes can be reduced to further reduce the guideblock size. In some embodiments, each of the guideblocks 2605, 2610, 2615, 2620 can include fiducial markers for localization of each block in a medical image and surgical planning. In some embodiments, each guideblock in a set can include a unique arrangement of fiducial markers so that each guideblock can be identified in a medical image without prior knowledge of which guideblock appears in the image. In some embodiments, the guide holes (eg 2622) can have loose clearance relative to the ablation probes and the ablation probes can be inserted in a non-predetermined configuration.

Figure 27A:
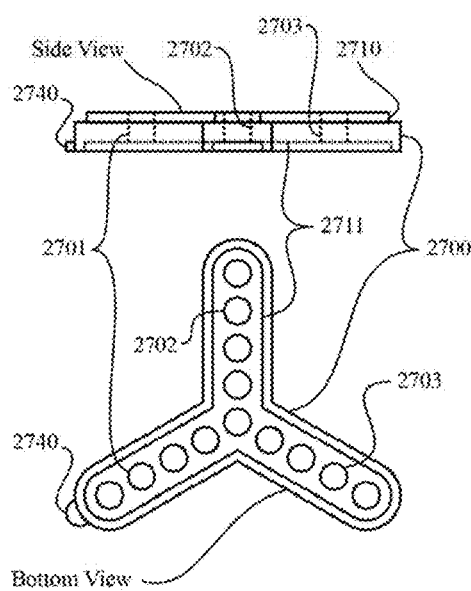
FIG. 27A is a schematic diagram showing, in two perpendicular views, a stackable ablation-probe guideblock having a mechanically-interlock feature and an interlock release tab.
Figure 27B:
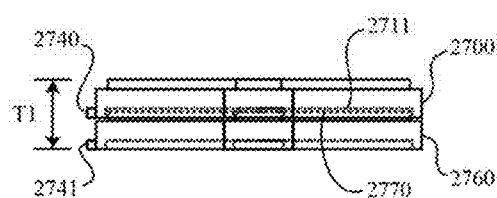
FIG. 27B is a schematic diagram showing a pair of stackable ablation-probe guideblocks having complementary mechanical-interlock features and interlock release tabs, wherein the guideblocks are shown in a mechanically-interlocked configuration; wherein the guideblocks are configured to guide two or more ablation probes through two or more parallel guideholes, in parallel, into a body, in one of a variety of parallel-ablation-probe configurations; wherein each guidehole is a hole through the guideblock; wherein a user can push the guideblocks together to minimize the space they occupy, and the mechanical-interlock features are configured to help keep the guideblocks aligned and held together; and wherein a user can slide the guideblocks apart along one or more ablation probes already inserted through the guideblocks and into the body, and then insert an additional ablation probe through corresponding guideholes in the guideblocks, thereby aligning the additional ablation probe parallel to the already-inserted ablation probes over a distance larger than the thickness of the guideblocks.
Figure 27C:
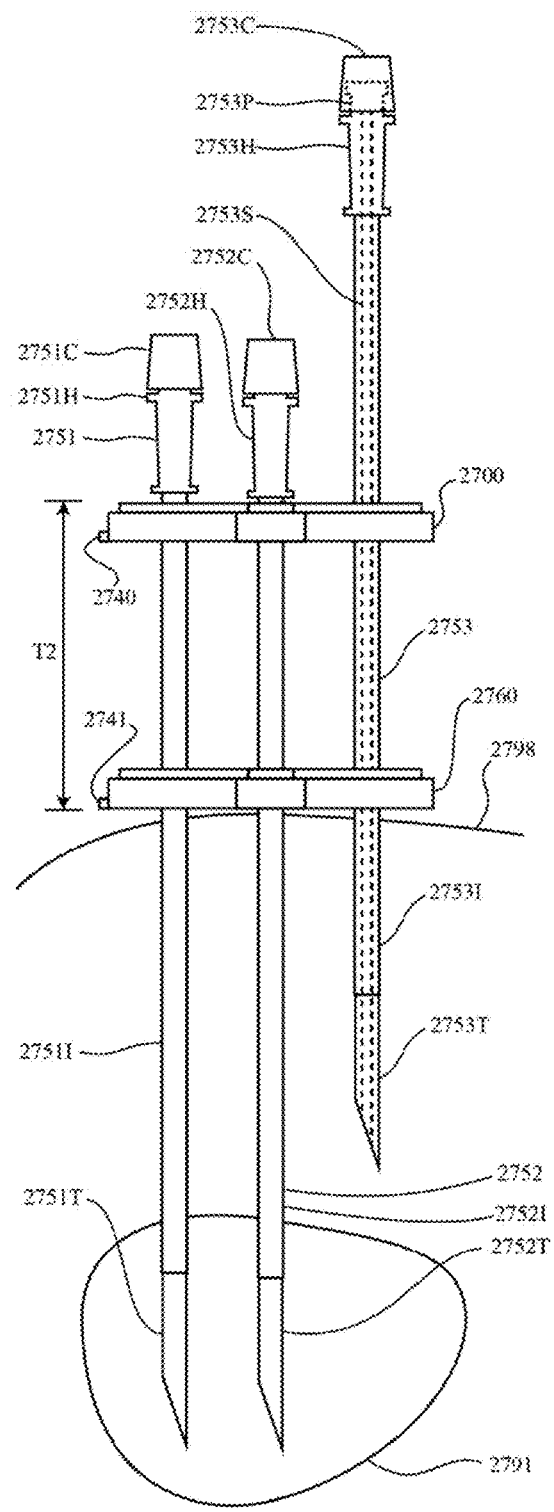
FIG. 27C is a schematic diagram showing a pair of stackable ablation-probe guideblocks having complementary mechanical-interlock features and interlock release tabs, wherein the guideblocks are shown in a separated configuration and are used in a method of aligning multiple ablation probes in a parallel configuration, as the ablation probes are inserted into a body.

Referring now to FIG. 27, one embodiment of a pair of stackable guideblocks 2700, 2760 is presented in several schematic diagrams, in accordance with several aspects of the present invention. FIG. 27 refers collectively to FIG. 27A, FIG. 27B, and FIG. 27C. Guideblocks 2700 and 2760 are identical. In FIG. 27A, block 2700 is shown in tow perpendicular external views, a view of the block's bottom labeled "Bottom View", and a view of one side of the block labeled "Side View". Like block 2500, block 2700 has thirteen guideholes (such as 2701, 2702 and 2703) that pass clear through the thickness of the guideblock from top to bottom. All guideholes of block 2700 are shown in the Bottom View, but only holes 2701, 2702, 2703 are shown through the side walls of the block 2700 as dashed lines in the Size View of FIG. 27A. The guideblock 2700 has a maximum top-to-bottom thickness of 3 mm. In some embodiments, the thickness of block 2700 can be in the range 1-10 mm. The block 2700 includes an interlock feature 2710 on its top surface that is complementary to the interlock feature 2711 on its bottom surface. In the Side View of FIG. 1A, the recessed interlock area 2711 is shown through the side walls of the block 2700 as dotted lines 2711. The interlock prominence 2710 and interlock recessed area 2711 are sized so that the top of an identical copy of block 2700 (such as block 2760) can fit into the bottom of block 2700 with an interference fit, and so that the bottom of an identical copy of block 2700 (such as block 2760) can fit over the top of block 2700 with an interference fit. The interference fits are configured such that when two blocks, such as 2700 and 2760, are interlocked as shown in FIG. 27B in an external side view, the blocks will not separate or rotate relative to each other unless they are manipulated. In FIG. 27B, the interlock tab 2770 on the top of block 2760 is shown through the side wall of block 2700 as a dotted line, and the tab 2770 fits into the interlock slot 2711 on the bottom of block 2700, the slot 2711 being shown as a dashed line through the side wall of block 2700. One advantage of interlocking guideblocks 2700 and 2760 is that they can be moved as a single piece along the shafts of ablation probes. One advantage of interlocking guideblocks 2700 and 2760 is that the combined guideblock thickness T1, shown in FIG. 27B, can be small to produce minimal obstruction of the surgical site, particularly when using ultrasound guidance. The block 2700 further includes release tab 2740, and block 2760 further includes release tab 2741, so that when the blocks 2700 and 2760 are interlocked as shown in FIG. 27B, a physician can easily separate the blocks 2700, 2760 by manipulation of the release tabs 2740, 2741 even when the physician is wearing sterile plastic gloves. In some embodiments, the interlock and release mechanisms can take other forms, such as a latch, clip, pin into hole, or other forms of mechanical interlock and release mechanisms. In some embodiments, the interlock features can only loosely engage the two blocks 2700, 2760 to help prevent rotational misalignment of the blocks, but not hold the blocks together; an advantage of this configuration is that the blocks can be more easily and quickly moved relatively to each other. In some embodiments of block 2700, the interlock features 2710 and 2711 can be omitted. In some embodiments of block 2700, the manipulation tab 2740 can be omitted. In some embodiments, the manipulation tab 2740 can take other forms or be included in multiplicity, for example on each branch of the block 2700.

Referring now to FIG. 27C, three RF cannula 2751, 2752, 2753 are inserted through guideblocks 2700 and 2760, through the skin surface 2798 of a body containing a tumor 2791. The RF cannula 2751, 2752, 2753 can each be configured to be used with an internally-cooled RF electrode (such as shown, in one embodiment, in relation to ablation probe 150 in FIG. 1A) or a non-cooled RF electrode. Cannula 2751 includes female luer hub 1751H, a cylindrical stainless steel hypotube shaft covered by a thin layer of electrical insulation in proximal region 2751I and having metallic active tip 2751T at it distal end, and a removable stylet including hub cap 2751C and solid stylet shaft inserted into the inner lumen of the hypotube shaft and having a distal sharp bevel point that is match ground to the distal bevel point of the hypotube shaft. Cannula 2752 includes female luer hub 1752H, a cylindrical stainless steel hypotube shaft covered by a thin layer of electrical insulation in proximal region 2752I and having metallic active tip 2752T at it distal end, and a removable stylet including hub cap 2752C and solid stylet shaft inserted into the inner lumen of the hypotube shaft and having a distal bevel point match ground to the distal sharp bevel point of the hypotube shaft. Cannula 2753 includes female luer hub 1753H, a cylindrical stainless steel hypotube shaft covered by a thin layer of insulation in proximal region 2753I and having metallic active tip 2753T at it distal end, and a removable stylet including hub cap 2753C and solid stylet shaft 2753S inserted into the inner lumen of the hypotube shaft and having a distal bevel point match ground to the distal sharp bevel point of the hypotube shaft. The stylet shaft 2753S is shown within the lumen of the cannula hypotube shaft 2753I, 2753T as a dotted line. The luer port stem 2753P of hub 2753H is shown within cap 2753C as a dotted line. Cannula 2751, 2752, 2753 are inserted through holes 2701, 2702, 2703 of guideblock 2700, and through the corresponding holes of guideblock 2760, respectively, thereby forming a parallel-shaft, equilateral-triangle probe configuration having an inter-probe spacing of 15 mm. Cannula 2751 and 2752 are positioned in the tumor 2798, and the guideblocks 2700 and 2760 are separated to produce an effective guideblock thickness T2, which is much larger than the thickness of the individual guideblocks 2700, 2760, and much larger than the thickness T1 of the combination of the guideblocks shown in FIG. 27B. The large effective guideblock thickness T2 constrains the orientation of ablation cannula 2753, and thus keeps cannula 2753 parallel to probes 2751 and 2752, as cannula 2753 is inserted into tumor 2798 which resides at a depth in tissue below the skin surface 2791. In some embodiments, the target structure 2798 can be an anatomical structure other than a tumor, such as a nerve, an osteoid osteoma, a blood vessel, the interior of a vertebra into which bone cement will be injected, or a region of tissue in which it is desired to coagulate blood flow. In some embodiments, the cannulae 2751, 2752, 2753 can be inserted to different depths relative to skin 2798, block 2700, or block 2760, for example as in the state shown in FIG. 27C; thereby a single lesion volume can be created with an irregular shape, separate lesion volumes can be created, and non-predetermined cannula configurations can be created.

Referring to FIG. 27, one advantage of the stackable guideblock pair 2700, 2760 is that, during an ablation procedure, a physician can reduce the combined thickness of the pair (for example, to thickness T1) to reduce obstruction at the surgical site, to allow an ultrasound transducer to be brought close to ablation probes aligned by the block, to allow an ultrasound transducer to be manipulated around ablation probes aligned by the blocks, to allow more length of the probe shafts to be inserted to the body, and to less restrict the orientation the probes 2751, 2752, 2753 passing through the guideholes thereby allowing a physician more flexibility in placing the probes through the guideblocks; and a physician can also increase the combined thickness of the guideblock pair (for example to thickness T2) to increasingly constrain the relative orientation of multiple ablation probes as they are inserted into a body. The interlock and release features of blocks 2700 and 2760 provide an important ergonomic advantage for the use of the stackable guideblocks, particularly when using ultrasound guidance, because the physician generally has one hand occupied by holding the ultrasound transducer. The use electrode-cannula-type RF ablation probe (one example of which is ablation probe 150 of FIG. 1A) with a guideblock has the advantage of reducing obstruction and encumbrance from electrode cables and tubes during probe placement, because the electrodes are not introduced until the cannula are positioned in the patient body and manipulation of the guideblock and other surgical guidance tools is complete; this is especially an advantage when it is desired to use a guideblock with cooled RF ablation probes requiring coolant tubing, and/or when a stackable guideblock having multiple parts is used. This is a special advantage for ultrasound-guidance and combined generator-ultrasound imaging systems having multiple ablation probes (many examples of which are presented in the present invention), because reduction of obstruction to the ultrasound transducer is important for proper and smooth ultrasound-guidance. The guideblocks 2700, 2760 can also be used with other types of HF ablation probes, including integral RF electrodes and MW antennae. In some embodiments, guideblock 2700 and 2760 can be non-identical, for example having different but complementary interlock and release features. In some embodiments, each of the guideblocks 2605, 2610, 2615, 2620 of FIG. 26 can be adapted to be stackable, for example, by reducing the block thickness, by include an interlock feature, and/or by including a interlock release feature. In some embodiments, more than two interlocking guideblocks can be used to guide probes into the body. In some embodiments, the guideholes of block 2700 can take the form of a slot.

In accordance with several aspects of the present invention, the guideblocks 2700 and 2760 are one example of a pair of guideblocks that can be used in a method for alignment of ablation probes in a body (hereinafter "Method A") comprising: inserting a first ablation probe through a first guidehole in a first guideblock, through a second guidehole in a second guideblock, and into bodily tissue; separating the first guideblock and the second guideblock along the shaft of the first ablation probe; inserting a second ablation probe through a third guidehole in the first guideblock, through a fourth guidehole in the second guideblock, and into the bodily tissue. Method A and further comprising: sliding the first guideblock and the second guideblock toward each other to make room for an ultrasound transducer at the surface of the bodily tissue. Method A and further comprising: inserting a third ablation probe through a fifth guidehole in the first guideblock, through a sixth guidehole in the second guideblock, and into the bodily tissue.

Figure 28:
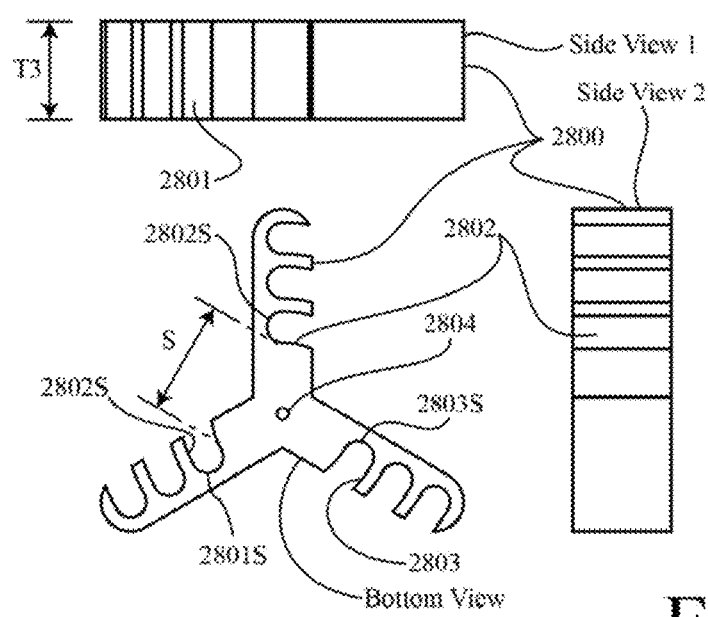
FIG. 28 is a schematic diagram showing, in three perpendicular views, an ablation-probe guideblock that can removed from ablation probes having hubs that pass through the guideblock and into bodily tissue, without removing the ablation probes from the bodily tissue; wherein the guideblock includes a cross-section having three branches, at least one guide-slot on each branch; wherein each guide-slots is slot through the guideblock that is open at a side of the guideblock, that follows a circumferential path around a single common point in the guideblock and in a single common plane, and that has a semi-cylindrical reference surface that is parallel to the semi-cylindrical reference surfaces of the other guide-slots; wherein the guideblock can be used to guide two or more ablation probes, through two or more guide-slots, into a body, in parallel, and in one of a variety of linear or triangular configurations, by alignment of each ablation probe to a semi-cylindrical reference surface of a guide-slot; wherein the guideblock has thin walls around the guideholes to reduce guideblock weight, to allow an ultrasound transducer to be positioned close to the shafts of the ablation probes at the surface of the body; wherein the thickness of the guideblock is configured to be less than the minimum spacing between the semi-cylindrical reference surfaces of any two guide-slots.

Referring now to FIG. 28, one embodiment of a guideblock 2800 for alignment of two or more ablation probes within a body is presented as a schematic diagram showing three perpendicular external views of the guideblock, in accordance with several aspects of the present invention. The guideblock 2800 is shown in a bottom view labeled "Bottom View", a first side view labeled "Side View 1", and a second second view "Side View 2". The block 2800 includes nine guide-slots through the top-to-bottom thickness T3 of the block 2800. For example slots 2801, 2802, and 2803 are shown in the Bottom View. Slot 2801 is visible in Side View 1. Slot 2802 is visible in Side View 2. The guideblock 2800 include a central through hole 2804. Each guide-slot (eg 2801, 2802, 2803) cuts through the top-to-bottom thickness T3 of the block 2800, is open at one side of the block, and has a semi-cylindrical reference surface (eg 2801S, 2802S, 2803S, respectively) that is parallel to the other semi-cylindrical slot reference surfaces and against which an ablation probe can be guided into bodily tissue in parallel with other ablation probes that are guided into the bodily tissue against the reference surfaces of other slots. For example, three ablation proves can be inserted into bodily tissue in a parallel-shaft, equilateral triangle configuration by aligning each of the probe against one of the reference surfaces 2801S, 2802S, and 2803S. Each slot further has a constant width and follows a path that is equidistant from the center of the guideblock (which is intersects with the central axis of the hole 2804) and that is parallel to the bottom surface of the guideblock 2800. The thickness T3 of the block 2800 is less than the minimum distance between the semi-cylindrical reference surfaces of the guide-slots. As such, after ablation probes, each having a large hub at its proximal end, have been inserted into bodily tissue through the guideblock 2800, wherein each probe is aligned against the reference surface of a slot, the block 2800 can be rotated around the axis of the central hole 2804 (for example by 30 degrees) such that the probes slide through the slots are exit the side of the block 2800, and the block 2800 can be rotated off the surface of the bodily tissue onto one of its ends and passed between the ablation probes, still inserted in the bodily tissue, providing there is sufficient clearance between the block 2800 and the hubs of the probes. One advantage of the block 2800 is that it can be removed after initial alignment of ablation probes in bodily tissue, thereby allowing the probes to be further advanced into the tissue. In some embodiments, two copies of block 2800 can be stacked one atop the other, with one block flipped 180 degrees top over bottom, and thereby produce a combined guideblock that has cylindrical through holes and that can be removed from ablation probes inserted through it into bodily tissue. In some embodiments, said two copies can be adapted to interlock, for example, by the methods and apparatuses shown in relation to blocks 2700 and 2760 in FIG. 27. In some embodiments that reference surfaces (eg 2801S, 2802S, 2803S) can be a different shape than cylindrical, for example flat or a surface having a curvature greater than the width of the slots (eg 2801, 2802, 2803, respectively). In some embodiments, the central hole 2804 can be omitted.

Paragraph 1: A system for tissue ablation including: a generator of high-frequency signal output; an electrode including an shaft portion adapted to be inserted into the body and adapted to be connected to the generator, the shaft portion having a tip portion so adapted such that when said shaft portion is inserted into the body, the signal output is delivered through the tip portion to the bodily tissue to be ablated, said shaft portion having an inner space that can accept circulation of coolant to cool said tip portion; a coolant system adapted to connect to said electrode and supply circulation of coolant to the electrode inner space to cool the electrode tip portion; a measuring system adapted to measure in real time at least one signal output parameter from the list of impedance, current, voltage, and power; a control system including an automatic controller adapted to control the at least one measured signal output parameter, including modulating the signal output to maintain the at least one measured signal output parameter at a desired level; a computer graphic display adapted to plot in real time at least one measured signal output parameter as a function of a time scale axis.

Paragraph 2: The system of Paragraph 1 wherein the measuring system measures in real time at least two signal output parameters from the list of impedance, current, voltage, and power; and wherein the computer graphic display plots in real time at least two measured signal output parameters on the same time scale, either next to each other on separate time scale axes, or overlapping each other on the same time scale axis, to provide a dynamic visual relationship of the variation of these signal output parameters.

Paragraph 3: The system of Paragraph 1 wherein the control system switches the level of the signal output between an ablation range configured to heat tissue substantially, and a cooling range configured to allow for cooling of the heated tissue, wherein the control system performs the switching in response to at least one of the measured signal output parameter in accordance with the automatic controller.

Paragraph 4: The system of Paragraph 1 wherein the control system alternately switches the level of the signal output between an ablation range configured to provide for substantial tissue heating, and a cooling range configured to provide for tissue, and thereby produces a sequence of signal output levels configured to maintain at least one of the measured signal output parameters in a desired range, in accordance with the automatic controller.

Paragraph 5: The system of Paragraph 1 wherein the control system produces a sequence of up times and down times; wherein during each up time, the signal output level is set to a high level configured to raise tissue temperatures substantially; wherein during each down time, the signal output level is set to a low level configured to allow for cooling of tissue cool that was heated into the boiling range; and wherein the control system, according to the automatic controller, stabilizes the duration of the up times, the duration of down times, and the signal output level during the up times to achieve a desired ablation size for a prescribed total duration of the ablation process.

Paragraph 6: The system of Paragraph 5 wherein the durations of the up times and the durations of the down times are each stabilized to a value in the range 5 to 40 seconds.

Paragraph 7: The system of Paragraph 1 wherein the control system, by means of the automatic controller, begins the process of abating tissue by means of the electrode by automatically ramping up the signal output level until the at least one signal output parameter reaches a prescribed level, and then the control system continues the process of ablating tissue by automatically modulating the signal output level according to the automatic controller to maintain at least one measured signal output parameter at desired levels to optimize ablation size.

Paragraph 8: The system of Paragraph 1 wherein the tip portion contains a temperature sensor; wherein the measuring system includes a temperature measuring system adapted to connect to the temperature sensor and to produce a temperature signal indicative of the temperature in the tip portion; wherein the computer graphic display is adapted to plot the temperature signal in real time on the same time scale as the time scale of a plotted signal output parameter.

Paragraph 9: The system of Paragraph 1 wherein the computer graphic display plots in real time either power, or current, or both, and at least one additional parameter selected from the list voltage, impedance, and temperature, as a function of the same time scale axis.

Paragraph 10: The system of Paragraph 9 wherein the graphic display parameters is color-coded so the parameters can be easily visually differentiated from each other.

Paragraph 11: The system of Paragraph 1 wherein the range of the time scale axis is at least 720 seconds.

Paragraph 12: The system of Paragraph 1 wherein if one of the displayed signal output parameters is impedance, then the range of the impedance measurement includes at least the range to 120 ohms.

Paragraph 13: The system of Paragraph 1 wherein if one of the displayed signal output parameters is current, then the range of said current output measurement includes at least the range 0 to 2000 mA.

Paragraph 14: The system of Paragraph 1 wherein the generator can produce more than 50 Watts of high-frequency signal output.

Paragraph 15: The system of Paragraph 1 wherein the generator can produce at least 200 Watts of high-frequency signal output.

Paragraph 16: The system of Paragraph 1 wherein the generator can produce at least 400 Watts of high-frequency signal output.

Paragraph 17: The system of Paragraph 1 wherein the generator is configured for tumor ablation.

Paragraph 18: The system of Paragraph 5 wherein during each up time, the signal output is on; and wherein during each down time, the signal output is off.

Paragraph 19: A system for ablation of tissue in the body including a generator of radiofrequency or microwave signal output; an electrode including a shaft portion adapted to be inserted into tissue of a body and adapted to be connected to the generator, the shaft portion having a tip portion so adapted that when the shaft portion is inserted into the body, the signal output is delivered through the tip portion to the tissue to be ablated, said shaft portion having an inner space that can accept circulation of coolant to cool said tip portion; a coolant system adapted to connect to said electrode and supply circulation of coolant to the inner space to cool said tip portion; a measuring system adapted to measure in real time the impedance of the signal output and at least one signal output level parameter in the list of power, voltage, and current; a control system including an automatic controller adapted to control the impedance, wherein the automatic controller modulates at least one of the signal output level parameters in the list of power, voltage, and current, wherein the modulation is configured to maintain the impedance at desired levels; a computer graphic display adapted to plot in real time the impedance on a first time axis, and the at least one measured signal output level parameter on a second time axis, wherein the time axes are registered to the same time scale to provide a dynamic visual relationship of the variation of the impedance and the at least one measured signal output level parameter.

Paragraph 20: The system of Paragraph 19 wherein the time axis of the impedance and the time axis of the at least one measured signal output level parameter are positioned next to each other.

Paragraph 21: The system of Paragraph 19 wherein the time axis of the impedance and the time axis of the at least one measured signal output level parameter are the same time axis.

Paragraph 22: The system of Paragraph 19 wherein the control system switches the level of the signal output between an ablation range configured to heat tissue substantially, and a cooling range configured to allow for cooling of the heated tissue, wherein the control system performs the switching in response to the impedance, in accordance with the automatic controller.

Paragraph 23: The system of Paragraph 19 wherein the modulation of signal output level by the automatic controller includes repeated alternations of up times wherein the signal output is higher, and down times wherein the signal output is lower, to achieve a stable pattern of impedance, output level modulations, up-time durations, and down-time durations, until an overall duration of signal output has been delivered to produce a desired ablation size; wherein during each up time, by means of the automatic controller, the control system maintains or increases the output level until the impedance rises above a threshold value; wherein during each down time, by means of the automatic controller, the control system produces a low output level for a duration configured to reduce the impedance to a baseline value.

Paragraph 24: The system of Paragraph 23 wherein the output signal is shut off during each down time; and wherein the output signal is turned on during each up time.

Paragraph 25: The system of Paragraph 19 wherein the tip portion contains a temperature sensor; wherein the measuring system includes a temperature measuring system adapted to connect to the temperature sensor and to produce a temperature signal indicative of the temperature in the tip portion; wherein the computer graphic display is adapted to plot the temperature signal in real time on the same time scale as the time scale of the impedance and the at least one measured signal output level parameter.

Paragraph 26: The system of Paragraph 25 wherein the measuring system is adapted to measure the parameters impedance, current, voltage, power, and temperature, and the computer graphic display is adapted to plot all of these parameters in real time, and on the same time scale axis.

Paragraph 27: The system of Paragraph 25 wherein the plots of the measured parameters are color coded so they can be easily visually differentiated.

Paragraph 28: The system of Paragraph 23 wherein after repeated alternations of up time and down time, the duration of the up times and the duration of the down times both stabilize to values in the range 5 to 40 seconds.

Paragraph 29: The system of Paragraph 19 wherein each time axis has a range of at least 720 seconds.

Paragraph 30: The system of Paragraph 19 wherein the range of impedance measurement includes at least the range 40 to 120 ohms.

Paragraph 31: The system of Paragraph 19 wherein if current is one of the measured signal output level, then current-measurement range includes at least the range 0 to 2000 mA.

Paragraph 32: The system of Paragraph 19 wherein the electrode shaft portion includes a metal tube that is insulated over its surface except for the tip portion which is uninsulated so that when said shaft portion is inserted into the tissue of the body, and said generator is connected electrically to the metal tube of the shaft portion, then the signal output current flows into the tissue only from of the tip portion to produce heating of the tissue.

Paragraph 33: The system of Paragraph 19 wherein a surface portion of the electrode tip portion is made echogenic by a surface treatment that reflects ultrasound signals preferentially so that when an ultrasound imaging machine is used to image bodily tissue in which the electrode tip portion is inserted, the echogenic surface portion is prominently visible to indicate the position of the tip portion in the tissue.

Paragraph 34: The system of Paragraph 33 wherein the echogenic surface portion includes a multiplicity of surface indentations in the surface of the tip portion.

Paragraph 35: A system for tissue ablation that includes a radiofrequency generator and a graphic display, wherein the radiofrequency generator is configured to apply a radiofrequency signal to an ablation electrode that is in contact with bodily tissue; wherein the graphic display is configured plot in real time and on one time axis, two or more parameters of the signal delivered to the ablation electrode; wherein each parameter is selected from the list: impedance; voltage; current; power; a measurement of the signal; mathematical functions taking one or more of the arguments impedance, voltage, current, power, and a measurement of the signal.

Paragraph 36: The system of Paragraph 35 and further including a controller configured to automatically alternate the signal level between a first range configured to heat tissue, and a second range configured to allow for cooling of heated tissue.

Paragraph 37: The system of Paragraph 36 wherein the controller switches the signal level from the first range to the second range based in whole or in part on an indication of boiling or impending boiling in tissue heated by the ablation electrode, and wherein the controller switches the signal level from the second range to the first range after a duration configured to allow for dissipation of gas bubbles formed in the tissue due to boiling.

Paragraph 38: The system of Paragraph 36 wherein the controller changes the signal level from the first range to the second range based in whole or in part on an increase in a measured impedance.

Paragraph 39: The system of Paragraph 38 wherein one of the plotted parameters is impedance, one of the plotted parameters is current, and the first range is a range of radiofrequency current levels.

Paragraph 40: The system of Paragraph 36 wherein the controller changes the signal level from the first range to the second range based in whole or in part on a change in one or more measured parameters in the list voltage, current, power.

Paragraph 41: The system of Paragraph 36 wherein the controller changes the signal level from the second range to the first range based on in whole or in part a measured impedance.

Paragraph 42: The system of Paragraph 36 wherein the ablation electrode is internally-cooled and the controller is configured to optimize a parameter of tissue heating by the ablation electrode.

Paragraph 43: The system of Paragraph 36 wherein the ablation electrode is internally-cooled and the controller is configured to maximize the volume of tissue heated by the internally-cooled ablation electrode.

Paragraph 44: The system of Paragraph 36 wherein the first range is a range of signal levels of one type, wherein the type is selected from the list current, power, voltage.

Paragraph 45: The system of Paragraph 36 wherein the first range is a range radiofrequency current values.

Paragraph 46: The system of Paragraph 35 wherein the ablation electrode is internally-cooled.

Paragraph 47: The system of Paragraph 35 wherein the ablation electrode is not internally-cooled.

Paragraph 48: The system of Paragraph 35 wherein the ablation electrode includes a temperature sensor.

Paragraph 49: The system of Paragraph 35 wherein the ablation electrode does not include a temperature sensor.

Paragraph 50: The system of Paragraph 35 wherein one of the plotted parameters is impedance.

Paragraph 51: The system of Paragraph 35 wherein one of the plotted parameters is current.

Paragraph 52: The system of Paragraph 35 wherein one of the plotted parameters is impedance, and one of the plotted parameters is current.

Paragraph 53: The system of Paragraph 35 wherein the graphic display is further configured to plot a temperature of the ablation electrode in real time on the time axis.

Paragraph 54: The system of Paragraph 35 wherein one of the plotted parameters is impedance, one of the plotted parameters is current, and the graphic display is further configured to plot a temperature of the ablation electrode in real time on the time axis.

Paragraph 55: The system of Paragraph 35 wherein the graphic display is further configured to plot a temperature measured at a distance from the ablation electrode.

Paragraph 56: The system of Paragraph 35 and further including a controller that can automatically regulate the signal level delivered to the ablation electrode, wherein the signal level is a parameter of the signal selected from the list: impedance; voltage; current; power, a measurement of the signal; a mathematical function taking one or more of the arguments impedance, voltage, current, power, and a measurement of the signal.

Paragraph 57: The system of Paragraph 35 wherein the radiofrequency generator delivers one or more radiofrequency signals to one or more ablation electrodes, and for each ablation electrode, the graphic display plots in real time and on a time axis, two or more parameters of the signal delivered to the ablation electrode; wherein each parameter is selected from the list: impedance; voltage; current; power; a measurement of the signal delivered to the ablation electrode; mathematical functions taking one or more of the arguments impedance, voltage, current, power, and a measurement of the signal delivered to the ablation electrode.

Paragraph 58: The system of Paragraph 57 wherein the graphic display positions all the plots of more than one electrode on the same time axis.

Paragraph 59: The system of Paragraph 57 wherein the graphic display includes a different time axis for the plots of each of the one or more ablation electrodes.

Paragraph 60: A system for tissue ablation that includes a radiofrequency generator, a controller, and a graphic display, wherein the radiofrequency generator delivers a radiofrequency signal output to an electrode inserted into bodily tissue; wherein the controller automatically alternates between a first state and a second state; wherein in the first state, the controller maintains the signal output at a higher level configured to raise the temperature of a substantial portion of the bodily tissue to a destructive temperature; wherein in the second state, the controller maintains the signal output at a lower level configured to allow the temperature of heated bodily tissue to cool substantially; wherein the graphic display plots one or more parameters of the signal output as a function of time; wherein each parameter can be selected from the list: impedance, current, power, voltage, duty cycle, temperature, time, a signal output level, a measurement of the signal output, a parameter of the signal output, a time average of a parameter of the signal output, the RMS value of a parameter of the signal output over a time window, a mathematical function of one or more parameters of the signal output.

Paragraph 61: The system of Paragraph 60 and further including a coolant supply, wherein the electrode is cooled by the coolant supply.

Paragraph 62: The system of Paragraph 60 or Paragraph 61 wherein the controller switches from the first state to the second state when a measurement indicates the presence of high-temperature vapor in tissue near the electrode.

Paragraph 63: The system of Paragraph 60 or Paragraph 61 wherein the controller switches from the first state to the second state in response to a change in a measured impedance.

Paragraph 64: The system of Paragraph 60 or Paragraph 61 wherein the duration for which the controller remains in the second state before switching to the first state is configured to provide for dissipation of high-temperature vapor in tissue near the electrode active tip.

Paragraph 65: The system of Paragraph 60 or Paragraph 61 wherein the controller prevents switching from the second state to the first state unless an elevated impedance decreases to a lower value.

Paragraph 66: The system of Paragraph 60 or Paragraph 61 wherein the higher level is an RF current level or a range of RF current levels.

Paragraph 67: The system of Paragraph 60 or Paragraph 61 wherein the higher level is an RF power level or a range of RF power levels.

Paragraph 68: The system of Paragraph 60 or Paragraph 61 wherein the higher level is an RF voltage level or a range of RF voltage levels.

Paragraph 69: The system of Paragraph 60 or Paragraph 61 wherein the duration of an instance of the first state or of an instance of the second state is greater than 5 seconds.

Paragraph 70: A system for tissue ablation that includes a radiofrequency generator and a controller, wherein the radiofrequency generator is configured to deliver a radiofrequency signal to bodily tissue via a radiofrequency electrode; wherein the controller automatically produces a sequence of on periods and off periods; wherein during each on period, the controller configures the signal level to heat tissue in order to increase the volume ablated tissue; wherein during each off period, the controller configures the signal level to allow for cooling of heated tissue; wherein after the signal is first configured to heat tissue in order to increase the volume ablated tissue, the controller both increases and decreases the signal level delivered during on periods.

Paragraph 71: The system of Paragraph 70 wherein the radiofrequency electrode is internally-cooled.

Paragraph 72: The system of Paragraph 70 wherein the duration of at least one on period or off period is 5 seconds or longer.

Paragraph 73: The system of Paragraph 70 wherein the controller switches from an on period to an off period is based in whole or in part on an indication of tissue boiling.

Paragraph 74: The system of Paragraph 70 wherein the controller switches from an on period to an off period is based in whole or in part on an impedance.

Paragraph 75: The system of Paragraph 70 wherein the controller configures the duration of an off period to provide for dissipation of gaseous vapor formed by boiling within the tissue.

Paragraph 76: The system of Paragraph 70 wherein the controller regulates a parameter of the signal level during each on period, wherein the parameter is selected from the list current, voltage, power.

Paragraph 77: The system of Paragraph 70 wherein the controller automatically regulates a parameter of the signal level during each off period, wherein the parameter is selected from the list current, voltage, power.

Paragraph 78: The system of Paragraph 70 wherein the controller increases the signal level during an on period.

Paragraph 79: The system of Paragraph 78 wherein the controller increases the signal level in steps over time.

Paragraph 80: The system of Paragraph 79 wherein the controller sets the initial signal level of an on period to be less than the final signal level of the latest preceding on period by an amount that is influenced by the duration of the final step in the signal level during the latest preceding on period.

Paragraph 81: The system of Paragraph 79 wherein a step increase in the signal level during a first on period is reversed by the controller to set the initial signal level for the next on period, if the duration of the step increase is less than a threshold value.

Paragraph 82: The system of Paragraph 78 wherein the controller increases the signal level as a smooth function of time after a delay of at least zero seconds.

Paragraph 83: The system of Paragraph 78 wherein the controller sets the initial signal level of a first on period to be less than the final signal level of the last preceding on period, wherein the difference between the final signal level of the last preceding on period and the initial signal level of the first on period is influenced by the duration and degree of signal level increase during the last preceding on period.

Paragraph 84: The system of Paragraph 70 wherein the signal level during a first on period is less than the signal level during a second on period, wherein the first on period comes before the second on period.

Paragraph 85: The system of Paragraph 84 wherein the increase in signal level from the first on period to the second on period is influenced by the duration of the first on period.

Paragraph 86: The system of Paragraph 70 wherein the controller sets the initial signal level of an on period to a value that is less than the final signal level of the latest preceding on period, wherein the value is influenced a parameter of the latest preceding on period.

Paragraph 87: The system of Paragraph 70 wherein the controller sets the initial signal level of an on period to a value that is less than the final signal level of the latest preceding on period if the duration of the latest preceding on period is less than a threshold value.

Paragraph 88: The system of Paragraph 70 wherein the increases and decreases in the signal level delivered during on periods are configured to maximize the volume ablated tissue.

Paragraph 89: The system of Paragraph 70 wherein the increases and decreases in the signal level delivered during on periods are configured to optimize a feature of the ablation process.

Paragraph 90: The system of Paragraph 70 further including a first user setting that sets the initial signal level of the initial on period in the sequence, and a second user setting that sets the maximum signal level of all on periods in the sequence.

Paragraph 91: A system for tissue ablation that includes a radiofrequency generator and a controller; wherein the radiofrequency generator is configured to deliver a radiofrequency signal to bodily tissue via a radiofrequency electrode; wherein the controller automatically produces a sequence of on periods and off periods; wherein during each on period, the controller configures the signal level to heat tissue in order to increase the volume ablated tissue; wherein during each off period, the controller configures the signal level to allow for cooling of heated tissue; wherein the duration of a first off period is different from the duration of a second off period.

Paragraph 92: The system of Paragraph 91 wherein the controller switches from an on period to an off period when continued application of the signal level of the on period no longer increases volume of ablated tissue; wherein the controller increases the duration of an off period relative to the duration of a preceding off period if the duration of a preceding on period is less than a threshold value.

Paragraph 93: The system of Paragraph 91 wherein the controller increases the duration of the off periods monotonically as a function of the elapsed time of the sequence.

Paragraph 94: The system of Paragraph 91 wherein the controller sets the duration of an off period as a function of a measurement of tissue temperature at a distance from the electrode active tip.

Paragraph 95: The system of Paragraph 91 wherein the controller sets the duration of an off period as a function of an impedance measurement.

Paragraph 96: The system of Paragraph 91 wherein the controller sets the duration of the off period as a function of the duration over which an impedance decreases from an elevated level induced by tissue heating during the previous on period.

Paragraph 97: A system for tissue ablation that includes a radiofrequency generator and a controller; wherein the radiofrequency generator is configured to deliver a radiofrequency signal to bodily tissue via a radiofrequency electrode; wherein the controller automatically produces a sequence of on periods and off periods; wherein during each on period, the controller configures the signal level to heat tissue in order to increase the volume ablated tissue; wherein during each off period, the controller configures the signal level to allow for cooling of heated tissue; wherein after the signal is first configured to heat tissue, the controller both increases and decreases the signal level delivered during on periods; and wherein the duration of a first off period is different from the duration of a second off period.

Paragraph 98: A method of pulsed-radiofrequency, cooled-radiofrequency tissue ablation comprising: generating a sequence of radiofrequency pulses; terminating a pulse when there is an indication of tissue boiling; after the beginning of the initial pulse of the sequence, increasing the radiofrequency signal amplitude delivered during a pulse relative to an earlier radiofrequency signal amplitude delivered during a pulse; and decreasing the radiofrequency signal amplitude delivered during a pulse relative to an earlier radiofrequency signal amplitude delivered during a pulse.

Paragraph 99: The method of Paragraph 98 wherein the indication of tissue boiling includes the impedance encountered by the pulse current rising above an impedance threshold.

Paragraph 100: The method of Paragraph 98 performed in whole or in part by an automated controller.

Paragraph 101: A method of pulsed-radiofrequency, cooled-radiofrequency tissue ablation comprising: generating a sequence of radiofrequency pulses; terminating a pulse based in whole or in part on an indication of tissue boiling; generating a pulse that includes a higher radiofrequency signal amplitude than does a preceding pulse.

Paragraph 102: A method of pulsed-radiofrequency, cooled-radiofrequency tissue ablation comprising: generating a sequence of radiofrequency pulses; terminating a pulse when tissue boiling is detected; setting the duration an inter-pulse period to be different from the duration of an earlier inter-pulse period.

Paragraph 103: A method of pulsed-radiofrequency, cooled-radiofrequency tissue ablation comprising: generating a sequence of radiofrequency pulses; terminating a pulse based in whole or in part on an indication of tissue boiling; after the beginning of the initial pulse of the sequence, increasing the radiofrequency signal amplitude delivered during a pulse relative to an earlier radiofrequency signal amplitude delivered during a pulse; decreasing the radiofrequency signal amplitude delivered during a pulse relative to an earlier radiofrequency signal amplitude delivered during a pulse; and setting the duration an inter-pulse period to be different from the duration of an earlier inter-pulse period.

Paragraph 104: A method of pulsed-radiofrequency, cooled-radiofrequency tissue ablation comprising: generating a sequence of radiofrequency pulses; terminating a pulse based in whole or in part on an indication of tissue boiling; and stopping the sequence when the number of radiofrequency pulses exceeds a count threshold.

Paragraph 105: A method of pulsed-radiofrequency, cooled-radiofrequency tissue ablation comprising: generating a sequence of radiofrequency pulses; terminating a pulse when tissue boiling is detected; and stopping the sequence when the sum of the durations of generated pulses exceeds a time threshold.

Paragraph 106: A method of pulsed-radiofrequency, cooled-radiofrequency tissue ablation comprising: generating a sequence of radiofrequency pulses; terminating a pulse when there is an indication of tissue boiling; and stopping the sequence if the time-integrated mean-squared radiofrequency current delivered during the sequence exceeds a current threshold.

Paragraph 107: A method of pulsed-radiofrequency, cooled-radiofrequency tissue ablation comprising: generating a sequence of radiofrequency pulses; terminating a pulse when a measurement indicated tissue boiling; and stopping the sequence if the time-integrated radiofrequency power delivered during the sequence exceeds a power threshold.

Paragraph 108: A method of pulsed-radiofrequency, cooled-radiofrequency tissue ablation comprising: generating a sequence of radiofrequency pulses; terminating a pulse when there is an indication of tissue boiling; and stopping the sequence if the total energy delivered during the sequence exceeds an energy threshold.

Paragraph 109: A method of pulsed-radiofrequency, cooled-radiofrequency tissue ablation comprising: generating a sequence of radiofrequency pulses; terminating a pulse based in whole or in part on a measurement indicative of tissue boiling; reducing the amplitude of a pulse if the duration of a preceding pulse is less than a time threshold; and stopping the sequence if the amplitude of a pulse falls below an amplitude threshold.

Paragraph 110: The method of Paragraph 109 further comprising: adjusting the value of the amplitude threshold based in whole or in part on the amplitude of a preceding pulse.

Paragraph 111: The method of Paragraph 109 further comprising: setting the value of the amplitude threshold relative to the maximum pulse amplitude of the sequence.

Paragraph 112: A method of pulsed-radiofrequency, cooled-radiofrequency tissue ablation comprising: generating a sequence of radiofrequency pulses; terminating a pulse based in whole or in part on an indicator of tissue boiling; reducing the amplitude of a pulse or increasing the duration of an inter-pulse period if the duration of a preceding pulse is less than a duration threshold; stopping the sequence if the average radiofrequency signal amplitude over at least one consecutive pulse and inter-pulse period is less than an amplitude threshold, wherein the amplitude threshold is a function of a parameter selected from the list current, power, voltage.

Paragraph 113: A method of pulsed-radiofrequency, cooled-radiofrequency tissue ablation comprising: generating a sequence of radiofrequency pulses; terminating a pulse is conditioned on an indicator of tissue boiling; increasing the duration of an inter-pulse period if the duration of a preceding pulse is less than a time threshold; and stopping the sequence if the duty cycle over at least one consecutive pulse and inter-pulse period is less than a duty-cycle threshold.

Paragraph 114: A method of pulsed-radiofrequency, cooled-radiofrequency tissue ablation comprising: generating a sequence of radiofrequency pulses; terminating a pulse based in whole or in part on an indication of tissue boiling; increasing the duration of an inter-pulse period if the duration of a preceding pulse is below a first time threshold; and stopping the sequence if the duration of an inter-pulse period is greater than an second time threshold.

Paragraph 115: A system for tissue ablation including a radiofrequency signal generator, an ablation electrode, at least two ground pads, and current-measurement circuit for each ground pad; wherein current from the radiofrequency signal generator flows between the electrode and each ground pad through a living body at the same time; wherein the system measures the current flowing through each ground pad.

Paragraph 116: A system for tissue ablation that includes a radiofrequency signal generator, a user interface, an ablation electrode, at least two ground pads, and a current-measurement system; wherein current from the radiofrequency signal generator flows between the electrode and each ground pad through a living body; wherein the current-measurement system measures the current flowing through each ground pad; and wherein the user interface includes a display for a ground pad.

Paragraph 117: The system of Paragraph 116 wherein the display for a ground pad includes a display of the current flowing through the ground pad.

Paragraph 118: The system of Paragraph 116 wherein the display for a ground pad includes a display of the RMS value of the radiofrequency current flowing through the ground pad.

Paragraph 119: The system of Paragraph 116 wherein the display for a ground pad includes a display of the impedance between the ablation electrode and the ground pad.

Paragraph 120: The system of Paragraph 116 wherein the display for a ground pad includes a display of the temperature of the ground pad.

Paragraph 121: The system of Paragraph 116 wherein the display for a ground pad includes a display of the portion of the total current flowing through all ground pads, that is flowing to the ground pad.

Paragraph 122: The system of Paragraph 121 wherein the portion is displayed as a fraction, a percentage, a fraction relative to a desired fraction, a fraction minus the quotient of one (I) divided by the total number of ground pads, a percentage relative to a desired percentage, or a percentage minus the quotient of one hundred (100) dividend by the total number of ground pads.

Paragraph 123: The system of Paragraph 116 wherein the display for a ground pad includes a display of a quotient wherein the dividend is the current flowing through the ground pad and the devisor is the total current flowing through all ground pads.

Paragraph 124: The system of Paragraph 116 wherein the display for a ground pad includes a display of a measurement of the portion of the total radiofrequency current flowing to all ground pads, that is flowing to the ground pad.

Paragraph 125: The system of Paragraph 116 wherein the display for a ground pad includes a display of a mathematical function of the current flowing through the ground pad and the current flowing through another ground pad.

Paragraph 126: The system of Paragraph 116 wherein the display for a ground pad includes a display of an average of the current flowing through the ground pad over a time window.

Paragraph 127: The system of Paragraph 116 wherein the display for a ground pad includes a display of the root-mean-square average of the current flowing through the ground pad over a time window.

Paragraph 128: The system of Paragraph 116 wherein the display for a ground pad includes a numerical display.

Paragraph 129: The system of Paragraph 116 wherein the display for a ground pad includes a digital display.

Paragraph 130: The system of Paragraph 116 wherein the display for a ground pad includes a graphical display.

Paragraph 131: The system of Paragraph 116 wherein the display for a ground pad includes a bar graph.

Paragraph 132: The system of Paragraph 116 wherein the display for a ground pad includes a plot of a measured parameter of the ground pad as function of a time axis.

Paragraph 133: The system of Paragraph 116 wherein the user interface includes a display for each ground pad.

Paragraph 134: The system of Paragraph 116 and further including a switch for each ground pad wherein opening a switch disconnects a ground pad from the radiofrequency signal generator and substantially stops the flow of current from the radiofrequency signal generator through the ground pad, and wherein closing a switch connects a ground pad to the radiofrequency signal generator and allows the flow of current from the radiofrequency signal generator through the ground pad; and further including a controller that automatically opens and closes the switch of a ground pad to regulate the displayed parameter for the ground pad.

Paragraph 135: The system of Paragraph 134 wherein the display for a ground pad includes a display of a moving average of the current flowing through the ground pad over at least one time period during which at least one ground-pad switch either opens or closes.

Paragraph 136: The system of Paragraph 134 wherein the display for a ground pad includes a display of a root-mean-square moving average of the current flowing through the ground pad over at least one time window during which at least one ground-pad switch either opens or closes.

Paragraph 137: The system of Paragraph 116 and further including more than one ablation electrode wherein current from the radiofrequency signal generator flows between each electrode and each ground pad through the living body.

Paragraph 138: The system of Paragraph 116 and further including a nerve-stimulation signal generator wherein current from the nerve-stimulation signal generator flows between the electrode and at least one of the ground pads through the living body.

Paragraph 139: A method for distributing radiofrequency current from an ablation electrode, through a living body, between at least two ground pads comprising: measuring the current flowing through a ground pad, and displaying the measured current in real-time.

Paragraph 140: The method of Paragraph 139 wherein the measured current is displayed numerically, digitally, by an analog indicator, graphically, as a bar graph, as a line graph, or as a function of a time axis.

Paragraph 141: The method of Paragraph 139 wherein the measured current is displayed as a value of the measured current at an instant in time, an average value of the measured current over a time period, a moving average of the measured current, the root-mean-squared average of the measured current over a time period, the root-mean-square average of the measured current over a moving time window, a fraction, a percentage, a fraction relative to a desired fraction, a percentage relative to a desired percentage, the portion of the current flowing through the ablation electrode that is flowing through the ground pad, a quotient wherein the dividend is the current flowing through the ground pad and the devisor is the total current flowing through all ground pads, or a mathematical function of the current flowing through the ground pad and the current flowing through at least one other ground pad.

Paragraph 142: A system for tissue ablation including a radiofrequency signal generator, a nerve-stimulation signal generator, at least one ablation electrode connected to a first pole of the radiofrequency signal generator, at least two ground pads connected to a second pole of the radiofrequency signal generator, and a circuit that measures the current of each ground pad; wherein, in a first operating mode, current from the radiofrequency signal generator flows between at least one ablation electrode and each ground pad through a living body; wherein, in a second operating mode, current from the nerve-stimulation signal generator flows between at least one ablation electrode and at least one of the ground pads through the living body.

Paragraph 143: The system of Paragraph 142 wherein the first operating mode and the second operating mode are active at the same time.

Paragraph 144: The system of Paragraph 142 wherein the first operating mode and the second operating mode are not active at the same time.

Paragraph 145: The system of Paragraph 142 and further including a user interface that includes a display of the current flowing through a ground pad.

Paragraph 146: The system of Paragraph 142 wherein the radiofrequency signal generator can produce more than 50 Watts of power.

Paragraph 147: The system of Paragraph 142 wherein the number of ablation electrodes is greater than four.

Paragraph 148: The system of Paragraph 142 and further including a controller and a switch; wherein a ground pad is connected to the radiofrequency signal generator through the switch; wherein the controller alternately connects and disconnects the ground pad from the radiofrequency signal generator by means of the switch.

Paragraph 149: The system of Paragraph 148 wherein the controller alternately connects and disconnects the ground pad from the radiofrequency signal generator to regulate the current flowing through the ground pad.

Paragraph 150: The system of Paragraph 148 wherein the controller alternately connects and disconnects the ground pad from the radiofrequency signal generator to regulate the temperature of tissue in contact with the ground pad.

Paragraph 151: The system of Paragraph 148 wherein the controller disables the radiofrequency signal generator while the switch is in the process of connecting or disconnecting the ground pad from the radiofrequency signal generator.

Paragraph 152: The system of Paragraph 142 and further including a controller and a switch; wherein a ground pad is connected to the nerve-stimulation signal generator through the switch; wherein the controller alternately connects and disconnects the ground pad from the nerve-stimulation signal generator by means of the switch.

Paragraph 153: The system of Paragraph 152 wherein the controller disables the nerve-stimulation signal generator while the switch is in the process of connecting or disconnecting the ground pad from the nerve-stimulation signal generator.

Paragraph 154: The system of Paragraph 142 and further including a controller and a switch; wherein an ablation electrode is connected to the radiofrequency signal generator through the switch; wherein the controller alternately connects and disconnects the ablation electrode from the radiofrequency signal generator by means of the switch.

Paragraph 155: The system of Paragraph 154 wherein the controller disables the radiofrequency signal generator while the switch is in the process of connecting or disconnecting the ablation electrode from the radiofrequency signal generator.

Paragraph 156: The system of Paragraph 142 and further including a controller and a switch; wherein an ablation electrode is connected to the nerve-stimulation signal generator through the switch; wherein the controller alternately connects and disconnects the ablation electrode from the nerve-stimulation signal generator by means of the switch.

Paragraph 157: The system of Paragraph 156 wherein the controller disables the nerve-stimulation signal generator while the switch is in the process of connecting or disconnecting the ablation electrode from the nerve-stimulation signal generator.

Paragraph 158: A system for tissue ablation that includes a radiofrequency signal generator, a controller, an ablation electrode, at least two ground pads, and circuit that measures the current of each ground pad; wherein current from the radiofrequency signal generator flows between the electrode and each ground pad through a living body at the same time; and wherein the controller automatically produces a sequence in which a ground pad is repeatedly connected to and disconnected from the radiofrequency signal generator by a switch to regulate the current of the ground pad during a tissue ablation process.

Paragraph 159: A system for tissue ablation that includes a radiofrequency signal generator, a controller, an ablation electrode, at least two ground pads, and an individual current-measurement device for each ground pad; wherein current from the radiofrequency signal generator flows between the electrode and each ground pad through a living body; and wherein the controller automatically produces a sequence in which a ground pad is alternately connected and disconnected from the radiofrequency signal generator during a tissue ablation process.

Paragraph 160: A system for tissue ablation that includes a radiofrequency signal generator, a controller, an ablation electrode, at least two ground pads, and a switch between each ground pad and the radiofrequency signal generator; wherein the controller automatically generates a sequence that includes at least two steps; wherein, in a first step having a first duration, the switch for a first ground pad is closed, the switch for a second ground pad is closed, and current generated by the radiofrequency signal generator flows from the ablation electrode to both a first ground pad and a second ground pad through a living body; wherein, in a second step having a second duration, the switch for the first ground pad is open, the switch for the second ground pad is closed, current from the radiofrequency signal generator does not flow substantially through the first ground pad, and current generated by the radiofrequency signal generator flows from the ablation electrode to the second ground pad through the living body; wherein the identity of the first ground pad is not predetermined.

Paragraph 161: The system of Paragraph 160 wherein the controller measures the current flowing through each ground pad during the first step, and the controller determines the identity of the first ground pad as that ground pad which has the higher current measurement.

Paragraph 162: The system of Paragraph 160 wherein the controller measures the current flowing through each ground pad before the second step, and the controller determines the identity of the first ground pad as that ground pad which has the higher current measurement.

Paragraph 163: The system of Paragraph 160 wherein the controller measures the temperature of each ground pad, and the controller determines the identity of the first ground pad as that ground pad which has the higher temperature measurement.

Paragraph 164: The system of Paragraph 160 wherein the controller determines the identity of the first ground pad, the identity of the second ground pad, the duration of the first step, the duration of the second step, the number of repetitions of the first step, or the number of repetitions of the second step in order to regulate a parameter influenced by the current flowing through a ground pad.

Paragraph 165: The system of Paragraph 164 wherein the controller determines the identity of the first ground pad or the identity of the second ground pad in order to reduce the number of steps in the sequence, to increase of the number of switches closed at the same time, to increase the duration for which more switches are closed at the same time, to increase the duration for which all switches are closed at the same time, or to reduce the duration during which only one switch is closed.

Paragraph 166: The system of Paragraph 160 wherein the first step precedes the second step.

Paragraph 167: The system of Paragraph 160 wherein the second step precedes the first step.

Paragraph 168: A system for tissue ablation that includes a radiofrequency signal generator, a controller, an ablation electrode, and at least two ground pads; wherein the controller automatically generates a sequence of at least two configurations; wherein, in a first configuration having a first duration, both a first ground pad and a second ground pad are connected to the radiofrequency signal generator, and current generated by the radiofrequency signal generator flows from the ablation electrode to both the first ground pad and the second ground pad through a living body; wherein, in a second configuration having a second duration, the first ground pad is disconnected from the radiofrequency signal generator, the second ground pad is connected to the radiofrequency signal generator, current generated by the radiofrequency signal generator flows from the ablation electrode to the second ground pad through the living body, and current from the radiofrequency signal generator does not flow substantially through the first ground pad; the identity of the first ground pad is not predetermined.

Paragraph 169: The system of Paragraph 168 wherein the controller selects the duration of the first configuration, the duration of the second configuration, the identity of the first ground pad, or the identity of the second ground pad based in whole or in part on a measured parameter of a ground pad.

Paragraph 170: The system of Paragraph 168 wherein the time schedule of the sequence is not predetermined.

Paragraph 171: The system of Paragraph 168 wherein at no time in the sequence does the controller switch an application of voltage first between the ablation electrode and the first ground pad, and second between the ablation electrode and the second ground pad.

Paragraph 172: The system of Paragraph 168 wherein the controller configures the sequence to regulate a parameter of a ground pad.

Paragraph 173: The system of Paragraph 172 wherein the parameter of a ground pad is the current carried by the ground pad.

Paragraph 174: The system of Paragraph 172 wherein the parameter of a ground pad is the root-mean-squared current carried by the ground pad.

Paragraph 175: The system of Paragraph 172 wherein the parameter of a ground pad is a temperature.

Paragraph 176: The system of Paragraph 172 wherein the controller disables the radiofrequency signal generator if the parameter exceeds a limit.

Paragraph 177: The system of Paragraph 172 wherein the controller configures the sequence to minimize the number of configurations, to maximize the number of ground pads that simultaneously carry radiofrequency current from the ablation electrode, or to maximize the total capacity of the ground pads to carry current from the ablation electrode without burning tissue in contact with any of the ground pads.

Paragraph 178: The system of Paragraph 168 wherein the controller configures the sequence to equalize the RMS current flowing to each ground pad over a time period.

Paragraph 179: The system of Paragraph 168 wherein the sequence includes a nested-simultaneous switching pattern.

Paragraph 180: The system of Paragraph 179 wherein the nested-simultaneous switching pattern is determined and then fixed at the beginning of the sequence.

Paragraph 181: The system of Paragraph 168 wherein each ground pad is connected to, and disconnected from, the radiofrequency signal generator by a switch.

Paragraph 182: A system for tissue ablation that includes a radiofrequency signal generator, a controller, an ablation electrode, and at least two ground pads; wherein the controller can connect each ground pad to the radiofrequency signal generator so that current flows between the ablation electrode and the ground pad through a living body, and the controller can disconnect each ground pad from the radiofrequency signal generator so that current does not substantially flow between the ablation electrode and the ground pad; wherein the controller disconnects the ground pads from the radiofrequency signal generator in an order, each ground pad being disconnected either after or at the same time as the preceding ground pad in the order; wherein the controller connects the ground pads to the radiofrequency signal generator in the order, each ground pad being connected either before or at the same time as the preceding ground pad in the order; wherein the order is not predetermined.

Paragraph 183: The system of Paragraph 182 wherein the order or timing by which the controller connects or disconnects ground pads is configured to regulate a measured parameter of each ground pad.

Paragraph 184: The system of Paragraph 183 wherein the parameter of each ground pad is the current flowing through each ground pad.

Paragraph 185: The system of Paragraph 183 wherein the parameter of each ground pad is the root-mean-squared current flowing through each ground pad over a time window.

Paragraph 186: The system of Paragraph 183 wherein the parameter of each ground pad is the temperature of each ground pad.

Paragraph 187: The system of Paragraph 183 wherein the order in which ground pads are disconnected is configured to minimize the total duration for which any of the ground pads is disconnected during the tissue ablation.

Paragraph 188: The system of Paragraph 183 wherein the order in which ground pads are disconnected is configured to maximize the number of ground pads connected at the same time during the tissue ablation.

Paragraph 189: The system of Paragraph 182 wherein when a ground pad is disconnected, it presently carries the most current among the presently connected ground pads.

Paragraph 190: The system of Paragraph 182 wherein when a ground pad is disconnected, it presently has the highest temperature among the presently connected ground pads.

Paragraph 191: The system of Paragraph 182 wherein the order is monotonically decreasing in the current carried by each pad when all ground pads are connected.

Paragraph 192: The system of Paragraph 182 wherein the order is monotonically decreasing in rate of increase in the temperature of each ground pad when all ground pads are connected.

Paragraph 193: The system of Paragraph 182 wherein the controller repeatedly disconnects the ground pads from the radiofrequency signal generator in the order, each ground pad being disconnected either after or at the same time as the preceding ground pad in the order; and repeatedly connects the ground pads to the radiofrequency signal generator in the order, each ground pad being connected either before or at the same time as the preceding ground pad in the order.

Paragraph 194: The system of Paragraph 182 wherein each ground pad is connected to and disconnected from the radiofrequency signal generator by means of a switch.

Paragraph 195: A method for distributing radiofrequency current from an ablation electrode, through a living body, between at least two ground pads comprising: connecting each of the ground pads to the current source so that current flows through each ground pad at the same time; selecting at least one of the ground pads to be disconnected based on at least one measurement; both disconnecting the selected ground pads from the current source, and connecting each of the non-selected ground pads to the current source, so that current does not substantially flow through any of the selected ground pads, and current flows through each of the non-selected ground pads, at the same time.

Paragraph 196: The method of Paragraph 195 performed in whole or in part by an automated controller.

Paragraph 197: The method of Paragraph 195 configured for preventing burning of tissue in contact with a ground pad.

Paragraph 198: The method of Paragraph 195 wherein the at least one measurement includes a measurement of the current flowing through a ground pad, or a measurement of the temperature of a ground pad.

Paragraph 199: The method of Paragraph 195 configured to regulate at least one measured parameter of a ground pad.

Paragraph 200: The method of Paragraph 199 wherein the at least one measured and regulated parameter includes the current flowing through a selected ground pad, the current flowing through a non-selected ground pad, the temperature of a selected ground pad, or the temperature of a non-selected ground pad.

Paragraph 201: The method of Paragraph 199 wherein regulating a measured parameter comprises hold the parameter below a limit.

Paragraph 202: The method of Paragraph 199 wherein regulating at least one measured parameter of a ground pad comprises equalizing the measured parameter of each of at least two ground pads.

Paragraph 203: The method of Paragraph 195 wherein the at least one measurement includes a measurement of the current flowing through each ground pad when current flows through each ground pad at the same time; and said selecting at least one of the ground pads to be disconnected based on at least one measurement comprises selecting the one or more ground pads having the highest current measurement, to be disconnected.

Paragraph 204: The method of Paragraph 195 wherein the at least one measurement includes a measurement of root-mean-squared current for each ground pad over a time period, and selecting at least one of the ground pads to be disconnected based on at least one measurement comprises selecting the one or more ground pads having the highest current measurement, to be disconnected.

Paragraph 205: The method of Paragraph 195 wherein the at least one measurement includes a measurement of temperature for each ground pad, and selecting at least one of the ground pads to be disconnected based on at least one measurement comprises selecting the one or more ground pads having the highest temperature measurement, to be disconnected.

Paragraph 206: The method of Paragraph 195 wherein the duration of said connecting each of the ground pads to the current source so that current flows through each ground pad at the same time; or the duration of said both disconnecting the selected ground pads from the current source, and connecting each of the non-selected ground pads to the current source, so that current does not substantially flow through any of the selected ground pads, and current flows through each of the non-selected ground pads, at the same time; is short relative to the thermal response time of the ground pads.

Paragraph 207: The method of Paragraph 195 and further comprising at least one repetition of the method of Paragraph 195 during a single radiofrequency ablation process.

Paragraph 208: The method of Paragraph 207 wherein the same at least one of the ground pads are selected in each repetition.

Paragraph 209: The method of Paragraph 195 wherein connecting each of the ground pads to the current source so that current flows through each ground pad at the same time precedes both disconnecting the selected ground pads from the current source, and connecting each of the non-selected ground pads to the current source, so that current does not substantially flow through any of the selected ground pads, and current flows through each of the non-selected ground pads, at the same time.

Paragraph 210: The method of Paragraph 195 wherein both disconnecting the selected ground pads from the current source, and connecting each of the non-selected ground pads to the current source, so that current does not substantially flow through any of the selected ground pads, and current flows through each of the non-selected ground pads, at the same time precedes connecting each of the ground pads to the current source so that current flows through each ground pad at the same time.

Paragraph 211: The method of Paragraph 195 wherein connecting a ground pad to the current source, and disconnecting the ground pad from the current source, is performed by means of a switch that is connected to both the ground and the current source.

Paragraph 212: The method of Paragraph 195 and further comprising applying the method of Paragraph 195 to the non-selected ground pads.

Paragraph 213: The method of Paragraph 195 and further comprising recursively applying the method of Paragraph 195 to the non-selected ground pads of each of at least one recursion of the method of Paragraph 195.

Paragraph 214: The method of Paragraph 213 and further comprising one or more repetitions of the method of Paragraph 213 during a single radiofrequency ablation process.

Paragraph 215: The method of Paragraph 214 wherein the selected ground pads of each recursion of the method of Paragraph 195 are the same for each repetition of the Paragraph 214.

Paragraph 216: The method of Paragraph 195 wherein distributing radiofrequency current from an ablation electrode, through a living body, between at least two ground pads comprises holding a function of current for each of the ground pads below a limit.

Paragraph 217: The method of Paragraph 216 wherein the function of current is the root-mean-squared current over a time window.

Paragraph 218: The method of Paragraph 195 wherein distributing radiofrequency current from an ablation electrode, through a living body, between at least two ground pads comprises equalizing a function of current for each of the ground pads.

Paragraph 219: The method of Paragraph 218 wherein the function of current is the root-mean-squared current over a time window.

Paragraph 220: The method of Paragraph 195 and further comprising displaying the at least one measurement to a person in real-time.

Paragraph 221: The method of Paragraph 195 and further comprising displaying to person a measurement of a ground pad in real-time.

Paragraph 222: A method for distributing radiofrequency current from an ablation electrode among at least two ground pads comprising: selecting a first ground pad based in whole or in part on at least one measurement of a ground pad; and switching among at least two states; wherein the states include a first state in which the first ground pad and a second ground pad each carry some or all of the current; wherein the states include a second state in which the first ground pad does not carry a substantial portion of the current, and the second ground pad carries some or all of the current.

Paragraph 223: The method of Paragraph 222 wherein the at least one measurement of a ground pad includes the current flowing through a ground pad, the power dissipated in the tissue near the ground pad, or the temperature of a ground pad.

Paragraph 224: The method of Paragraph 222 wherein said switching among at least two states comprises repeatedly changing the configuration of a switching system that connect each ground pad to the source of the current, in order to produce the states.

Paragraph 225: The method of Paragraph 222 performed by an automated controller.

Paragraph 226: The method of Paragraph 222 configured to regulate at least one measurement of a ground pad.

Paragraph 227: The method of Paragraph 222 configured to regulate at least one measurement for each ground pad.

Paragraph 228: The method of Paragraph 222 wherein the states can occur in any order, and each state can occur one or more times.

Paragraph 229: The method of Paragraph 222 wherein at one additional electrode carries some or all of the current.

Paragraph 230: The method of Paragraph 222 wherein the states include a state in which no ground pad carries a substantial portion of the current.

Paragraph 231: The method of Paragraph 222 wherein there is one or more ground pad that does not carry a substantial portion of the current.

Paragraph 232: The method of Paragraph 222 and further comprising changing the selection of the first ground pad at least once during said switching among at least two states, based in whole or in part on at least one measurement of a ground pad.

Paragraph 233: The method Paragraph 222 wherein the states further include at least one state in which a subset of the ground pads do not carry a substantial portion of the current, and each of the ground pads that are not in the subset carries some or all of the current.

Paragraph 234: The method Paragraph 222 wherein at least two of the ground pads are combined into a single pad structure within which each pad is electrically isolated from the other ground pads.

Paragraph 235: The method of Paragraph 222 and further comprising selecting each of the second through (N−1)-th ground pads based in whole or in part on at least one measurement of a ground pad; wherein in the first state, the second through the (N−1)-th ground pads and an N-th through P-th ground pads each carry some or all of the current; wherein for each integer M in the range two to N, the states include an M-th state in which each of the first through (M−1)-th ground pads do not carry a substantial portion of the current, and each of the M-th through P-th ground pads carries some or all of the current; N being an integer number greater than two, and P being an integer number that is greater than or equal to N.

Paragraph 236: The method of Paragraph 235 and further comprising changing the selection any one or more of the first through (N−1)-th ground pads at least once, changing the value of N, or changing the value of P, during said switching among at least two states, based in whole or in part on at least one measurement of a ground pad.

Paragraph 237: The method of Paragraph 235 wherein the states include an (N+1)-th state in which none of the first through P-th ground pads carries a substantial portion of the current.

Paragraph 238: A system for tissue ablation that includes a radiofrequency signal generator, a controller, an ablation electrode, at least two ground pads, and a switching system by means of which each ground pad can be connected to and disconnected from the radiofrequency signal generator; wherein current from the radiofrequency signal generator flows between the electrode and each ground pad through a living body; wherein the controller turns off the radiofrequency signal generator when a ground pad is being connected or disconnected from the radiofrequency signal generator during a tissue ablation process.

Paragraph 239: A system for tissue ablation that includes a radiofrequency signal generator, a controller, an ablation electrode, and at least two ground pads; wherein current from the radiofrequency signal generator flows between the electrode and each ground pad through a living body; wherein the controller reduces the current when a ground pad is being connected or disconnected from the radiofrequency signal generator by a switch in order to prevent undesired stimulation of excitable tissue in the living body.

Paragraph 240: A method of avoiding undesired electrical stimulation of excitable tissue during a radiofrequency tissue ablation process in which a ground pad is connected to or disconnected from the source of the radiofrequency signal, comprising reducing or turning off the radiofrequency signal output while a ground pad is in the process of being either connected to or disconnected from the source of radiofrequency signal.

Paragraph 241: The method of Paragraph 240 wherein the ground pad is connected to or disconnected from the source by means of a switch.

Paragraph 242: A method of avoiding undesired electrical stimulation of excitable tissue during a multi-electrode radiofrequency tissue ablation process in which an ablation electrode is connected to or disconnected from the source of the radiofrequency signal, comprising reducing or turning off the radiofrequency signal output while the ablation electrode is in the process of being either connected to or disconnected from the source of radiofrequency signal.

Paragraph 243: The method of Paragraph 242 wherein the ablation electrode is connected to or disconnected from the source by means of a switch.

Paragraph 244: The method Paragraph 242 wherein the multi-electrode radiofrequency tissue ablation process is multi-electrode cooled radiofrequency tissue ablation process.

Paragraph 245: The method Paragraph 242 wherein ablated tissue includes a tumor.

Paragraph 246: The method Paragraph 242 wherein ablated tissue includes a nerve.

Paragraph 247: The method Paragraph 242 wherein ablated tissue is within a large organ, including but not limited to an organ in the list: liver, kidney, lung, pancreas, bone.

Paragraph 248: A system comprising at least one electrode, a nerve-stimulation signal generator, and a high-frequency ablation signal generator, wherein the system delivers a nerve-stimulation signal to a nerve through a first electrode, and the system delivers a high-frequency-ablation signal to tissue through a second electrode, such that the nerve is stimulated while tissue is being ablated.

Paragraph 249: The system of Paragraph 248 wherein the high-frequency ablation signal is a signal selected from the group: a radiofrequency ablation signal, a microwave ablation signal, a direct current ablation signal, a pulsed radiofrequency signal configured to hold the temperature measured by the second electrode below the neurolytic range, a superposition of a radiofrequency ablation signal and a direct current ablation signal, a superposition of a radiofrequency ablation signal and a direct current ablation signal, a superposition of a radiofrequency ablation signal and a microwave ablation signal.

Paragraph 250: The system of Paragraph 248 or 249 wherein the nerve-stimulation signal is a signal selected from the group: a biphasic signal, a signal comprising a sequence of biphasic square pulses, a signal comprising a sequence of biphasic square pulses having pulse width in the range 0.1-3 milliseconds, a signal comprising a sequence of biphasic square pulses having pulse frequency in the range 1 Hz to 200 Hz, a signal comprising sinusoidal bursts, a motor nerve stimulation signal, a nerve-stimulation signal with a frequency in the range 1 Hz to 10 Hz, a nerve-stimulation signal with a frequency 2 Hz, a nerve-stimulation signal with a frequency in the range 5 Hz, a sensory-nerve stimulation signal, a nerve-stimulation signal with a frequency in the range 50 Hz to 200 Hz, a nerve-stimulation signal with a frequency 50 Hz, a peripheral-nerve stimulation signal, a central-nerve stimulation signal, a high-frequency-block signal, a signal with frequency 2,000 Hz to 50,000 Hz, a nerve stimulation signal configured to block transmission of action potentials, a nerve stimulation signal with frequency less than 50,000 kHz.

Paragraph 251: The system of Paragraph 248, 249, or 250 wherein the first electrode and the second electrode are the same electrode.

Paragraph 252: The system of Paragraph 248, 249, or 250 wherein the first electrode and the second electrode are the same active tip on a single electrode.

Paragraph 253: The system of Paragraph 248, 249, or 250 wherein first electrode and the second electrode are physically separate.

Paragraph 254: The system of Paragraph 248, 249, 250, or 251 wherein the tissue being ablated includes a nerve.

Paragraph 255: The system of Paragraph 248, 249, 250, or 251 wherein the tissue being ablated includes the nerve that is stimulated.

Paragraph 256: The system of Paragraph 255 wherein the nerve is a peripheral nerve.

Paragraph 257: The system of Paragraph 248, 249, 250, or 251 wherein the tissue being ablated does not include the nerve that is stimulated.

Paragraph 258: The system of Paragraph 248, 249, 250, 251, 252, 253, 254, 255, 256, or 257 wherein the nerve-stimulation signal and the high-frequency ablation signal are delivered at the same time.

Paragraph 259: The system of Paragraph 248, 249, 250, 251, 252, 253, 254, 255, 256, or 257 wherein the nerve-stimulation signal and the high-frequency ablation signal are interleaved in time such that they are not delivered at the same time.

Paragraph 260: The system of Paragraph 248, 249, 250, 251, 252, 253, 254, 255, 256, 257, 258, or 259 and further including a recording electrode and monitoring device for measuring electrical signals on the stimulated nerve, while it is being stimulated.

Paragraph 261: A method for reducing or blocking a patient's perception of a tissue ablation process comprising applying an electrical stimulation signal to a nerve during the tissue ablation process.

Paragraph 262; The method of Paragraph 261 wherein the tissue ablation process comprises a high-frequency electrical tissue ablation process.

Paragraph 263: The method of Paragraph 261 or 262 wherein the tissue ablation comprises a radiofrequency ablation process.

Paragraph 264: The method of Paragraph 261 or 262 wherein the tissue ablation is selected from the group: high-frequency ablation, radiofrequency ablation, pulsed radiofrequency neuromodulation, microwave ablation, cryogenic ablation, laser ablation, ablation by heating a resistive coil heating, ablation by beating a probe.

Paragraph 265: The method of Paragraph 261 wherein the patient's perception includes pain.

Paragraph 266: The method of Paragraph 261 wherein the electrical stimulation signal is a high-frequency nerve block signal.

Paragraph 267: The method of Paragraph 261 wherein tissue ablation process and the electrical stimulation signal performed by a single system.

Paragraph 268: The method of Paragraph 261 wherein the ablated tissue includes a nerve.

Paragraph 269: The method of Paragraph 268 wherein the ablated nerve is the same nerve as the stimulated nerve.

Paragraph 270: The method of Paragraph 261 wherein tissue ablation process and the electrical stimulation signal are performed by a single electrode.

Paragraph 271: The method of Paragraph 261 and further including stopping the ablation process, stopping the electrical stimulation signal, and then testing the result of the ablation process based in whole or in part of the patient's perception of pain before and after the ablation process.

Paragraph 272: A method for monitoring the progress of a nerve ablation process comprising: stimulating a nerve during the process of ablating the nerve, and monitoring the response of the nerve to the stimulation.

Paragraph 273: The method of Paragraph 272 wherein monitoring comprises monitoring the conduction of action potentials through the region of the nerve that is intended to be ablated.

Paragraph 274: The method of Paragraph 272 wherein monitoring comprising monitoring the conduction of action potentials through the region of the nerve that is proximate to an ablation probe active tip.

Paragraph 275: The method of Paragraph 272 wherein the location of the nerve ablation process is positioned along the nerve between the location nerve stimulation and the location of the monitoring of the response of the nerve to the stimulation.

Paragraph 276: The method of Paragraphs 272, 273, 274, or 275 wherein monitoring is performed by one or more of the methods selected form the group: measuring an electrical signal conducted by the nerve, observing a physiological response influenced by the nerve, observing twitching from a muscle innervated by the nerve, monitoring the patient's perception of the stimulation signal.

Paragraph 277: The method of Paragraph 272, 273, 274, 275, or 276, and further comprising: stopping the nerve ablation process when the response of the nerve to the stimulation is reduced to below a threshold.

Paragraph 278: The method of Paragraphs 272, 273, 274, 275, 276, or 277 wherein the nerve ablation process is of one or more of the types selected from the group: a radiofrequency ablation, a microwave ablation, a direct current, a pulsed radiofrequency configured to hold the temperature measured by the second electrode below the neurolytic range, combined radiofrequency and direct current ablation, cooled RF ablation, perfusion RF ablation, combined radiofrequency and microwave ablation.

Paragraph 279: The system of Paragraph 272, 273, 274, 275, 276, 277, or 278 wherein the nerve stimulation is of one or more of the types selected from the group: electrical nerve stimulation, an electrical signal configured to induce repeated nerve firing, a biphasic signal, a signal comprising a sequence of biphasic square pulses, a signal comprising a sequence of biphasic square pulses having pulse width in the range 0.1-3 milliseconds, a signal comprising a sequence of biphasic square pulses having pulse frequency in the range 1 Hz to 200 Hz, a signal comprising sinusoidal bursts, a motor nerve stimulation signal, a nerve-stimulation signal with a frequency in the range 1 Hz to 10 Hz, a nerve-stimulation signal with a frequency 2 Hz, a nerve-stimulation signal with a frequency in the range 5 Hz, a sensory-nerve stimulation signal, a nerve-stimulation signal with a frequency in the range 50 Hz to 200 Hz, a nerve-stimulation signal with a frequency 50 Hz, a peripheral-nerve stimulation signal, a central-nerve stimulation signal, mechanical stimulation of the nerve, stimulation of a receptor that stimulates the nerve, stimulation of a physiologic process that stimulates the nerve, mechanical manipulation of the patient that stimulates the nerve.

Paragraph 280: A method wherein an electrical stimulation signal is applied to a nerve and is configured to block the perception of pain generated by the ablation of the nerve.

Paragraph 281: The method of Paragraph 280 wherein the electrical stimulation signal induces a high-frequency conduction block.

Paragraph 282: The method of Paragraph 280 wherein the nerve is a peripheral nerve and wherein the electrical stimulation signal is applied to a location on the nerve that is closer to the spinal cord than the ablation at which the nerve is being ablated.

Paragraph 283: The method of Paragraph 280 wherein the ablation of the nerve is produced by a high-frequency electrical signal delivered to an electrode.

Paragraph 284: The method of Paragraph 280 wherein the electrical stimulation signal and the high-frequency electrical signal are produced by the same electrosurgical generator unit.

Paragraph 285: The method of Paragraph 280 wherein the high-frequency electrical signal is a radiofrequency signal.

Paragraph 286: A method wherein an electrical stimulation signal is applied to a nerve at a first location, an ablation process is applied to the nerve at a second location, and the transmission of nerve signals generated at the first location through the second location are monitored during the ablation process.

Paragraph 287: The method of Paragraphs 286 wherein the ablation process is a high-frequency ablation process.

Paragraph 288: The method of Paragraph 286 wherein the electrical stimulation signal and the high-frequency ablation process are produced by the same electrosurgical generator unit.

Paragraph 289: The method of Paragraph 286 wherein the ablation process is a radiofrequency ablation process.

Paragraph 290: The method of Paragraph 286 wherein the ablation process is a laser ablation process.

Paragraph 291: The method of Paragraph 286 wherein the transmission is monitored by placing a recording electrode at a third location along the nerve, wherein the second location is between the first location and the third location along the nerve.

Paragraph 292: The method of Paragraph 286 wherein the transmission is monitored by placing a recording electrode within a muscle innervated by the nerve, and the second location is between the first location and the muscle along the nerve.

Paragraph 293: The method of Paragraph 286 wherein the transmission is monitored by observation of contractions in a muscle innervated by the nerve, and the second location is between the first location and the muscle along the nerve.

Paragraph 294: A system including a radiofrequency generator and an ultrasound imaging machine wherein the radiofrequency generator can measure and control the operations of the ultrasound imaging machine, and the ultrasound imaging machine can measure and control the operations of the radiofrequency generator.

Paragraph 295: A high-frequency electrosurgical generator that can monitor and control an ultrasound imaging machine.

Paragraph 296: The system of Paragraph 295 wherein the high-frequency generator is a radiofrequency generator.

Paragraph 297: The system of Paragraph 295 wherein the high-frequency generator is a microwave generator.

Paragraph 298: The system of Paragraph 295 wherein the high-frequency generator includes a display on which ultrasound data is displayed.

Paragraph 299: The system of Paragraph 295 wherein the high-frequency generator includes a display on which ultrasound settings are displayed.

Paragraph 300: The system of Paragraph 295 wherein the high-frequency generator includes user interface elements for control of the settings and operations of the ultrasound machine.

Paragraph 301: The system of Paragraph 295 wherein the high-frequency generator adjusts its signal output in response to data measured from the ultrasound imaging machine.

Paragraph 302: The system of Paragraph 295 wherein the high-frequency generator automatically adjusts the operation of the ultrasound imagine in response to measurements of an ablation process.

Paragraph 303: The system of Paragraph 295 wherein the ultrasound machine and high-frequency generator are in same chassis.

Paragraph 304: The system of Paragraph 295 wherein a single user interface includes both high-frequency generator and ultrasound machine control functions.

Paragraph 305: The system of Paragraph 295 wherein the control of ultrasound machine is by means of a standardized interface for connecting a high-frequency electrosurgical generator to an ultrasound imaging machine.

Paragraph 306: The system of Paragraph 295 wherein the high-frequency generator includes a common procedure record including both ultrasound and radiofrequency data.

Paragraph 307: The system of Paragraph 295 wherein the high-frequency generator is of a type selected from the group: radiofrequency generator, microwave generator, cooled radiofrequency generator and pump, impedance-controlled cooled radiofrequency tissue ablation, nerve radiofrequency ablation generator, neurological radiofrequency ablation generator, radiofrequency ablation generator that includes an integrated nerve stimulator.

Paragraph 308: An ultrasound imaging machine that can monitor and control a high-frequency electrosurgical generator.

Paragraph 309: The system of Paragraph 308 wherein the high-frequency generator is a radiofrequency generator.

Paragraph 310: The system of Paragraph 308 wherein the high-frequency generator is a microwave generator.

Paragraph 311: The system of Paragraph 308 wherein the ultrasound machine includes a display on which high-frequency generator data is displayed.

Paragraph 312: The system of Paragraph 308 wherein the ultrasound machine includes a display on which high-frequency generator settings are displayed.

Paragraph 313: The system of Paragraph 308 wherein the ultrasound machine includes user interface elements for control of the high-frequency generator settings and operations.

Paragraph 314: The system of Paragraph 308 wherein the ultrasound machine automatically adjusts its data acquisition process in response a measurement collected by the high-frequency generator.

Paragraph 315: The system of Paragraph 308 wherein the ultrasound machine automatically adjusts the operation of the high-frequency generator in response to an ultrasound measurement.

Paragraph 316: The system of Paragraph 308 wherein the ultrasound machine and high-frequency generator are in same chassis.

Paragraph 317: The system of Paragraph 308 wherein a single user interface includes control function of both the high-frequency generator and the ultrasound imaging machine.

Paragraph 318: The system of Paragraph 308 wherein the high-frequency generator includes a standardized interface by means of which an ultrasound imaging machine can control the high-frequency generator.

Paragraph 319: The system of Paragraph 308 wherein the ultrasound machine produces a common procedure record including both ultrasound and radiofrequency data.

Paragraph 320: A system that includes an ultrasound imaging apparatus, an electrosurgical tissue ablation generator, and a user interface which includes user controls and a data display for both the ultrasound imaging apparatus and the electrosurgical tissue ablation generator.

Paragraph 321: The system of Paragraph 320 wherein the user interface is a single user console.

Paragraph 322: A tissue ablation apparatus including an interface to which an ultrasound imaging machine can connect and thereby control the operations of the tissue ablation apparatus either automatically or by user input into the user interface of the ultrasound imaging machine, read data from the tissue ablation apparatus, and display data from the tissue ablation apparatus to the user by means of the user interface of the ultrasound imaging machine.

Paragraph 323: The system of Paragraph 322 wherein the ultrasound imaging machine can be selected from one or more ultrasound imaging machines configured to connect to the tissue ablation apparatus.

Paragraph 324: The system of Paragraph 322 and further including published specifications for the interface.

Paragraph 325: The system of Paragraph 322 wherein the tissue ablation apparatus is configured to be housed inside the ultrasound imaging machine's chassis.

Paragraph 326: A ultrasound imaging apparatus including an interface to which an tissue ablation apparatus can connect and thereby control the operations of the ultrasound imaging apparatus either automatically or by user input into the tissue ablation machine user interface, read data from the ultrasound imaging apparatus, and display data from the ultrasound imaging apparatus to the user by means of the user interface of the tissue ablation apparatus.

Paragraph 327: The system of Paragraph 326 wherein the tissue ablation apparatus can be selected from one or more tissue ablation apparatuses configured to connect to the ultrasound imaging apparatus.

Paragraph 328: The system of Paragraph 326 and further including published specifications for the interface.

Paragraph 329: The system of Paragraph 326 wherein the ultrasound imaging apparatus is configured to be housed inside the chassis of the tissue ablation apparatus.

Paragraph 330: A method for marketing a tissue ablation apparatus comprising constructing a tissue ablation apparatus having a data connection that provides for monitoring and control of the tissue ablation apparatus, and publishing the specification of the data connection.

Paragraph 331: A method for marketing a medical imaging apparatus comprising constructing a medical imaging apparatus having a data connection that provides for monitoring and control of the medical imaging apparatus, and publishing the specification of the data connection.

Paragraph 134A. The system of Paragraph 116 and further including a switching system by means of which each ground pad can be connected to and disconnected from the radiofrequency signal generator, wherein connecting a ground pad to the radiofrequency signal generator allows the flow of current from the radiofrequency signal generator through the ground pad, and wherein disconnecting a ground pad from the radiofrequency signal generator substantially stops the flow of current from the radiofrequency signal generator through the ground pad; and further including a controller that automatically connects and disconnects a ground pad from the radiofrequency signal generator to regulate the displayed parameter for the ground pad.

Paragraph 135A. The system of Paragraph 134A wherein the display for a ground pad includes a display of a moving average of the current flowing through the ground pad over at least one time period during which at least one ground-pad switch either opens or closes.

Paragraph 136A. The system of Paragraph 134A wherein the display for a ground pad includes a display of a root-mean-square moving average of the current flowing through the ground pad over at least one time window during which at least one ground-pad switch either opens or closes.

Paragraph 137A. The system of Paragraph 134A wherein the controller turns off the radiofrequency signal generator while a ground pad is being connected or disconnected from the radiofrequency signal generator during a tissue ablation process.

Paragraph 138A. The system of Paragraph 134A wherein the switching system includes a switch for each ground pad, wherein opening the switch for a ground pad disconnects the ground pad from the radiofrequency signal generator, and wherein closing the switch for a ground pad disconnects the ground pad from the radiofrequency signal generator.

Paragraph 139A. The system of Paragraph 134A wherein controller that automatically connects and disconnects one or more ground pads from the radiofrequency signal generator to regulate the displayed parameter for each ground pad.

Paragraph 60A. The system of Paragraph 36 and further including numerical display of the duration of each instance of the signal level being in the first range, each instance of the signal level being in the second range, or both.

Paragraph 61A. The system of Paragraph 35 and further including numerical display of the two or more parameters.

Paragraph 195A. The system of Paragraph 182 and further including a nerve-stimulation signal generator that can deliver a nerve-stimulation signal to the ablation electrode.

Paragraph 196A. The system of Paragraph 183 and further including a user display of the measured parameter of each ground pad.

Paragraph 197A. The system of Paragraph 182 wherein the controller turns off the radiofrequency signal generator while a ground pad is in the process of being connected to the radiofrequency signal generator or in the process of being disconnected from the radiofrequency signal generator.

A number of embodiments of the invention have been described. Nevertheless, it will be understood that various modifications may be made without departing from the spirit and scope of the invention. Accordingly, other embodiments are within the scope of the following claims. What we claim are the following.

What is claimed is:

1. A system for tissue ablation that includes a radiofrequency signal generator, a user interface, an ablation electrode, at least two ground pads, and a current-measurement system; wherein current from the radiofrequency signal generator is adapted to flow between the electrode and each ground pad through a living body; wherein the current-measurement system measures the current flowing through each ground pad; and wherein the user interface includes a numerical or graphical display of the currents measured for the ground pads.

2. The system of claim 1 wherein the display includes a display of the current measured for a ground pad.

3. The system of claim 1 wherein the display includes a display of the RMS value of the radiofrequency current measured for a ground pad.

4. The system of claim 1 wherein the display includes a display of a mathematical function of the current measured for a ground pad.

5. The system of claim 1 wherein the display includes a display of the current measured for each ground pad.

6. The system of claim 1 wherein the display includes a display of the portion of the total current flowing through all ground pads, that is flowing to ground pad.

7. The system of claim 6 wherein the portion is displayed as a fraction, a percentage, a fraction relative to a desired fraction, a fraction minus the quotient of one (1) divided by the total number of ground pads, a percentage relative to a desired percentage, or a percentage minus the quotient of one hundred (100) divided by the total number of ground pads.

8. The system of claim 1 wherein the display includes a display of a quotient wherein the dividend is the current measured for a ground pad and the devisor is the sum of the currents measured for all ground pads.

9. The system of claim 1 wherein the display includes a display of a measurement of the portion of the total current flowing to all ground pads, that is flowing to each ground pad.

10. The system of claim 1 wherein the display includes a display of a mathematical function of the current measured for a first ground pad and the current measured for a second ground pad.

11. The system of claim 1 wherein the display includes a display of an average of the current measured for a ground pad over a time window.

12. The system of claim 1 wherein the display includes a display of the root-mean-square value of the current flowing through a ground pad over a time window.

13. The system of claim 1 wherein the display includes a substantially real-time display of the current measured for a ground pad.

14. The system of claim 1 wherein the display includes a digital display.

15. The system of claim 1 wherein the display includes a display of the root-mean-squared current measured for each ground pad.

16. The system of claim 1 wherein the display includes a bar graph.

17. The system of claim 1 wherein the display includes a plot of a measured current as function of a time axis.

18. The system of claim 1 wherein the display includes a graph of the current measured for each ground pad as a function of time.

19. The system of claim 1 and further including a switching system by means of which each ground pad can be connected to and disconnected from the radiofrequency signal generator, wherein connecting a ground pad to the radiofrequency signal generator allows the flow of current from the radiofrequency signal generator through the ground pad, and wherein disconnecting a ground pad from the radiofrequency signal generator substantially stops the flow of current from the radiofrequency signal generator through the ground pad; and further including a controller that automatically connects and disconnects a ground pad from the radiofrequency signal generator to regulate the parameter that is measured and displayed for the ground pad.

20. The system of claim 19 wherein the display includes a display of a moving average of the current flowing through a ground pad over at least one time period during which at least one ground-pad switch either opens or closes.

21. The system of claim 19 wherein the display includes a display of a root-mean-square moving average of the current flowing through a ground pad over at least one time window during which at least one ground-pad switch either opens or doses.

22. The system of claim 19 wherein the controller turns off the radiofrequency signal generator during the time periods when the switching system is in the process of connecting a ground pad to the radiofrequency signal generator, and during the time periods when the switching system is in the process of disconnecting a ground pad from the radiofrequency signal generator, during a tissue ablation process.

23. The system of claim 19 wherein the switching system includes a switch for each ground pad, wherein opening the switch for a ground pad disconnects the ground pad from the radiofrequency signal generator, and wherein closing the switch for a ground pad connects the ground pad to the radiofrequency signal generator.

24. The system of claim 19 wherein the controller automatically connects and disconnects one or more ground pads from the radiofrequency signal generator to regulate the current that is measured and displayed for each ground pad.

25. The system of claim 1 and further including more than one ablation electrodes wherein current from the radiofrequency signal generator is adapted to flow between each electrode and each ground pad through the living body.

26. The system of claim 1 and further including a nerve-stimulation signal generator wherein current from the nerve-stimulation signal generator is adapted to flow between the electrode and at least one of the ground pads through the living body.

27. The system of claim 1 wherein the displayed currents are real-time operating measurements selected from the list: current, portion of total current flowing to all ground pads, or a function thereof.

28. The system of claim 9 wherein for each of all but one ground pad, the display includes a display of a measurement of the portion of the total current flowing to all ground pads, that is flowing to the ground pad, and wherein for the said one ground pad, the display includes a display of a measurement of the total current flowing to all ground pads.

* * * * *